US008603779B2

(12) United States Patent
Foster et al.

(10) Patent No.: US 8,603,779 B2
(45) **Date of Patent: *Dec. 10, 2013**

(54) NON-CYTOTOXIC PROTEIN CONJUGATES

(75) Inventors: Keith Foster, Salisbury (GB); John Chaddock, Salisbury (GB); Charles Penn, Salisbury (GB); Kei Roger Aoki, Irvine, CA (US); Joseph Francis, Irvine, CA (US); Lance Steward, Irvine, CA (US)

(73) Assignees: Syntaxin, Ltd., Abingdon (GB); Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/343,892

(22) Filed: Jan. 5, 2012

(65) Prior Publication Data

US 2012/0156186 A1 Jun. 21, 2012

Related U.S. Application Data

(63) Continuation-in-part of application No. 11/791,979, filed as application No. PCT/GB2005/004598 on Dec. 1, 2005, now Pat. No. 8,187,834.

(30) Foreign Application Priority Data

Dec. 1, 2004 (GB) .................................. 0426394.3
Mar. 10, 2005 (GB) .................................. 0504964.8
Mar. 10, 2005 (GB) .................................. 0504966.3

(51) Int. Cl.

| | |
|---|---|
| ***C07K 14/00*** | (2006.01) |
| ***A61K 38/16*** | (2006.01) |
| ***C12P 21/04*** | (2006.01) |
| ***C12P 21/06*** | (2006.01) |

(52) U.S. Cl.

USPC ........ 435/69.7; 435/69.1; 514/21.2; 530/350; 536/23.2

(58) Field of Classification Search

USPC ..................... 435/69.7, 69.1, 320.1; 530/350; 514/21.2; 536/23.2; 30/350

See application file for complete search history.

(56) References Cited

U.S. PATENT DOCUMENTS

| | | | |
|---|---|---|---|
| 5,668,255 | A | 9/1997 | Murphy |
| 5,989,545 | A | 11/1999 | Foster et al. |
| 5,998,375 | A | 12/1999 | Thgersen et al. |
| 6,136,564 | A | 10/2000 | Kopetzki |
| 6,395,513 | B1 | 5/2002 | Foster |
| 6,461,617 | B1 | 10/2002 | Shone |
| 6,632,440 | B1 | 10/2003 | Quinn |
| 6,776,990 | B2 | 8/2004 | Sachs |
| 6,843,998 | B1 | 1/2005 | Steward |
| 6,962,703 | B2 | 11/2005 | Foster |
| 7,052,702 | B1 | 5/2006 | Duggan |
| 7,056,729 | B2 | 6/2006 | Donovan |
| 7,132,259 | B1 | 11/2006 | Dolly |
| 7,192,596 | B2 | 3/2007 | Shone |
| 7,208,466 | B1 | 4/2007 | Foster |
| 7,244,436 | B2 | 7/2007 | Donovan |
| 7,244,437 | B2 | 7/2007 | Donovan |
| 7,262,291 | B2 | 8/2007 | Donovan |
| 7,276,473 | B2 | 10/2007 | Sachs |
| 7,413,742 | B2 | 8/2008 | Donovan |
| 7,419,676 | B2 | 9/2008 | Dolly |
| 7,422,877 | B2 | 9/2008 | Dolly |
| 7,452,543 | B2 | 11/2008 | Chaddock |
| 7,494,661 | B2 | 2/2009 | Sanders |
| 7,514,088 | B2 | 4/2009 | Steward |
| 7,658,933 | B2 | 2/2010 | Foster et al. |
| 7,659,092 | B2 | 2/2010 | Foster et al. |
| 7,709,228 | B2 | 5/2010 | Dolly |
| 7,736,659 | B2 | 6/2010 | Donovan |
| 7,740,868 | B2 | 6/2010 | Steward |
| 7,749,514 | B2 | 7/2010 | Steward |
| 7,780,968 | B2 | 8/2010 | Donovan |
| 7,785,606 | B2 | 8/2010 | Ichtchenko |

(Continued)

FOREIGN PATENT DOCUMENTS

| | | |
|---|---|---|
| EP | 1 422 240 A2 | 5/2004 |
| EP | 1422240 | 5/2004 |
| WO | 96/33273 | 10/1996 |
| WO | WO 96/33273 | 10/1996 |
| WO | WO 97/07208 | 2/1997 |
| WO | WO 98/07864 | 2/1998 |
| WO | WO 99/17806 | 4/1999 |
| WO | WO 00/57897 | 10/2000 |
| WO | WO 01/14570 A1 | 3/2001 |
| WO | 01/58936 | 8/2001 |

(Continued)

OTHER PUBLICATIONS

Translation of Japanese Office Action dated Jun. 28, 2011 in JP 2007-543906.

(Continued)

*Primary Examiner* — Chih-Min Kam

(74) *Attorney, Agent, or Firm* — Roylance, Abrams, Berdo & Goodman, L.L.P.

(57) ABSTRACT

The present invention is directed to non-cytotoxic protein conjugates for inhibition or reduction of exocytic fusion in a nociceptive sensory afferent cell. The protein conjugates comprise: (i) a galanin Targeting Moiety (TM), wherein the TM is an agonist of a receptor present on a nociceptive sensory afferent cell, and wherein the receptor undergoes endocytosis to be incorporated into an endosome within the nociceptive sensory afferent cell; (ii) a non-cytotoxic protease or a fragment thereof, wherein the protease or protease fragment is capable of cleaving a protein of the exocytic fusion apparatus of the nociceptive sensory afferent cell; and (iii) a Translocation Domain, wherein the Translocation Domain translocates the protease or protease fragment from within the endosome, across the endosomal membrane, and into the cytosol of the nociceptive sensory afferent cell. Nucleic acid sequences encoding the protein conjugates, methods of preparing same and uses thereof are is also described.

15 Claims, 28 Drawing Sheets

(56) References Cited

U.S. PATENT DOCUMENTS

| | | | |
|---|---|---|---|
| 7,811,584 | B2 | 10/2010 | Steward et al. |
| 7,833,535 | B2 | 11/2010 | Donovan |
| 7,887,810 | B2 | 2/2011 | Foster |
| 7,892,560 | B2 | 2/2011 | Foster |
| 7,897,157 | B2 | 3/2011 | Steward |
| 8,067,200 | B2 | 11/2011 | Foster et al. |
| 8,187,834 | B2 | 5/2012 | Foster et al. |
| 2003/0049264 | A1 | 3/2003 | Foster et al. |
| 2003/0180289 | A1 | 9/2003 | Foster |
| 2004/0071736 | A1 | 4/2004 | Quinn |
| 2004/0115727 | A1 | 6/2004 | Steward |
| 2005/0095251 | A1 | 5/2005 | Steward |
| 2005/0244435 | A1 | 11/2005 | Shone |
| 2006/0051356 | A1 | 3/2006 | Foster |
| 2006/0110410 | A1 | 5/2006 | Shone |
| 2006/0216283 | A1 | 9/2006 | Foster |
| 2007/0010447 | A1 | 1/2007 | Quinn |
| 2007/0010475 | A1 | 1/2007 | Richardson |
| 2007/0066559 | A1 | 3/2007 | Richardson |
| 2007/0184048 | A1 | 8/2007 | Foster |
| 2007/0184070 | A1 | 8/2007 | Shone |
| 2007/0248626 | A1 | 10/2007 | Shone |
| 2008/0025994 | A1 | 1/2008 | Steward |
| 2008/0032928 | A1 | 2/2008 | Quinn |
| 2008/0032931 | A1 | 2/2008 | Steward |
| 2008/0038274 | A1 | 2/2008 | Foster |
| 2008/0070278 | A1 | 3/2008 | North |
| 2008/0182294 | A1 | 7/2008 | Dolly |
| 2008/0311622 | A1 | 12/2008 | Dolly |
| 2009/0004224 | A1 | 1/2009 | Steward |
| 2009/0005313 | A1 | 1/2009 | Steward |
| 2009/0018081 | A1 | 1/2009 | Steward |
| 2009/0030182 | A1 | 1/2009 | Dolly |
| 2009/0030188 | A1 | 1/2009 | Dolly |
| 2009/0042270 | A1 | 2/2009 | Dolly |
| 2009/0069238 | A1 | 3/2009 | Steward |
| 2009/0081730 | A1 | 3/2009 | Dolly |
| 2009/0087458 | A1 | 4/2009 | Dolly |
| 2009/0104234 | A1 | 4/2009 | Francis |
| 2009/0117157 | A1 | 5/2009 | Brin |
| 2009/0162341 | A1 | 6/2009 | Foster et al. |
| 2010/0034802 | A1 | 2/2010 | Foster |
| 2010/0055761 | A1 | 3/2010 | Seed |
| 2010/0196421 | A1 | 8/2010 | Ichtchenko |
| 2010/0209955 | A1 | 8/2010 | Oyler |
| 2010/0303757 | A1 | 12/2010 | Francis |
| 2010/0303789 | A1 | 12/2010 | Francis |
| 2010/0303791 | A1 | 12/2010 | Francis |
| 2011/0091437 | A1 | 4/2011 | Foster |

FOREIGN PATENT DOCUMENTS

| | | |
|---|---|---|
| WO | WO 02/007759 A3 | 1/2002 |
| WO | WO 2004/024909 A2 | 3/2004 |
| WO | WO 2005/023309 A2 | 3/2005 |
| WO | 2006/026780 | 3/2006 |
| WO | 2006/059093 | 6/2006 |
| WO | 2006/059105 | 6/2006 |
| WO | 2006/059113 | 6/2006 |
| WO | WO 2006/059113 | 6/2006 |
| WO | 2007/138339 | 12/2007 |

OTHER PUBLICATIONS

Translation of Japanese Office Acton dated Jun. 28, 2011 in JP 2007-543908.

Sagane et al., Dichain structure of botulinum neurotoxin : Identification of clevage in Tyles C, D, and F neurotoxin molecules, J. Protein Chemistry 18(8) :855-892 (1999).

Chaddock, et al., "Retargeted Clostridial Endopeptidases: Inhibition of Nociceptive Neurotransmitter Release in Vitro, and Antinociceptive Activity in in Vivo Models of Pain," Movement Disorders, vol. 19, pp. S42-S47; Sep. 8, 2004.

U.S. Appl. No. 12/862,948, filed Aug. 25, 2010, Pending.

U.S. Appl. No. 13/239,573, filed Sep. 22, 2011, Pending.

U.S. Appl. No. 13/072,865, filed Mar. 28, 2011, Pending.

U.S. Appl. No. 13/212,868, filed Aug. 18, 2011, Pending.

U.S. Appl. No. 13/418,453, filed Mar. 13, 2012, Pending.

U.S. Appl. No. 12/303,078, filed Sep. 21, 2009, Abandoned.

U.S. Appl. No. 12/868,510, filed Aug. 25, 2010, Pending.

U.S. Appl. No. 13/419,381, filed Mar. 13, 2012, Pending.

U.S. Appl. No. 13/360,565, filed Jan. 27, 2012, Pending.

Office Action issued Sep. 10, 2012 in EP 10 166 556.0

Office Action issued Sep. 10, 2012 in EP 10 184 150.0.

Office Action issued Sep. 10, 2012 in EP 10 184 114.6.

Office Action issued Sep. 10, 2012 in EP 05 810 711.1.

Office Action issues Aug. 22, 2012 in CA 2,595,115.

Blanc, Jacky P. et al., Examination of the Requirement for an Amphiphilic Helical Structure in B-Endorphin through the Design, Synthesis, and Study of Model Peptides, The Journal of Biological Chemistry, vol. 258, No. 13, 1983, pp. 8277-8284.

Shone, Clifford C. et al., A 50-kDa fragment from the NH2-terminus of the heavy subunit of Clostridium botulinum type A neurotoxin forms channels in lipid vesicies, Eur. J Biochem. 167, 175-180, 1987.

Wagner, Ernst et al., Influenza virus hemagglutinin HA-2 N-terminal fusogenic peptides augment gene transfer by transferrin-polysine-DNA complexes: Toward a synthetic virus-like gene-transfer vehicle, Proc. Natl. Acad. Sci., USA, vol. 89, pp. 7934-7938, 1992.

Plank, Christian et al., The Influence of Endosome-disruptive Peptides on Gene Transfer Using Synthetic Virus-like Gene Transfer Systems, The Journal of Biological Chemistry, vol. 269, No. 17, 1994, pp. 12918-12924.

Dooley, Colette T., et al., Binding and in Vitro Activities of Peptides with High Affinity for the Nociceptin/Orphanin FQ Receptor, ORL1, The Journal of Pharmacology and Experimental Therapeutics, 1997, vol. 283, No. 2, pp. 735-741.

Vergnoillie, N et al., Proteinase-activated receptor-2 and hyperalgesia: A novel pain pathway, Nature Medicine, vol. 7, No. 7, 2001, pp. 821-826.

Rizzi, Daniela et al., [Arg14, LYS15]Nociceptin, a Highly Potent Agonist of the Nociceptin/Orphanin FQ Receptor: in Vitro and in Vivo Studies, The Journal of Pharmacology and Experimental Therapeutics, 2002, vol. 300, No. 1, pp. 57-63.

Turton, Kathryn et al., Botulinum and tetanus neurotoxins: structure, function an therapeutic utility, TRENDS in Biochemical Sciences, vol. 27, No. 11, 2002, pp. 552-558.

Maile, Rebecca et al., Effects of nociceptin and analogues of nociceptin upon spontaneous dorsal root activity recorded from an in vitro preparation of rat spinal cord, Neuroscience Letters 350 (2003) 190-192.

Craddock, John A. et al., Manipulation of Signal Transduction by Botulinum Neurotoxins and their Derivatives, Current Signal Transduction Therapy, 2007, 2, 221-225.

Guerrini, Remo et al., Address and Message Sequences for the Nociceptin Receptor: A Structure-Activity Study of Nociceptin-(1-13)-peptide amide, J. Med. Chem., 1997, 40, 1739-1793.

Scriavo, Giampietro et al., Neurotoxins Affecting Neuroexocytosis, Physiological Reviews, vol. 80, No. 2, 2000, pp. 717-766.

X.J. et al., Galanin and spinal nociceptive mechanisms: recent advances and therapeutic implications, Neuropeptides, 2000, 34(3 &4), 137-147.

Okada Kazushi et al., Highly Potent Nociceptin Analog Conte ning the Arg-Lys Triple Repeat, Biochemical and Biophysical Research Communications, 273, 493-498, 2000.

Mogil, Jeffrey S. et al., The Molecular and Behavioral Pharmacology of the Orphan FQ/Nociceptin Peptide, and Receptor Family, Pharmalogical Revews, 2001, vol. 53, No. 3, pp. 381-415.

Craddock, J.A., et al., A Conjugate Composed of Nerve Growth Factor Coupled to a Non-Toxic Derivative of Clostridium botulinum Neurotoxin Type A Can Inhibit Neurotransmitter Release in Vitro, Growth Factors 18(2):147-155, 2000.

Craddock, J.A., et al., Expression and Purification of Catalytically Active, Non-Toxic Endopeptidase Derivative of Clostridium botulinum Toxin Type A, Protein Expression and Purification 25(2):219-228, 2002.

(56) References Cited

OTHER PUBLICATIONS

Craddock, J.A., et al., Inhibition of Vesicular Secretion in Both Neuronal and Nonneuronal Cells by Retargeted Endopeptidase Derivative of Clostridium botulinum Neurotoxin Type A, Infection and Immunity 88(5).2587-2593, 2000.
Cui, M., et al., Retargeted Clostridial Endopeptidase: Antinociceptive Activity in Preclinical Models of Pain, Naunynn-Schmiedeberg's Archives of Pharmacology:R16, 2002.
Duggan, M. J., et al., Inhibition of Release of Neurotransmitters from Rat Dorsal Root Ganglia by a Novel Conjugate of a Clostridium Botulinum Toxin A Endopeptidase Fragment and Erythrina cristagalli Lectin, Journal of Biological Chemistry 277(38):34846-34852, 2002.
Foster, K.A., et al., Re-Engineering the Target Specificity of Clostridial Neurotoxins: A Route to Novel Therapeutics, Neurotoxicity Research 9(2,3):101-107 , 2006.
Inoue, M., et al., Nociceptin/Orphannin FQ-Induced Nociceptive Responses Through Substance P Release From Peripheral Nerve Endings in Nice, ONAS (Proceedings of the National Academy of Sciences USA), 95(18):10949-10953, 1998.
Sutton, J.M., et al., Preparation of Specifically Activatable Endopeptidase Derivatives of Clostridium bottulinum Toxins Type A, B, and C and Their Applications, Protein Expression and Purification 40(1):31-41 , 2005.
English Translation of Office Action issues Jun. 26, 2012 in JP 2007-543906.
English Translation of Office Action issues Jun. 26, 2012 in JP 2007-543908.
English Translation of Office Action issues Jun. 29, 2012 in CN 200780028089.0.
U.S. Appl. No. 11/798,610, Quinn.
U.S. Appl. No. 08/513,878, filed Dec. 1, 1995, North.
U.S. Appl. No. 09/572,431, filed May 17, 2000, North.
U.S. Appl. No. 11/819, 648, filed Jun. 28, 2007, Foster.
Okada et al., *Biochem. Biophys. Res. Comm.* 278 :493-498 (2000).
Chinese Office Action issued Mar. 25, 2013, from the Chinese Patent Office in related Chinese Patent Application No. 200780028089.0, and English translation.
English Translation of Japanese Office Action issued Feb. 19, 2013, from the Japanese Patent Office in related Japanese Patent Application No. JP 2011-258137.
Office Action dated Jul. 29, 2013, from the Mexican Patent Office in related Mexican Patent Application No. Application No. MX/a/2008/015227, and English summary thereof.

Duration of action following eDRG exposure for 1 Day

| Lab book reference | $pIC_{50}$ | pIC50 s.e.mean | $IC_{50}$ (nM) |
|---|---|---|---|
| Mean ±.s.e. mean | -6.19 | 0.10 | 639.24 |

| Ligand/ Molecule | $pEC_{50}$ ± sem | $n_H$ ± sem |
|---|---|---|
| Galanin 1-29 | 9.22 ± 0.14 | 0.79 ± 0.08 |
| Galanin fusion protein | 7.27 ± 0.08 | 1.14 ± 0.15 |

SEQUENCE LISTING

<160> NUMBER OF SEQ ID NOS: 123

<210> SEQ ID NO 1
<211> LENGTH: 51
<212> TYPE: DNA
<213> ORGANISM: Artificial Sequence
<220> FEATURE:
<223> OTHER INFORMATION: Synthetic

<400> SEQUENCE: 1
tttggcggtt tcacgggcgc acgcaaatca gcgcgtaaat tagctaacca g 51

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Phe Gly Gly Phe Thr Gly Ala Arg Lys Ser Ala Arg Lys Leu Ala Asn
1 5 10 15

Gln

<210> SEQ ID NO 3
<211> LENGTH: 33
<212> TYPE: DNA
<213> ORGANISM: Artificial Sequence
<220> FEATURE:
<223> OTHER INFORMATION: Synthetic

<400> SEQUENCE: 3
tttggcggtt tcacgggcgc acgcaaatca gcg 33

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Phe Gly Gly Phe Thr Gly Ala Arg Lys Ser Ala
1 5 10

<210> SEQ ID NO 5
<211> LENGTH: 33
<212> TYPE: DNA
<213> ORGANISM: Artificial Sequence
<220> FEATURE:
<223> OTHER INFORMATION: Synthetic

<400> SEQUENCE: 5
tttggcggtt tcacgggcgc acgcaaatat gcg 33

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Phe Gly Gly Phe Thr Gly Ala Arg Lys Tyr Ala
1 5 10

<210> SEQ ID NO 7
<211> LENGTH: 33
<212> TYPE: DNA
<213> ORGANISM: Artificial Sequence
<220> FEATURE:
<223> OTHER INFORMATION: Synthetic

<400> SEQUENCE: 7
tttggcggtt tcacgggcgc acgcaaatca tat 33

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

Phe Gly Gly Phe Thr Gly Ala Arg Lys Ser Tyr
1 5 10

<210> SEQ ID NO 9
<211> LENGTH: 51
<212> TYPE: DNA
<213> ORGANISM: Artificial Sequence
<220> FEATURE:
<223> OTHER INFORMATION: Synthetic

<400> SEQUENCE: 9
tttggcggtt tcacgggcgc acgcaaatca gcgcgtaaat atgctaacca g 51

<210> SEQ ID NO 10
<211> LENGTH: 17
<212> TYPE: PRT
<213> ORGANISM: Artificial Sequence
<220> FEATURE:
<223> OTHER INFORMATION: Synthetic

<400> SEQUENCE: 10

Phe Gly Gly Phe Thr Gly Ala Arg Lys Ser Ala Arg Lys Tyr Ala Asn
1 5 10 15

Gln

<210> SEQ ID NO 11
<211> LENGTH: 39
<212> TYPE: DNA
<213> ORGANISM: Artificial Sequence
<220> FEATURE:
<223> OTHER INFORMATION: Synthetic

<400> SEQUENCE: 11
tttggcggtt tcacgggcgc acgcaaatca gcgcgtaaa 39

<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

Phe Gly Gly Phe Thr Gly Ala Arg Lys Ser Ala Arg Lys
1 5 10

<210> SEQ ID NO 13
<211> LENGTH: 51
<212> TYPE: DNA
<213> ORGANISM: Artificial Sequence
<220> FEATURE:
<223> OTHER INFORMATION: Synthetic

<400> SEQUENCE: 13
tttggcggtt tcacgggcgc acgcaaatca gcgcgtaaac gcaaaaacca g 51

<210> SEQ ID NO 14
<211> LENGTH: 17
<212> TYPE: PRT
<213> ORGANISM: Artificial Sequence
<220> FEATURE:
<223> OTHER INFORMATION: Synthetic

<400> SEQUENCE: 14

Phe Gly Gly Phe Thr Gly Ala Arg Lys Ser Ala Arg Lys Arg Lys Asn
1 5 10 15

Gln

<210> SEQ ID NO 15
<211> LENGTH: 2736
<212> TYPE: DNA
<213> ORGANISM: Artificial Sequence
<220> FEATURE:
<223> OTHER INFORMATION: Synthetic

<400> SEQUENCE: 15
ctcgggattg agggtcgttt tggcggtttc acgggcgcac gcaaatcagc gcgtaaatta 60
gctaaccaga ctagtggcgg tgggggtagt ggcggtggcg gttcgggcgg gggtgggagc 120
cctaggggat ccatggagtt cgttaacaaa cagttcaact ataaagaccc agttaacggt 180
gttgacattg cttacatcaa aatcccgaac gctggccaga tgcagccggt aaaggcattc 240
aaaatccaca acaaaatctg ggttatcccg gaacgtgata cctttactaa cccggaagaa 300
ggtgacctga acccgccacc ggaagcgaaa caggtgccgg tatcttacta tgactccacc 360
tacctgtcta ccgataacga aaaggacaac tacctgaaag gtgttactaa actgttcgag 420
cgtatttact ccaccgacct gggccgtatg ctgctgacta gcatcgttcg cggtatcccg 480
ttctggggcg gttctaccat cgataccgaa ctgaaagtaa tcgacactaa ctgcatcaac 540
gttattcagc cggacggttc ctatcgttcc gaagaactga acctggtgat catcggcccg 600
tctgctgata tcatccagtt cgagtgtaag agctttggtc acgaagttct gaacctcacc 660
cgtaacggct acggttccac tcagtacatc cgtttctctc cggacttcac cttcggtttt 720
gaagaatccc tggaagtaga cacgaaccca ctgctgggcg ctggtaaatt cgcaactgat 780
cctgcggtta ccctggctca cgaactgatt catgcaggcc accgcctgta cggtatcgcc 840
atcaatccga accgtgtctt caaagttaac accaacgcgt attacgagat gtccggtctg 900
gaagttagct tcgaagaact gcgtactttt ggcggtcacg acgctaaatt catcgactct 960
ctgcaagaaa acgagttccg tctgtactac tataacaagt tcaaagatat cgcatccacc 1020
ctgaacaaag cgaaatccat cgtgggtacc actgcttctc tccagtacat gaagaacgtt 1080
tttaaagaaa aatacctgct cagcgaagac acctccggca aattctctgt agacaagttg 1140
aaattcgata aactttacaa aatgctgact gaaatttaca ccgaagacaa cttcgttaag 1200
ttctttaaag ttctgaaccg caaaacctat ctgaacttcg acaaggcagt attcaaaatc 1260
aacatcgtgc cgaaagttaa ctacactatc tacgatggtt tcaacctgcg taacaccaac 1320

-continued

```
ctggctgcta attttaacgg ccagaacacg gaaatcaaca acatgaactt cacaaaactg   1380

aaaaacttca ctggtctgtt cgagttttac aagctgctgt gcgtcgacgg catcattacc   1440

tccaaaacta aatctctgat agaaggtaga aacaaagcgc tgaacgacct ctgtatcaag   1500

gttaacaact gggatttatt cttcagcccg agtgaagaca acttcaccaa cgacctgaac   1560

aaaggtgaag aaatcacctc agatactaac atcgaagcag ccgaagaaaa catctcgctg   1620

gacctgatcc agcagtacta cctgaccttt aatttcgaca acgagccgga aaacatttct   1680

atcgaaaacc tgagctctga tatcatcggc cagctggaac tgatgccgaa catcgaacgt   1740

ttcccaaacg gtaaaaagta cgagctggac aaatatacca tgttccacta cctgcgcgcg   1800

caggaatttg aacacggcaa atcccgtatc gcactgacta actccgttaa cgaagctctg   1860

ctcaacccgt cccgtgtata caccttcttc tctagcgact acgtgaaaaa ggtcaacaaa   1920

gcgactgaag ctgcaatgtt cttgggttgg gttgaacagc ttgtttatga ttttaccgac   1980

gagacgtccg aagtatctac taccgacaaa attgcggata tcactatcat catcccgtac   2040

atcggtccgg ctctgaacat tggcaacatg ctgtacaaag acgacttcgt tggcgcactg   2100

atcttctccg gtgcggtgat cctgctggag ttcatcccgg aaatcgccat cccggtactg   2160

ggcacctttg ctctggtttc ttacattgca aacaaggttc tgactgtaca aaccatcgac   2220

aacgcgctga gcaaacgtaa cgaaaaatgg gatgaagttt acaaatatat cgtgaccaac   2280

tggctggcta aggttaatac tcagatcgac ctcatccgca aaaaaatgaa agaagcactg   2340

gaaaaccagg cggaagctac caaggcaatc attaactacc agtacaacca gtacaccgag   2400

gaagaaaaaa acaacatcaa cttcaacatc gacgatctgt cctctaaact gaacgaatcc   2460

atcaacaaag ctatgatcaa catcaacaag ttcctgaacc agtgctctgt aagctatctg   2520

atgaactcca tgatcccgta cggtgttaaa cgtctggagg acttcgatgc gtctctgaaa   2580

gacgccctgc tgaaatacat ttacgacaac cgtggcactc tgatcggtca ggttgatcgt   2640

ctgaaggaca aagtgaacaa taccttatcg accgacatcc cttttcagct cagtaaatat   2700

gtcgataacc aacgcctttt gtccactcta gactag                             2736
```

```
<210> SEQ ID NO 16
<211> LENGTH: 911
<212> TYPE: PRT
<213> ORGANISM: Artificial Sequence
<220> FEATURE:
<223> OTHER INFORMATION: Synthetic

<400> SEQUENCE: 16

Leu Gly Ile Glu Gly Arg Phe Gly Gly Phe Thr Gly Ala Arg Lys Ser
1               5                   10                  15

Ala Arg Lys Leu Ala Asn Gln Thr Ser Gly Gly Gly Gly Ser Gly Gly
            20                  25                  30

Gly Gly Ser Gly Gly Gly Gly Ser Pro Arg Gly Ser Met Glu Phe Val
        35                  40                  45

Asn Lys Gln Phe Asn Tyr Lys Asp Pro Val Asn Gly Val Asp Ile Ala
    50                  55                  60

Tyr Ile Lys Ile Pro Asn Ala Gly Gln Met Gln Pro Val Lys Ala Phe
65                  70                  75                  80

Lys Ile His Asn Lys Ile Trp Val Ile Pro Glu Arg Asp Thr Phe Thr
                85                  90                  95

Asn Pro Glu Glu Gly Asp Leu Asn Pro Pro Pro Glu Ala Lys Gln Val
            100                 105                 110

Pro Val Ser Tyr Tyr Asp Ser Thr Tyr Leu Ser Thr Asp Asn Glu Lys
```

-continued

```
        115                 120                 125

Asp Asn Tyr Leu Lys Gly Val Thr Lys Leu Phe Glu Arg Ile Tyr Ser
    130                 135                 140

Thr Asp Leu Gly Arg Met Leu Leu Thr Ser Ile Val Arg Gly Ile Pro
145                 150                 155                 160

Phe Trp Gly Gly Ser Thr Ile Asp Thr Glu Leu Lys Val Ile Asp Thr
                165                 170                 175

Asn Cys Ile Asn Val Ile Gln Pro Asp Gly Ser Tyr Arg Ser Glu Glu
            180                 185                 190

Leu Asn Leu Val Ile Ile Gly Pro Ser Ala Asp Ile Ile Gln Phe Glu
        195                 200                 205

Cys Lys Ser Phe Gly His Glu Val Leu Asn Leu Thr Arg Asn Gly Tyr
    210                 215                 220

Gly Ser Thr Gln Tyr Ile Arg Phe Ser Pro Asp Phe Thr Phe Gly Phe
225                 230                 235                 240

Glu Glu Ser Leu Glu Val Asp Thr Asn Pro Leu Leu Gly Ala Gly Lys
                245                 250                 255

Phe Ala Thr Asp Pro Ala Val Thr Leu Ala His Glu Leu Ile His Ala
            260                 265                 270

Gly His Arg Leu Tyr Gly Ile Ala Ile Asn Pro Asn Arg Val Phe Lys
        275                 280                 285

Val Asn Thr Asn Ala Tyr Tyr Glu Met Ser Gly Leu Glu Val Ser Phe
    290                 295                 300

Glu Glu Leu Arg Thr Phe Gly Gly His Asp Ala Lys Phe Ile Asp Ser
305                 310                 315                 320

Leu Gln Glu Asn Glu Phe Arg Leu Tyr Tyr Tyr Asn Lys Phe Lys Asp
                325                 330                 335

Ile Ala Ser Thr Leu Asn Lys Ala Lys Ser Ile Val Gly Thr Thr Ala
            340                 345                 350

Ser Leu Gln Tyr Met Lys Asn Val Phe Lys Glu Lys Tyr Leu Leu Ser
        355                 360                 365

Glu Asp Thr Ser Gly Lys Phe Ser Val Asp Lys Leu Lys Phe Asp Lys
    370                 375                 380

Leu Tyr Lys Met Leu Thr Glu Ile Tyr Thr Glu Asp Asn Phe Val Lys
385                 390                 395                 400

Phe Phe Lys Val Leu Asn Arg Lys Thr Tyr Leu Asn Phe Asp Lys Ala
                405                 410                 415

Val Phe Lys Ile Asn Ile Val Pro Lys Val Asn Tyr Thr Ile Tyr Asp
            420                 425                 430

Gly Phe Asn Leu Arg Asn Thr Asn Leu Ala Ala Asn Phe Asn Gly Gln
        435                 440                 445

Asn Thr Glu Ile Asn Asn Met Asn Phe Thr Lys Leu Lys Asn Phe Thr
    450                 455                 460

Gly Leu Phe Glu Phe Tyr Lys Leu Leu Cys Val Asp Gly Ile Ile Thr
465                 470                 475                 480

Ser Lys Thr Lys Ser Leu Ile Glu Gly Arg Asn Lys Ala Leu Asn Asp
                485                 490                 495

Leu Cys Ile Lys Val Asn Asn Trp Asp Leu Phe Phe Ser Pro Ser Glu
            500                 505                 510

Asp Asn Phe Thr Asn Asp Leu Asn Lys Gly Glu Glu Ile Thr Ser Asp
        515                 520                 525

Thr Asn Ile Glu Ala Ala Glu Glu Asn Ile Ser Leu Asp Leu Ile Gln
    530                 535                 540
```

-continued

```
Gln Tyr Tyr Leu Thr Phe Asn Phe Asp Asn Glu Pro Glu Asn Ile Ser
545                 550                 555                 560

Ile Glu Asn Leu Ser Ser Asp Ile Ile Gly Gln Leu Glu Leu Met Pro
                565                 570                 575

Asn Ile Glu Arg Phe Pro Asn Gly Lys Lys Tyr Glu Leu Asp Lys Tyr
            580                 585                 590

Thr Met Phe His Tyr Leu Arg Ala Gln Glu Phe Glu His Gly Lys Ser
        595                 600                 605

Arg Ile Ala Leu Thr Asn Ser Val Asn Glu Ala Leu Leu Asn Pro Ser
    610                 615                 620

Arg Val Tyr Thr Phe Phe Ser Ser Asp Tyr Val Lys Lys Val Asn Lys
625                 630                 635                 640

Ala Thr Glu Ala Ala Met Phe Leu Gly Trp Val Glu Gln Leu Val Tyr
                645                 650                 655

Asp Phe Thr Asp Glu Thr Ser Glu Val Ser Thr Thr Asp Lys Ile Ala
            660                 665                 670

Asp Ile Thr Ile Ile Ile Pro Tyr Ile Gly Pro Ala Leu Asn Ile Gly
        675                 680                 685

Asn Met Leu Tyr Lys Asp Asp Phe Val Gly Ala Leu Ile Phe Ser Gly
    690                 695                 700

Ala Val Ile Leu Leu Glu Phe Ile Pro Glu Ile Ala Ile Pro Val Leu
705                 710                 715                 720

Gly Thr Phe Ala Leu Val Ser Tyr Ile Ala Asn Lys Val Leu Thr Val
                725                 730                 735

Gln Thr Ile Asp Asn Ala Leu Ser Lys Arg Asn Glu Lys Trp Asp Glu
            740                 745                 750

Val Tyr Lys Tyr Ile Val Thr Asn Trp Leu Ala Lys Val Asn Thr Gln
        755                 760                 765

Ile Asp Leu Ile Arg Lys Lys Met Lys Glu Ala Leu Glu Asn Gln Ala
    770                 775                 780

Glu Ala Thr Lys Ala Ile Ile Asn Tyr Gln Tyr Asn Gln Tyr Thr Glu
785                 790                 795                 800

Glu Glu Lys Asn Asn Ile Asn Phe Asn Ile Asp Asp Leu Ser Ser Lys
                805                 810                 815

Leu Asn Glu Ser Ile Asn Lys Ala Met Ile Asn Ile Asn Lys Phe Leu
            820                 825                 830

Asn Gln Cys Ser Val Ser Tyr Leu Met Asn Ser Met Ile Pro Tyr Gly
        835                 840                 845

Val Lys Arg Leu Glu Asp Phe Asp Ala Ser Leu Lys Asp Ala Leu Leu
    850                 855                 860

Lys Tyr Ile Tyr Asp Asn Arg Gly Thr Leu Ile Gly Gln Val Asp Arg
865                 870                 875                 880

Leu Lys Asp Lys Val Asn Asn Thr Leu Ser Thr Asp Ile Pro Phe Gln
                885                 890                 895

Leu Ser Lys Tyr Val Asp Asn Gln Arg Leu Leu Ser Thr Leu Asp
            900                 905                 910
```

<210> SEQ ID NO 17
<211> LENGTH: 2700
<212> TYPE: DNA
<213> ORGANISM: Artificial Sequence
<220> FEATURE:
<223> OTHER INFORMATION: Synthetic

<400> SEQUENCE: 17

```
tttggcggtt tcacgggcgc acgcaaatca tatactagtg gcggtggggg tagtggcggt      60
```

-continued

```
ggcggttcgg gcgggggtgg gagccctagg ggatccatgg agttcgttaa caaacagttc    120
aactataaag acccagttaa cggtgttgac attgcttaca tcaaaatccc gaacgctggc    180
cagatgcagc cggtaaaggc attcaaaatc cacaacaaaa tctgggttat cccggaacgt    240
gataccttta ctaacccgga agaaggtgac ctgaacccgc caccggaagc gaaacaggtg    300
ccggtatctt actatgactc cacctacctg tctaccgata acgaaaagga caactacctg    360
aaaggtgtta ctaaactgtt cgagcgtatt tactccaccg acctgggccg tatgctgctg    420
actagcatcg ttcgcggtat cccgttctgg ggcggttcta ccatcgatac cgaactgaaa    480
gtaatcgaca ctaactgcat caacgttatt cagccggacg gttcctatcg ttccgaagaa    540
ctgaacctgg tgatcatcgg cccgtctgct gatatcatcc agttcgagtg taagagcttt    600
ggtcacgaag ttctgaacct cacccgtaac ggctacggtt ccactcagta catccgtttc    660
tctccggact tcaccttcgg ttttgaagaa tccctggaag tagacacgaa cccactgctg    720
ggcgctggta aattcgcaac tgatcctgcg gttaccctgg ctcacgaact gattcatgca    780
ggccaccgcc tgtacggtat cgccatcaat ccgaaccgtg tcttcaaagt taacaccaac    840
gcgtattacg agatgtccgg tctggaagtt agcttcgaag aactgcgtac ttttggcggt    900
cacgacgcta aattcatcga ctctctgcaa gaaaacgagt tccgtctgta ctactataac    960
aagttcaaag atatcgcatc caccctgaac aaagcgaaat ccatcgtggg taccactgct   1020
tctctccagt acatgaagaa cgtttttaaa gaaaaatacc tgctcagcga agacacctcc   1080
ggcaaattct ctgtagacaa gttgaaattc gataaacttt acaaaatgct gactgaaatt   1140
tacaccgaag acaacttcgt taagttcttt aaagttctga accgcaaaac ctatctgaac   1200
ttcgacaagg cagtattcaa aatcaacatc gtgccgaaag ttaactacac tatctacgat   1260
ggtttcaacc tgcgtaacac caacctggct gctaatttta acggccagaa cacggaaatc   1320
aacaacatga acttcacaaa actgaaaaac ttcactggtc tgttcgagtt ttacaagctg   1380
ctgtgcgtcg acggcatcat tacctccaaa actaaatctc tgatagaagg tagaaacaaa   1440
gcgctgaacg acctctgtat caaggttaac aactgggatt tattcttcag cccgagtgaa   1500
gacaacttca ccaacgacct gaacaaaggt gaagaaatca cctcagatac taacatcgaa   1560
gcagccgaag aaaacatctc gctggacctg atccagcagt actacctgac ctttaatttc   1620
gacaacgagc cggaaaacat ttctatcgaa aacctgagct ctgatatcat cggccagctg   1680
gaactgatgc cgaacatcga acgtttccca aacggtaaaa agtacgagct ggacaaatat   1740
accatgttcc actacctgcg cgcgcaggaa tttgaacacg gcaaatcccg tatcgcactg   1800
actaactccg ttaacgaagc tctgctcaac ccgtcccgtg tatacacctt cttctctagc   1860
gactacgtga aaaaggtcaa caaagcgact gaagctgcaa tgttcttggg ttgggttgaa   1920
cagcttgttt atgattttac cgacgagacg tccgaagtat ctactaccga caaaattgcg   1980
gatatcacta tcatcatccc gtacatcggt ccggctctga acattggcaa catgctgtac   2040
aaagacgact tcgttggcgc actgatcttc tccggtgcgg tgatcctgct ggagttcatc   2100
ccggaaatcg ccatcccggt actgggcacc tttgctctgg tttcttacat tgcaaacaag   2160
gttctgactg tacaaaccat cgacaacgcg ctgagcaaac gtaacgaaaa atgggatgaa   2220
gtttacaaat atatcgtgac caactggctg gctaaggtta atactcagat cgacctcatc   2280
cgcaaaaaaa tgaaagaagc actggaaaac caggcggaag ctaccaaggc aatcattaac   2340
taccagtaca accagtacac cgaggaagaa aaaaacaaca tcaacttcaa catcgacgat   2400
ctgtcctcta aactgaacga atccatcaac aaagctatga tcaacatcaa caagttcctg   2460
```

-continued aaccagtgct ctgtaagcta tctgatgaac tccatgatcc cgtacggtgt taaacgtctg 2520
gaggacttcg atgcgtctct gaaagacgcc ctgctgaaat acatttacga caaccgtggc 2580
actctgatcg gtcaggttga tcgtctgaag gacaaagtga acaatacctt atcgaccgac 2640
atcccttttc agctcagtaa atatgtcgat aaccaacgcc ttttgtccac tctagactag 2700

<210> SEQ ID NO 18
<211> LENGTH: 899
<212> TYPE: PRT
<213> ORGANISM: Artificial Sequence
<220> FEATURE:
<223> OTHER INFORMATION: Synthetic

<400> SEQUENCE: 18

Phe Gly Gly Phe Thr Gly Ala Arg Lys Ser Tyr Thr Ser Gly Gly Gly
1 5 10 15

Gly Ser Gly Gly Gly Gly Ser Gly Gly Gly Gly Ser Pro Arg Gly Ser
20 25 30

Met Glu Phe Val Asn Lys Gln Phe Asn Tyr Lys Asp Pro Val Asn Gly
35 40 45

Val Asp Ile Ala Tyr Ile Lys Ile Pro Asn Ala Gly Gln Met Gln Pro
50 55 60

Val Lys Ala Phe Lys Ile His Asn Lys Ile Trp Val Ile Pro Glu Arg
65 70 75 80

Asp Thr Phe Thr Asn Pro Glu Glu Gly Asp Leu Asn Pro Pro Pro Glu
85 90 95

Ala Lys Gln Val Pro Val Ser Tyr Tyr Asp Ser Thr Tyr Leu Ser Thr
100 105 110

Asp Asn Glu Lys Asp Asn Tyr Leu Lys Gly Val Thr Lys Leu Phe Glu
115 120 125

Arg Ile Tyr Ser Thr Asp Leu Gly Arg Met Leu Leu Thr Ser Ile Val
130 135 140

Arg Gly Ile Pro Phe Trp Gly Gly Ser Thr Ile Asp Thr Glu Leu Lys
145 150 155 160

Val Ile Asp Thr Asn Cys Ile Asn Val Ile Gln Pro Asp Gly Ser Tyr
165 170 175

Arg Ser Glu Glu Leu Asn Leu Val Ile Ile Gly Pro Ser Ala Asp Ile
180 185 190

Ile Gln Phe Glu Cys Lys Ser Phe Gly His Glu Val Leu Asn Leu Thr
195 200 205

Arg Asn Gly Tyr Gly Ser Thr Gln Tyr Ile Arg Phe Ser Pro Asp Phe
210 215 220

Thr Phe Gly Phe Glu Glu Ser Leu Glu Val Asp Thr Asn Pro Leu Leu
225 230 235 240

Gly Ala Gly Lys Phe Ala Thr Asp Pro Ala Val Thr Leu Ala His Glu
245 250 255

Leu Ile His Ala Gly His Arg Leu Tyr Gly Ile Ala Ile Asn Pro Asn
260 265 270

Arg Val Phe Lys Val Asn Thr Asn Ala Tyr Tyr Glu Met Ser Gly Leu
275 280 285

Glu Val Ser Phe Glu Glu Leu Arg Thr Phe Gly Gly His Asp Ala Lys
290 295 300

Phe Ile Asp Ser Leu Gln Glu Asn Glu Phe Arg Leu Tyr Tyr Tyr Asn
305 310 315 320

Lys Phe Lys Asp Ile Ala Ser Thr Leu Asn Lys Ala Lys Ser Ile Val

```
                325                 330                 335

Gly Thr Thr Ala Ser Leu Gln Tyr Met Lys Asn Val Phe Lys Glu Lys
            340                 345                 350

Tyr Leu Leu Ser Glu Asp Thr Ser Gly Lys Phe Ser Val Asp Lys Leu
        355                 360                 365

Lys Phe Asp Lys Leu Tyr Lys Met Leu Thr Glu Ile Tyr Thr Glu Asp
    370                 375                 380

Asn Phe Val Lys Phe Phe Lys Val Leu Asn Arg Lys Thr Tyr Leu Asn
385                 390                 395                 400

Phe Asp Lys Ala Val Phe Lys Ile Asn Ile Val Pro Lys Val Asn Tyr
                405                 410                 415

Thr Ile Tyr Asp Gly Phe Asn Leu Arg Asn Thr Asn Leu Ala Ala Asn
            420                 425                 430

Phe Asn Gly Gln Asn Thr Glu Ile Asn Asn Met Asn Phe Thr Lys Leu
        435                 440                 445

Lys Asn Phe Thr Gly Leu Phe Glu Phe Tyr Lys Leu Leu Cys Val Asp
    450                 455                 460

Gly Ile Ile Thr Ser Lys Thr Lys Ser Leu Ile Glu Gly Arg Asn Lys
465                 470                 475                 480

Ala Leu Asn Asp Leu Cys Ile Lys Val Asn Asn Trp Asp Leu Phe Phe
                485                 490                 495

Ser Pro Ser Glu Asp Asn Phe Thr Asn Asp Leu Asn Lys Gly Glu Glu
            500                 505                 510

Ile Thr Ser Asp Thr Asn Ile Glu Ala Ala Glu Glu Asn Ile Ser Leu
        515                 520                 525

Asp Leu Ile Gln Gln Tyr Tyr Leu Thr Phe Asn Phe Asp Asn Glu Pro
    530                 535                 540

Glu Asn Ile Ser Ile Glu Asn Leu Ser Ser Asp Ile Ile Gly Gln Leu
545                 550                 555                 560

Glu Leu Met Pro Asn Ile Glu Arg Phe Pro Asn Gly Lys Lys Tyr Glu
                565                 570                 575

Leu Asp Lys Tyr Thr Met Phe His Tyr Leu Arg Ala Gln Glu Phe Glu
            580                 585                 590

His Gly Lys Ser Arg Ile Ala Leu Thr Asn Ser Val Asn Glu Ala Leu
        595                 600                 605

Leu Asn Pro Ser Arg Val Tyr Thr Phe Phe Ser Ser Asp Tyr Val Lys
    610                 615                 620

Lys Val Asn Lys Ala Thr Glu Ala Ala Met Phe Leu Gly Trp Val Glu
625                 630                 635                 640

Gln Leu Val Tyr Asp Phe Thr Asp Glu Thr Ser Glu Val Ser Thr Thr
                645                 650                 655

Asp Lys Ile Ala Asp Ile Thr Ile Ile Ile Pro Tyr Ile Gly Pro Ala
            660                 665                 670

Leu Asn Ile Gly Asn Met Leu Tyr Lys Asp Asp Phe Val Gly Ala Leu
        675                 680                 685

Ile Phe Ser Gly Ala Val Ile Leu Leu Glu Phe Ile Pro Glu Ile Ala
    690                 695                 700

Ile Pro Val Leu Gly Thr Phe Ala Leu Val Ser Tyr Ile Ala Asn Lys
705                 710                 715                 720

Val Leu Thr Val Gln Thr Ile Asp Asn Ala Leu Ser Lys Arg Asn Glu
                725                 730                 735

Lys Trp Asp Glu Val Tyr Lys Tyr Ile Val Thr Asn Trp Leu Ala Lys
            740                 745                 750
```

-continued

```
Val Asn Thr Gln Ile Asp Leu Ile Arg Lys Lys Met Lys Glu Ala Leu
        755                 760                 765

Glu Asn Gln Ala Glu Ala Thr Lys Ala Ile Ile Asn Tyr Gln Tyr Asn
    770                 775                 780

Gln Tyr Thr Glu Glu Glu Lys Asn Asn Ile Asn Phe Asn Ile Asp Asp
785                 790                 795                 800

Leu Ser Ser Lys Leu Asn Glu Ser Ile Asn Lys Ala Met Ile Asn Ile
                805                 810                 815

Asn Lys Phe Leu Asn Gln Cys Ser Val Ser Tyr Leu Met Asn Ser Met
            820                 825                 830

Ile Pro Tyr Gly Val Lys Arg Leu Glu Asp Phe Asp Ala Ser Leu Lys
        835                 840                 845

Asp Ala Leu Leu Lys Tyr Ile Tyr Asp Asn Arg Gly Thr Leu Ile Gly
    850                 855                 860

Gln Val Asp Arg Leu Lys Asp Lys Val Asn Asn Thr Leu Ser Thr Asp
865                 870                 875                 880

Ile Pro Phe Gln Leu Ser Lys Tyr Val Asp Asn Gln Arg Leu Leu Ser
                885                 890                 895

Thr Leu Asp
```

<210> SEQ ID NO 19
<211> LENGTH: 2706
<212> TYPE: DNA
<213> ORGANISM: Artificial Sequence
<220> FEATURE:
<223> OTHER INFORMATION: Synthetic

<400> SEQUENCE: 19

```
tttggcggtt tcacgggcgc acgcaaatca gcgcgtaaaa ctagtggcgg tgggggtagt     60

ggcggtggcg gttcgggcgg gggtgggagc cctaggggat ccatggagtt cgttaacaaa    120

cagttcaact ataaagaccc agttaacggt gttgacattg cttacatcaa aatcccgaac    180

gctggccaga tgcagccggt aaaggcattc aaaatccaca acaaaatctg ggttatcccg    240

gaacgtgata cctttactaa cccggaagaa ggtgacctga acccgccacc ggaagcgaaa    300

caggtgccgg tatcttacta tgactccacc tacctgtcta ccgataacga aaaggacaac    360

tacctgaaag gtgttactaa actgttcgag cgtatttact ccaccgacct gggccgtatg    420

ctgctgacta gcatcgttcg cggtatcccg ttctggggcg gttctaccat cgataccgaa    480

ctgaaagtaa tcgacactaa ctgcatcaac gttattcagc cggacggttc ctatcgttcc    540

gaagaactga acctggtgat catcggcccg tctgctgata tcatccagtt cgagtgtaag    600

agctttggtc acgaagttct gaacctcacc cgtaacggct acggttccac tcagtacatc    660

cgtttctctc cggacttcac cttcggtttt gaagaatccc tggaagtaga cacgaaccca    720

ctgctgggcg ctggtaaatt cgcaactgat cctgcggtta ccctggctca cgaactgatt    780

catgcaggcc accgcctgta cggtatcgcc atcaatccga accgtgtctt caaagttaac    840

accaacgcgt attacgagat gtccggtctg gaagttagct tcgaagaact gcgtactttt    900

ggcggtcacg acgctaaatt catcgactct ctgcaagaaa acgagttccg tctgtactac    960

tataacaagt tcaaagatat cgcatccacc ctgaacaaag cgaaatccat cgtgggtacc   1020

actgcttctc tccagtacat gaagaacgtt tttaaagaaa aatacctgct cagcgaagac   1080

acctccggca aattctctgt agacaagttg aaattcgata aactttacaa aatgctgact   1140

gaaatttaca ccgaagacaa cttcgttaag ttctttaaag ttctgaaccg caaaacctat   1200

ctgaacttcg acaaggcagt attcaaaatc aacatcgtgc cgaaagttaa ctacactatc   1260
```

-continued

```
tacgatggtt tcaacctgcg taacaccaac ctggctgcta attttaacgg ccagaacacg   1320

gaaatcaaca acatgaactt cacaaaactg aaaaacttca ctggtctgtt cgagttttac   1380

aagctgctgt gcgtcgacgg catcattacc tccaaaacta aatctctgat agaaggtaga   1440

aacaaagcgc tgaacgacct ctgtatcaag gttaacaact gggatttatt cttcagcccg   1500

agtgaagaca acttcaccaa cgacctgaac aaaggtgaag aaatcacctc agatactaac   1560

atcgaagcag ccgaagaaaa catctcgctg gacctgatcc agcagtacta cctgaccttt   1620

aatttcgaca acgagccgga aaacatttct atcgaaaacc tgagctctga tatcatcggc   1680

cagctggaac tgatgccgaa catcgaacgt ttcccaaacg gtaaaaagta cgagctggac   1740

aaatatacca tgttccacta cctgcgcgcg caggaatttg aacacggcaa atcccgtatc   1800

gcactgacta actccgttaa cgaagctctg ctcaacccgt cccgtgtata caccttcttc   1860

tctagcgact acgtgaaaaa ggtcaacaaa gcgactgaag ctgcaatgtt cttgggttgg   1920

gttgaacagc ttgtttatga ttttaccgac gagacgtccg aagtatctac taccgacaaa   1980

attgcggata tcactatcat catcccgtac atcggtccgg ctctgaacat tggcaacatg   2040

ctgtacaaag acgacttcgt tggcgcactg atcttctccg gtgcggtgat cctgctggag   2100

ttcatcccgg aaatcgccat cccggtactg ggcacctttg ctctggtttc ttacattgca   2160

aacaaggttc tgactgtaca aaccatcgac aacgcgctga gcaaacgtaa cgaaaaatgg   2220

gatgaagttt acaaatatat cgtgaccaac tggctggcta aggttaatac tcagatcgac   2280

ctcatccgca aaaaaatgaa agaagcactg gaaaaccagg cggaagctac caaggcaatc   2340

attaactacc agtacaacca gtacaccgag gaagaaaaaa acaacatcaa cttcaacatc   2400

gacgatctgt cctctaaact gaacgaatcc atcaacaaag ctatgatcaa catcaacaag   2460

ttcctgaacc agtgctctgt aagctatctg atgaactcca tgatcccgta cggtgttaaa   2520

cgtctggagg acttcgatgc gtctctgaaa gacgccctgc tgaaatacat ttacgacaac   2580

cgtggcactc tgatcggtca ggttgatcgt ctgaaggaca aagtgaacaa taccttatcg   2640

accgacatcc cttttcagct cagtaaatat gtcgataacc aacgcctttt gtccactcta   2700

gactag                                                              2706
```

```
<210> SEQ ID NO 20
<211> LENGTH: 901
<212> TYPE: PRT
<213> ORGANISM: Artificial Sequence
<220> FEATURE:
<223> OTHER INFORMATION: Synthetic

<400> SEQUENCE: 20

Phe Gly Gly Phe Thr Gly Ala Arg Lys Ser Ala Arg Lys Thr Ser Gly
1               5                   10                  15

Gly Gly Gly Ser Gly Gly Gly Gly Ser Gly Gly Gly Gly Ser Pro Arg
            20                  25                  30

Gly Ser Met Glu Phe Val Asn Lys Gln Phe Asn Tyr Lys Asp Pro Val
        35                  40                  45

Asn Gly Val Asp Ile Ala Tyr Ile Lys Ile Pro Asn Ala Gly Gln Met
    50                  55                  60

Gln Pro Val Lys Ala Phe Lys Ile His Asn Lys Ile Trp Val Ile Pro
65                  70                  75                  80

Glu Arg Asp Thr Phe Thr Asn Pro Glu Glu Gly Asp Leu Asn Pro Pro
                85                  90                  95

Pro Glu Ala Lys Gln Val Pro Val Ser Tyr Tyr Asp Ser Thr Tyr Leu
```

-continued

```
            100                 105                 110

Ser Thr Asp Asn Glu Lys Asp Asn Tyr Leu Lys Gly Val Thr Lys Leu
        115                 120                 125

Phe Glu Arg Ile Tyr Ser Thr Asp Leu Gly Arg Met Leu Leu Thr Ser
    130                 135                 140

Ile Val Arg Gly Ile Pro Phe Trp Gly Gly Ser Thr Ile Asp Thr Glu
145                 150                 155                 160

Leu Lys Val Ile Asp Thr Asn Cys Ile Asn Val Ile Gln Pro Asp Gly
                165                 170                 175

Ser Tyr Arg Ser Glu Glu Leu Asn Leu Val Ile Ile Gly Pro Ser Ala
            180                 185                 190

Asp Ile Ile Gln Phe Glu Cys Lys Ser Phe Gly His Glu Val Leu Asn
        195                 200                 205

Leu Thr Arg Asn Gly Tyr Gly Ser Thr Gln Tyr Ile Arg Phe Ser Pro
    210                 215                 220

Asp Phe Thr Phe Gly Phe Glu Glu Ser Leu Glu Val Asp Thr Asn Pro
225                 230                 235                 240

Leu Leu Gly Ala Gly Lys Phe Ala Thr Asp Pro Ala Val Thr Leu Ala
                245                 250                 255

His Glu Leu Ile His Ala Gly His Arg Leu Tyr Gly Ile Ala Ile Asn
            260                 265                 270

Pro Asn Arg Val Phe Lys Val Asn Thr Asn Ala Tyr Tyr Glu Met Ser
        275                 280                 285

Gly Leu Glu Val Ser Phe Glu Glu Leu Arg Thr Phe Gly Gly His Asp
    290                 295                 300

Ala Lys Phe Ile Asp Ser Leu Gln Glu Asn Glu Phe Arg Leu Tyr Tyr
305                 310                 315                 320

Tyr Asn Lys Phe Lys Asp Ile Ala Ser Thr Leu Asn Lys Ala Lys Ser
                325                 330                 335

Ile Val Gly Thr Thr Ala Ser Leu Gln Tyr Met Lys Asn Val Phe Lys
            340                 345                 350

Glu Lys Tyr Leu Leu Ser Glu Asp Thr Ser Gly Lys Phe Ser Val Asp
        355                 360                 365

Lys Leu Lys Phe Asp Lys Leu Tyr Lys Met Leu Thr Glu Ile Tyr Thr
    370                 375                 380

Glu Asp Asn Phe Val Lys Phe Phe Lys Val Leu Asn Arg Lys Thr Tyr
385                 390                 395                 400

Leu Asn Phe Asp Lys Ala Val Phe Lys Ile Asn Ile Val Pro Lys Val
                405                 410                 415

Asn Tyr Thr Ile Tyr Asp Gly Phe Asn Leu Arg Asn Thr Asn Leu Ala
            420                 425                 430

Ala Asn Phe Asn Gly Gln Asn Thr Glu Ile Asn Asn Met Asn Phe Thr
        435                 440                 445

Lys Leu Lys Asn Phe Thr Gly Leu Phe Glu Phe Tyr Lys Leu Leu Cys
    450                 455                 460

Val Asp Gly Ile Ile Thr Ser Lys Thr Lys Ser Leu Ile Glu Gly Arg
465                 470                 475                 480

Asn Lys Ala Leu Asn Asp Leu Cys Ile Lys Val Asn Asn Trp Asp Leu
                485                 490                 495

Phe Phe Ser Pro Ser Glu Asp Asn Phe Thr Asn Asp Leu Asn Lys Gly
            500                 505                 510

Glu Glu Ile Thr Ser Asp Thr Asn Ile Glu Ala Ala Glu Glu Asn Ile
        515                 520                 525
```

```
Ser Leu Asp Leu Ile Gln Gln Tyr Tyr Leu Thr Phe Asn Phe Asp Asn
    530                 535                 540

Glu Pro Glu Asn Ile Ser Ile Glu Asn Leu Ser Ser Asp Ile Ile Gly
545                 550                 555                 560

Gln Leu Glu Leu Met Pro Asn Ile Glu Arg Phe Pro Asn Gly Lys Lys
                565                 570                 575

Tyr Glu Leu Asp Lys Tyr Thr Met Phe His Tyr Leu Arg Ala Gln Glu
            580                 585                 590

Phe Glu His Gly Lys Ser Arg Ile Ala Leu Thr Asn Ser Val Asn Glu
        595                 600                 605

Ala Leu Leu Asn Pro Ser Arg Val Tyr Thr Phe Phe Ser Ser Asp Tyr
    610                 615                 620

Val Lys Lys Val Asn Lys Ala Thr Glu Ala Ala Met Phe Leu Gly Trp
625                 630                 635                 640

Val Glu Gln Leu Val Tyr Asp Phe Thr Asp Glu Thr Ser Glu Val Ser
                645                 650                 655

Thr Thr Asp Lys Ile Ala Asp Ile Thr Ile Ile Ile Pro Tyr Ile Gly
            660                 665                 670

Pro Ala Leu Asn Ile Gly Asn Met Leu Tyr Lys Asp Asp Phe Val Gly
        675                 680                 685

Ala Leu Ile Phe Ser Gly Ala Val Ile Leu Leu Glu Phe Ile Pro Glu
    690                 695                 700

Ile Ala Ile Pro Val Leu Gly Thr Phe Ala Leu Val Ser Tyr Ile Ala
705                 710                 715                 720

Asn Lys Val Leu Thr Val Gln Thr Ile Asp Asn Ala Leu Ser Lys Arg
                725                 730                 735

Asn Glu Lys Trp Asp Glu Val Tyr Lys Tyr Ile Val Thr Asn Trp Leu
            740                 745                 750

Ala Lys Val Asn Thr Gln Ile Asp Leu Ile Arg Lys Lys Met Lys Glu
        755                 760                 765

Ala Leu Glu Asn Gln Ala Glu Ala Thr Lys Ala Ile Ile Asn Tyr Gln
    770                 775                 780

Tyr Asn Gln Tyr Thr Glu Glu Glu Lys Asn Asn Ile Asn Phe Asn Ile
785                 790                 795                 800

Asp Asp Leu Ser Ser Lys Leu Asn Glu Ser Ile Asn Lys Ala Met Ile
                805                 810                 815

Asn Ile Asn Lys Phe Leu Asn Gln Cys Ser Val Ser Tyr Leu Met Asn
            820                 825                 830

Ser Met Ile Pro Tyr Gly Val Lys Arg Leu Glu Asp Phe Asp Ala Ser
        835                 840                 845

Leu Lys Asp Ala Leu Leu Lys Tyr Ile Tyr Asp Asn Arg Gly Thr Leu
    850                 855                 860

Ile Gly Gln Val Asp Arg Leu Lys Asp Lys Val Asn Asn Thr Leu Ser
865                 870                 875                 880

Thr Asp Ile Pro Phe Gln Leu Ser Lys Tyr Val Asp Asn Gln Arg Leu
                885                 890                 895

Leu Ser Thr Leu Asp
            900


<210> SEQ ID NO 21
<211> LENGTH: 2691
<212> TYPE: DNA
<213> ORGANISM: Artificial Sequence
<220> FEATURE:
<223> OTHER INFORMATION: Synthetic
```

-continued

<400> SEQUENCE: 21

```
atggagttcg ttaacaaaca gttcaactat aaagacccag ttaacggtgt tgacattgct      60
tacatcaaaa tcccgaacgc tggccagatg cagccggtaa aggcattcaa aatccacaac     120
aaaatctggg ttatcccgga acgtgatacc tttactaacc cggaagaagg tgacctgaac     180
ccgccaccgg aagcgaaaca ggtgccggta tcttactatg actccaccta cctgtctacc     240
gataacgaaa aggacaacta cctgaaaggt gttactaaac tgttcgagcg tatttactcc     300
accgacctgg gccgtatgct gctgactagc atcgttcgcg gtatcccgtt ctggggcggt     360
tctaccatcg ataccgaact gaaagtaatc gacactaact gcatcaacgt tattcagccg     420
gacggttcct atcgttccga agaactgaac ctggtgatca tcggcccgtc tgctgatatc     480
atccagttcg agtgtaagag ctttggtcac gaagttctga acctcacccg taacggctac     540
ggttccactc agtacatccg tttctctccg gacttcacct tcggttttga agaatccctg     600
gaagtagaca cgaacccact gctgggcgct ggtaaattcg caactgatcc tgcggttacc     660
ctggctcacg aactgattca tgcaggccac cgcctgtacg gtatcgccat caatccgaac     720
cgtgtcttca aagttaacac caacgcgtat tacgagatgt ccggtctgga agttagcttc     780
gaagaactgc gtacttttgg cggtcacgac gctaaattca tcgactctct gcaagaaaac     840
gagttccgtc tgtactacta taacaagttc aaagatatcg catccaccct gaacaaagcg     900
aaatccatcg tgggtaccac tgcttctctc cagtacatga agaacgtttt taaagaaaaa     960
tacctgctca gcgaagacac ctccggcaaa ttctctgtag acaagttgaa attcgataaa    1020
ctttacaaaa tgctgactga aatttacacc gaagacaact tcgttaagtt ctttaaagtt    1080
ctgaaccgca aaacctatct gaacttcgac aaggcagtat tcaaaatcaa catcgtgccg    1140
aaagttaact acactatcta cgatggtttc aacctgcgta acaccaacct ggctgctaat    1200
tttaacggcc agaacacgga aatcaacaac atgaacttca caaaactgaa aaacttcact    1260
ggtctgttcg agttttacaa gctgctgtgc gtcgacggca tcattacctc caaaactaaa    1320
tctctgatag aaggtagaaa caaagcgctg aacgacctct gtatcaaggt taacaactgg    1380
gatttattct tcagcccgag tgaagacaac ttcaccaacg acctgaacaa aggtgaagaa    1440
atcacctcag atactaacat cgaagcagcc gaagaaaaca tctcgctgga cctgatccag    1500
cagtactacc tgacctttaa tttcgacaac gagccggaaa acatttctat cgaaaacctg    1560
agctctgata tcatcggcca gctggaactg atgccgaaca tcgaacgttt cccaaacggt    1620
aaaaagtacg agctggacaa atataccatg ttccactacc tgcgcgcgca ggaatttgaa    1680
cacggcaaat cccgtatcgc actgactaac tccgttaacg aagctctgct caacccgtcc    1740
cgtgtataca ccttcttctc tagcgactac gtgaaaaagg tcaacaaagc gactgaagct    1800
gcaatgttct tgggttgggt tgaacagctt gtttatgatt ttaccgacga gacgtccgaa    1860
gtatctacta ccgacaaaat tgcggatatc actatcatca tcccgtacat cggtccggct    1920
ctgaacattg gcaacatgct gtacaaagac gacttcgttg gcgcactgat cttctccggt    1980
gcggtgatcc tgctggagtt catcccggaa atcgccatcc cggtactggg cacctttgct    2040
ctggtttctt acattgcaaa caaggttctg actgtacaaa ccatcgacaa cgcgctgagc    2100
aaacgtaacg aaaaatggga tgaagtttac aaatatatcg tgaccaactg gctggctaag    2160
gttaatactc agatcgacct catccgcaaa aaaatgaaag aagcactgga aaaccaggcg    2220
gaagctacca aggcaatcat taactaccag tacaaccagt acaccgagga agaaaaaaac    2280
aacatcaact tcaacatcga cgatctgtcc tctaaactga acgaatccat caacaaagct    2340
```

```
atgatcaaca tcaacaagtt cctgaaccag tgctctgtaa gctatctgat gaactccatg   2400

atcccgtacg gtgttaaacg tctggaggac ttcgatgcgt ctctgaaaga cgccctgctg   2460

aaatacattt acgacaaccg tggcactctg atcggtcagg ttgatcgtct gaaggacaaa   2520

gtgaacaata ccttatcgac cgacatccct tttcagctca gtaaatatgt cgataaccaa   2580

cgcctttttgt ccactggcgg tgggggtagt ggcggtggcg gttcgggcgg gggtgggagc   2640

tttggcggtt tcacgggcgc acgcaaatca gcgcgtaaat tagctaacca g            2691
```

```
<210> SEQ ID NO 22
<211> LENGTH: 897
<212> TYPE: PRT
<213> ORGANISM: Artificial Sequence
<220> FEATURE:
<223> OTHER INFORMATION: Synthetic

<400> SEQUENCE: 22

Met Glu Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
```

-continued

```
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Asp
            420                 425                 430

Gly Ile Ile Thr Ser Lys Thr Lys Ser Leu Ile Glu Gly Arg Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735
```

```
Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Gly Gly Gly Gly Ser Gly Gly Gly Gly Ser Gly Gly Gly Gly Ser
865                 870                 875                 880

Phe Gly Gly Phe Thr Gly Ala Arg Lys Ser Ala Arg Lys Leu Ala Asn
                885                 890                 895

Gln
```

<210> SEQ ID NO 23
<211> LENGTH: 2676
<212> TYPE: DNA
<213> ORGANISM: Artificial Sequence
<220> FEATURE:
<223> OTHER INFORMATION: Synthetic

<400> SEQUENCE: 23

```
atgccaataa caattaacaa ctttaattat tcagatcctg ttgataataa aaatatttta     60

tatttagata ctcatttaaa tacactagct aatgagcctg aaaaagcctt tcgcattaca    120

ggaaatatat gggtaatacc tgatagattt tcaagaaatt ctaatccaaa tttaaataaa    180

cctcctcgag ttacaagccc taaaagtggt tattatgatc ctaattattt gagtactgat    240

tctgacaaag atacattttt aaaagaaatt ataaagttat ttaaaagaat taattctaga    300

gaaataggag aagaattaat atatagactt tcgacagata taccctttcc tgggaataac    360

aatactccaa ttaatacctt tgattttgat gtagatttta acagtgttga tgttaaaact    420

agacaaggta acaactgggt taaaactggt agcataaatc ctagtgttat aataactgga    480

cctagagaaa acattataga tccagaaact tctacgttta aattaactaa caataccttt    540

gcggcacaag aaggatttgg tgctttatca ataatttcaa tatcacctag atttatgcta    600

acatatagta atgcaactaa tgatgtagga gagggtagat tttctaagtc tgaattttgc    660

atggatccaa tactaatttt aatgcatgaa cttaatcatg caatgcataa tttatatgga    720

atagctatac caaatgatca aacaatttca tctgtaacta gtaatatttt ttattctcaa    780

tataatgtga aattagagta tgcagaaata tatgcatttg gaggtccaac tatagacctt    840

attcctaaaa gtgcaaggaa atattttgag gaaaaggcat tggattatta tagatctata    900

gctaaaagac ttaatagtat aactactgca aatccttcaa gctttaataa atatataggg    960

gaatataaac agaaacttat tagaaagtat agattcgtag tagaatcttc aggtgaagtt   1020

acagtaaatc gtaataagtt tgttgagtta tataatgaac ttacacaaat atttacagaa   1080

tttaactacg ctaaaatata taatgtacaa aataggaaaa tatatctttc aaatgtatat   1140
```

actccggtta cggcgaatat attagacgat aatgtttatg atatacaaaa tggatttaat 1200
atacctaaaa gtaatttaaa tgtactattt atgggtcaaa atttatctcg aaatccagca 1260
ttaagaaaag tcaatcctga aaatatgctt tatttattta caaaattttg tcataaagca 1320
atagatggta gatcattata taataaaaca ttagattgta gagagctttt agttaaaaat 1380
actgacttac cctttatagg tgatattagt gatgttaaaa ctgatatatt tttaagaaaa 1440
gatattaatg aagaaactga agttatatac tatccggaca atgtttcagt agatcaagtt 1500
attctcagta agaatacctc agaacatgga caactagatt tattataccc tagtattgac 1560
agtgagagtg aaatattacc aggggagaat caagtctttt atgataatag aactcaaaat 1620
gttgattatt tgaattctta ttattaccta gaatctcaaa aactaagtga taatgttgaa 1680
gattttactt ttacgagatc aattgaggag gctttggata atagtgcaaa agtatatact 1740
tactttccta cactagctaa taaagtaaat gcgggtgttc aaggtggttt atttttaatg 1800
tgggcaaatg atgtagttga agattttact acaaatattc taagaaaaga tacattagat 1860
aaaatatcag atgtatcagc tattattccc tatataggac ccgcattaaa tataagtaat 1920
tctgtaagaa gaggaaattt tactgaagca tttgcagtta ctggtgtaac tattttatta 1980
gaagcatttc ctgaatttac aatacctgca cttggtgcat ttgtgattta tagtaaggtt 2040
caagaaagaa acgagattat taaaactata gataattgtt tagaacaaag gattaagaga 2100
tggaaagatt catatgaatg gatgatggga acgtggttat ccaggattat tactcaattt 2160
aataatataa gttatcaaat gtatgattct ttaaattatc aggcaggtgc aatcaaagct 2220
aaaatagatt tagaatataa aaaatattca ggaagtgata aagaaaatat aaaaagtcaa 2280
gttgaaaatt taaaaaatag tttagatgta aaaatttcgg aagcaatgaa taatataaat 2340
aaatttatac gagaatgttc cgtaacatat ttatttaaaa atatgttacc taaagtaatt 2400
gatgaattaa atgagtttga tcgaaatact aaagcaaaat taattaatct tatagatagt 2460
cataatatta ttctagttgg tgaagtagat aaattaaaag caaaagtaaa taatagcttt 2520
caaaatacaa taccctttaa tatttttttca tatactaata attctttatt aaaagatata 2580
attaatgaat atttcaatgg cggtgggggt agtggcggtg gcggttcggg cgggggtggg 2640
agctttggcg gtttcacggg cgcacgcaaa tcagcg 2676

<210> SEQ ID NO 24
<211> LENGTH: 892
<212> TYPE: PRT
<213> ORGANISM: Artificial Sequence
<220> FEATURE:
<223> OTHER INFORMATION: Synthetic

<400> SEQUENCE: 24

Met Pro Ile Thr Ile Asn Asn Phe Asn Tyr Ser Asp Pro Val Asp Asn
1 5 10 15

Lys Asn Ile Leu Tyr Leu Asp Thr His Leu Asn Thr Leu Ala Asn Glu
20 25 30

Pro Glu Lys Ala Phe Arg Ile Thr Gly Asn Ile Trp Val Ile Pro Asp
35 40 45

Arg Phe Ser Arg Asn Ser Asn Pro Asn Leu Asn Lys Pro Pro Arg Val
50 55 60

Thr Ser Pro Lys Ser Gly Tyr Tyr Asp Pro Asn Tyr Leu Ser Thr Asp
65 70 75 80

Ser Asp Lys Asp Thr Phe Leu Lys Glu Ile Ile Lys Leu Phe Lys Arg
85 90 95

-continued

```
Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445

Lys Thr Leu Asp Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525
```

```
Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860

Phe Asn Gly Gly Gly Gly Ser Gly Gly Gly Gly Ser Gly Gly Gly Gly
865                 870                 875                 880

Ser Phe Gly Gly Phe Thr Gly Ala Arg Lys Ser Ala
                885                 890
```

<210> SEQ ID NO 25
<211> LENGTH: 2712
<212> TYPE: DNA
<213> ORGANISM: Artificial Sequence
<220> FEATURE:
<223> OTHER INFORMATION: Synthetic

<400> SEQUENCE: 25

-continued

```
tttggcggtt tcacgggcgc acgcaaatca gcgcgtaaat atgctaacca gactagtggc     60
ggtgggggta gtggcggtgg cggttcgggc gggggtggga gccctagggg atccatgcca    120
ataacaatta acaactttaa ttattcagat cctgttgata ataaaaatat tttatattta    180
gatactcatt taaatacact agctaatgag cctgaaaaag cctttcgcat tacaggaaat    240
atatgggtaa tacctgatag attttcaaga aattctaatc caaatttaaa taaacctcct    300
cgagttacaa gccctaaaag tggttattat gatcctaatt atttgagtac tgattctgac    360
aaagatacat ttttaaaaga aattataaag ttatttaaaa gaattaattc tagagaaata    420
ggagaagaat taatatatag actttcgaca gatataccct ttcctgggaa taacaatact    480
ccaattaata cctttgattt tgatgtagat tttaacagtg ttgatgttaa aactagacaa    540
ggtaacaact gggttaaaac tggtagcata aatcctagtg ttataataac tggacctaga    600
gaaaacatta tagatccaga aacttctacg tttaaattaa ctaacaatac ctttgcggca    660
caagaaggat ttggtgcttt atcaataatt tcaatatcac ctagatttat gctaacatat    720
agtaatgcaa ctaatgatgt aggagagggt agattttcta agtctgaatt ttgcatggat    780
ccaatactaa ttttaatgca tgaacttaat catgcaatgc ataatttata tggaatagct    840
ataccaaatg atcaaacaat ttcatctgta actagtaata tttttattc tcaatataat    900
gtgaaattag agtatgcaga aatatatgca tttggaggtc caactataga ccttattcct    960
aaaagtgcaa ggaaatattt tgaggaaaag gcattggatt attatagatc tatagctaaa   1020
agacttaata gtataactac tgcaaatcct tcaagcttta ataaatatat aggggaatat   1080
aaacagaaac ttattagaaa gtatagattc gtagtagaat cttcaggtga agttacagta   1140
aatcgtaata agtttgttga gttatataat gaacttacac aaatatttac agaatttaac   1200
tacgctaaaa tatataatgt acaaaatagg aaaatatatc tttcaaatgt atatactccg   1260
gttacggcga atatattaga cgataatgtt tatgatatac aaaatggatt taatatacct   1320
aaaagtaatt taaatgtact atttatgggt caaaatttat ctcgaaatcc agcattaaga   1380
aaagtcaatc ctgaaaatat gctttattta tttacaaaat tttgtcataa agcaatagat   1440
ggtagatcat tatataataa aacattagat tgtagagagc ttttagttaa aaatactgac   1500
ttacccttta taggtgatat tagtgatgtt aaaactgata tatttttaag aaaagatatt   1560
aatgaagaaa ctgaagttat atactatccg gacaatgttt cagtagatca agttattctc   1620
agtaagaata cctcagaaca tggacaacta gatttattat accctagtat tgacagtgag   1680
agtgaaatat taccagggga gaatcaagtc ttttatgata atagaactca aaatgttgat   1740
tatttgaatt cttattatta cctagaatct caaaaactaa gtgataatgt tgaagatttt   1800
acttttacga gatcaattga ggaggctttg gataatagtg caaaagtata tacttacttt   1860
cctacactag ctaataaagt aaatgcgggt gttcaaggtg gtttattttt aatgtgggca   1920
aatgatgtag ttgaagattt tactacaaat attctaagaa aagatacatt agataaaata   1980
tcagatgtat cagctattat tccctatata ggacccgcat taaatataag taattctgta   2040
agaagaggaa attttactga agcatttgca gttactggtg taactatttt attagaagca   2100
tttcctgaat ttacaatacc tgcacttggt gcatttgtga tttatagtaa ggttcaagaa   2160
agaaacgaga ttattaaaac tatagataat tgtttagaac aaaggattaa gagatggaaa   2220
gattcatatg aatggatgat gggaacgtgg ttatccagga ttattactca atttaataat   2280
ataagttatc aaatgtatga ttctttaaat tatcaggcag gtgcaatcaa agctaaaata   2340
gatttagaat ataaaaaata ttcaggaagt gataaagaaa atataaaaag tcaagttgaa   2400
```

-continued aatttaaaaa atagtttaga tgtaaaaatt tcggaagcaa tgaataatat aaataaattt 2460
atacgagaat gttccgtaac atatttattt aaaaatatgt tacctaaagt aattgatgaa 2520
ttaaatgagt ttgatcgaaa tactaaagca aaattaatta atcttataga tagtcataat 2580
attattctag ttggtgaagt agataaatta aaagcaaaag taaataatag ctttcaaaat 2640
acaataccct ttaatatttt ttcatatact aataattctt tattaaaaga tataattaat 2700
gaatatttca at 2712

<210> SEQ ID NO 26
<211> LENGTH: 904
<212> TYPE: PRT
<213> ORGANISM: Artificial Sequence
<220> FEATURE:
<223> OTHER INFORMATION: Synthetic

<400> SEQUENCE: 26

Phe Gly Gly Phe Thr Gly Ala Arg Lys Ser Ala Arg Lys Tyr Ala Asn
1               5                   10                  15

Gln Thr Ser Gly Gly Gly Gly Ser Gly Gly Gly Gly Ser Gly Gly Gly
            20                  25                  30

Gly Ser Pro Arg Gly Ser Met Pro Ile Thr Ile Asn Asn Phe Asn Tyr
        35                  40                  45

Ser Asp Pro Val Asp Asn Lys Asn Ile Leu Tyr Leu Asp Thr His Leu
    50                  55                  60

Asn Thr Leu Ala Asn Glu Pro Glu Lys Ala Phe Arg Ile Thr Gly Asn
65                  70                  75                  80

Ile Trp Val Ile Pro Asp Arg Phe Ser Arg Asn Ser Asn Pro Asn Leu
                85                  90                  95

Asn Lys Pro Pro Arg Val Thr Ser Pro Lys Ser Gly Tyr Tyr Asp Pro
            100                 105                 110

Asn Tyr Leu Ser Thr Asp Ser Asp Lys Asp Thr Phe Leu Lys Glu Ile
        115                 120                 125

Ile Lys Leu Phe Lys Arg Ile Asn Ser Arg Glu Ile Gly Glu Glu Leu
    130                 135                 140

Ile Tyr Arg Leu Ser Thr Asp Ile Pro Phe Pro Gly Asn Asn Asn Thr
145                 150                 155                 160

Pro Ile Asn Thr Phe Asp Phe Asp Val Asp Phe Asn Ser Val Asp Val
                165                 170                 175

Lys Thr Arg Gln Gly Asn Asn Trp Val Lys Thr Gly Ser Ile Asn Pro
            180                 185                 190

Ser Val Ile Ile Thr Gly Pro Arg Glu Asn Ile Ile Asp Pro Glu Thr
        195                 200                 205

Ser Thr Phe Lys Leu Thr Asn Asn Thr Phe Ala Ala Gln Glu Gly Phe
    210                 215                 220

Gly Ala Leu Ser Ile Ile Ser Ile Ser Pro Arg Phe Met Leu Thr Tyr
225                 230                 235                 240

Ser Asn Ala Thr Asn Asp Val Gly Glu Gly Arg Phe Ser Lys Ser Glu
                245                 250                 255

Phe Cys Met Asp Pro Ile Leu Ile Leu Met His Glu Leu Asn His Ala
            260                 265                 270

Met His Asn Leu Tyr Gly Ile Ala Ile Pro Asn Asp Gln Thr Ile Ser
        275                 280                 285

Ser Val Thr Ser Asn Ile Phe Tyr Ser Gln Tyr Asn Val Lys Leu Glu
    290                 295                 300

Tyr Ala Glu Ile Tyr Ala Phe Gly Gly Pro Thr Ile Asp Leu Ile Pro

```
305                 310                 315                 320

Lys Ser Ala Arg Lys Tyr Phe Glu Glu Lys Ala Leu Asp Tyr Tyr Arg
                325                 330                 335

Ser Ile Ala Lys Arg Leu Asn Ser Ile Thr Thr Ala Asn Pro Ser Ser
            340                 345                 350

Phe Asn Lys Tyr Ile Gly Glu Tyr Lys Gln Lys Leu Ile Arg Lys Tyr
        355                 360                 365

Arg Phe Val Val Glu Ser Ser Gly Glu Val Thr Val Asn Arg Asn Lys
    370                 375                 380

Phe Val Glu Leu Tyr Asn Glu Leu Thr Gln Ile Phe Thr Glu Phe Asn
385                 390                 395                 400

Tyr Ala Lys Ile Tyr Asn Val Gln Asn Arg Lys Ile Tyr Leu Ser Asn
                405                 410                 415

Val Tyr Thr Pro Val Thr Ala Asn Ile Leu Asp Asp Asn Val Tyr Asp
            420                 425                 430

Ile Gln Asn Gly Phe Asn Ile Pro Lys Ser Asn Leu Asn Val Leu Phe
        435                 440                 445

Met Gly Gln Asn Leu Ser Arg Asn Pro Ala Leu Arg Lys Val Asn Pro
    450                 455                 460

Glu Asn Met Leu Tyr Leu Phe Thr Lys Phe Cys His Lys Ala Ile Asp
465                 470                 475                 480

Gly Arg Ser Leu Tyr Asn Lys Thr Leu Asp Cys Arg Glu Leu Leu Val
                485                 490                 495

Lys Asn Thr Asp Leu Pro Phe Ile Gly Asp Ile Ser Asp Val Lys Thr
            500                 505                 510

Asp Ile Phe Leu Arg Lys Asp Ile Asn Glu Glu Thr Glu Val Ile Tyr
        515                 520                 525

Tyr Pro Asp Asn Val Ser Val Asp Gln Val Ile Leu Ser Lys Asn Thr
    530                 535                 540

Ser Glu His Gly Gln Leu Asp Leu Leu Tyr Pro Ser Ile Asp Ser Glu
545                 550                 555                 560

Ser Glu Ile Leu Pro Gly Glu Asn Gln Val Phe Tyr Asp Asn Arg Thr
                565                 570                 575

Gln Asn Val Asp Tyr Leu Asn Ser Tyr Tyr Tyr Leu Glu Ser Gln Lys
            580                 585                 590

Leu Ser Asp Asn Val Glu Asp Phe Thr Phe Thr Arg Ser Ile Glu Glu
        595                 600                 605

Ala Leu Asp Asn Ser Ala Lys Val Tyr Thr Tyr Phe Pro Thr Leu Ala
    610                 615                 620

Asn Lys Val Asn Ala Gly Val Gln Gly Gly Leu Phe Leu Met Trp Ala
625                 630                 635                 640

Asn Asp Val Val Glu Asp Phe Thr Thr Asn Ile Leu Arg Lys Asp Thr
                645                 650                 655

Leu Asp Lys Ile Ser Asp Val Ser Ala Ile Ile Pro Tyr Ile Gly Pro
            660                 665                 670

Ala Leu Asn Ile Ser Asn Ser Val Arg Arg Gly Asn Phe Thr Glu Ala
        675                 680                 685

Phe Ala Val Thr Gly Val Thr Ile Leu Leu Glu Ala Phe Pro Glu Phe
    690                 695                 700

Thr Ile Pro Ala Leu Gly Ala Phe Val Ile Tyr Ser Lys Val Gln Glu
705                 710                 715                 720

Arg Asn Glu Ile Ile Lys Thr Ile Asp Asn Cys Leu Glu Gln Arg Ile
                725                 730                 735
```

-continued

```
Lys Arg Trp Lys Asp Ser Tyr Glu Trp Met Met Gly Thr Trp Leu Ser
            740                 745                 750

Arg Ile Ile Thr Gln Phe Asn Asn Ile Ser Tyr Gln Met Tyr Asp Ser
        755                 760                 765

Leu Asn Tyr Gln Ala Gly Ala Ile Lys Ala Lys Ile Asp Leu Glu Tyr
    770                 775                 780

Lys Lys Tyr Ser Gly Ser Asp Lys Glu Asn Ile Lys Ser Gln Val Glu
785                 790                 795                 800

Asn Leu Lys Asn Ser Leu Asp Val Lys Ile Ser Glu Ala Met Asn Asn
                805                 810                 815

Ile Asn Lys Phe Ile Arg Glu Cys Ser Val Thr Tyr Leu Phe Lys Asn
            820                 825                 830

Met Leu Pro Lys Val Ile Asp Glu Leu Asn Glu Phe Asp Arg Asn Thr
        835                 840                 845

Lys Ala Lys Leu Ile Asn Leu Ile Asp Ser His Asn Ile Ile Leu Val
    850                 855                 860

Gly Glu Val Asp Lys Leu Lys Ala Lys Val Asn Asn Ser Phe Gln Asn
865                 870                 875                 880

Thr Ile Pro Phe Asn Ile Phe Ser Tyr Thr Asn Asn Ser Leu Leu Lys
                885                 890                 895

Asp Ile Ile Asn Glu Tyr Phe Asn
            900
```

<210> SEQ ID NO 27
<211> LENGTH: 1302
<212> TYPE: DNA
<213> ORGANISM: Artificial Sequence
<220> FEATURE:
<223> OTHER INFORMATION: Synthetic

<400> SEQUENCE: 27

```
ggatccatgg agttcgttaa caaacagttc aactataaag acccagttaa cggtgttgac      60

attgcttaca tcaaaatccc gaacgctggc cagatgcagc cggtaaaggc attcaaaatc     120

cacaacaaaa tctgggttat cccggaacgt gataccttta ctaacccgga agaaggtgac     180

ctgaacccgc caccggaagc gaaacaggtg ccggtatctt actatgactc cacctacctg     240

tctaccgata acgaaaagga caactacctg aaaggtgtta ctaaactgtt cgagcgtatt     300

tactccaccg acctgggccg tatgctgctg actagcatcg ttcgcggtat cccgttctgg     360

ggcggttcta ccatcgatac cgaactgaaa gtaatcgaca ctaactgcat caacgttatt     420

cagccggacg gttcctatcg ttccgaagaa ctgaacctgg tgatcatcgg cccgtctgct     480

gatatcatcc agttcgagtg taagagcttt ggtcacgaag ttctgaacct cacccgtaac     540

ggctacggtt ccactcagta catccgtttc tctccggact tcaccttcgg ttttgaagaa     600

tccctggaag tagacacgaa cccactgctg ggcgctggta aattcgcaac tgatcctgcg     660

gttaccctgg ctcacgaact gattcatgca ggccaccgcc tgtacggtat cgccatcaat     720

ccgaaccgtg tcttcaaagt taacaccaac gcgtattacg agatgtccgg tctggaagtt     780

agcttcgaag aactgcgtac ttttggcggt cacgacgcta aattcatcga ctctctgcaa     840

gaaaacgagt tccgtctgta ctactataac aagttcaaag atatcgcatc caccctgaac     900

aaagcgaaat ccatcgtggg taccactgct tctctccagt acatgaagaa cgtttttaaa     960

gaaaaatacc tgctcagcga agacacctcc ggcaaattct ctgtagacaa gttgaaattc    1020

gataaacttt acaaaatgct gactgaaatt tacaccgaag acaacttcgt taagttcttt    1080

aaagttctga accgcaaaac ctatctgaac ttcgacaagg cagtattcaa aatcaacatc    1140
```

```
gtgccgaaag ttaactacac tatctacgat ggtttcaacc tgcgtaacac caacctggct   1200

gctaatttta acggccagaa cacggaaatc aacaacatga acttcacaaa actgaaaaac   1260

ttcactggtc tgttcgagtt ttacaagctg ctgtgcgtcg ac                      1302
```

<210> SEQ ID NO 28
<211> LENGTH: 1257
<212> TYPE: DNA
<213> ORGANISM: Artificial Sequence
<220> FEATURE:
<223> OTHER INFORMATION: Synthetic

<400> SEQUENCE: 28

```
ctgcagtgta tcaaggttaa caactgggat ttattcttca gcccgagtga agacaacttc     60

accaacgacc tgaacaaagg tgaagaaatc acctcagata ctaacatcga agcagccgaa    120

gaaaacatct cgctggacct gatccagcag tactacctga cctttaattt cgacaacgag    180

ccggaaaaca tttctatcga aaacctgagc tctgatatca tcggccagct ggaactgatg    240

ccgaacatcg aacgtttccc aaacggtaaa aagtacgagc tggacaaata taccatgttc    300

cactacctgc gcgcgcagga atttgaacac ggcaaatccc gtatcgcact gactaactcc    360

gttaacgaag ctctgctcaa cccgtcccgt gtatacacct tcttctctag cgactacgtg    420

aaaaaggtca acaaagcgac tgaagctgca atgttcttgg gttgggttga acagcttgtt    480

tatgatttta ccgacgagac gtccgaagta tctactaccg acaaaattgc ggatatcact    540

atcatcatcc cgtacatcgg tccggctctg aacattggca acatgctgta caaagacgac    600

ttcgttggcg cactgatctt ctccggtgcg gtgatcctgc tggagttcat cccggaaatc    660

gccatcccgg tactgggcac ctttgctctg gtttcttaca ttgcaaacaa ggttctgact    720

gtacaaacca tcgacaacgc gctgagcaaa cgtaacgaaa aatgggatga agtttacaaa    780

tatatcgtga ccaactggct ggctaaggtt aatactcaga tcgacctcat ccgcaaaaaa    840

atgaaagaag cactggaaaa ccaggcggaa gctaccaagg caatcattaa ctaccagtac    900

aaccagtaca ccgaggaaga aaaaaacaac atcaacttca acatcgacga tctgtcctct    960

aaactgaacg aatccatcaa caaagctatg atcaacatca acaagttcct gaaccagtgc   1020

tctgtaagct atctgatgaa ctccatgatc ccgtacggtg ttaaacgtct ggaggacttc   1080

gatgcgtctc tgaaagacgc cctgctgaaa tacatttacg acaaccgtgg cactctgatc   1140

ggtcaggttg atcgtctgaa ggacaaagtg aacaatacct tatcgaccga catccctttt   1200

cagctcagta aatatgtcga taaccaacgc cttttgtcca ctctagacta gaagctt      1257
```

<210> SEQ ID NO 29
<211> LENGTH: 1323
<212> TYPE: DNA
<213> ORGANISM: Artificial Sequence
<220> FEATURE:
<223> OTHER INFORMATION: Synthetic

<400> SEQUENCE: 29

```
ggatccatgc cggttaccat caacaacttc aactacaacg acccgatcga caacaacaac     60

atcattatga tggaaccgcc gttcgcacgt ggtaccggac gttactacaa ggcttttaag    120

atcaccgacc gtatctggat catcccggaa cgttacacct tcggttacaa acctgaggac    180

ttcaacaaga gtagcgggat tttcaatcgt gacgtctgcg agtactatga tccagattat    240

ctgaatacca acgataagaa gaacatattc cttcagacta tgattaaact cttcaaccgt    300

atcaaaagca aaccgctcgg tgaaaaactc ctcgaaatga ttatcaacgg tatcccgtac    360
```

ctcggtgacc gtcgtgtccc gcttgaagag ttcaacacca acatcgcaag cgtcaccgtc 420
aacaaactca tcagcaaccc aggtgaagtc gaacgtaaaa aaggtatctt cgcaaacctc 480
atcatcttcg gtccgggtcc ggtcctcaac gaaaacgaaa ccatcgacat cggtatccag 540
aaccacttcg caagccgtga aggtttcggt ggtatcatgc agatgaaatt ctgcccggaa 600
tacgtcagtg tcttcaacaa cgtccaggaa aacaaaggtg caagcatctt caaccgtcgt 660
ggttacttca gcgacccggc actcatcctc atgcatgaac tcatccacgt cctccacggt 720
ctctacggta tcaaagttga cgacctcccg atcgtcccga acgagaagaa attcttcatg 780
cagagcaccg acgcaatcca ggctgaggaa ctctacacct tcggtggcca agacccaagt 840
atcataaccc cgtccaccga caaaagcatc tacgacaaag tcctccagaa cttcaggggt 900
atcgtggaca gactcaacaa agtcctcgtc tgcatcagcg acccgaacat caatatcaac 960
atatacaaga acaagttcaa agacaagtac aaattcgtcg aggacagcga aggcaaatac 1020
agcatcgacg tagaaagttt cgacaagctc tacaaaagcc tcatgttcgg tttcaccgaa 1080
accaacatcg ccgagaacta caagatcaag acaagggcaa gttacttcag cgacagcctc 1140
ccgcctgtca aaatcaagaa cctcttagac aacgagattt acacaattga agagggcttc 1200
aacatcagtg acaaagacat ggagaaggaa tacagaggtc agaacaaggc tatcaacaaa 1260
caggcatacg aggagatcag caaagaacac ctcgcagtct acaagatcca gatgtgcgtc 1320
gac 1323

<210> SEQ ID NO 30
<211> LENGTH: 1260
<212> TYPE: DNA
<213> ORGANISM: Artificial Sequence
<220> FEATURE:
<223> OTHER INFORMATION: Synthetic

<400> SEQUENCE: 30
ctgcagtgca tcgacgttga caacgaagac ctgttcttca tcgctgacaa aaacagcttc 60
agtgacgacc tgagcaaaaa cgaacgtatc gaatacaaca cccagagcaa ctacatcgaa 120
aacgacttcc cgatcaacga actgatcctg gacaccgacc tgataagtaa aatcgaactg 180
ccgagcgaaa acaccgaaag tctgaccgac ttcaacgttg acgttccggt ttacgaaaaa 240
cagccggcta tcaagaaaat cttcaccgac gaaaacacca tcttccagta cctgtacagc 300
cagaccttcc cgctggacat ccgtgacatc agtctgacca gcagtttcga cgacgctctg 360
ctgttcagca acaaagttta cagtttcttc agcatggact acatcaaaac cgctaacaaa 420
gttgttgaag cagggctgtt cgctggttgg gttaaacaga tcgttaacga cttcgttatc 480
gaagctaaca aaagcaacac tatggacaaa atcgctgaca tcagtctgat cgttccgtac 540
atcggtctgg ctctgaacgt tggtaacgaa accgctaaag gtaactttga aaacgctttc 600
gagatcgctg gtgcaagcat cctgctggag ttcatcccgg aactgctgat cccggttgtt 660
ggtgctttcc tgctggaaag ttacatcgac aacaaaaaca agatcatcaa aaccatcgac 720
aacgctctga ccaaacgtaa cgaaaaatgg agtgatatgt acggtctgat cgttgctcag 780
tggctgagca ccgtcaacac ccagttctac accatcaaag aaggtatgta caaagctctg 840
aactaccagg ctcaggctct ggaagagatc atcaaatacc gttacaacat ctacagtgag 900
aaggaaaaga gtaacatcaa catcgacttc aacgacatca acagcaaact gaacgaaggt 960
atcaaccagg ctatcgacaa catcaacaac ttcatcaacg gttgcagtgt tagctacctg 1020
atgaagaaga tgatcccgct ggctgttgaa aaactgctgg acttcgacaa caccctgaaa 1080
aagaacctgc tgaactacat cgacgaaaac aagctgtacc tgatcggtag tgctgaatac 1140
gaaaaaagta aagtgaacaa atacctgaag accatcatgc cgttcgacct gagtatctac 1200
accaacgaca ccatcctgat cgaaatgttc aacaaataca actctctaga ctagaagctt 1260

<210> SEQ ID NO 31
<211> LENGTH: 1329
<212> TYPE: DNA
<213> ORGANISM: Artificial Sequence
<220> FEATURE:
<223> OTHER INFORMATION: Synthetic

<400> SEQUENCE: 31
ggatccgaat tcatgccgat caccatcaac aacttcaact acagcgatcc ggtggataac 60
aaaaacatcc tgtacctgga tacccatctg aataccctgg cgaacgaacc ggaaaaagcg 120
tttcgtatca ccggcaacat ttgggttatt ccggatcgtt ttagccgtaa cagcaacccg 180
aatctgaata aaccgccgcg tgttaccagc ccgaaaagcg gttattacga tccgaactat 240
ctgagcaccg atagcgataa agataccttc ctgaaagaaa tcatcaaact gttcaaacgc 300
atcaacagcc gtgaaattgg cgaagaactg atctatcgcc tgagcaccga tattccgttt 360
ccgggcaaca acaacacccc gatcaacacc tttgatttcg atgtggattt caacagcgtt 420
gatgttaaaa cccgccaggg taacaattgg gtgaaaaccg gcagcattaa cccgagcgtg 480
attattaccg gtccgcgcga aaacattatt gatccggaaa ccagcacctt taaactgacc 540
aacaacacct ttgcggcgca ggaaggtttt ggcgcgctga gcattattag cattagcccg 600
cgctttatgc tgacctatag caacgcgacc aacgatgttg gtgaaggccg tttcagcaaa 660
agcgaatttt gcatggaccc gatcctgatc ctgatgcatg aactgaacca tgcgatgcat 720
aacctgtatg gcatcgcgat tccgaacgat cagaccatta gcagcgtgac cagcaacatc 780
ttttacagcc agtacaacgt gaaactggaa tatgcggaaa tctatgcgtt tggcggtccg 840
accattgatc tgattccgaa aagcgcgcgc aaatacttcg aagaaaaagc gctggattac 900
tatcgcagca ttgcgaaacg tctgaacagc attaccaccg cgaatccgag cagcttcaac 960
aaatatatcg gcgaatataa acagaaactg atccgcaaat atcgctttgt ggtggaaagc 1020
agcggcgaag ttaccgttaa ccgcaataaa ttcgtggaac tgtacaacga actgacccag 1080
atcttcaccg aatttaacta tgcgaaaatc tataacgtgc agaaccgtaa aatctacctg 1140
agcaacgtgt ataccccggt gaccgcgaat attctggatg ataacgtgta cgatatccag 1200
aacggcttta acatcccgaa aagcaacctg aacgttctgt ttatgggcca gaacctgagc 1260
cgtaatccgg cgctgcgtaa agtgaacccg gaaaacatgc tgtacctgtt caccaaattt 1320
tgcgtcgac 1329

<210> SEQ ID NO 32
<211> LENGTH: 1263
<212> TYPE: DNA
<213> ORGANISM: Artificial Sequence
<220> FEATURE:
<223> OTHER INFORMATION: Synthetic

<400> SEQUENCE: 32
ctgcagtgtc gtgaactgct ggtgaaaaac accgatctgc cgtttattgg cgatatcagc 60
gatgtgaaaa ccgatatctt cctgcgcaaa gatatcaacg aagaaaccga agtgatctac 120
tacccggata acgtgagcgt tgatcaggtg atcctgagca aaaacaccag cgaacatggt 180
cagctggatc tgctgtatcc gagcattgat agcgaaagcg aaattctgcc gggcgaaaac 240

-continued

```
caggtgtttt acgataaccg tacccagaac gtggattacc tgaacagcta ttactacctg    300

gaaagccaga aactgagcga taacgtggaa gattttacct ttacccgcag cattgaagaa    360

gcgctggata acagcgcgaa agtttacacc tattttccga ccctggcgaa caaagttaat    420

gcgggtgttc agggcggtct gtttctgatg tgggcgaacg atgtggtgga agatttcacc    480

accaacatcc tgcgtaaaga taccctggat aaaatcagcg atgttagcgc gattattccg    540

tatattggtc cggcgctgaa cattagcaat agcgtgcgtc gtggcaattt taccgaagcg    600

tttgcggtta ccggtgtgac cattctgctg gaagcgtttc cggaatttac cattccggcg    660

ctgggtgcgt ttgtgatcta tagcaaagtg caggaacgca acgaaatcat caaaaccatc    720

gataactgcc tggaacagcg tattaaacgc tggaaagata gctatgaatg gatgatgggc    780

acctggctga gccgtattat cacccagttc aacaacatca gctaccagat gtacgatagc    840

ctgaactatc aggcgggtgc gattaaagcg aaaatcgatc tggaatacaa aaaatacagc    900

ggcagcgata aagaaaacat caaaagccag gttgaaaacc tgaaaaacag cctggatgtg    960

aaaattagcg aagcgatgaa taacatcaac aaattcatcc gcgaatgcag cgtgacctac   1020

ctgttcaaaa acatgctgcc gaaagtgatc gatgaactga acgaatttga tcgcaacacc   1080

aaagcgaaac tgatcaacct gatcgatagc cacaacatta ttctggtggg cgaagtggat   1140

aaactgaaag cgaaagttaa caacagcttc cagaacacca tcccgtttaa catcttcagc   1200

tataccaaca acagcctgct gaaagatatc atcaacgaat acttcaatct agactagaag   1260

ctt                                                                 1263


<210> SEQ ID NO 33
<211> LENGTH: 207
<212> TYPE: DNA
<213> ORGANISM: Artificial Sequence
<220> FEATURE:
<223> OTHER INFORMATION: Synthetic

<400> SEQUENCE: 33

ggatccacgc acgtcgacgg catcattacc tccaaaacta aatctctgat cgaaggtcgt     60

tttggcggtt tcacgggcgc acgcaaatca gcgcgtaaat tagctaacca ggcgctagcg    120

ggcggtggcg gtagcggcgg tggcggtagc ggcggtggcg gtagcgcact agtgctgcag    180

acgcacggtc tagaatgata aaagctt                                        207


<210> SEQ ID NO 34
<211> LENGTH: 108
<212> TYPE: DNA
<213> ORGANISM: Artificial Sequence
<220> FEATURE:
<223> OTHER INFORMATION: Synthetic

<400> SEQUENCE: 34

ggatccacgc acgtcgacgg catcattacc tccaaaacta aatctctgat agaaggtaga     60

aacaaagcgc tgaacctgca gacgcacggt ctagaatgat aaaagctt                 108


<210> SEQ ID NO 35
<211> LENGTH: 186
<212> TYPE: DNA
<213> ORGANISM: Artificial Sequence
<220> FEATURE:
<223> OTHER INFORMATION: Synthetic

<400> SEQUENCE: 35

catatgaata acctcgggat tgagggtcgt tttggcggtt tcacgggcgc acgcaaatca     60
```

-continued gcgcgtaaat tagctaacca gactagtggc ggtgggggta gtggcggtgg cggttcgggc 120
gggggtggga gccctagggg atccgtcgac ctgcagggtc tagaagcgct agcgtgataa 180
aagctt 186

<210> SEQ ID NO 36
<211> LENGTH: 180
<212> TYPE: DNA
<213> ORGANISM: Artificial Sequence
<220> FEATURE:
<223> OTHER INFORMATION: Synthetic

<400> SEQUENCE: 36
ggatccacgc acgtcgacgc gattgatggt cgttttggcg gtttcacggg cgcacgcaaa 60
tcagcgcgta aattagctaa ccaggcgcta gcgggcggtg gcggtagcgg cggtggcggt 120
agcggcggtg gcggtagcgc actagtgctg cagacgcacg gtctagaatg ataaaagctt 180

<210> SEQ ID NO 37
<211> LENGTH: 249
<212> TYPE: DNA
<213> ORGANISM: Artificial Sequence
<220> FEATURE:
<223> OTHER INFORMATION: Synthetic

<400> SEQUENCE: 37
ggatccacgc acgtcgacgg catcattacc tccaaaacta aatctctgat cgaaggtcgt 60
tacggtggtt tcatgacctc tgaaaaatct cagaccccgc tggttaccct gttcaaaaac 120
gctatcatca aaaacgctta caaaaaaggt gaagcgctag cgggtggtgg tggttctggt 180
ggtggtggtt ctggtggtgg tggttctgca ctagtgctgc agacgcacgg tctagaatga 240
taaaagctt 249

<210> SEQ ID NO 38
<211> LENGTH: 207
<212> TYPE: DNA
<213> ORGANISM: Artificial Sequence
<220> FEATURE:
<223> OTHER INFORMATION: Synthetic

<400> SEQUENCE: 38
ggatccacgc acgtcgacgg catcattacc tccaaaacta aatctctgat cgaaggtcgt 60
tttggcggtt tcacgggcgc acgcaaatca gcgcgtaaac gtaagaacca ggcgctagcg 120
ggcggtggcg gtagcggcgg tggcggtagc ggcggtggcg gtagcgcact agtgctgcag 180
acgcacggtc tagaatgata aaagctt 207

<210> SEQ ID NO 39
<211> LENGTH: 2709
<212> TYPE: DNA
<213> ORGANISM: Artificial Sequence
<220> FEATURE:
<223> OTHER INFORMATION: Synthetic

<400> SEQUENCE: 39
ggatccatgg agttcgttaa caaacagttc aactataaag acccagttaa cggtgttgac 60
attgcttaca tcaaaatccc gaacgctggc cagatgcagc cggtaaaggc attcaaaatc 120
cacaacaaaa tctgggttat cccggaacgt gataccttta ctaacccgga agaaggtgac 180
ctgaacccgc caccggaagc gaaacaggtg ccggtatctt actatgactc cacctacctg 240
tctaccgata acgaaaagga caactacctg aaaggtgtta ctaaactgtt cgagcgtatt 300

```
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg gttcctatcg ttccgaagaa ctgaacctgg tgatcatcgg cccgtctgct    480
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct tctctccagt acatgaagaa cgtttttaaa    960
gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa aatcaacatc   1140
gtgccgaaag ttaactacac tatctacgat ggtttcaacc tgcgtaacac caacctggct   1200
gctaatttta acggccagaa cacggaaatc aacaacatga acttcacaaa actgaaaaac   1260
ttcactggtc tgttcgagtt ttacaagctg ctgtgcgtcg acggcatcat tacctccaaa   1320
actaaatctc tgatagaagg tagatttggc ggtttcacgg gcgcacgcaa atcagcgcgt   1380
aaattagcta accaggcgct agcgggcggt ggcggtagcg gcggtggcgg tagcggcggt   1440
ggcggtagcg cactagtgct gcagtgtatc aaggttaaca actgggattt attcttcagc   1500
ccgagtgaag acaacttcac caacgacctg aacaaaggtg aagaaatcac ctcagatact   1560
aacatcgaag cagccgaaga aaacatctcg ctggacctga tccagcagta ctacctgacc   1620
tttaatttcg acaacgagcc ggaaaacatt tctatcgaaa acctgagctc tgatatcatc   1680
ggccagctgg aactgatgcc gaacatcgaa cgtttcccaa acggtaaaaa gtacgagctg   1740
gacaaatata ccatgttcca ctacctgcgc gcgcaggaat ttgaacacgg caaatcccgt   1800
atcgcactga ctaactccgt taacgaagct ctgctcaacc cgtcccgtgt atacaccttc   1860
ttctctagcg actacgtgaa aaaggtcaac aaagcgactg aagctgcaat gttcttgggt   1920
tgggttgaac agcttgttta tgattttacc gacgagacgt ccgaagtatc tactaccgac   1980
aaaattgcgg atatcactat catcatcccg tacatcggtc cggctctgaa cattggcaac   2040
atgctgtaca aagacgactt cgttggcgca ctgatcttct ccggtgcggt gatcctgctg   2100
gagttcatcc cggaaatcgc catcccggta ctgggcacct ttgctctggt ttcttacatt   2160
gcaaacaagg ttctgactgt acaaaccatc gacaacgcgc tgagcaaacg taacgaaaaa   2220
tgggatgaag tttacaaata tatcgtgacc aactggctgg ctaaggttaa tactcagatc   2280
gacctcatcc gcaaaaaaat gaaagaagca ctggaaaacc aggcggaagc taccaaggca   2340
atcattaact accagtacaa ccagtacacc gaggaagaaa aaaacaacat caacttcaac   2400
atcgacgatc tgtcctctaa actgaacgaa tccatcaaca aagctatgat caacatcaac   2460
aagttcctga accagtgctc tgtaagctat ctgatgaact ccatgatccc gtacggtgtt   2520
aaacgtctgg aggacttcga tgcgtctctg aaagacgccc tgctgaaata catttacgac   2580
aaccgtggca ctctgatcgg tcaggttgat cgtctgaagg acaaagtgaa caatacctta   2640
tcgaccgaca tccctttca gctcagtaaa tatgtcgata accaacgcct tttgtccact   2700
```

ctagactag 2709

<210> SEQ ID NO 40
<211> LENGTH: 902
<212> TYPE: PRT
<213> ORGANISM: Artificial Sequence
<220> FEATURE:
<223> OTHER INFORMATION: Synthetic

<400> SEQUENCE: 40

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
```

-continued

```
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Arg Lys Leu Ala Asn
    450                 455                 460

Gln Ala Leu Ala Gly Gly Gly Gly Ser Gly Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
            500                 505                 510

Gly Glu Glu Ile Thr Ser Asp Thr Asn Ile Glu Ala Ala Glu Glu Asn
        515                 520                 525

Ile Ser Leu Asp Leu Ile Gln Gln Tyr Tyr Leu Thr Phe Asn Phe Asp
    530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
            580                 585                 590

Glu Phe Glu His Gly Lys Ser Arg Ile Ala Leu Thr Asn Ser Val Asn
        595                 600                 605

Glu Ala Leu Leu Asn Pro Ser Arg Val Tyr Thr Phe Phe Ser Ser Asp
    610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Ile Pro Tyr Ile
            660                 665                 670

Gly Pro Ala Leu Asn Ile Gly Asn Met Leu Tyr Lys Asp Asp Phe Val
        675                 680                 685

Gly Ala Leu Ile Phe Ser Gly Ala Val Ile Leu Leu Glu Phe Ile Pro
    690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
                725                 730                 735

Arg Asn Glu Lys Trp Asp Glu Val Tyr Lys Tyr Ile Val Thr Asn Trp
            740                 745                 750

Leu Ala Lys Val Asn Thr Gln Ile Asp Leu Ile Arg Lys Lys Met Lys
        755                 760                 765

Glu Ala Leu Glu Asn Gln Ala Glu Ala Thr Lys Ala Ile Ile Asn Tyr
    770                 775                 780
```

-continued

```
Gln Tyr Asn Gln Tyr Thr Glu Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
        835                 840                 845

Ser Leu Lys Asp Ala Leu Leu Lys Tyr Ile Tyr Asp Asn Arg Gly Thr
    850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Asp
            900
```

<210> SEQ ID NO 41
<211> LENGTH: 2736
<212> TYPE: DNA
<213> ORGANISM: Artificial Sequence
<220> FEATURE:
<223> OTHER INFORMATION: Synthetic

<400> SEQUENCE: 41

```
ctcgggattg agggtcgttt tggcggtttc acgggcgcac gcaaatcagc gcgtaaatta     60

gctaaccaga ctagtggcgg tgggggtagt ggcggtggcg gttcgggcgg gggtgggagc    120

cctaggggat ccatggagtt cgttaacaaa cagttcaact ataaagaccc agttaacggt    180

gttgacattg cttacatcaa aatcccgaac gctggccaga tgcagccggt aaaggcattc    240

aaaatccaca acaaaatctg ggttatcccg gaacgtgata cctttactaa cccggaagaa    300

ggtgacctga acccgccacc ggaagcgaaa caggtgccgg tatcttacta tgactccacc    360

tacctgtcta ccgataacga aaaggacaac tacctgaaag gtgttactaa actgttcgag    420

cgtatttact ccaccgacct gggccgtatg ctgctgacta gcatcgttcg cggtatcccg    480

ttctggggcg gttctaccat cgataccgaa ctgaaagtaa tcgacactaa ctgcatcaac    540

gttattcagc cggacggttc ctatcgttcc gaagaactga acctggtgat catcggcccg    600

tctgctgata tcatccagtt cgagtgtaag agctttggtc acgaagttct gaacctcacc    660

cgtaacggct acggttccac tcagtacatc cgtttctctc cggacttcac cttcggtttt    720

gaagaatccc tggaagtaga cacgaaccca ctgctgggcg ctggtaaatt cgcaactgat    780

cctgcggtta ccctggctca cgaactgatt catgcaggcc accgcctgta cggtatcgcc    840

atcaatccga accgtgtctt caaagttaac accaacgcgt attacgagat gtccggtctg    900

gaagttagct tcgaagaact gcgtactttt ggcggtcacg acgctaaatt catcgactct    960

ctgcaagaaa acgagttccg tctgtactac tataacaagt tcaaagatat cgcatccacc   1020

ctgaacaaag cgaaatccat cgtgggtacc actgcttctc tccagtacat gaagaacgtt   1080

tttaaagaaa aatacctgct cagcgaagac acctccggca aattctctgt agacaagttg   1140

aaattcgata aactttacaa aatgctgact gaaatttaca ccgaagacaa cttcgttaag   1200

ttctttaaag ttctgaaccg caaaacctat ctgaacttcg acaaggcagt attcaaaatc   1260

aacatcgtgc cgaaagttaa ctacactatc tacgatggtt tcaacctgcg taacaccaac   1320

ctggctgcta attttaacgg ccagaacacg gaaatcaaca acatgaactt cacaaaactg   1380
```

-continued

```
aaaaacttca ctggtctgtt cgagttttac aagctgctgt gcgtcgacgg catcattacc   1440

tccaaaacta aatctctgat agaaggtaga aacaaagcgc tgaacgacct ctgtatcaag   1500

gttaacaact gggatttatt cttcagcccg agtgaagaca acttcaccaa cgacctgaac   1560

aaaggtgaag aaatcacctc agatactaac atcgaagcag ccgaagaaaa catctcgctg   1620

gacctgatcc agcagtacta cctgaccttt aatttcgaca acgagccgga aaacatttct   1680

atcgaaaacc tgagctctga tatcatcggc cagctggaac tgatgccgaa catcgaacgt   1740

ttcccaaacg gtaaaaagta cgagctggac aaatatacca tgttccacta cctgcgcgcg   1800

caggaatttg aacacggcaa atcccgtatc gcactgacta actccgttaa cgaagctctg   1860

ctcaacccgt cccgtgtata caccttcttc tctagcgact acgtgaaaaa ggtcaacaaa   1920

gcgactgaag ctgcaatgtt cttgggttgg gttgaacagc ttgtttatga ttttaccgac   1980

gagacgtccg aagtatctac taccgacaaa attgcggata tcactatcat catcccgtac   2040

atcggtccgg ctctgaacat tggcaacatg ctgtacaaag acgacttcgt tggcgcactg   2100

atcttctccg gtgcggtgat cctgctggag ttcatcccgg aaatcgccat cccggtactg   2160

ggcacctttg ctctggtttc ttacattgca aacaaggttc tgactgtaca aaccatcgac   2220

aacgcgctga gcaaacgtaa cgaaaaatgg gatgaagttt acaaatatat cgtgaccaac   2280

tggctggcta aggttaatac tcagatcgac ctcatccgca aaaaaatgaa agaagcactg   2340

gaaaaccagg cggaagctac caaggcaatc attaactacc agtacaacca gtacaccgag   2400

gaagaaaaaa acaacatcaa cttcaacatc gacgatctgt cctctaaact gaacgaatcc   2460

atcaacaaag ctatgatcaa catcaacaag ttcctgaacc agtgctctgt aagctatctg   2520

atgaactcca tgatcccgta cggtgttaaa cgtctggagg acttcgatgc gtctctgaaa   2580

gacgccctgc tgaaatacat ttacgacaac cgtggcactc tgatcggtca ggttgatcgt   2640

ctgaaggaca aagtgaacaa taccttatcg accgacatcc cttttcagct cagtaaatat   2700

gtcgataacc aacgcctttt gtccactcta gactag                             2736
```

<210> SEQ ID NO 42
<211> LENGTH: 911
<212> TYPE: PRT
<213> ORGANISM: Artificial Sequence
<220> FEATURE:
<223> OTHER INFORMATION: Synthetic

<400> SEQUENCE: 42

```
Leu Gly Ile Glu Gly Arg Phe Gly Gly Phe Thr Gly Ala Arg Lys Ser
1               5                   10                  15

Ala Arg Lys Leu Ala Asn Gln Thr Ser Gly Gly Gly Gly Ser Gly Gly
            20                  25                  30

Gly Gly Ser Gly Gly Gly Gly Ser Pro Arg Gly Ser Met Glu Phe Val
        35                  40                  45

Asn Lys Gln Phe Asn Tyr Lys Asp Pro Val Asn Gly Val Asp Ile Ala
    50                  55                  60

Tyr Ile Lys Ile Pro Asn Ala Gly Gln Met Gln Pro Val Lys Ala Phe
65                  70                  75                  80

Lys Ile His Asn Lys Ile Trp Val Ile Pro Glu Arg Asp Thr Phe Thr
                85                  90                  95

Asn Pro Glu Glu Gly Asp Leu Asn Pro Pro Pro Glu Ala Lys Gln Val
            100                 105                 110

Pro Val Ser Tyr Tyr Asp Ser Thr Tyr Leu Ser Thr Asp Asn Glu Lys
        115                 120                 125
```

```
Asp Asn Tyr Leu Lys Gly Val Thr Lys Leu Phe Glu Arg Ile Tyr Ser
    130                 135                 140

Thr Asp Leu Gly Arg Met Leu Leu Thr Ser Ile Val Arg Gly Ile Pro
145                 150                 155                 160

Phe Trp Gly Gly Ser Thr Ile Asp Thr Glu Leu Lys Val Ile Asp Thr
                165                 170                 175

Asn Cys Ile Asn Val Ile Gln Pro Asp Gly Ser Tyr Arg Ser Glu Glu
            180                 185                 190

Leu Asn Leu Val Ile Ile Gly Pro Ser Ala Asp Ile Ile Gln Phe Glu
        195                 200                 205

Cys Lys Ser Phe Gly His Glu Val Leu Asn Leu Thr Arg Asn Gly Tyr
    210                 215                 220

Gly Ser Thr Gln Tyr Ile Arg Phe Ser Pro Asp Phe Thr Phe Gly Phe
225                 230                 235                 240

Glu Glu Ser Leu Glu Val Asp Thr Asn Pro Leu Leu Gly Ala Gly Lys
                245                 250                 255

Phe Ala Thr Asp Pro Ala Val Thr Leu Ala His Glu Leu Ile His Ala
            260                 265                 270

Gly His Arg Leu Tyr Gly Ile Ala Ile Asn Pro Asn Arg Val Phe Lys
        275                 280                 285

Val Asn Thr Asn Ala Tyr Tyr Glu Met Ser Gly Leu Glu Val Ser Phe
    290                 295                 300

Glu Glu Leu Arg Thr Phe Gly Gly His Asp Ala Lys Phe Ile Asp Ser
305                 310                 315                 320

Leu Gln Glu Asn Glu Phe Arg Leu Tyr Tyr Tyr Asn Lys Phe Lys Asp
                325                 330                 335

Ile Ala Ser Thr Leu Asn Lys Ala Lys Ser Ile Val Gly Thr Thr Ala
            340                 345                 350

Ser Leu Gln Tyr Met Lys Asn Val Phe Lys Glu Lys Tyr Leu Leu Ser
        355                 360                 365

Glu Asp Thr Ser Gly Lys Phe Ser Val Asp Lys Leu Lys Phe Asp Lys
    370                 375                 380

Leu Tyr Lys Met Leu Thr Glu Ile Tyr Thr Glu Asp Asn Phe Val Lys
385                 390                 395                 400

Phe Phe Lys Val Leu Asn Arg Lys Thr Tyr Leu Asn Phe Asp Lys Ala
                405                 410                 415

Val Phe Lys Ile Asn Ile Val Pro Lys Val Asn Tyr Thr Ile Tyr Asp
            420                 425                 430

Gly Phe Asn Leu Arg Asn Thr Asn Leu Ala Ala Asn Phe Asn Gly Gln
        435                 440                 445

Asn Thr Glu Ile Asn Asn Met Asn Phe Thr Lys Leu Lys Asn Phe Thr
    450                 455                 460

Gly Leu Phe Glu Phe Tyr Lys Leu Leu Cys Val Asp Gly Ile Ile Thr
465                 470                 475                 480

Ser Lys Thr Lys Ser Leu Ile Glu Gly Arg Asn Lys Ala Leu Asn Asp
                485                 490                 495

Leu Cys Ile Lys Val Asn Asn Trp Asp Leu Phe Phe Ser Pro Ser Glu
            500                 505                 510

Asp Asn Phe Thr Asn Asp Leu Asn Lys Gly Glu Glu Ile Thr Ser Asp
        515                 520                 525

Thr Asn Ile Glu Ala Ala Glu Glu Asn Ile Ser Leu Asp Leu Ile Gln
    530                 535                 540

Gln Tyr Tyr Leu Thr Phe Asn Phe Asp Asn Glu Pro Glu Asn Ile Ser
545                 550                 555                 560
```

```
Ile Glu Asn Leu Ser Ser Asp Ile Ile Gly Gln Leu Glu Leu Met Pro
                565                 570                 575

Asn Ile Glu Arg Phe Pro Asn Gly Lys Lys Tyr Glu Leu Asp Lys Tyr
            580                 585                 590

Thr Met Phe His Tyr Leu Arg Ala Gln Glu Phe Glu His Gly Lys Ser
        595                 600                 605

Arg Ile Ala Leu Thr Asn Ser Val Asn Glu Ala Leu Leu Asn Pro Ser
    610                 615                 620

Arg Val Tyr Thr Phe Phe Ser Ser Asp Tyr Val Lys Lys Val Asn Lys
625                 630                 635                 640

Ala Thr Glu Ala Ala Met Phe Leu Gly Trp Val Glu Gln Leu Val Tyr
                645                 650                 655

Asp Phe Thr Asp Glu Thr Ser Glu Val Ser Thr Thr Asp Lys Ile Ala
            660                 665                 670

Asp Ile Thr Ile Ile Ile Pro Tyr Ile Gly Pro Ala Leu Asn Ile Gly
        675                 680                 685

Asn Met Leu Tyr Lys Asp Asp Phe Val Gly Ala Leu Ile Phe Ser Gly
    690                 695                 700

Ala Val Ile Leu Leu Glu Phe Ile Pro Glu Ile Ala Ile Pro Val Leu
705                 710                 715                 720

Gly Thr Phe Ala Leu Val Ser Tyr Ile Ala Asn Lys Val Leu Thr Val
                725                 730                 735

Gln Thr Ile Asp Asn Ala Leu Ser Lys Arg Asn Glu Lys Trp Asp Glu
            740                 745                 750

Val Tyr Lys Tyr Ile Val Thr Asn Trp Leu Ala Lys Val Asn Thr Gln
        755                 760                 765

Ile Asp Leu Ile Arg Lys Lys Met Lys Glu Ala Leu Glu Asn Gln Ala
    770                 775                 780

Glu Ala Thr Lys Ala Ile Ile Asn Tyr Gln Tyr Asn Gln Tyr Thr Glu
785                 790                 795                 800

Glu Glu Lys Asn Asn Ile Asn Phe Asn Ile Asp Asp Leu Ser Ser Lys
                805                 810                 815

Leu Asn Glu Ser Ile Asn Lys Ala Met Ile Asn Ile Asn Lys Phe Leu
            820                 825                 830

Asn Gln Cys Ser Val Ser Tyr Leu Met Asn Ser Met Ile Pro Tyr Gly
        835                 840                 845

Val Lys Arg Leu Glu Asp Phe Asp Ala Ser Leu Lys Asp Ala Leu Leu
    850                 855                 860

Lys Tyr Ile Tyr Asp Asn Arg Gly Thr Leu Ile Gly Gln Val Asp Arg
865                 870                 875                 880

Leu Lys Asp Lys Val Asn Asn Thr Leu Ser Thr Asp Ile Pro Phe Gln
                885                 890                 895

Leu Ser Lys Tyr Val Asp Asn Gln Arg Leu Leu Ser Thr Leu Asp
            900                 905                 910


<210> SEQ ID NO 43
<211> LENGTH: 2715
<212> TYPE: DNA
<213> ORGANISM: Artificial Sequence
<220> FEATURE:
<223> OTHER INFORMATION: Synthetic

<400> SEQUENCE: 43

ggatccgaat tcatgccgat caccatcaac aacttcaact acagcgatcc ggtggataac      60

aaaaacatcc tgtacctgga tacccatctg aataccctgg cgaacgaacc ggaaaaagcg     120
```

```
tttcgtatca ccggcaacat ttgggttatt ccggatcgtt ttagccgtaa cagcaacccg    180
aatctgaata aaccgccgcg tgttaccagc ccgaaaagcg gttattacga tccgaactat    240
ctgagcaccg atagcgataa agataccttc ctgaaagaaa tcatcaaact gttcaaacgc    300
atcaacagcc gtgaaattgg cgaagaactg atctatcgcc tgagcaccga tattccgttt    360
ccgggcaaca acaacacccc gatcaacacc tttgatttcg atgtggattt caacagcgtt    420
gatgttaaaa cccgccaggg taacaattgg gtgaaaaccg gcagcattaa cccgagcgtg    480
attattaccg gtccgcgcga aaacattatt gatccggaaa ccagcacctt taaactgacc    540
aacaacacct ttgcggcgca ggaaggtttt ggcgcgctga gcattattag cattagcccg    600
cgctttatgc tgacctatag caacgcgacc aacgatgttg gtgaaggccg tttcagcaaa    660
agcgaatttt gcatggaccc gatcctgatc ctgatgcatg aactgaacca tgcgatgcat    720
aacctgtatg gcatcgcgat tccgaacgat cagaccatta gcagcgtgac cagcaacatc    780
ttttacagcc agtacaacgt gaaactggaa tatgcggaaa tctatgcgtt tggcggtccg    840
accattgatc tgattccgaa aagcgcgcgc aaatacttcg aagaaaaagc gctggattac    900
tatcgcagca ttgcgaaacg tctgaacagc attaccaccg cgaatccgag cagcttcaac    960
aaatatatcg gcgaatataa acagaaactg atccgcaaat atcgctttgt ggtggaaagc   1020
agcggcgaag ttaccgttaa ccgcaataaa ttcgtggaac tgtacaacga actgacccag   1080
atcttcaccg aatttaacta tgcgaaaatc tataacgtgc agaaccgtaa aatctacctg   1140
agcaacgtgt ataccccggt gaccgcgaat attctggatg ataacgtgta cgatatccag   1200
aacggcttta acatcccgaa aagcaacctg aacgttctgt ttatgggcca gaacctgagc   1260
cgtaatccgg cgctgcgtaa agtgaacccg gaaaacatgc tgtacctgtt caccaaattt   1320
tgcgtcgacg cgatagatgg tagatttggc ggtttcacgg gcgcacgcaa atcagcgcgt   1380
aaattagcta accaggcgct agcgggcggt ggcggtagcg gcggtggcgg tagcggcggt   1440
ggcggtagcg cactagtgct gcagtgtcgt gaactgctgg tgaaaaacac cgatctgccg   1500
tttattggcg atatcagcga tgtgaaaacc gatatcttcc tgcgcaaaga tatcaacgaa   1560
gaaaccgaag tgatctacta cccggataac gtgagcgttg atcaggtgat cctgagcaaa   1620
aacaccagcg aacatggtca gctggatctg ctgtatccga gcattgatag cgaaagcgaa   1680
attctgccgg gcgaaaacca ggtgttttac gataaccgta cccagaacgt ggattacctg   1740
aacagctatt actacctgga aagccagaaa ctgagcgata acgtggaaga ttttaccttt   1800
acccgcagca ttgaagaagc gctggataac agcgcgaaag tttacaccta ttttccgacc   1860
ctggcgaaca aagttaatgc gggtgttcag ggcggtctgt ttctgatgtg ggcgaacgat   1920
gtggtggaag atttcaccac caacatcctg cgtaaagata ccctggataa aatcagcgat   1980
gttagcgcga ttattccgta tattggtccg gcgctgaaca ttagcaatag cgtgcgtcgt   2040
ggcaatttta ccgaagcgtt tgcggttacc ggtgtgacca ttctgctgga agcgtttccg   2100
gaatttacca ttccggcgct gggtgcgttt gtgatctata gcaaagtgca ggaacgcaac   2160
gaaatcatca aaaccatcga taactgcctg gaacagcgta ttaaacgctg gaaagatagc   2220
tatgaatgga tgatgggcac ctggctgagc cgtattatca cccagttcaa caacatcagc   2280
taccagatgt acgatagcct gaactatcag gcgggtgcga ttaaagcgaa aatcgatctg   2340
gaatacaaaa aatacagcgg cagcgataaa gaaaacatca aaagccaggt tgaaaacctg   2400
aaaaacagcc tggatgtgaa aattagcgaa gcgatgaata acatcaacaa attcatccgc   2460
gaatgcagcg tgacctacct gttcaaaaac atgctgccga aagtgatcga tgaactgaac   2520
```

gaatttgatc gcaacaccaa agcgaaactg atcaacctga tcgatagcca caacattatt 2580
ctggtgggcg aagtggataa actgaaagcg aaagttaaca acagcttcca gaacaccatc 2640
ccgtttaaca tcttcagcta taccaacaac agcctgctga aagatatcat caacgaatac 2700
ttcaatctag actag 2715

<210> SEQ ID NO 44
<211> LENGTH: 904
<212> TYPE: PRT
<213> ORGANISM: Artificial Sequence
<220> FEATURE:
<223> OTHER INFORMATION: Synthetic

<400> SEQUENCE: 44

Gly Ser Glu Phe Met Pro Ile Thr Ile Asn Asn Phe Asn Tyr Ser Asp
1 5 10 15

Pro Val Asp Asn Lys Asn Ile Leu Tyr Leu Asp Thr His Leu Asn Thr
20 25 30

Leu Ala Asn Glu Pro Glu Lys Ala Phe Arg Ile Thr Gly Asn Ile Trp
35 40 45

Val Ile Pro Asp Arg Phe Ser Arg Asn Ser Asn Pro Asn Leu Asn Lys
50 55 60

Pro Pro Arg Val Thr Ser Pro Lys Ser Gly Tyr Tyr Asp Pro Asn Tyr
65 70 75 80

Leu Ser Thr Asp Ser Asp Lys Asp Thr Phe Leu Lys Glu Ile Ile Lys
85 90 95

Leu Phe Lys Arg Ile Asn Ser Arg Glu Ile Gly Glu Glu Leu Ile Tyr
100 105 110

Arg Leu Ser Thr Asp Ile Pro Phe Pro Gly Asn Asn Asn Thr Pro Ile
115 120 125

Asn Thr Phe Asp Phe Asp Val Asp Phe Asn Ser Val Asp Val Lys Thr
130 135 140

Arg Gln Gly Asn Asn Trp Val Lys Thr Gly Ser Ile Asn Pro Ser Val
145 150 155 160

Ile Ile Thr Gly Pro Arg Glu Asn Ile Ile Asp Pro Glu Thr Ser Thr
165 170 175

Phe Lys Leu Thr Asn Asn Thr Phe Ala Ala Gln Glu Gly Phe Gly Ala
180 185 190

Leu Ser Ile Ile Ser Ile Ser Pro Arg Phe Met Leu Thr Tyr Ser Asn
195 200 205

Ala Thr Asn Asp Val Gly Glu Gly Arg Phe Ser Lys Ser Glu Phe Cys
210 215 220

Met Asp Pro Ile Leu Ile Leu Met His Glu Leu Asn His Ala Met His
225 230 235 240

Asn Leu Tyr Gly Ile Ala Ile Pro Asn Asp Gln Thr Ile Ser Ser Val
245 250 255

Thr Ser Asn Ile Phe Tyr Ser Gln Tyr Asn Val Lys Leu Glu Tyr Ala
260 265 270

Glu Ile Tyr Ala Phe Gly Gly Pro Thr Ile Asp Leu Ile Pro Lys Ser
275 280 285

Ala Arg Lys Tyr Phe Glu Glu Lys Ala Leu Asp Tyr Tyr Arg Ser Ile
290 295 300

Ala Lys Arg Leu Asn Ser Ile Thr Thr Ala Asn Pro Ser Ser Phe Asn
305 310 315 320

Lys Tyr Ile Gly Glu Tyr Lys Gln Lys Leu Ile Arg Lys Tyr Arg Phe

-continued

```
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
    370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Ala Ile Asp Gly Arg
        435                 440                 445

Phe Gly Gly Phe Thr Gly Ala Arg Lys Ser Ala Arg Lys Leu Ala Asn
    450                 455                 460

Gln Ala Leu Ala Gly Gly Gly Gly Ser Gly Gly Gly Gly Ser Gly Gly
465                 470                 475                 480

Gly Gly Ser Ala Leu Val Leu Gln Cys Arg Glu Leu Leu Val Lys Asn
                485                 490                 495

Thr Asp Leu Pro Phe Ile Gly Asp Ile Ser Asp Val Lys Thr Asp Ile
            500                 505                 510

Phe Leu Arg Lys Asp Ile Asn Glu Glu Thr Glu Val Ile Tyr Tyr Pro
        515                 520                 525

Asp Asn Val Ser Val Asp Gln Val Ile Leu Ser Lys Asn Thr Ser Glu
    530                 535                 540

His Gly Gln Leu Asp Leu Leu Tyr Pro Ser Ile Asp Ser Glu Ser Glu
545                 550                 555                 560

Ile Leu Pro Gly Glu Asn Gln Val Phe Tyr Asp Asn Arg Thr Gln Asn
                565                 570                 575

Val Asp Tyr Leu Asn Ser Tyr Tyr Tyr Leu Glu Ser Gln Lys Leu Ser
            580                 585                 590

Asp Asn Val Glu Asp Phe Thr Phe Thr Arg Ser Ile Glu Glu Ala Leu
        595                 600                 605

Asp Asn Ser Ala Lys Val Tyr Thr Tyr Phe Pro Thr Leu Ala Asn Lys
    610                 615                 620

Val Asn Ala Gly Val Gln Gly Gly Leu Phe Leu Met Trp Ala Asn Asp
625                 630                 635                 640

Val Val Glu Asp Phe Thr Thr Asn Ile Leu Arg Lys Asp Thr Leu Asp
                645                 650                 655

Lys Ile Ser Asp Val Ser Ala Ile Ile Pro Tyr Ile Gly Pro Ala Leu
            660                 665                 670

Asn Ile Ser Asn Ser Val Arg Arg Gly Asn Phe Thr Glu Ala Phe Ala
        675                 680                 685

Val Thr Gly Val Thr Ile Leu Leu Glu Ala Phe Pro Glu Phe Thr Ile
    690                 695                 700

Pro Ala Leu Gly Ala Phe Val Ile Tyr Ser Lys Val Gln Glu Arg Asn
705                 710                 715                 720

Glu Ile Ile Lys Thr Ile Asp Asn Cys Leu Glu Gln Arg Ile Lys Arg
                725                 730                 735

Trp Lys Asp Ser Tyr Glu Trp Met Met Gly Thr Trp Leu Ser Arg Ile
            740                 745                 750
```

-continued

Ile Thr Gln Phe Asn Asn Ile Ser Tyr Gln Met Tyr Asp Ser Leu Asn
        755                 760                 765

Tyr Gln Ala Gly Ala Ile Lys Ala Lys Ile Asp Leu Glu Tyr Lys Lys
    770                 775                 780

Tyr Ser Gly Ser Asp Lys Glu Asn Ile Lys Ser Gln Val Glu Asn Leu
785                 790                 795                 800

Lys Asn Ser Leu Asp Val Lys Ile Ser Glu Ala Met Asn Asn Ile Asn
                805                 810                 815

Lys Phe Ile Arg Glu Cys Ser Val Thr Tyr Leu Phe Lys Asn Met Leu
            820                 825                 830

Pro Lys Val Ile Asp Glu Leu Asn Glu Phe Asp Arg Asn Thr Lys Ala
        835                 840                 845

Lys Leu Ile Asn Leu Ile Asp Ser His Asn Ile Ile Leu Val Gly Glu
    850                 855                 860

Val Asp Lys Leu Lys Ala Lys Val Asn Asn Ser Phe Gln Asn Thr Ile
865                 870                 875                 880

Pro Phe Asn Ile Phe Ser Tyr Thr Asn Asn Ser Leu Leu Lys Asp Ile
                885                 890                 895

Ile Asn Glu Tyr Phe Asn Leu Asp
            900

<210> SEQ ID NO 45
<211> LENGTH: 2742
<212> TYPE: DNA
<213> ORGANISM: Artificial Sequence
<220> FEATURE:
<223> OTHER INFORMATION: Synthetic

<400> SEQUENCE: 45
ggatccgaat tcatgccgat caccatcaac aacttcaact acagcgatcc ggtggataac 60
aaaaacatcc tgtacctgga tacccatctg aataccctgg cgaacgaacc ggaaaaagcg 120
tttcgtatca ccggcaacat ttgggttatt ccggatcgtt ttagccgtaa cagcaacccg 180
aatctgaata aaccgccgcg tgttaccagc ccgaaaagcg gttattacga tccgaactat 240
ctgagcaccg atagcgataa agataccttc ctgaaagaaa tcatcaaact gttcaaacgc 300
atcaacagcc gtgaaattgg cgaagaactg atctatcgcc tgagcaccga tattccgttt 360
ccgggcaaca acaacacccc gatcaacacc tttgatttcg atgtggattt caacagcgtt 420
gatgttaaaa cccgccaggg taacaattgg gtgaaaaccg gcagcattaa cccgagcgtg 480
attattaccg gtccgcgcga aaacattatt gatccggaaa ccagcacctt taaactgacc 540
aacaacacct ttgcggcgca ggaaggtttt ggcgcgctga gcattattag cattagcccg 600
cgctttatgc tgacctatag caacgcgacc aacgatgttg gtgaaggccg tttcagcaaa 660
agcgaatttt gcatggaccc gatcctgatc ctgatgcatg aactgaacca tgcgatgcat 720
aacctgtatg gcatcgcgat tccgaacgat cagaccatta gcagcgtgac cagcaacatc 780
ttttacagcc agtacaacgt gaaactggaa tatgcggaaa tctatgcgtt tggcggtccg 840
accattgatc tgattccgaa aagcgcgcgc aaatacttcg aagaaaaagc gctggattac 900
tatcgcagca ttgcgaaacg tctgaacagc attaccaccg cgaatccgag cagcttcaac 960
aaatatatcg gcgaatataa acagaaactg atccgcaaat atcgctttgt ggtggaaagc 1020
agcggcgaag ttaccgttaa ccgcaataaa ttcgtggaac tgtacaacga actgacccag 1080
atcttcaccg aatttaacta tgcgaaaatc tataacgtgc agaaccgtaa aatctacctg 1140
agcaacgtgt ataccccggt gaccgcgaat attctggatg ataacgtgta cgatatccag 1200

```
aacggcttta acatcccgaa aagcaacctg aacgttctgt ttatgggcca gaacctgagc   1260

cgtaatccgg cgctgcgtaa agtgaacccg gaaaacatgc tgtacctgtt caccaaattt   1320

tgcgtcgacg gcatcattac ctccaaaact aaatctctga tagaaggtag atttggcggt   1380

ttcacgggcg cacgcaaatc agcgcgtaaa ttagctaacc aggcgctagc gggcggtggc   1440

ggtagcggcg gtggcggtag cggcggtggc ggtagcgcac tagtgctgca gtgtcgtgaa   1500

ctgctggtga aaaacaccga tctgccgttt attggcgata tcagcgatgt gaaaaccgat   1560

atcttcctgc gcaaagatat caacgaagaa accgaagtga tctactaccc ggataacgtg   1620

agcgttgatc aggtgatcct gagcaaaaac accagcgaac atggtcagct ggatctgctg   1680

tatccgagca ttgatagcga aagcgaaatt ctgccgggcg aaaaccaggt gttttacgat   1740

aaccgtaccc agaacgtgga ttacctgaac agctattact acctggaaag ccagaaactg   1800

agcgataacg tggaagattt tacctttacc cgcagcattg aagaagcgct ggataacagc   1860

gcgaaagttt acacctattt tccgaccctg gcgaacaaag ttaatgcggg tgttcagggc   1920

ggtctgtttc tgatgtgggc gaacgatgtg gtggaagatt tcaccaccaa catcctgcgt   1980

aaagataccc tggataaaat cagcgatgtt agcgcgatta ttccgtatat tggtccggcg   2040

ctgaacatta gcaatagcgt gcgtcgtggc aattttaccg aagcgtttgc ggttaccggt   2100

gtgaccattc tgctggaagc gtttccggaa tttaccattc cggcgctggg tgcgtttgtg   2160

atctatagca aagtgcagga acgcaacgaa atcatcaaaa ccatcgataa ctgcctggaa   2220

cagcgtatta aacgctggaa agatagctat gaatggatga tgggcacctg gctgagccgt   2280

attatcaccc agttcaacaa catcagctac cagatgtacg atagcctgaa ctatcaggcg   2340

ggtgcgatta aagcgaaaat cgatctggaa tacaaaaaat acagcggcag cgataaagaa   2400

aacatcaaaa gccaggttga aaacctgaaa aacagcctgg atgtgaaaat tagcgaagcg   2460

atgaataaca tcaacaaatt catccgcgaa tgcagcgtga cctacctgtt caaaaacatg   2520

ctgccgaaag tgatcgatga actgaacgaa tttgatcgca acaccaaagc gaaactgatc   2580

aacctgatcg atagccacaa cattattctg gtgggcgaag tggataaact gaaagcgaaa   2640

gttaacaaca gcttccagaa caccatcccg tttaacatct tcagctatac caacaacagc   2700

ctgctgaaag atatcatcaa cgaatacttc aatctagact ag                       2742
```

<210> SEQ ID NO 46
<211> LENGTH: 913
<212> TYPE: PRT
<213> ORGANISM: Artificial Sequence
<220> FEATURE:
<223> OTHER INFORMATION: Synthetic

<400> SEQUENCE: 46

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95
```

```
Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
    290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
    370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Gly Ile Ile Thr Ser
        435                 440                 445

Lys Thr Lys Ser Leu Ile Glu Gly Arg Phe Gly Gly Phe Thr Gly Ala
    450                 455                 460

Arg Lys Ser Ala Arg Lys Leu Ala Asn Gln Ala Leu Ala Gly Gly Gly
465                 470                 475                 480

Gly Ser Gly Gly Gly Gly Ser Gly Gly Gly Gly Ser Ala Leu Val Leu
                485                 490                 495

Gln Cys Arg Glu Leu Leu Val Lys Asn Thr Asp Leu Pro Phe Ile Gly
            500                 505                 510

Asp Ile Ser Asp Val Lys Thr Asp Ile Phe Leu Arg Lys Asp Ile Asn
        515                 520                 525
```

```
Glu Glu Thr Glu Val Ile Tyr Tyr Pro Asp Asn Val Ser Val Asp Gln
    530                 535                 540

Val Ile Leu Ser Lys Asn Thr Ser Glu His Gly Gln Leu Asp Leu Leu
545                 550                 555                 560

Tyr Pro Ser Ile Asp Ser Glu Ser Glu Ile Leu Pro Gly Glu Asn Gln
                565                 570                 575

Val Phe Tyr Asp Asn Arg Thr Gln Asn Val Asp Tyr Leu Asn Ser Tyr
            580                 585                 590

Tyr Tyr Leu Glu Ser Gln Lys Leu Ser Asp Asn Val Glu Asp Phe Thr
        595                 600                 605

Phe Thr Arg Ser Ile Glu Glu Ala Leu Asp Asn Ser Ala Lys Val Tyr
    610                 615                 620

Thr Tyr Phe Pro Thr Leu Ala Asn Lys Val Asn Ala Gly Val Gln Gly
625                 630                 635                 640

Gly Leu Phe Leu Met Trp Ala Asn Asp Val Val Glu Asp Phe Thr Thr
                645                 650                 655

Asn Ile Leu Arg Lys Asp Thr Leu Asp Lys Ile Ser Asp Val Ser Ala
            660                 665                 670

Ile Ile Pro Tyr Ile Gly Pro Ala Leu Asn Ile Ser Asn Ser Val Arg
        675                 680                 685

Arg Gly Asn Phe Thr Glu Ala Phe Ala Val Thr Gly Val Thr Ile Leu
    690                 695                 700

Leu Glu Ala Phe Pro Glu Phe Thr Ile Pro Ala Leu Gly Ala Phe Val
705                 710                 715                 720

Ile Tyr Ser Lys Val Gln Glu Arg Asn Glu Ile Ile Lys Thr Ile Asp
                725                 730                 735

Asn Cys Leu Glu Gln Arg Ile Lys Arg Trp Lys Asp Ser Tyr Glu Trp
            740                 745                 750

Met Met Gly Thr Trp Leu Ser Arg Ile Ile Thr Gln Phe Asn Asn Ile
        755                 760                 765

Ser Tyr Gln Met Tyr Asp Ser Leu Asn Tyr Gln Ala Gly Ala Ile Lys
    770                 775                 780

Ala Lys Ile Asp Leu Glu Tyr Lys Lys Tyr Ser Gly Ser Asp Lys Glu
785                 790                 795                 800

Asn Ile Lys Ser Gln Val Glu Asn Leu Lys Asn Ser Leu Asp Val Lys
                805                 810                 815

Ile Ser Glu Ala Met Asn Asn Ile Asn Lys Phe Ile Arg Glu Cys Ser
            820                 825                 830

Val Thr Tyr Leu Phe Lys Asn Met Leu Pro Lys Val Ile Asp Glu Leu
        835                 840                 845

Asn Glu Phe Asp Arg Asn Thr Lys Ala Lys Leu Ile Asn Leu Ile Asp
    850                 855                 860

Ser His Asn Ile Ile Leu Val Gly Glu Val Asp Lys Leu Lys Ala Lys
865                 870                 875                 880

Val Asn Asn Ser Phe Gln Asn Thr Ile Pro Phe Asn Ile Phe Ser Tyr
                885                 890                 895

Thr Asn Asn Ser Leu Leu Lys Asp Ile Ile Asn Glu Tyr Phe Asn Leu
            900                 905                 910

Asp
```

<210> SEQ ID NO 47
<211> LENGTH: 2673
<212> TYPE: DNA
<213> ORGANISM: Artificial Sequence
<220> FEATURE:
<223> OTHER INFORMATION: Synthetic

<400> SEQUENCE: 47

```
ggatccatgg agttcgttaa caaacagttc aactataaag acccagttaa cggtgttgac     60
attgcttaca tcaaaatccc gaacgctggc cagatgcagc cggtaaaggc attcaaaatc    120
cacaacaaaa tctgggttat cccggaacgt gatacccttta ctaacccgga agaaggtgac    180
ctgaacccgc caccggaagc gaaacaggtg ccggtatctt actatgactc cacctacctg    240
tctaccgata acgaaaagga caactacctg aaaggtgtta ctaaactgtt cgagcgtatt    300
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg gttcctatcg ttccgaagaa ctgaacctgg tgatcatcgg cccgtctgct    480
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct tctctccagt acatgaagaa cgtttttaaa    960
gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa aatcaacatc   1140
gtgccgaaag ttaactacac tatctacgat ggtttcaacc tgcgtaacac caacctggct   1200
gctaatttta acggccagaa cacggaaatc aacaacatga acttcacaaa actgaaaaac   1260
ttcactggtc tgttcgagtt ttacaagctg ctgtgcgtcg acggcatcat tacctccaaa   1320
actaaatctc tgatagaagg tagatacggt ggtttcatgg cgctagcggg cggtggcggt   1380
agcggcggtg gcggtagcgg cggtggcggt agcgcactag tgctgcagtg tatcaaggtt   1440
aacaactggg atttattctt cagcccgagt gaagacaact tcaccaacga cctgaacaaa   1500
ggtgaagaaa tcacctcaga tactaacatc gaagcagccg aagaaaacat ctcgctggac   1560
ctgatccagc agtactacct gacctttaat ttcgacaacg agccggaaaa catttctatc   1620
gaaaacctga gctctgatat catcggccag ctggaactga tgccgaacat cgaacgtttc   1680
ccaaacggta aaaagtacga gctggacaaa tataccatgt tccactacct gcgcgcgcag   1740
gaatttgaac acggcaaatc ccgtatcgca ctgactaact ccgttaacga agctctgctc   1800
aacccgtccc gtgtatacac cttcttctct agcgactacg tgaaaaaggt caacaaagcg   1860
actgaagctg caatgttctt gggttgggtt gaacagcttg tttatgattt taccgacgag   1920
acgtccgaag tatctactac cgacaaaatt gcggatatca ctatcatcat cccgtacatc   1980
ggtccggctc tgaacattgg caacatgctg tacaaagacg acttcgttgg cgcactgatc   2040
ttctccggtg cggtgatcct gctggagttc atcccggaaa tcgccatccc ggtactgggc   2100
acctttgctc tggtttctta cattgcaaac aaggttctga ctgtacaaac catcgacaac   2160
gcgctgagca aacgtaacga aaaatgggat gaagtttaca aatatatcgt gaccaactgg   2220
ctggctaagg ttaatactca gatcgacctc atccgcaaaa aaatgaaaga agcactggaa   2280
```

```
aaccaggcgg aagctaccaa ggcaatcatt aactaccagt acaaccagta caccgaggaa   2340

gaaaaaaaca acatcaactt caacatcgac gatctgtcct ctaaactgaa cgaatccatc   2400

aacaaagcta tgatcaacat caacaagttc ctgaaccagt gctctgtaag ctatctgatg   2460

aactccatga tcccgtacgg tgttaaacgt ctggaggact tcgatgcgtc tctgaaagac   2520

gccctgctga aatacattta cgacaaccgt ggcactctga tcggtcaggt tgatcgtctg   2580

aaggacaaag tgaacaatac cttatcgacc gacatccctt ttcagctcag taaatatgtc   2640

gataaccaac gccttttgtc cactctagac tag                                2673
```

<210> SEQ ID NO 48
<211> LENGTH: 890
<212> TYPE: PRT
<213> ORGANISM: Artificial Sequence
<220> FEATURE:
<223> OTHER INFORMATION: Synthetic

<400> SEQUENCE: 48

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
```

```
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Tyr Gly Gly Phe Met Ala Leu Ala Gly Gly Gly Gly Ser Gly Gly Gly
    450                 455                 460

Gly Ser Gly Gly Gly Gly Ser Ala Leu Val Leu Gln Cys Ile Lys Val
465                 470                 475                 480

Asn Asn Trp Asp Leu Phe Phe Ser Pro Ser Glu Asp Asn Phe Thr Asn
                485                 490                 495

Asp Leu Asn Lys Gly Glu Glu Ile Thr Ser Asp Thr Asn Ile Glu Ala
            500                 505                 510

Ala Glu Glu Asn Ile Ser Leu Asp Leu Ile Gln Gln Tyr Tyr Leu Thr
        515                 520                 525

Phe Asn Phe Asp Asn Glu Pro Glu Asn Ile Ser Ile Glu Asn Leu Ser
    530                 535                 540

Ser Asp Ile Ile Gly Gln Leu Glu Leu Met Pro Asn Ile Glu Arg Phe
545                 550                 555                 560

Pro Asn Gly Lys Lys Tyr Glu Leu Asp Lys Tyr Thr Met Phe His Tyr
                565                 570                 575

Leu Arg Ala Gln Glu Phe Glu His Gly Lys Ser Arg Ile Ala Leu Thr
            580                 585                 590

Asn Ser Val Asn Glu Ala Leu Leu Asn Pro Ser Arg Val Tyr Thr Phe
        595                 600                 605

Phe Ser Ser Asp Tyr Val Lys Lys Val Asn Lys Ala Thr Glu Ala Ala
    610                 615                 620

Met Phe Leu Gly Trp Val Glu Gln Leu Val Tyr Asp Phe Thr Asp Glu
625                 630                 635                 640

Thr Ser Glu Val Ser Thr Thr Asp Lys Ile Ala Asp Ile Thr Ile Ile
                645                 650                 655

Ile Pro Tyr Ile Gly Pro Ala Leu Asn Ile Gly Asn Met Leu Tyr Lys
            660                 665                 670

Asp Asp Phe Val Gly Ala Leu Ile Phe Ser Gly Ala Val Ile Leu Leu
        675                 680                 685

Glu Phe Ile Pro Glu Ile Ala Ile Pro Val Leu Gly Thr Phe Ala Leu
    690                 695                 700

Val Ser Tyr Ile Ala Asn Lys Val Leu Thr Val Gln Thr Ile Asp Asn
705                 710                 715                 720
```

```
Ala Leu Ser Lys Arg Asn Glu Lys Trp Asp Glu Val Tyr Lys Tyr Ile
                725                 730                 735

Val Thr Asn Trp Leu Ala Lys Val Asn Thr Gln Ile Asp Leu Ile Arg
            740                 745                 750

Lys Lys Met Lys Glu Ala Leu Glu Asn Gln Ala Glu Ala Thr Lys Ala
        755                 760                 765

Ile Ile Asn Tyr Gln Tyr Asn Gln Tyr Thr Glu Glu Glu Lys Asn Asn
    770                 775                 780

Ile Asn Phe Asn Ile Asp Asp Leu Ser Ser Lys Leu Asn Glu Ser Ile
785                 790                 795                 800

Asn Lys Ala Met Ile Asn Ile Asn Lys Phe Leu Asn Gln Cys Ser Val
                805                 810                 815

Ser Tyr Leu Met Asn Ser Met Ile Pro Tyr Gly Val Lys Arg Leu Glu
            820                 825                 830

Asp Phe Asp Ala Ser Leu Lys Asp Ala Leu Leu Lys Tyr Ile Tyr Asp
        835                 840                 845

Asn Arg Gly Thr Leu Ile Gly Gln Val Asp Arg Leu Lys Asp Lys Val
    850                 855                 860

Asn Asn Thr Leu Ser Thr Asp Ile Pro Phe Gln Leu Ser Lys Tyr Val
865                 870                 875                 880

Asp Asn Gln Arg Leu Leu Ser Thr Leu Asp
                885                 890
```

```
<210> SEQ ID NO 49
<211> LENGTH: 2751
<212> TYPE: DNA
<213> ORGANISM: Artificial Sequence
<220> FEATURE:
<223> OTHER INFORMATION: Synthetic

<400> SEQUENCE: 49

ggatccatgg agttcgttaa caaacagttc aactataaag acccagttaa cggtgttgac      60

attgcttaca tcaaaatccc gaacgctggc cagatgcagc cggtaaaggc attcaaaatc     120

cacaacaaaa tctgggttat cccggaacgt gataccttta ctaacccgga agaaggtgac     180

ctgaacccgc caccggaagc gaaacaggtg ccggtatctt actatgactc cacctacctg     240

tctaccgata acgaaaagga caactacctg aaaggtgtta ctaaactgtt cgagcgtatt     300

tactccaccg acctgggccg tatgctgctg actagcatcg ttcgcggtat cccgttctgg     360

ggcggttcta ccatcgatac cgaactgaaa gtaatcgaca ctaactgcat caacgttatt     420

cagccggacg gttcctatcg ttccgaagaa ctgaacctgg tgatcatcgg cccgtctgct     480

gatatcatcc agttcgagtg taagagcttt ggtcacgaag ttctgaacct cacccgtaac     540

ggctacggtt ccactcagta catccgtttc tctccggact tcaccttcgg ttttgaagaa     600

tccctggaag tagacacgaa cccactgctg ggcgctggta aattcgcaac tgatcctgcg     660

gttaccctgg ctcacgaact gattcatgca ggccaccgcc tgtacggtat cgccatcaat     720

ccgaaccgtg tcttcaaagt taacaccaac gcgtattacg agatgtccgg tctggaagtt     780

agcttcgaag aactgcgtac ttttggcggt cacgacgcta aattcatcga ctctctgcaa     840

gaaaacgagt tccgtctgta ctactataac aagttcaaag atatcgcatc caccctgaac     900

aaagcgaaat ccatcgtggg taccactgct tctctccagt acatgaagaa cgtttttaaa     960

gaaaaatacc tgctcagcga agacacctcc ggcaaattct ctgtagacaa gttgaaattc    1020

gataaacttt acaaaatgct gactgaaatt tacaccgaag acaacttcgt taagttcttt    1080

aaagttctga accgcaaaac ctatctgaac ttcgacaagg cagtattcaa aatcaacatc    1140
```

```
gtgccgaaag ttaactacac tatctacgat ggtttcaacc tgcgtaacac caacctggct   1200

gctaatttta acggccagaa cacggaaatc aacaacatga acttcacaaa actgaaaaac   1260

ttcactggtc tgttcgagtt ttacaagctg ctgtgcgtcg acggcatcat tacctccaaa   1320

actaaatctc tgatcgaagg tcgttacggt ggtttcatga cctctgaaaa atctcagacc   1380

ccgctggtta ccctgttcaa aaacgctatc atcaaaaacg cttacaaaaa aggtgaagcg   1440

ctagcgggtg gtggtggttc tggtggtggt ggttctggtg gtggtggttc tgcactagtg   1500

ctgcagtgta tcaaggttaa caactgggat ttattcttca gcccgagtga agacaacttc   1560

accaacgacc tgaacaaagg tgaagaaatc acctcagata ctaacatcga agcagccgaa   1620

gaaaacatct cgctggacct gatccagcag tactacctga cctttaattt cgacaacgag   1680

ccggaaaaca tttctatcga aaacctgagc tctgatatca tcggccagct ggaactgatg   1740

ccgaacatcg aacgtttccc aaacggtaaa aagtacgagc tggacaaata taccatgttc   1800

cactacctgc gcgcgcagga atttgaacac ggcaaatccc gtatcgcact gactaactcc   1860

gttaacgaag ctctgctcaa cccgtcccgt gtatacacct tcttctctag cgactacgtg   1920

aaaaaggtca acaaagcgac tgaagctgca atgttcttgg gttgggttga acagcttgtt   1980

tatgatttta ccgacgagac gtccgaagta tctactaccg acaaaattgc ggatatcact   2040

atcatcatcc cgtacatcgg tccggctctg aacattggca acatgctgta caaagacgac   2100

ttcgttggcg cactgatctt ctccggtgcg gtgatcctgc tggagttcat cccggaaatc   2160

gccatcccgg tactgggcac ctttgctctg gtttcttaca ttgcaaacaa ggttctgact   2220

gtacaaacca tcgacaacgc gctgagcaaa cgtaacgaaa aatgggatga agtttacaaa   2280

tatatcgtga ccaactggct ggctaaggtt aatactcaga tcgacctcat ccgcaaaaaa   2340

atgaaagaag cactggaaaa ccaggcggaa gctaccaagg caatcattaa ctaccagtac   2400

aaccagtaca ccgaggaaga aaaaaacaac atcaacttca acatcgacga tctgtcctct   2460

aaactgaacg aatccatcaa caaagctatg atcaacatca acaagttcct gaaccagtgc   2520

tctgtaagct atctgatgaa ctccatgatc ccgtacggtg ttaaacgtct ggaggacttc   2580

gatgcgtctc tgaaagacgc cctgctgaaa tacatttacg acaaccgtgg cactctgatc   2640

ggtcaggttg atcgtctgaa ggacaaagtg aacaatacct tatcgaccga catccctttt   2700

cagctcagta aatatgtcga taaccaacgc cttttgtcca ctctagacta g            2751
```

<210> SEQ ID NO 50
<211> LENGTH: 916
<212> TYPE: PRT
<213> ORGANISM: Artificial Sequence
<220> FEATURE:
<223> OTHER INFORMATION: Synthetic

<400> SEQUENCE: 50

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80
```

```
Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Tyr Gly Gly Phe Met Thr Ser Glu Lys Ser Gln Thr Pro Leu Val Thr
    450                 455                 460

Leu Phe Lys Asn Ala Ile Ile Lys Asn Ala Tyr Lys Lys Gly Glu Ala
465                 470                 475                 480

Leu Ala Gly Gly Gly Gly Ser Gly Gly Gly Gly Ser Gly Gly Gly Gly
                485                 490                 495

Ser Ala Leu Val Leu Gln Cys Ile Lys Val Asn Asn Trp Asp Leu Phe
            500                 505                 510
```

```
Phe Ser Pro Ser Glu Asp Asn Phe Thr Asn Asp Leu Asn Lys Gly Glu
        515                 520                 525

Glu Ile Thr Ser Asp Thr Asn Ile Glu Ala Ala Glu Glu Asn Ile Ser
    530                 535                 540

Leu Asp Leu Ile Gln Gln Tyr Tyr Leu Thr Phe Asn Phe Asp Asn Glu
545                 550                 555                 560

Pro Glu Asn Ile Ser Ile Glu Asn Leu Ser Ser Asp Ile Ile Gly Gln
                565                 570                 575

Leu Glu Leu Met Pro Asn Ile Glu Arg Phe Pro Asn Gly Lys Lys Tyr
            580                 585                 590

Glu Leu Asp Lys Tyr Thr Met Phe His Tyr Leu Arg Ala Gln Glu Phe
        595                 600                 605

Glu His Gly Lys Ser Arg Ile Ala Leu Thr Asn Ser Val Asn Glu Ala
    610                 615                 620

Leu Leu Asn Pro Ser Arg Val Tyr Thr Phe Phe Ser Ser Asp Tyr Val
625                 630                 635                 640

Lys Lys Val Asn Lys Ala Thr Glu Ala Ala Met Phe Leu Gly Trp Val
                645                 650                 655

Glu Gln Leu Val Tyr Asp Phe Thr Asp Glu Thr Ser Glu Val Ser Thr
            660                 665                 670

Thr Asp Lys Ile Ala Asp Ile Thr Ile Ile Ile Pro Tyr Ile Gly Pro
        675                 680                 685

Ala Leu Asn Ile Gly Asn Met Leu Tyr Lys Asp Asp Phe Val Gly Ala
    690                 695                 700

Leu Ile Phe Ser Gly Ala Val Ile Leu Leu Glu Phe Ile Pro Glu Ile
705                 710                 715                 720

Ala Ile Pro Val Leu Gly Thr Phe Ala Leu Val Ser Tyr Ile Ala Asn
                725                 730                 735

Lys Val Leu Thr Val Gln Thr Ile Asp Asn Ala Leu Ser Lys Arg Asn
            740                 745                 750

Glu Lys Trp Asp Glu Val Tyr Lys Tyr Ile Val Thr Asn Trp Leu Ala
        755                 760                 765

Lys Val Asn Thr Gln Ile Asp Leu Ile Arg Lys Lys Met Lys Glu Ala
    770                 775                 780

Leu Glu Asn Gln Ala Glu Ala Thr Lys Ala Ile Ile Asn Tyr Gln Tyr
785                 790                 795                 800

Asn Gln Tyr Thr Glu Glu Glu Lys Asn Asn Ile Asn Phe Asn Ile Asp
                805                 810                 815

Asp Leu Ser Ser Lys Leu Asn Glu Ser Ile Asn Lys Ala Met Ile Asn
            820                 825                 830

Ile Asn Lys Phe Leu Asn Gln Cys Ser Val Ser Tyr Leu Met Asn Ser
        835                 840                 845

Met Ile Pro Tyr Gly Val Lys Arg Leu Glu Asp Phe Asp Ala Ser Leu
    850                 855                 860

Lys Asp Ala Leu Leu Lys Tyr Ile Tyr Asp Asn Arg Gly Thr Leu Ile
865                 870                 875                 880

Gly Gln Val Asp Arg Leu Lys Asp Lys Val Asn Asn Thr Leu Ser Thr
                885                 890                 895

Asp Ile Pro Phe Gln Leu Ser Lys Tyr Val Asp Asn Gln Arg Leu Leu
            900                 905                 910

Ser Thr Leu Asp
        915
```

<210> SEQ ID NO 51
<211> LENGTH: 2709
<212> TYPE: DNA
<213> ORGANISM: Artificial Sequence
<220> FEATURE:
<223> OTHER INFORMATION: Synthetic

<400> SEQUENCE: 51

```
ggatccatgg agttcgttaa caaacagttc aactataaag acccagttaa cggtgttgac     60

attgcttaca tcaaaatccc gaacgctggc cagatgcagc cggtaaaggc attcaaaatc    120

cacaacaaaa tctgggttat cccggaacgt gataccttta ctaacccgga agaaggtgac    180

ctgaacccgc caccggaagc gaaacaggtg ccggtatctt actatgactc cacctacctg    240

tctaccgata acgaaaagga caactacctg aaaggtgtta ctaaactgtt cgagcgtatt    300

tactccaccg acctgggccg tatgctgctg actagcatcg ttcgcggtat cccgttctgg    360

ggcggttcta ccatcgatac cgaactgaaa gtaatcgaca ctaactgcat caacgttatt    420

cagccggacg gttcctatcg ttccgaagaa ctgaacctgg tgatcatcgg cccgtctgct    480

gatatcatcc agttcgagtg taagagcttt ggtcacgaag ttctgaacct cacccgtaac    540

ggctacggtt ccactcagta catccgtttc tctccggact tcaccttcgg ttttgaagaa    600

tccctggaag tagacacgaa cccactgctg ggcgctggta aattcgcaac tgatcctgcg    660

gttaccctgg ctcacgaact gattcatgca ggccaccgcc tgtacggtat cgccatcaat    720

ccgaaccgtg tcttcaaagt taacaccaac gcgtattacg agatgtccgg tctggaagtt    780

agcttcgaag aactgcgtac ttttggcggt cacgacgcta aattcatcga ctctctgcaa    840

gaaaacgagt tccgtctgta ctactataac aagttcaaag atatcgcatc caccctgaac    900

aaagcgaaat ccatcgtggg taccactgct tctctccagt acatgaagaa cgtttttaaa    960

gaaaaatacc tgctcagcga agacacctcc ggcaaattct ctgtagacaa gttgaaattc   1020

gataaacttt acaaaatgct gactgaaatt tacaccgaag acaacttcgt taagttcttt   1080

aaagttctga accgcaaaac ctatctgaac ttcgacaagg cagtattcaa aatcaacatc   1140

gtgccgaaag ttaactacac tatctacgat ggtttcaacc tgcgtaacac caacctggct   1200

gctaatttta acggccagaa cacggaaatc aacaacatga acttcacaaa actgaaaaac   1260

ttcactggtc tgttcgagtt ttacaagctg ctgtgcgtcg acggcatcat tacctccaaa   1320

actaaatctc tgatagaagg tagatttggc ggtttcacgg gcgcacgcaa atcagcgcgt   1380

aaacgtaaga accaggcgct agcgggcggt ggcggtagcg gcggtggcgg tagcggcggt   1440

ggcggtagcg cactagtgct gcagtgtatc aaggttaaca actgggattt attcttcagc   1500

ccgagtgaag acaacttcac caacgacctg aacaaaggtg aagaaatcac ctcagatact   1560

aacatcgaag cagccgaaga aaacatctcg ctggacctga tccagcagta ctacctgacc   1620

tttaatttcg acaacgagcc ggaaaacatt tctatcgaaa acctgagctc tgatatcatc   1680

ggccagctgg aactgatgcc gaacatcgaa cgtttcccaa acggtaaaaa gtacgagctg   1740

gacaaatata ccatgttcca ctacctgcgc gcgcaggaat ttgaacacgg caaatcccgt   1800

atcgcactga ctaactccgt taacgaagct ctgctcaacc cgtcccgtgt atacaccttc   1860

ttctctagcg actacgtgaa aaaggtcaac aaagcgactg aagctgcaat gttcttgggt   1920

tgggttgaac agcttgttta tgattttacc gacgagacgt ccgaagtatc tactaccgac   1980

aaaattgcgg atatcactat catcatcccg tacatcggtc cggctctgaa cattggcaac   2040

atgctgtaca aagacgactt cgttggcgca ctgatcttct ccggtgcggt gatcctgctg   2100

gagttcatcc cggaaatcgc catcccggta ctgggcacct ttgctctggt ttcttacatt   2160
```

```
gcaaacaagg ttctgactgt acaaaccatc gacaacgcgc tgagcaaacg taacgaaaaa   2220

tgggatgaag tttacaaata tatcgtgacc aactggctgg ctaaggttaa tactcagatc   2280

gacctcatcc gcaaaaaaat gaaagaagca ctggaaaacc aggcggaagc taccaaggca   2340

atcattaact accagtacaa ccagtacacc gaggaagaaa aaaacaacat caacttcaac   2400

atcgacgatc tgtcctctaa actgaacgaa tccatcaaca aagctatgat caacatcaac   2460

aagttcctga accagtgctc tgtaagctat ctgatgaact ccatgatccc gtacggtgtt   2520

aaacgtctgg aggacttcga tgcgtctctg aaagacgccc tgctgaaata catttacgac   2580

aaccgtggca ctctgatcgg tcaggttgat cgtctgaagg acaaagtgaa caatacctta   2640

tcgaccgaca tccctttca gctcagtaaa tatgtcgata accaacgcct tttgtccact   2700

ctagactag                                                           2709
```

<210> SEQ ID NO 52
<211> LENGTH: 902
<212> TYPE: PRT
<213> ORGANISM: Artificial Sequence
<220> FEATURE:
<223> OTHER INFORMATION: Synthetic

<400> SEQUENCE: 52

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
```

```
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Arg Lys Arg Lys Asn
    450                 455                 460

Gln Ala Leu Ala Gly Gly Gly Gly Ser Gly Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
            500                 505                 510

Gly Glu Glu Ile Thr Ser Asp Thr Asn Ile Glu Ala Ala Glu Glu Asn
        515                 520                 525

Ile Ser Leu Asp Leu Ile Gln Gln Tyr Tyr Leu Thr Phe Asn Phe Asp
    530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
            580                 585                 590

Glu Phe Glu His Gly Lys Ser Arg Ile Ala Leu Thr Asn Ser Val Asn
        595                 600                 605

Glu Ala Leu Leu Asn Pro Ser Arg Val Tyr Thr Phe Phe Ser Ser Asp
    610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Ile Pro Tyr Ile
            660                 665                 670

Gly Pro Ala Leu Asn Ile Gly Asn Met Leu Tyr Lys Asp Asp Phe Val
        675                 680                 685
```

```
Gly Ala Leu Ile Phe Ser Gly Ala Val Ile Leu Leu Glu Phe Ile Pro
    690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
                725                 730                 735

Arg Asn Glu Lys Trp Asp Glu Val Tyr Lys Tyr Ile Val Thr Asn Trp
            740                 745                 750

Leu Ala Lys Val Asn Thr Gln Ile Asp Leu Ile Arg Lys Lys Met Lys
        755                 760                 765

Glu Ala Leu Glu Asn Gln Ala Glu Ala Thr Lys Ala Ile Ile Asn Tyr
    770                 775                 780

Gln Tyr Asn Gln Tyr Thr Glu Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
        835                 840                 845

Ser Leu Lys Asp Ala Leu Leu Lys Tyr Ile Tyr Asp Asn Arg Gly Thr
    850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Asp
            900


<210> SEQ ID NO 53
<211> LENGTH: 2691
<212> TYPE: DNA
<213> ORGANISM: Artificial Sequence
<220> FEATURE:
<223> OTHER INFORMATION: Synthetic

<400> SEQUENCE: 53

ggatccatgg agttcgttaa caaacagttc aactataaag acccagttaa cggtgttgac      60

attgcttaca tcaaaatccc gaacgctggc cagatgcagc cggtaaaggc attcaaaatc     120

cacaacaaaa tctgggttat cccggaacgt gataccttta ctaacccgga agaaggtgac     180

ctgaacccgc caccggaagc gaaacaggtg ccggtatctt actatgactc cacctacctg     240

tctaccgata acgaaaagga caactacctg aaaggtgtta ctaaactgtt cgagcgtatt     300

tactccaccg acctgggccg tatgctgctg actagcatcg ttcgcggtat cccgttctgg     360

ggcggttcta ccatcgatac cgaactgaaa gtaatcgaca ctaactgcat caacgttatt     420

cagccggacg gttcctatcg ttccgaagaa ctgaacctgg tgatcatcgg cccgtctgct     480

gatatcatcc agttcgagtg taagagcttt ggtcacgaag ttctgaacct cacccgtaac     540

ggctacggtt ccactcagta catccgtttc tctccggact tcaccttcgg ttttgaagaa     600

tccctggaag tagacacgaa cccactgctg ggcgctggta aattcgcaac tgatcctgcg     660

gttaccctgg ctcacgaact gattcatgca ggccaccgcc tgtacggtat cgccatcaat     720

ccgaaccgtg tcttcaaagt taacaccaac gcgtattacg agatgtccgg tctggaagtt     780

agcttcgaag aactgcgtac ttttggcggt cacgacgcta aattcatcga ctctctgcaa     840
```

```
gaaaacgagt tccgtctgta ctactataac aagttcaaag atatcgcatc caccctgaac    900
aaagcgaaat ccatcgtggg taccactgct tctctccagt acatgaagaa cgtttttaaa    960
gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa aatcaacatc   1140
gtgccgaaag ttaactacac tatctacgat ggtttcaacc tgcgtaacac caacctggct   1200
gctaatttta acggccagaa cacggaaatc aacaacatga acttcacaaa actgaaaaac   1260
ttcactggtc tgttcgagtt ttacaagctg ctgtgcgtcg acggcatcat tacctccaaa   1320
actaaatctc tgatagaagg tagatttggc ggtttcacgg gcgcacgcaa atcagcggcg   1380
ctagcgggcg gtggcggtag cggcggtggc ggtagcggcg gtggcggtag cgcactagtg   1440
ctgcagtgta tcaaggttaa caactgggat ttattcttca gcccgagtga agacaacttc   1500
accaacgacc tgaacaaagg tgaagaaatc acctcagata ctaacatcga agcagccgaa   1560
gaaaacatct cgctggacct gatccagcag tactacctga cctttaattt cgacaacgag   1620
ccggaaaaca tttctatcga aaacctgagc tctgatatca tcggccagct ggaactgatg   1680
ccgaacatcg aacgtttccc aaacggtaaa aagtacgagc tggacaaata taccatgttc   1740
cactacctgc gcgcgcagga atttgaacac ggcaaatccc gtatcgcact gactaactcc   1800
gttaacgaag ctctgctcaa cccgtcccgt gtatacacct tcttctctag cgactacgtg   1860
aaaaaggtca acaaagcgac tgaagctgca atgttcttgg gttgggttga acagcttgtt   1920
tatgatttta ccgacgagac gtccgaagta tctactaccg acaaaattgc ggatatcact   1980
atcatcatcc cgtacatcgg tccggctctg aacattggca acatgctgta caaagacgac   2040
ttcgttggcg cactgatctt ctccggtgcg gtgatcctgc tggagttcat cccggaaatc   2100
gccatcccgg tactgggcac ctttgctctg gtttcttaca ttgcaaacaa ggttctgact   2160
gtacaaacca tcgacaacgc gctgagcaaa cgtaacgaaa aatgggatga agtttacaaa   2220
tatatcgtga ccaactggct ggctaaggtt aatactcaga tcgacctcat ccgcaaaaaa   2280
atgaaagaag cactggaaaa ccaggcggaa gctaccaagg caatcattaa ctaccagtac   2340
aaccagtaca ccgaggaaga aaaaaacaac atcaacttca acatcgacga tctgtcctct   2400
aaactgaacg aatccatcaa caaagctatg atcaacatca acaagttcct gaaccagtgc   2460
tctgtaagct atctgatgaa ctccatgatc ccgtacggtg ttaaacgtct ggaggacttc   2520
gatgcgtctc tgaaagacgc cctgctgaaa tacatttacg acaaccgtgg cactctgatc   2580
ggtcaggttg atcgtctgaa ggacaaagtg aacaatacct tatcgaccga catccctttt   2640
cagctcagta aatatgtcga taaccaacgc cttttgtcca ctctagacta g            2691
```

```
<210> SEQ ID NO 54
<211> LENGTH: 896
<212> TYPE: PRT
<213> ORGANISM: Artificial Sequence
<220> FEATURE:
<223> OTHER INFORMATION: Synthetic

<400> SEQUENCE: 54

Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45
```

-continued

```
Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Ala Leu Ala Gly Gly
    450                 455                 460

Gly Gly Ser Gly Gly Gly Gly Ser Gly Gly Gly Gly Ser Ala Leu Val
```

```
465                 470                 475                 480

Leu Gln Cys Ile Lys Val Asn Asn Trp Asp Leu Phe Phe Ser Pro Ser
                485                 490                 495

Glu Asp Asn Phe Thr Asn Asp Leu Asn Lys Gly Glu Glu Ile Thr Ser
            500                 505                 510

Asp Thr Asn Ile Glu Ala Ala Glu Glu Asn Ile Ser Leu Asp Leu Ile
        515                 520                 525

Gln Gln Tyr Tyr Leu Thr Phe Asn Phe Asp Asn Glu Pro Glu Asn Ile
    530                 535                 540

Ser Ile Glu Asn Leu Ser Ser Asp Ile Ile Gly Gln Leu Glu Leu Met
545                 550                 555                 560

Pro Asn Ile Glu Arg Phe Pro Asn Gly Lys Lys Tyr Glu Leu Asp Lys
                565                 570                 575

Tyr Thr Met Phe His Tyr Leu Arg Ala Gln Glu Phe Glu His Gly Lys
            580                 585                 590

Ser Arg Ile Ala Leu Thr Asn Ser Val Asn Glu Ala Leu Leu Asn Pro
        595                 600                 605

Ser Arg Val Tyr Thr Phe Phe Ser Ser Asp Tyr Val Lys Lys Val Asn
    610                 615                 620

Lys Ala Thr Glu Ala Ala Met Phe Leu Gly Trp Val Glu Gln Leu Val
625                 630                 635                 640

Tyr Asp Phe Thr Asp Glu Thr Ser Glu Val Ser Thr Thr Asp Lys Ile
                645                 650                 655

Ala Asp Ile Thr Ile Ile Ile Pro Tyr Ile Gly Pro Ala Leu Asn Ile
            660                 665                 670

Gly Asn Met Leu Tyr Lys Asp Asp Phe Val Gly Ala Leu Ile Phe Ser
        675                 680                 685

Gly Ala Val Ile Leu Leu Glu Phe Ile Pro Glu Ile Ala Ile Pro Val
    690                 695                 700

Leu Gly Thr Phe Ala Leu Val Ser Tyr Ile Ala Asn Lys Val Leu Thr
705                 710                 715                 720

Val Gln Thr Ile Asp Asn Ala Leu Ser Lys Arg Asn Glu Lys Trp Asp
                725                 730                 735

Glu Val Tyr Lys Tyr Ile Val Thr Asn Trp Leu Ala Lys Val Asn Thr
            740                 745                 750

Gln Ile Asp Leu Ile Arg Lys Lys Met Lys Glu Ala Leu Glu Asn Gln
        755                 760                 765

Ala Glu Ala Thr Lys Ala Ile Ile Asn Tyr Gln Tyr Asn Gln Tyr Thr
    770                 775                 780

Glu Glu Glu Lys Asn Asn Ile Asn Phe Asn Ile Asp Asp Leu Ser Ser
785                 790                 795                 800

Lys Leu Asn Glu Ser Ile Asn Lys Ala Met Ile Asn Ile Asn Lys Phe
                805                 810                 815

Leu Asn Gln Cys Ser Val Ser Tyr Leu Met Asn Ser Met Ile Pro Tyr
            820                 825                 830

Gly Val Lys Arg Leu Glu Asp Phe Asp Ala Ser Leu Lys Asp Ala Leu
        835                 840                 845

Leu Lys Tyr Ile Tyr Asp Asn Arg Gly Thr Leu Ile Gly Gln Val Asp
    850                 855                 860

Arg Leu Lys Asp Lys Val Asn Asn Thr Leu Ser Thr Asp Ile Pro Phe
865                 870                 875                 880

Gln Leu Ser Lys Tyr Val Asp Asn Gln Arg Leu Leu Ser Thr Leu Asp
                885                 890                 895
```

<210> SEQ ID NO 55
<211> LENGTH: 2691
<212> TYPE: DNA
<213> ORGANISM: Artificial Sequence
<220> FEATURE:
<223> OTHER INFORMATION: Synthetic

<400> SEQUENCE: 55

```
ggatccatgg agttcgttaa caaacagttc aactataaag acccagttaa cggtgttgac     60

attgcttaca tcaaaatccc gaacgctggc cagatgcagc cggtaaaggc attcaaaatc    120

cacaacaaaa tctgggttat cccggaacgt gataccttta ctaacccgga agaaggtgac    180

ctgaacccgc caccggaagc gaaacaggtg ccggtatctt actatgactc cacctacctg    240

tctaccgata acgaaaagga caactacctg aaaggtgtta ctaaactgtt cgagcgtatt    300

tactccaccg acctgggccg tatgctgctg actagcatcg ttcgcggtat cccgttctgg    360

ggcggttcta ccatcgatac cgaactgaaa gtaatcgaca ctaactgcat caacgttatt    420

cagccggacg gttcctatcg ttccgaagaa ctgaacctgg tgatcatcgg cccgtctgct    480

gatatcatcc agttcgagtg taagagcttt ggtcacgaag ttctgaacct cacccgtaac    540

ggctacggtt ccactcagta catccgtttc tctccggact tcaccttcgg ttttgaagaa    600

tccctggaag tagacacgaa cccactgctg ggcgctggta aattcgcaac tgatcctgcg    660

gttaccctgg ctcacgaact gattcatgca ggccaccgcc tgtacggtat cgccatcaat    720

ccgaaccgtg tcttcaaagt taacaccaac gcgtattacg agatgtccgg tctggaagtt    780

agcttcgaag aactgcgtac ttttggcggt cacgacgcta aattcatcga ctctctgcaa    840

gaaaacgagt tccgtctgta ctactataac aagttcaaag atatcgcatc caccctgaac    900

aaagcgaaat ccatcgtggg taccactgct tctctccagt acatgaagaa cgtttttaaa    960

gaaaaatacc tgctcagcga agacacctcc ggcaaattct ctgtagacaa gttgaaattc   1020

gataaacttt acaaaatgct gactgaaatt tacaccgaag acaacttcgt taagttcttt   1080

aaagttctga accgcaaaac ctatctgaac ttcgacaagg cagtattcaa aatcaacatc   1140

gtgccgaaag ttaactacac tatctacgat ggtttcaacc tgcgtaacac caacctggct   1200

gctaatttta acggccagaa cacggaaatc aacaacatga acttcacaaa actgaaaaac   1260

ttcactggtc tgttcgagtt ttacaagctg ctgtgcgtcg acggcatcat tacctccaaa   1320

actaaatctc tgatagaagg tagatttggc ggtttcacgg gcgcacgcaa atatgcggcg   1380

ctagcgggcg gtggcggtag cggcggtggc ggtagcggcg gtggcggtag cgcactagtg   1440

ctgcagtgta tcaaggttaa caactgggat ttattcttca gcccgagtga agacaacttc   1500

accaacgacc tgaacaaagg tgaagaaatc acctcagata ctaacatcga agcagccgaa   1560

gaaaacatct cgctggacct gatccagcag tactacctga cctttaattt cgacaacgag   1620

ccggaaaaca tttctatcga aaacctgagc tctgatatca tcggccagct ggaactgatg   1680

ccgaacatcg aacgtttccc aaacggtaaa aagtacgagc tggacaaata taccatgttc   1740

cactacctgc gcgcgcagga atttgaacac ggcaaatccc gtatcgcact gactaactcc   1800

gttaacgaag ctctgctcaa cccgtcccgt gtatacacct tcttctctag cgactacgtg   1860

aaaaaggtca acaaagcgac tgaagctgca atgttcttgg gttgggttga acagcttgtt   1920

tatgatttta ccgacgagac gtccgaagta tctactaccg acaaaattgc ggatatcact   1980

atcatcatcc cgtacatcgg tccggctctg aacattggca acatgctgta caaagacgac   2040

ttcgttggcg cactgatctt ctccggtgcg gtgatcctgc tggagttcat cccggaaatc   2100
```

```
gccatcccgg tactgggcac ctttgctctg gtttcttaca ttgcaaacaa ggttctgact   2160

gtacaaacca tcgacaacgc gctgagcaaa cgtaacgaaa aatgggatga agtttacaaa   2220

tatatcgtga ccaactggct ggctaaggtt aatactcaga tcgacctcat ccgcaaaaaa   2280

atgaaagaag cactggaaaa ccaggcggaa gctaccaagg caatcattaa ctaccagtac   2340

aaccagtaca ccgaggaaga aaaaaacaac atcaacttca acatcgacga tctgtcctct   2400

aaactgaacg aatccatcaa caaagctatg atcaacatca acaagttcct gaaccagtgc   2460

tctgtaagct atctgatgaa ctccatgatc ccgtacggtg ttaaacgtct ggaggacttc   2520

gatgcgtctc tgaaagacgc cctgctgaaa tacatttacg acaaccgtgg cactctgatc   2580

ggtcaggttg atcgtctgaa ggacaaagtg aacaatacct tatcgaccga catccctttt   2640

cagctcagta aatatgtcga taaccaacgc cttttgtcca ctctagacta g           2691
```

<210> SEQ ID NO 56
<211> LENGTH: 896
<212> TYPE: PRT
<213> ORGANISM: Artificial Sequence
<220> FEATURE:
<223> OTHER INFORMATION: Synthetic

<400> SEQUENCE: 56

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270
```

```
Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Tyr Ala Ala Leu Ala Gly Gly
    450                 455                 460

Gly Gly Ser Gly Gly Gly Gly Ser Gly Gly Gly Gly Ser Ala Leu Val
465                 470                 475                 480

Leu Gln Cys Ile Lys Val Asn Asn Trp Asp Leu Phe Phe Ser Pro Ser
                485                 490                 495

Glu Asp Asn Phe Thr Asn Asp Leu Asn Lys Gly Glu Glu Ile Thr Ser
            500                 505                 510

Asp Thr Asn Ile Glu Ala Ala Glu Glu Asn Ile Ser Leu Asp Leu Ile
        515                 520                 525

Gln Gln Tyr Tyr Leu Thr Phe Asn Phe Asp Asn Glu Pro Glu Asn Ile
    530                 535                 540

Ser Ile Glu Asn Leu Ser Ser Asp Ile Ile Gly Gln Leu Glu Leu Met
545                 550                 555                 560

Pro Asn Ile Glu Arg Phe Pro Asn Gly Lys Lys Tyr Glu Leu Asp Lys
                565                 570                 575

Tyr Thr Met Phe His Tyr Leu Arg Ala Gln Glu Phe Glu His Gly Lys
            580                 585                 590

Ser Arg Ile Ala Leu Thr Asn Ser Val Asn Glu Ala Leu Leu Asn Pro
        595                 600                 605

Ser Arg Val Tyr Thr Phe Phe Ser Ser Asp Tyr Val Lys Lys Val Asn
    610                 615                 620

Lys Ala Thr Glu Ala Ala Met Phe Leu Gly Trp Val Glu Gln Leu Val
625                 630                 635                 640

Tyr Asp Phe Thr Asp Glu Thr Ser Glu Val Ser Thr Thr Asp Lys Ile
                645                 650                 655

Ala Asp Ile Thr Ile Ile Ile Pro Tyr Ile Gly Pro Ala Leu Asn Ile
            660                 665                 670

Gly Asn Met Leu Tyr Lys Asp Asp Phe Val Gly Ala Leu Ile Phe Ser
        675                 680                 685

Gly Ala Val Ile Leu Leu Glu Phe Ile Pro Glu Ile Ala Ile Pro Val
```

```
    690                 695                 700

Leu Gly Thr Phe Ala Leu Val Ser Tyr Ile Ala Asn Lys Val Leu Thr
705                 710                 715                 720

Val Gln Thr Ile Asp Asn Ala Leu Ser Lys Arg Asn Glu Lys Trp Asp
                725                 730                 735

Glu Val Tyr Lys Tyr Ile Val Thr Asn Trp Leu Ala Lys Val Asn Thr
            740                 745                 750

Gln Ile Asp Leu Ile Arg Lys Lys Met Lys Glu Ala Leu Glu Asn Gln
        755                 760                 765

Ala Glu Ala Thr Lys Ala Ile Ile Asn Tyr Gln Tyr Asn Gln Tyr Thr
    770                 775                 780

Glu Glu Glu Lys Asn Asn Ile Asn Phe Asn Ile Asp Asp Leu Ser Ser
785                 790                 795                 800

Lys Leu Asn Glu Ser Ile Asn Lys Ala Met Ile Asn Ile Asn Lys Phe
                805                 810                 815

Leu Asn Gln Cys Ser Val Ser Tyr Leu Met Asn Ser Met Ile Pro Tyr
            820                 825                 830

Gly Val Lys Arg Leu Glu Asp Phe Asp Ala Ser Leu Lys Asp Ala Leu
        835                 840                 845

Leu Lys Tyr Ile Tyr Asp Asn Arg Gly Thr Leu Ile Gly Gln Val Asp
    850                 855                 860

Arg Leu Lys Asp Lys Val Asn Asn Thr Leu Ser Thr Asp Ile Pro Phe
865                 870                 875                 880

Gln Leu Ser Lys Tyr Val Asp Asn Gln Arg Leu Leu Ser Thr Leu Asp
                885                 890                 895


<210> SEQ ID NO 57
<211> LENGTH: 2691
<212> TYPE: DNA
<213> ORGANISM: Artificial Sequence
<220> FEATURE:
<223> OTHER INFORMATION: Synthetic

<400> SEQUENCE: 57

ggatccatgg agttcgttaa caaacagttc aactataaag acccagttaa cggtgttgac      60

attgcttaca tcaaaatccc gaacgctggc cagatgcagc cggtaaaggc attcaaaatc     120

cacaacaaaa tctgggttat cccggaacgt gataccttta ctaacccgga agaaggtgac     180

ctgaacccgc caccggaagc gaaacaggtg ccggtatctt actatgactc cacctacctg     240

tctaccgata acgaaaagga caactacctg aaaggtgtta ctaaactgtt cgagcgtatt     300

tactccaccg acctgggccg tatgctgctg actagcatcg ttcgcggtat cccgttctgg     360

ggcggttcta ccatcgatac cgaactgaaa gtaatcgaca ctaactgcat caacgttatt     420

cagccggacg gttcctatcg ttccgaagaa ctgaacctgg tgatcatcgg cccgtctgct     480

gatatcatcc agttcgagtg taagagcttt ggtcacgaag ttctgaacct cacccgtaac     540

ggctacggtt ccactcagta catccgtttc tctccggact tcaccttcgg ttttgaagaa     600

tccctggaag tagacacgaa cccactgctg ggcgctggta aattcgcaac tgatcctgcg     660

gttaccctgg ctcacgaact gattcatgca ggccaccgcc tgtacggtat cgccatcaat     720

ccgaaccgtg tcttcaaagt taacaccaac gcgtattacg agatgtccgg tctggaagtt     780

agcttcgaag aactgcgtac ttttggcggt cacgacgcta aattcatcga ctctctgcaa     840

gaaaacgagt tccgtctgta ctactataac aagttcaaag atatcgcatc caccctgaac     900

aaagcgaaat ccatcgtggg taccactgct tctctccagt acatgaagaa cgtttttaaa     960
```

-continued gaaaaatacc tgctcagcga agacacctcc ggcaaattct ctgtagacaa gttgaaattc 1020
gataaacttt acaaaatgct gactgaaatt tacaccgaag acaacttcgt taagttcttt 1080
aaagttctga accgcaaaac ctatctgaac ttcgacaagg cagtattcaa aatcaacatc 1140
gtgccgaaag ttaactacac tatctacgat ggtttcaacc tgcgtaacac caacctggct 1200
gctaatttta acggccagaa cacggaaatc aacaacatga acttcacaaa actgaaaaac 1260
ttcactggtc tgttcgagtt ttacaagctg ctgtgcgtcg acggcatcat tacctccaaa 1320
actaaatctc tgatagaagg tagatttggc ggtttcacgg gcgcacgcaa atcatatgcg 1380
ctagcgggcg gtggcggtag cggcggtggc ggtagcggcg gtggcggtag cgcactagtg 1440
ctgcagtgta tcaaggttaa caactgggat ttattcttca gcccgagtga agacaacttc 1500
accaacgacc tgaacaaagg tgaagaaatc acctcagata ctaacatcga agcagccgaa 1560
gaaaacatct cgctggacct gatccagcag tactacctga cctttaattt cgacaacgag 1620
ccggaaaaca tttctatcga aaacctgagc tctgatatca tcggccagct ggaactgatg 1680
ccgaacatcg aacgtttccc aaacggtaaa aagtacgagc tggacaaata taccatgttc 1740
cactacctgc gcgcgcagga atttgaacac ggcaaatccc gtatcgcact gactaactcc 1800
gttaacgaag ctctgctcaa cccgtcccgt gtatacacct tcttctctag cgactacgtg 1860
aaaaaggtca acaaagcgac tgaagctgca atgttcttgg gttgggttga acagcttgtt 1920
tatgatttta ccgacgagac gtccgaagta tctactaccg acaaaattgc ggatatcact 1980
atcatcatcc cgtacatcgg tccggctctg aacattggca acatgctgta caaagacgac 2040
ttcgttggcg cactgatctt ctccggtgcg gtgatcctgc tggagttcat cccggaaatc 2100
gccatcccgg tactgggcac ctttgctctg gtttcttaca ttgcaaacaa ggttctgact 2160
gtacaaacca tcgacaacgc gctgagcaaa cgtaacgaaa aatgggatga agtttacaaa 2220
tatatcgtga ccaactggct ggctaaggtt aatactcaga tcgacctcat ccgcaaaaaa 2280
atgaaagaag cactggaaaa ccaggcggaa gctaccaagg caatcattaa ctaccagtac 2340
aaccagtaca ccgaggaaga aaaaaacaac atcaacttca acatcgacga tctgtcctct 2400
aaactgaacg aatccatcaa caaagctatg atcaacatca acaagttcct gaaccagtgc 2460
tctgtaagct atctgatgaa ctccatgatc ccgtacggtg ttaaacgtct ggaggacttc 2520
gatgcgtctc tgaaagacgc cctgctgaaa tacatttacg acaaccgtgg cactctgatc 2580
ggtcaggttg atcgtctgaa ggacaaagtg aacaatacct tatcgaccga catccctttt 2640
cagctcagta aatatgtcga taaccaacgc cttttgtcca ctctagacta g 2691

<210> SEQ ID NO 58
<211> LENGTH: 896
<212> TYPE: PRT
<213> ORGANISM: Artificial Sequence
<220> FEATURE:
<223> OTHER INFORMATION: Synthetic

<400> SEQUENCE: 58

Gly Ser Met Glu Phe Val Asn Lys Gln Phe Asn Tyr Lys Asp Pro Val
1 5 10 15

Asn Gly Val Asp Ile Ala Tyr Ile Lys Ile Pro Asn Ala Gly Gln Met
20 25 30

Gln Pro Val Lys Ala Phe Lys Ile His Asn Lys Ile Trp Val Ile Pro
35 40 45

Glu Arg Asp Thr Phe Thr Asn Pro Glu Glu Gly Asp Leu Asn Pro Pro
50 55 60

-continued

```
Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Tyr Ala Leu Ala Gly Gly
    450                 455                 460

Gly Gly Ser Gly Gly Gly Gly Ser Gly Gly Gly Gly Ser Ala Leu Val
465                 470                 475                 480

Leu Gln Cys Ile Lys Val Asn Asn Trp Asp Leu Phe Phe Ser Pro Ser
                485                 490                 495
```

```
Glu Asp Asn Phe Thr Asn Asp Leu Asn Lys Gly Glu Glu Ile Thr Ser
            500                 505                 510

Asp Thr Asn Ile Glu Ala Ala Glu Glu Asn Ile Ser Leu Asp Leu Ile
        515                 520                 525

Gln Gln Tyr Tyr Leu Thr Phe Asn Phe Asp Asn Glu Pro Glu Asn Ile
    530                 535                 540

Ser Ile Glu Asn Leu Ser Ser Asp Ile Ile Gly Gln Leu Glu Leu Met
545                 550                 555                 560

Pro Asn Ile Glu Arg Phe Pro Asn Gly Lys Lys Tyr Glu Leu Asp Lys
                565                 570                 575

Tyr Thr Met Phe His Tyr Leu Arg Ala Gln Glu Phe Glu His Gly Lys
            580                 585                 590

Ser Arg Ile Ala Leu Thr Asn Ser Val Asn Glu Ala Leu Leu Asn Pro
        595                 600                 605

Ser Arg Val Tyr Thr Phe Phe Ser Ser Asp Tyr Val Lys Lys Val Asn
    610                 615                 620

Lys Ala Thr Glu Ala Ala Met Phe Leu Gly Trp Val Glu Gln Leu Val
625                 630                 635                 640

Tyr Asp Phe Thr Asp Glu Thr Ser Glu Val Ser Thr Thr Asp Lys Ile
                645                 650                 655

Ala Asp Ile Thr Ile Ile Ile Pro Tyr Ile Gly Pro Ala Leu Asn Ile
            660                 665                 670

Gly Asn Met Leu Tyr Lys Asp Asp Phe Val Gly Ala Leu Ile Phe Ser
        675                 680                 685

Gly Ala Val Ile Leu Leu Glu Phe Ile Pro Glu Ile Ala Ile Pro Val
    690                 695                 700

Leu Gly Thr Phe Ala Leu Val Ser Tyr Ile Ala Asn Lys Val Leu Thr
705                 710                 715                 720

Val Gln Thr Ile Asp Asn Ala Leu Ser Lys Arg Asn Glu Lys Trp Asp
                725                 730                 735

Glu Val Tyr Lys Tyr Ile Val Thr Asn Trp Leu Ala Lys Val Asn Thr
            740                 745                 750

Gln Ile Asp Leu Ile Arg Lys Lys Met Lys Glu Ala Leu Glu Asn Gln
        755                 760                 765

Ala Glu Ala Thr Lys Ala Ile Ile Asn Tyr Gln Tyr Asn Gln Tyr Thr
    770                 775                 780

Glu Glu Glu Lys Asn Asn Ile Asn Phe Asn Ile Asp Asp Leu Ser Ser
785                 790                 795                 800

Lys Leu Asn Glu Ser Ile Asn Lys Ala Met Ile Asn Ile Asn Lys Phe
                805                 810                 815

Leu Asn Gln Cys Ser Val Ser Tyr Leu Met Asn Ser Met Ile Pro Tyr
            820                 825                 830

Gly Val Lys Arg Leu Glu Asp Phe Asp Ala Ser Leu Lys Asp Ala Leu
        835                 840                 845

Leu Lys Tyr Ile Tyr Asp Asn Arg Gly Thr Leu Ile Gly Gln Val Asp
    850                 855                 860

Arg Leu Lys Asp Lys Val Asn Asn Thr Leu Ser Thr Asp Ile Pro Phe
865                 870                 875                 880

Gln Leu Ser Lys Tyr Val Asp Asn Gln Arg Leu Leu Ser Thr Leu Asp
                885                 890                 895
```

<210> SEQ ID NO 59
<211> LENGTH: 2709
<212> TYPE: DNA

<213> ORGANISM: Artificial Sequence
<220> FEATURE:
<223> OTHER INFORMATION: Synthetic

<400> SEQUENCE: 59
ggatccatgg agttcgttaa caaacagttc aactataaag acccagttaa cggtgttgac 60
attgcttaca tcaaaatccc gaacgctggc cagatgcagc cggtaaaggc attcaaaatc 120
cacaacaaaa tctgggttat cccggaacgt gataccttta ctaacccgga agaaggtgac 180
ctgaacccgc caccggaagc gaaacaggtg ccggtatctt actatgactc cacctacctg 240
tctaccgata acgaaaagga caactacctg aaaggtgtta ctaaactgtt cgagcgtatt 300
tactccaccg acctgggccg tatgctgctg actagcatcg ttcgcggtat cccgttctgg 360
ggcggttcta ccatcgatac cgaactgaaa gtaatcgaca ctaactgcat caacgttatt 420
cagccggacg gttcctatcg ttccgaagaa ctgaacctgg tgatcatcgg cccgtctgct 480
gatatcatcc agttcgagtg taagagcttt ggtcacgaag ttctgaacct cacccgtaac 540
ggctacggtt ccactcagta catccgtttc tctccggact tcaccttcgg ttttgaagaa 600
tccctggaag tagacacgaa cccactgctg ggcgctggta aattcgcaac tgatcctgcg 660
gttaccctgg ctcacgaact gattcatgca ggccaccgcc tgtacggtat cgccatcaat 720
ccgaaccgtg tcttcaaagt taacaccaac gcgtattacg agatgtccgg tctggaagtt 780
agcttcgaag aactgcgtac ttttggcggt cacgacgcta aattcatcga ctctctgcaa 840
gaaaacgagt tccgtctgta ctactataac aagttcaaag atatcgcatc caccctgaac 900
aaagcgaaat ccatcgtggg taccactgct tctctccagt acatgaagaa cgtttttaaa 960
gaaaaatacc tgctcagcga agacacctcc ggcaaattct ctgtagacaa gttgaaattc 1020
gataaacttt acaaaatgct gactgaaatt tacaccgaag acaacttcgt taagttcttt 1080
aaagttctga accgcaaaac ctatctgaac ttcgacaagg cagtattcaa aatcaacatc 1140
gtgccgaaag ttaactacac tatctacgat ggtttcaacc tgcgtaacac caacctggct 1200
gctaatttta acggccagaa cacggaaatc aacaacatga acttcacaaa actgaaaaac 1260
ttcactggtc tgttcgagtt ttacaagctg ctgtgcgtcg acggcatcat tacctccaaa 1320
actaaatctc tgatagaagg tagatttggc ggtttcacgg gcgcacgcaa atcagcgcgt 1380
aaatatgcta accaggcgct agcgggcggt ggcggtagcg gcggtggcgg tagcggcggt 1440
ggcggtagcg cactagtgct gcagtgtatc aaggttaaca actgggattt attcttcagc 1500
ccgagtgaag acaacttcac caacgacctg aacaaaggtg aagaaatcac ctcagatact 1560
aacatcgaag cagccgaaga aaacatctcg ctggacctga tccagcagta ctacctgacc 1620
tttaatttcg acaacgagcc ggaaaacatt tctatcgaaa acctgagctc tgatatcatc 1680
ggccagctgg aactgatgcc gaacatcgaa cgtttcccaa acggtaaaaa gtacgagctg 1740
gacaaatata ccatgttcca ctacctgcgc gcgcaggaat ttgaacacgg caaatcccgt 1800
atcgcactga ctaactccgt taacgaagct ctgctcaacc cgtcccgtgt atacaccttc 1860
ttctctagcg actacgtgaa aaaggtcaac aaagcgactg aagctgcaat gttcttgggt 1920
tgggttgaac agcttgttta tgattttacc gacgagacgt ccgaagtatc tactaccgac 1980
aaaattgcgg atatcactat catcatcccg tacatcggtc cggctctgaa cattggcaac 2040
atgctgtaca aagacgactt cgttggcgca ctgatcttct ccggtgcggt gatcctgctg 2100
gagttcatcc cggaaatcgc catcccggta ctgggcacct ttgctctggt ttcttacatt 2160
gcaaacaagg ttctgactgt acaaaccatc gacaacgcgc tgagcaaacg taacgaaaaa 2220

```
tgggatgaag tttacaaata tatcgtgacc aactggctgg ctaaggttaa tactcagatc   2280

gacctcatcc gcaaaaaaat gaaagaagca ctggaaaacc aggcggaagc taccaaggca   2340

atcattaact accagtacaa ccagtacacc gaggaagaaa aaaacaacat caacttcaac   2400

atcgacgatc tgtcctctaa actgaacgaa tccatcaaca aagctatgat caacatcaac   2460

aagttcctga accagtgctc tgtaagctat ctgatgaact ccatgatccc gtacggtgtt   2520

aaacgtctgg aggacttcga tgcgtctctg aaagacgccc tgctgaaata catttacgac   2580

aaccgtggca ctctgatcgg tcaggttgat cgtctgaagg acaaagtgaa caatacctta   2640

tcgaccgaca tccctttttca gctcagtaaa tatgtcgata accaacgcct tttgtccact   2700

ctagactag                                                           2709
```

```
<210> SEQ ID NO 60
<211> LENGTH: 902
<212> TYPE: PRT
<213> ORGANISM: Artificial Sequence
<220> FEATURE:
<223> OTHER INFORMATION: Synthetic

<400> SEQUENCE: 60

Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
```

-continued

```
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Arg Lys Tyr Ala Asn
    450                 455                 460

Gln Ala Leu Ala Gly Gly Gly Gly Ser Gly Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
            500                 505                 510

Gly Glu Glu Ile Thr Ser Asp Thr Asn Ile Glu Ala Ala Glu Glu Asn
        515                 520                 525

Ile Ser Leu Asp Leu Ile Gln Gln Tyr Tyr Leu Thr Phe Asn Phe Asp
    530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
            580                 585                 590

Glu Phe Glu His Gly Lys Ser Arg Ile Ala Leu Thr Asn Ser Val Asn
        595                 600                 605

Glu Ala Leu Leu Asn Pro Ser Arg Val Tyr Thr Phe Phe Ser Ser Asp
    610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Ile Pro Tyr Ile
            660                 665                 670

Gly Pro Ala Leu Asn Ile Gly Asn Met Leu Tyr Lys Asp Asp Phe Val
        675                 680                 685

Gly Ala Leu Ile Phe Ser Gly Ala Val Ile Leu Leu Glu Phe Ile Pro
    690                 695                 700
```

-continued

```
Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
                725                 730                 735

Arg Asn Glu Lys Trp Asp Glu Val Tyr Lys Tyr Ile Val Thr Asn Trp
            740                 745                 750

Leu Ala Lys Val Asn Thr Gln Ile Asp Leu Ile Arg Lys Lys Met Lys
        755                 760                 765

Glu Ala Leu Glu Asn Gln Ala Glu Ala Thr Lys Ala Ile Ile Asn Tyr
    770                 775                 780

Gln Tyr Asn Gln Tyr Thr Glu Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
        835                 840                 845

Ser Leu Lys Asp Ala Leu Leu Lys Tyr Ile Tyr Asp Asn Arg Gly Thr
    850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Asp
            900
```

<210> SEQ ID NO 61
<211> LENGTH: 2697
<212> TYPE: DNA
<213> ORGANISM: Artificial Sequence
<220> FEATURE:
<223> OTHER INFORMATION: Synthetic

<400> SEQUENCE: 61

```
ggatccatgg agttcgttaa caaacagttc aactataaag acccagttaa cggtgttgac      60

attgcttaca tcaaaatccc gaacgctggc cagatgcagc cggtaaaggc attcaaaatc     120

cacaacaaaa tctgggttat cccggaacgt gataccttta ctaacccgga agaaggtgac     180

ctgaacccgc caccggaagc gaaacaggtg ccggtatctt actatgactc cacctacctg     240

tctaccgata acgaaaagga caactacctg aaaggtgtta ctaaactgtt cgagcgtatt     300

tactccaccg acctgggccg tatgctgctg actagcatcg ttcgcggtat cccgttctgg     360

ggcggttcta ccatcgatac cgaactgaaa gtaatcgaca ctaactgcat caacgttatt     420

cagccggacg gttcctatcg ttccgaagaa ctgaacctgg tgatcatcgg cccgtctgct     480

gatatcatcc agttcgagtg taagagcttt ggtcacgaag ttctgaacct cacccgtaac     540

ggctacggtt ccactcagta catccgtttc tctccggact tcaccttcgg ttttgaagaa     600

tccctggaag tagacacgaa cccactgctg ggcgctggta aattcgcaac tgatcctgcg     660

gttaccctgg ctcacgaact gattcatgca ggccaccgcc tgtacggtat cgccatcaat     720

ccgaaccgtg tcttcaaagt taacaccaac gcgtattacg agatgtccgg tctggaagtt     780

agcttcgaag aactgcgtac ttttggcggt cacgacgcta aattcatcga ctctctgcaa     840

gaaaacgagt tccgtctgta ctactataac aagttcaaag atatcgcatc caccctgaac     900

aaagcgaaat ccatcgtggg taccactgct tctctccagt acatgaagaa cgtttttaaa     960
```

-continued

```
gaaaaatacc tgctcagcga agacacctcc ggcaaattct ctgtagacaa gttgaaattc   1020

gataaacttt acaaaatgct gactgaaatt tacaccgaag acaacttcgt taagttcttt   1080

aaagttctga accgcaaaac ctatctgaac ttcgacaagg cagtattcaa aatcaacatc   1140

gtgccgaaag ttaactacac tatctacgat ggtttcaacc tgcgtaacac caacctggct   1200

gctaatttta acggccagaa cacggaaatc aacaacatga acttcacaaa actgaaaaac   1260

ttcactggtc tgttcgagtt ttacaagctg ctgtgcgtcg acggcatcat tacctccaaa   1320

actaaatctc tgatagaagg tagatttggc ggtttcacgg gcgcacgcaa atcagcgcgt   1380

aaagcgctag cgggcggtgg cggtagcggc ggtggcggta gcggcggtgg cggtagcgca   1440

ctagtgctgc agtgtatcaa ggttaacaac tgggatttat tcttcagccc gagtgaagac   1500

aacttcacca acgacctgaa caaaggtgaa gaaatcacct cagatactaa catcgaagca   1560

gccgaagaaa acatctcgct ggacctgatc cagcagtact acctgacctt taatttcgac   1620

aacgagccgg aaaacatttc tatcgaaaac ctgagctctg atatcatcgg ccagctggaa   1680

ctgatgccga acatcgaacg tttcccaaac ggtaaaaagt acgagctgga caaatatacc   1740

atgttccact acctgcgcgc gcaggaattt gaacacggca aatcccgtat cgcactgact   1800

aactccgtta acgaagctct gctcaacccg tcccgtgtat acaccttctt ctctagcgac   1860

tacgtgaaaa aggtcaacaa agcgactgaa gctgcaatgt tcttgggttg ggttgaacag   1920

cttgtttatg attttaccga cgagacgtcc gaagtatcta ctaccgacaa aattgcggat   1980

atcactatca tcatcccgta catcggtccg gctctgaaca ttggcaacat gctgtacaaa   2040

gacgacttcg ttggcgcact gatcttctcc ggtgcggtga tcctgctgga gttcatcccg   2100

gaaatcgcca tcccggtact gggcaccttt gctctggttt cttacattgc aaacaaggtt   2160

ctgactgtac aaaccatcga caacgcgctg agcaaacgta acgaaaaatg ggatgaagtt   2220

tacaaatata tcgtgaccaa ctggctggct aaggttaata ctcagatcga cctcatccgc   2280

aaaaaaatga aagaagcact ggaaaaccag gcggaagcta ccaaggcaat cattaactac   2340

cagtacaacc agtacaccga ggaagaaaaa aacaacatca acttcaacat cgacgatctg   2400

tcctctaaac tgaacgaatc catcaacaaa gctatgatca acatcaacaa gttcctgaac   2460

cagtgctctg taagctatct gatgaactcc atgatcccgt acggtgttaa acgtctggag   2520

gacttcgatg cgtctctgaa agacgccctg ctgaaataca tttacgacaa ccgtggcact   2580

ctgatcggtc aggttgatcg tctgaaggac aaagtgaaca ataccttatc gaccgacatc   2640

ccttttcagc tcagtaaata tgtcgataac caacgccttt tgtccactct agactag      2697
```

<210> SEQ ID NO 62
<211> LENGTH: 898
<212> TYPE: PRT
<213> ORGANISM: Artificial Sequence
<220> FEATURE:
<223> OTHER INFORMATION: Synthetic

<400> SEQUENCE: 62

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60
```

-continued

```
Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Arg Lys Ala Leu Ala
    450                 455                 460

Gly Gly Gly Gly Ser Gly Gly Gly Gly Ser Gly Gly Gly Gly Ser Ala
465                 470                 475                 480

Leu Val Leu Gln Cys Ile Lys Val Asn Asn Trp Asp Leu Phe Phe Ser
```

-continued

```
                485                 490                 495

Pro Ser Glu Asp Asn Phe Thr Asn Asp Leu Asn Lys Gly Glu Glu Ile
            500                 505                 510

Thr Ser Asp Thr Asn Ile Glu Ala Ala Glu Glu Asn Ile Ser Leu Asp
        515                 520                 525

Leu Ile Gln Gln Tyr Tyr Leu Thr Phe Asn Phe Asp Asn Glu Pro Glu
    530                 535                 540

Asn Ile Ser Ile Glu Asn Leu Ser Ser Asp Ile Ile Gly Gln Leu Glu
545                 550                 555                 560

Leu Met Pro Asn Ile Glu Arg Phe Pro Asn Gly Lys Lys Tyr Glu Leu
                565                 570                 575

Asp Lys Tyr Thr Met Phe His Tyr Leu Arg Ala Gln Glu Phe Glu His
            580                 585                 590

Gly Lys Ser Arg Ile Ala Leu Thr Asn Ser Val Asn Glu Ala Leu Leu
        595                 600                 605

Asn Pro Ser Arg Val Tyr Thr Phe Phe Ser Ser Asp Tyr Val Lys Lys
    610                 615                 620

Val Asn Lys Ala Thr Glu Ala Ala Met Phe Leu Gly Trp Val Glu Gln
625                 630                 635                 640

Leu Val Tyr Asp Phe Thr Asp Glu Thr Ser Glu Val Ser Thr Thr Asp
                645                 650                 655

Lys Ile Ala Asp Ile Thr Ile Ile Ile Pro Tyr Ile Gly Pro Ala Leu
            660                 665                 670

Asn Ile Gly Asn Met Leu Tyr Lys Asp Asp Phe Val Gly Ala Leu Ile
        675                 680                 685

Phe Ser Gly Ala Val Ile Leu Leu Glu Phe Ile Pro Glu Ile Ala Ile
    690                 695                 700

Pro Val Leu Gly Thr Phe Ala Leu Val Ser Tyr Ile Ala Asn Lys Val
705                 710                 715                 720

Leu Thr Val Gln Thr Ile Asp Asn Ala Leu Ser Lys Arg Asn Glu Lys
                725                 730                 735

Trp Asp Glu Val Tyr Lys Tyr Ile Val Thr Asn Trp Leu Ala Lys Val
            740                 745                 750

Asn Thr Gln Ile Asp Leu Ile Arg Lys Lys Met Lys Glu Ala Leu Glu
        755                 760                 765

Asn Gln Ala Glu Ala Thr Lys Ala Ile Ile Asn Tyr Gln Tyr Asn Gln
    770                 775                 780

Tyr Thr Glu Glu Glu Lys Asn Asn Ile Asn Phe Asn Ile Asp Asp Leu
785                 790                 795                 800

Ser Ser Lys Leu Asn Glu Ser Ile Asn Lys Ala Met Ile Asn Ile Asn
                805                 810                 815

Lys Phe Leu Asn Gln Cys Ser Val Ser Tyr Leu Met Asn Ser Met Ile
            820                 825                 830

Pro Tyr Gly Val Lys Arg Leu Glu Asp Phe Asp Ala Ser Leu Lys Asp
        835                 840                 845

Ala Leu Leu Lys Tyr Ile Tyr Asp Asn Arg Gly Thr Leu Ile Gly Gln
    850                 855                 860

Val Asp Arg Leu Lys Asp Lys Val Asn Asn Thr Leu Ser Thr Asp Ile
865                 870                 875                 880

Pro Phe Gln Leu Ser Lys Tyr Val Asp Asn Gln Arg Leu Leu Ser Thr
                885                 890                 895

Leu Asp
```

<210> SEQ ID NO 63
<211> LENGTH: 2736
<212> TYPE: DNA
<213> ORGANISM: Artificial Sequence
<220> FEATURE:
<223> OTHER INFORMATION: Synthetic

<400> SEQUENCE: 63

```
ctcgggattg agggtcgttt tggcggtttc acgggcgcac gcaaatcagc gcgtaaatta     60
gctaaccaga ctagtggcgg tgggggtagt ggcggtggcg gttcgggcgg gggtgggagc    120
cctaggggat ccatggagtt cgttaacaaa cagttcaact ataaagaccc agttaacggt    180
gttgacattg cttacatcaa aatcccgaac gctggccaga tgcagccggt aaaggcattc    240
aaaatccaca acaaaatctg ggttatcccg gaacgtgata cctttactaa cccggaagaa    300
ggtgacctga acccgccacc ggaagcgaaa caggtgccgg tatcttacta tgactccacc    360
tacctgtcta ccgataacga aaaggacaac tacctgaaag gtgttactaa actgttcgag    420
cgtatttact ccaccgacct gggccgtatg ctgctgacta gcatcgttcg cggtatcccg    480
ttctggggcg gttctaccat cgataccgaa ctgaaagtaa tcgacactaa ctgcatcaac    540
gttattcagc cggacggttc ctatcgttcc gaagaactga acctggtgat catcggcccg    600
tctgctgata tcatccagtt cgagtgtaag agctttggtc acgaagttct gaacctcacc    660
cgtaacggct acggttccac tcagtacatc cgtttctctc cggacttcac cttcggtttt    720
gaagaatccc tggaagtaga cacgaaccca ctgctgggcg ctggtaaatt cgcaactgat    780
cctgcggtta ccctggctca cgaactgatt catgcaggcc accgcctgta cggtatcgcc    840
atcaatccga accgtgtctt caaagttaac accaacgcgt attacgagat gtccggtctg    900
gaagttagct tcgaagaact gcgtactttt ggcggtcacg acgctaaatt catcgactct    960
ctgcaagaaa acgagttccg tctgtactac tataacaagt tcaaagatat cgcatccacc   1020
ctgaacaaag cgaaatccat cgtgggtacc actgcttctc tccagtacat gaagaacgtt   1080
tttaaagaaa aatacctgct cagcgaagac acctccggca aattctctgt agacaagttg   1140
aaattcgata aactttacaa aatgctgact gaaatttaca ccgaagacaa cttcgttaag   1200
ttctttaaag ttctgaaccg caaaacctat ctgaacttcg acaaggcagt attcaaaatc   1260
aacatcgtgc cgaaagttaa ctacactatc tacgatggtt tcaacctgcg taacaccaac   1320
ctggctgcta attttaacgg ccagaacacg gaaatcaaca acatgaactt cacaaaactg   1380
aaaaacttca ctggtctgtt cgagttttac aagctgctgt gcgtcgacgg catcattacc   1440
tccaaaacta aatctctgat agaaggtaga aacaaagcgc tgaacctgca gtgtatcaag   1500
gttaacaact gggatttatt cttcagcccg agtgaagaca acttcaccaa cgacctgaac   1560
aaaggtgaag aaatcacctc agatactaac atcgaagcag ccgaagaaaa catctcgctg   1620
gacctgatcc agcagtacta cctgaccttt aatttcgaca acgagccgga aaacatttct   1680
atcgaaaacc tgagctctga tatcatcggc cagctggaac tgatgccgaa catcgaacgt   1740
ttcccaaacg gtaaaaagta cgagctggac aaatatacca tgttccacta cctgcgcgcg   1800
caggaatttg aacacggcaa atcccgtatc gcactgacta actccgttaa cgaagctctg   1860
ctcaacccgt cccgtgtata caccttcttc tctagcgact acgtgaaaaa ggtcaacaaa   1920
gcgactgaag ctgcaatgtt cttgggttgg gttgaacagc ttgtttatga ttttaccgac   1980
gagacgtccg aagtatctac taccgacaaa attgcggata tcactatcat catcccgtac   2040
atcggtccgg ctctgaacat tggcaacatg ctgtacaaag acgacttcgt tggcgcactg   2100
atcttctccg gtgcggtgat cctgctggag ttcatcccgg aaatcgccat cccggtactg   2160
```

```
ggcacctttg ctctggtttc ttacattgca aacaaggttc tgactgtaca aaccatcgac   2220

aacgcgctga gcaaacgtaa cgaaaaatgg gatgaagttt acaaatatat cgtgaccaac   2280

tggctggcta aggttaatac tcagatcgac ctcatccgca aaaaaatgaa agaagcactg   2340

gaaaaccagg cggaagctac caaggcaatc attaactacc agtacaacca gtacaccgag   2400

gaagaaaaaa acaacatcaa cttcaacatc gacgatctgt cctctaaact gaacgaatcc   2460

atcaacaaag ctatgatcaa catcaacaag ttcctgaacc agtgctctgt aagctatctg   2520

atgaactcca tgatcccgta cggtgttaaa cgtctggagg acttcgatgc gtctctgaaa   2580

gacgccctgc tgaaatacat ttacgacaac cgtggcactc tgatcggtca ggttgatcgt   2640

ctgaaggaca aagtgaacaa taccttatcg accgacatcc cttttcagct cagtaaatat   2700

gtcgataacc aacgcctttt gtccactcta gactag                             2736
```

<210> SEQ ID NO 64
<211> LENGTH: 911
<212> TYPE: PRT
<213> ORGANISM: Artificial Sequence
<220> FEATURE:
<223> OTHER INFORMATION: Synthetic

<400> SEQUENCE: 64

```
Leu Gly Ile Glu Gly Arg Phe Gly Gly Phe Thr Gly Ala Arg Lys Ser
1               5                   10                  15

Ala Arg Lys Leu Ala Asn Gln Thr Ser Gly Gly Gly Gly Ser Gly Gly
            20                  25                  30

Gly Gly Ser Gly Gly Gly Gly Ser Pro Arg Gly Ser Met Glu Phe Val
        35                  40                  45

Asn Lys Gln Phe Asn Tyr Lys Asp Pro Val Asn Gly Val Asp Ile Ala
    50                  55                  60

Tyr Ile Lys Ile Pro Asn Ala Gly Gln Met Gln Pro Val Lys Ala Phe
65                  70                  75                  80

Lys Ile His Asn Lys Ile Trp Val Ile Pro Glu Arg Asp Thr Phe Thr
                85                  90                  95

Asn Pro Glu Glu Gly Asp Leu Asn Pro Pro Pro Glu Ala Lys Gln Val
            100                 105                 110

Pro Val Ser Tyr Tyr Asp Ser Thr Tyr Leu Ser Thr Asp Asn Glu Lys
        115                 120                 125

Asp Asn Tyr Leu Lys Gly Val Thr Lys Leu Phe Glu Arg Ile Tyr Ser
    130                 135                 140

Thr Asp Leu Gly Arg Met Leu Leu Thr Ser Ile Val Arg Gly Ile Pro
145                 150                 155                 160

Phe Trp Gly Gly Ser Thr Ile Asp Thr Glu Leu Lys Val Ile Asp Thr
                165                 170                 175

Asn Cys Ile Asn Val Ile Gln Pro Asp Gly Ser Tyr Arg Ser Glu Glu
            180                 185                 190

Leu Asn Leu Val Ile Ile Gly Pro Ser Ala Asp Ile Ile Gln Phe Glu
        195                 200                 205

Cys Lys Ser Phe Gly His Glu Val Leu Asn Leu Thr Arg Asn Gly Tyr
    210                 215                 220

Gly Ser Thr Gln Tyr Ile Arg Phe Ser Pro Asp Phe Thr Phe Gly Phe
225                 230                 235                 240

Glu Glu Ser Leu Glu Val Asp Thr Asn Pro Leu Leu Gly Ala Gly Lys
                245                 250                 255

Phe Ala Thr Asp Pro Ala Val Thr Leu Ala His Glu Leu Ile His Ala
```

```
            260                 265                 270

Gly His Arg Leu Tyr Gly Ile Ala Ile Asn Pro Asn Arg Val Phe Lys
        275                 280                 285

Val Asn Thr Asn Ala Tyr Tyr Glu Met Ser Gly Leu Glu Val Ser Phe
    290                 295                 300

Glu Glu Leu Arg Thr Phe Gly Gly His Asp Ala Lys Phe Ile Asp Ser
305                 310                 315                 320

Leu Gln Glu Asn Glu Phe Arg Leu Tyr Tyr Tyr Asn Lys Phe Lys Asp
                325                 330                 335

Ile Ala Ser Thr Leu Asn Lys Ala Lys Ser Ile Val Gly Thr Thr Ala
            340                 345                 350

Ser Leu Gln Tyr Met Lys Asn Val Phe Lys Glu Lys Tyr Leu Leu Ser
        355                 360                 365

Glu Asp Thr Ser Gly Lys Phe Ser Val Asp Lys Leu Lys Phe Asp Lys
    370                 375                 380

Leu Tyr Lys Met Leu Thr Glu Ile Tyr Thr Glu Asp Asn Phe Val Lys
385                 390                 395                 400

Phe Phe Lys Val Leu Asn Arg Lys Thr Tyr Leu Asn Phe Asp Lys Ala
                405                 410                 415

Val Phe Lys Ile Asn Ile Val Pro Lys Val Asn Tyr Thr Ile Tyr Asp
            420                 425                 430

Gly Phe Asn Leu Arg Asn Thr Asn Leu Ala Ala Asn Phe Asn Gly Gln
        435                 440                 445

Asn Thr Glu Ile Asn Asn Met Asn Phe Thr Lys Leu Lys Asn Phe Thr
    450                 455                 460

Gly Leu Phe Glu Phe Tyr Lys Leu Leu Cys Val Asp Gly Ile Ile Thr
465                 470                 475                 480

Ser Lys Thr Lys Ser Leu Ile Glu Gly Arg Asn Lys Ala Leu Asn Leu
                485                 490                 495

Gln Cys Ile Lys Val Asn Asn Trp Asp Leu Phe Phe Ser Pro Ser Glu
            500                 505                 510

Asp Asn Phe Thr Asn Asp Leu Asn Lys Gly Glu Glu Ile Thr Ser Asp
        515                 520                 525

Thr Asn Ile Glu Ala Ala Glu Glu Asn Ile Ser Leu Asp Leu Ile Gln
    530                 535                 540

Gln Tyr Tyr Leu Thr Phe Asn Phe Asp Asn Glu Pro Glu Asn Ile Ser
545                 550                 555                 560

Ile Glu Asn Leu Ser Ser Asp Ile Ile Gly Gln Leu Glu Leu Met Pro
                565                 570                 575

Asn Ile Glu Arg Phe Pro Asn Gly Lys Lys Tyr Glu Leu Asp Lys Tyr
            580                 585                 590

Thr Met Phe His Tyr Leu Arg Ala Gln Glu Phe Glu His Gly Lys Ser
        595                 600                 605

Arg Ile Ala Leu Thr Asn Ser Val Asn Glu Ala Leu Leu Asn Pro Ser
    610                 615                 620

Arg Val Tyr Thr Phe Phe Ser Ser Asp Tyr Val Lys Lys Val Asn Lys
625                 630                 635                 640

Ala Thr Glu Ala Ala Met Phe Leu Gly Trp Val Glu Gln Leu Val Tyr
                645                 650                 655

Asp Phe Thr Asp Glu Thr Ser Glu Val Ser Thr Thr Asp Lys Ile Ala
            660                 665                 670

Asp Ile Thr Ile Ile Ile Pro Tyr Ile Gly Pro Ala Leu Asn Ile Gly
        675                 680                 685
```

```
Asn Met Leu Tyr Lys Asp Asp Phe Val Gly Ala Leu Ile Phe Ser Gly
    690                 695                 700

Ala Val Ile Leu Leu Glu Phe Ile Pro Glu Ile Ala Ile Pro Val Leu
705                 710                 715                 720

Gly Thr Phe Ala Leu Val Ser Tyr Ile Ala Asn Lys Val Leu Thr Val
                725                 730                 735

Gln Thr Ile Asp Asn Ala Leu Ser Lys Arg Asn Glu Lys Trp Asp Glu
            740                 745                 750

Val Tyr Lys Tyr Ile Val Thr Asn Trp Leu Ala Lys Val Asn Thr Gln
        755                 760                 765

Ile Asp Leu Ile Arg Lys Lys Met Lys Glu Ala Leu Glu Asn Gln Ala
    770                 775                 780

Glu Ala Thr Lys Ala Ile Ile Asn Tyr Gln Tyr Asn Gln Tyr Thr Glu
785                 790                 795                 800

Glu Glu Lys Asn Asn Ile Asn Phe Asn Ile Asp Asp Leu Ser Ser Lys
                805                 810                 815

Leu Asn Glu Ser Ile Asn Lys Ala Met Ile Asn Ile Asn Lys Phe Leu
            820                 825                 830

Asn Gln Cys Ser Val Ser Tyr Leu Met Asn Ser Met Ile Pro Tyr Gly
        835                 840                 845

Val Lys Arg Leu Glu Asp Phe Asp Ala Ser Leu Lys Asp Ala Leu Leu
    850                 855                 860

Lys Tyr Ile Tyr Asp Asn Arg Gly Thr Leu Ile Gly Gln Val Asp Arg
865                 870                 875                 880

Leu Lys Asp Lys Val Asn Asn Thr Leu Ser Thr Asp Ile Pro Phe Gln
                885                 890                 895

Leu Ser Lys Tyr Val Asp Asn Gln Arg Leu Leu Ser Thr Leu Asp
            900                 905                 910


<210> SEQ ID NO 65
<211> LENGTH: 177
<212> TYPE: DNA
<213> ORGANISM: Artificial Sequence
<220> FEATURE:
<223> OTHER INFORMATION: Synthetic

<400> SEQUENCE: 65

ggatccacgc acgtcgacgg catcattacc tccaaaacta aatctctgat agaaggtaga      60

tttggcggtt tcacgggcgc acgcaaatca gcgcgtaaat tagctaacca ggcgctagcg     120

ggtggtggtg gttctgcact agtgctgcag acgcacggtc tagaatgata aaagctt        177


<210> SEQ ID NO 66
<211> LENGTH: 192
<212> TYPE: DNA
<213> ORGANISM: Artificial Sequence
<220> FEATURE:
<223> OTHER INFORMATION: Synthetic

<400> SEQUENCE: 66

ggatccacgc acgtcgacgg catcattacc tccaaaacta aatctctgat agaaggtaga      60

tttggcggtt tcacgggcgc acgcaaatca gcgcgtaaat tagctaacca ggcgctagcg     120

ggtggtggtg gttctggtgg tggtggttct gcactagtgc tgcagacgca cggtctagaa     180

tgataaaagc tt                                                         192


<210> SEQ ID NO 67
<211> LENGTH: 222
<212> TYPE: DNA
```

<213> ORGANISM: Artificial Sequence
<220> FEATURE:
<223> OTHER INFORMATION: Synthetic

<400> SEQUENCE: 67
ggatccacgc acgtcgacgg catcattacc tccaaaacta aatctctgat agaaggtaga 60
tttggcggtt tcacgggcgc acgcaaatca gcgcgtaaat tagctaacca ggcgctagcg 120
ggtggtggtg gttctggtgg tggtggttct ggtggtggtg gttctggtgg tggtggttct 180
gcactagtgc tgcagacgca cggtctagaa tgataaaagc tt 222

<210> SEQ ID NO 68
<211> LENGTH: 237
<212> TYPE: DNA
<213> ORGANISM: Artificial Sequence
<220> FEATURE:
<223> OTHER INFORMATION: Synthetic

<400> SEQUENCE: 68
ggatccacgc acgtcgacgg catcattacc tccaaaacta aatctctgat agaaggtaga 60
tttggcggtt tcacgggcgc acgcaaatca gcgcgtaaat tagctaacca ggcgctagcg 120
ggtggtggtg gttctggtgg tggtggttct ggtggtggtg gttctggtgg tggtggttct 180
ggtggtggtg gttctgcact agtgctgcag acgcacggtc tagaatgata aaagctt 237

<210> SEQ ID NO 69
<211> LENGTH: 228
<212> TYPE: DNA
<213> ORGANISM: Artificial Sequence
<220> FEATURE:
<223> OTHER INFORMATION: Synthetic

<400> SEQUENCE: 69
ggatccacgc acgtcgacgg catcattacc tccaaaacta aatctctgat agaaggtaga 60
tttggcggtt tcacgggcgc acgcaaatca gcgcgtaaat tagctaacca ggcgctagcg 120
gctgaagctg ctgctaaaga agctgctgct aaagaagctg ctgctaaagc tggtggcggt 180
ggttccgcac tagtgctgca gacgcacggt ctagaatgat aaaagctt 228

<210> SEQ ID NO 70
<211> LENGTH: 2694
<212> TYPE: DNA
<213> ORGANISM: Artificial Sequence
<220> FEATURE:
<223> OTHER INFORMATION: Synthetic

<400> SEQUENCE: 70
ggatccatgg agttcgttaa caaacagttc aactataaag acccagttaa cggtgttgac 60
attgcttaca tcaaaatccc gaacgctggc cagatgcagc cggtaaaggc attcaaaatc 120
cacaacaaaa tctgggttat cccggaacgt gataccttta ctaacccgga agaaggtgac 180
ctgaacccgc caccggaagc gaaacaggtg ccggtatctt actatgactc cacctacctg 240
tctaccgata acgaaaagga caactacctg aaaggtgtta ctaaactgtt cgagcgtatt 300
tactccaccg acctgggccg tatgctgctg actagcatcg ttcgcggtat cccgttctgg 360
ggcggttcta ccatcgatac cgaactgaaa gtaatcgaca ctaactgcat caacgttatt 420
cagccggacg gttcctatcg ttccgaagaa ctgaacctgg tgatcatcgg cccgtctgct 480
gatatcatcc agttcgagtg taagagcttt ggtcacgaag ttctgaacct cacccgtaac 540
ggctacggtt ccactcagta catccgtttc tctccggact tcaccttcgg ttttgaagaa 600

-continued tccctggaag tagacacgaa cccactgctg ggcgctggta aattcgcaac tgatcctgcg 660
gttaccctgg ctcacgaact gattcatgca ggccaccgcc tgtacggtat cgccatcaat 720
ccgaaccgtg tcttcaaagt taacaccaac gcgtattacg agatgtccgg tctggaagtt 780
agcttcgaag aactgcgtac ttttggcggt cacgacgcta aattcatcga ctctctgcaa 840
gaaaacgagt tccgtctgta ctactataac aagttcaaag atatcgcatc caccctgaac 900
aaagcgaaat ccatcgtggg taccactgct tctctccagt acatgaagaa cgtttttaaa 960
gaaaaatacc tgctcagcga agacacctcc ggcaaattct ctgtagacaa gttgaaattc 1020
gataaacttt acaaaatgct gactgaaatt tacaccgaag acaacttcgt taagttcttt 1080
aaagttctga accgcaaaac ctatctgaac ttcgacaagg cagtattcaa aatcaacatc 1140
gtgccgaaag ttaactacac tatctacgat ggtttcaacc tgcgtaacac caacctggct 1200
gctaatttta acggccagaa cacggaaatc aacaacatga acttcacaaa actgaaaaac 1260
ttcactggtc tgttcgagtt ttacaagctg ctgtgcgtcg acggcatcat tacctccaaa 1320
actaaatctc tgatagaagg tagatttggc ggtttcacgg gcgcacgcaa atcagcgcgt 1380
aaattagcta accaggcgct agcgggtggt ggtggttctg gtggtggtgg ttctgcacta 1440
gtgctgcagt gtatcaaggt taacaactgg gatttattct tcagcccgag tgaagacaac 1500
ttcaccaacg acctgaacaa aggtgaagaa atcacctcag atactaacat cgaagcagcc 1560
gaagaaaaca tctcgctgga cctgatccag cagtactacc tgacctttaa tttcgacaac 1620
gagccggaaa acatttctat cgaaaacctg agctctgata tcatcggcca gctggaactg 1680
atgccgaaca tcgaacgttt cccaaacggt aaaaagtacg agctggacaa atataccatg 1740
ttccactacc tgcgcgcgca ggaatttgaa cacggcaaat cccgtatcgc actgactaac 1800
tccgttaacg aagctctgct caacccgtcc cgtgtataca ccttcttctc tagcgactac 1860
gtgaaaaagg tcaacaaagc gactgaagct gcaatgttct tgggttgggt tgaacagctt 1920
gtttatgatt ttaccgacga gacgtccgaa gtatctacta ccgacaaaat tgcggatatc 1980
actatcatca tcccgtacat cggtccggct ctgaacattg gcaacatgct gtacaaagac 2040
gacttcgttg gcgcactgat cttctccggt gcggtgatcc tgctggagtt catcccggaa 2100
atcgccatcc cggtactggg cacctttgct ctggtttctt acattgcaaa caaggttctg 2160
actgtacaaa ccatcgacaa cgcgctgagc aaacgtaacg aaaaatggga tgaagtttac 2220
aaatatatcg tgaccaactg gctggctaag gttaatactc agatcgacct catccgcaaa 2280
aaaatgaaag aagcactgga aaaccaggcg gaagctacca aggcaatcat taactaccag 2340
tacaaccagt acaccgagga agaaaaaaac aacatcaact tcaacatcga cgatctgtcc 2400
tctaaactga acgaatccat caacaaagct atgatcaaca tcaacaagtt cctgaaccag 2460
tgctctgtaa gctatctgat gaactccatg atcccgtacg gtgttaaacg tctggaggac 2520
ttcgatgcgt ctctgaaaga cgccctgctg aaatacattt acgacaaccg tggcactctg 2580
atcggtcagg ttgatcgtct gaaggacaaa gtgaacaata ccttatcgac cgacatccct 2640
tttcagctca gtaaatatgt cgataaccaa cgccttttgt ccactctaga ctag 2694

<210> SEQ ID NO 71
<211> LENGTH: 897
<212> TYPE: PRT
<213> ORGANISM: Artificial Sequence
<220> FEATURE:
<223> OTHER INFORMATION: Synthetic

<400> SEQUENCE: 71

-continued

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430
```

```
Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Arg Lys Leu Ala Asn
    450                 455                 460

Gln Ala Leu Ala Gly Gly Gly Gly Ser Gly Gly Gly Gly Ser Ala Leu
465                 470                 475                 480

Val Leu Gln Cys Ile Lys Val Asn Asn Trp Asp Leu Phe Phe Ser Pro
                485                 490                 495

Ser Glu Asp Asn Phe Thr Asn Asp Leu Asn Lys Gly Glu Glu Ile Thr
            500                 505                 510

Ser Asp Thr Asn Ile Glu Ala Ala Glu Glu Asn Ile Ser Leu Asp Leu
        515                 520                 525

Ile Gln Gln Tyr Tyr Leu Thr Phe Asn Phe Asp Asn Glu Pro Glu Asn
    530                 535                 540

Ile Ser Ile Glu Asn Leu Ser Ser Asp Ile Ile Gly Gln Leu Glu Leu
545                 550                 555                 560

Met Pro Asn Ile Glu Arg Phe Pro Asn Gly Lys Lys Tyr Glu Leu Asp
                565                 570                 575

Lys Tyr Thr Met Phe His Tyr Leu Arg Ala Gln Glu Phe Glu His Gly
            580                 585                 590

Lys Ser Arg Ile Ala Leu Thr Asn Ser Val Asn Glu Ala Leu Leu Asn
        595                 600                 605

Pro Ser Arg Val Tyr Thr Phe Phe Ser Ser Asp Tyr Val Lys Lys Val
    610                 615                 620

Asn Lys Ala Thr Glu Ala Ala Met Phe Leu Gly Trp Val Glu Gln Leu
625                 630                 635                 640

Val Tyr Asp Phe Thr Asp Glu Thr Ser Glu Val Ser Thr Thr Asp Lys
                645                 650                 655

Ile Ala Asp Ile Thr Ile Ile Ile Pro Tyr Ile Gly Pro Ala Leu Asn
            660                 665                 670

Ile Gly Asn Met Leu Tyr Lys Asp Asp Phe Val Gly Ala Leu Ile Phe
        675                 680                 685

Ser Gly Ala Val Ile Leu Leu Glu Phe Ile Pro Glu Ile Ala Ile Pro
    690                 695                 700

Val Leu Gly Thr Phe Ala Leu Val Ser Tyr Ile Ala Asn Lys Val Leu
705                 710                 715                 720

Thr Val Gln Thr Ile Asp Asn Ala Leu Ser Lys Arg Asn Glu Lys Trp
                725                 730                 735

Asp Glu Val Tyr Lys Tyr Ile Val Thr Asn Trp Leu Ala Lys Val Asn
            740                 745                 750

Thr Gln Ile Asp Leu Ile Arg Lys Lys Met Lys Glu Ala Leu Glu Asn
        755                 760                 765

Gln Ala Glu Ala Thr Lys Ala Ile Ile Asn Tyr Gln Tyr Asn Gln Tyr
    770                 775                 780

Thr Glu Glu Glu Lys Asn Asn Ile Asn Phe Asn Ile Asp Asp Leu Ser
785                 790                 795                 800

Ser Lys Leu Asn Glu Ser Ile Asn Lys Ala Met Ile Asn Ile Asn Lys
                805                 810                 815

Phe Leu Asn Gln Cys Ser Val Ser Tyr Leu Met Asn Ser Met Ile Pro
            820                 825                 830

Tyr Gly Val Lys Arg Leu Glu Asp Phe Asp Ala Ser Leu Lys Asp Ala
        835                 840                 845

Leu Leu Lys Tyr Ile Tyr Asp Asn Arg Gly Thr Leu Ile Gly Gln Val
```

-continued

```
    850                 855                 860

Asp Arg Leu Lys Asp Lys Val Asn Asn Thr Leu Ser Thr Asp Ile Pro
865                 870                 875                 880

Phe Gln Leu Ser Lys Tyr Val Asp Asn Gln Arg Leu Leu Ser Thr Leu
                885                 890                 895

Asp


<210> SEQ ID NO 72
<211> LENGTH: 2724
<212> TYPE: DNA
<213> ORGANISM: Artificial Sequence
<220> FEATURE:
<223> OTHER INFORMATION: Synthetic

<400> SEQUENCE: 72

ggatccatgg agttcgttaa caaacagttc aactataaag acccagttaa cggtgttgac     60

attgcttaca tcaaaatccc gaacgctggc cagatgcagc cggtaaaggc attcaaaatc    120

cacaacaaaa tctgggttat cccggaacgt gatacccttta ctaacccgga agaaggtgac   180

ctgaacccgc caccggaagc gaaacaggtg ccggtatctt actatgactc cacctacctg    240

tctaccgata acgaaaagga caactacctg aaaggtgtta ctaaactgtt cgagcgtatt    300

tactccaccg acctgggccg tatgctgctg actagcatcg ttcgcggtat cccgttctgg    360

ggcggttcta ccatcgatac cgaactgaaa gtaatcgaca ctaactgcat caacgttatt    420

cagccggacg gttcctatcg ttccgaagaa ctgaacctgg tgatcatcgg cccgtctgct    480

gatatcatcc agttcgagtg taagagcttt ggtcacgaag ttctgaacct cacccgtaac    540

ggctacggtt ccactcagta catccgtttc tctccggact tcaccttcgg ttttgaagaa    600

tccctggaag tagacacgaa cccactgctg ggcgctggta aattcgcaac tgatcctgcg    660

gttaccctgg ctcacgaact gattcatgca ggccaccgcc tgtacggtat cgccatcaat    720

ccgaaccgtg tcttcaaagt taacaccaac gcgtattacg agatgtccgg tctggaagtt    780

agcttcgaag aactgcgtac ttttggcggt cacgacgcta aattcatcga ctctctgcaa    840

gaaaacgagt tccgtctgta ctactataac aagttcaaag atatcgcatc caccctgaac    900

aaagcgaaat ccatcgtggg taccactgct tctctccagt acatgaagaa cgtttttaaa    960

gaaaaatacc tgctcagcga agacacctcc ggcaaattct ctgtagacaa gttgaaattc   1020

gataaacttt acaaaatgct gactgaaatt tacaccgaag acaacttcgt taagttcttt   1080

aaagttctga accgcaaaac ctatctgaac ttcgacaagg cagtattcaa aatcaacatc   1140

gtgccgaaag ttaactacac tatctacgat ggtttcaacc tgcgtaacac caacctggct   1200

gctaatttta acggccagaa cacggaaatc aacaacatga acttcacaaa actgaaaaac   1260

ttcactggtc tgttcgagtt ttacaagctg ctgtgcgtcg acggcatcat tacctccaaa   1320

actaaatctc tgatagaagg tagatttggc ggtttcacgg gcgcacgcaa atcagcgcgt   1380

aaattagcta accaggcgct agcgggtggt ggtggttctg gtggtggtgg ttctggtggt   1440

ggtggttctg gtggtggtgg ttctgcacta gtgctgcagt gtatcaaggt taacaactgg   1500

gatttattct tcagcccgag tgaagacaac ttcaccaacg acctgaacaa aggtgaagaa   1560

atcacctcag atactaacat cgaagcagcc gaagaaaaca tctcgctgga cctgatccag   1620

cagtactacc tgacctttaa tttcgacaac gagccggaaa acatttctat cgaaaacctg   1680

agctctgata tcatcggcca gctggaactg atgccgaaca tcgaacgttt cccaaacggt   1740

aaaaagtacg agctggacaa atataccatg ttccactacc tgcgcgcgca ggaatttgaa   1800
```

-continued

```
cacggcaaat cccgtatcgc actgactaac tccgttaacg aagctctgct caacccgtcc   1860

cgtgtataca ccttcttctc tagcgactac gtgaaaaagg tcaacaaagc gactgaagct   1920

gcaatgttct tgggttgggt tgaacagctt gtttatgatt ttaccgacga gacgtccgaa   1980

gtatctacta ccgacaaaat tgcggatatc actatcatca tcccgtacat cggtccggct   2040

ctgaacattg gcaacatgct gtacaaagac gacttcgttg gcgcactgat cttctccggt   2100

gcggtgatcc tgctggagtt catcccggaa atcgccatcc cggtactggg cacctttgct   2160

ctggtttctt acattgcaaa caaggttctg actgtacaaa ccatcgacaa cgcgctgagc   2220

aaacgtaacg aaaaatggga tgaagtttac aaatatatcg tgaccaactg gctggctaag   2280

gttaatactc agatcgacct catccgcaaa aaaatgaaag aagcactgga aaaccaggcg   2340

gaagctacca aggcaatcat taactaccag tacaaccagt acaccgagga agaaaaaaac   2400

aacatcaact tcaacatcga cgatctgtcc tctaaactga acgaatccat caacaaagct   2460

atgatcaaca tcaacaagtt cctgaaccag tgctctgtaa gctatctgat gaactccatg   2520

atcccgtacg gtgttaaacg tctggaggac ttcgatgcgt ctctgaaaga cgccctgctg   2580

aaatacattt acgacaaccg tggcactctg atcggtcagg ttgatcgtct gaaggacaaa   2640

gtgaacaata ccttatcgac cgacatccct tttcagctca gtaaatatgt cgataaccaa   2700

cgccttttgt ccactctaga ctag                                          2724
```

<210> SEQ ID NO 73
<211> LENGTH: 907
<212> TYPE: PRT
<213> ORGANISM: Artificial Sequence
<220> FEATURE:
<223> OTHER INFORMATION: Synthetic

<400> SEQUENCE: 73

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205
```

-continued

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Arg Lys Leu Ala Asn
    450                 455                 460

Gln Ala Leu Ala Gly Gly Gly Gly Ser Gly Gly Gly Gly Ser Gly Gly
465                 470                 475                 480

Gly Gly Ser Gly Gly Gly Gly Ser Ala Leu Val Leu Gln Cys Ile Lys
                485                 490                 495

Val Asn Asn Trp Asp Leu Phe Phe Ser Pro Ser Glu Asp Asn Phe Thr
            500                 505                 510

Asn Asp Leu Asn Lys Gly Glu Glu Ile Thr Ser Asp Thr Asn Ile Glu
        515                 520                 525

Ala Ala Glu Glu Asn Ile Ser Leu Asp Leu Ile Gln Gln Tyr Tyr Leu
    530                 535                 540

Thr Phe Asn Phe Asp Asn Glu Pro Glu Asn Ile Ser Ile Glu Asn Leu
545                 550                 555                 560

Ser Ser Asp Ile Ile Gly Gln Leu Glu Leu Met Pro Asn Ile Glu Arg
                565                 570                 575

Phe Pro Asn Gly Lys Lys Tyr Glu Leu Asp Lys Tyr Thr Met Phe His
            580                 585                 590

Tyr Leu Arg Ala Gln Glu Phe Glu His Gly Lys Ser Arg Ile Ala Leu
        595                 600                 605

Thr Asn Ser Val Asn Glu Ala Leu Leu Asn Pro Ser Arg Val Tyr Thr
    610                 615                 620

Phe Phe Ser Ser Asp Tyr Val Lys Lys Val Asn Lys Ala Thr Glu Ala

-continued

```
625                 630                 635                 640

Ala Met Phe Leu Gly Trp Val Glu Gln Leu Val Tyr Asp Phe Thr Asp
                645                 650                 655

Glu Thr Ser Glu Val Ser Thr Thr Asp Lys Ile Ala Asp Ile Thr Ile
            660                 665                 670

Ile Ile Pro Tyr Ile Gly Pro Ala Leu Asn Ile Gly Asn Met Leu Tyr
        675                 680                 685

Lys Asp Asp Phe Val Gly Ala Leu Ile Phe Ser Gly Ala Val Ile Leu
    690                 695                 700

Leu Glu Phe Ile Pro Glu Ile Ala Ile Pro Val Leu Gly Thr Phe Ala
705                 710                 715                 720

Leu Val Ser Tyr Ile Ala Asn Lys Val Leu Thr Val Gln Thr Ile Asp
                725                 730                 735

Asn Ala Leu Ser Lys Arg Asn Glu Lys Trp Asp Glu Val Tyr Lys Tyr
            740                 745                 750

Ile Val Thr Asn Trp Leu Ala Lys Val Asn Thr Gln Ile Asp Leu Ile
        755                 760                 765

Arg Lys Lys Met Lys Glu Ala Leu Glu Asn Gln Ala Glu Ala Thr Lys
    770                 775                 780

Ala Ile Ile Asn Tyr Gln Tyr Asn Gln Tyr Thr Glu Glu Glu Lys Asn
785                 790                 795                 800

Asn Ile Asn Phe Asn Ile Asp Asp Leu Ser Ser Lys Leu Asn Glu Ser
                805                 810                 815

Ile Asn Lys Ala Met Ile Asn Ile Asn Lys Phe Leu Asn Gln Cys Ser
            820                 825                 830

Val Ser Tyr Leu Met Asn Ser Met Ile Pro Tyr Gly Val Lys Arg Leu
        835                 840                 845

Glu Asp Phe Asp Ala Ser Leu Lys Asp Ala Leu Leu Lys Tyr Ile Tyr
    850                 855                 860

Asp Asn Arg Gly Thr Leu Ile Gly Gln Val Asp Arg Leu Lys Asp Lys
865                 870                 875                 880

Val Asn Asn Thr Leu Ser Thr Asp Ile Pro Phe Gln Leu Ser Lys Tyr
                885                 890                 895

Val Asp Asn Gln Arg Leu Leu Ser Thr Leu Asp
            900                 905
```

<210> SEQ ID NO 74
<211> LENGTH: 207
<212> TYPE: DNA
<213> ORGANISM: Artificial Sequence
<220> FEATURE:
<223> OTHER INFORMATION: Synthetic

<400> SEQUENCE: 74

```
ggatccacgc acgtcgacgg catcattacc tccaaaacta aatctgacga tgacgataaa      60

tttggcggtt tcacgggcgc acgcaaatca gcgcgtaaac gtaagaacca ggcgctagcg     120

ggcggtggcg gtagcggcgg tggcggtagc ggcggtggcg gtagcgcact agtgctgcag     180

acgcacggtc tagaatgata aaagctt                                         207
```

<210> SEQ ID NO 75
<211> LENGTH: 2709
<212> TYPE: DNA
<213> ORGANISM: Artificial Sequence
<220> FEATURE:
<223> OTHER INFORMATION: Synthetic

<400> SEQUENCE: 75

-continued

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc caccggaagc gaaacaggtg ccggtatctt actatgactc cacctacctg     240
tctaccgata acgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg gttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt tccgtctgta ctactataac aagttcaaag atatcgcatc caccctgaac     900
aaagcgaaat ccatcgtggg taccactgct tctctccagt acatgaagaa cgtttttaaa     960
gaaaaatacc tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa aatcaacatc    1140
gtgccgaaag ttaactacac tatctacgat ggtttcaacc tgcgtaacac caacctggct    1200
gctaatttta acggccagaa cacggaaatc aacaacatga acttcacaaa actgaaaaac    1260
ttcactggtc tgttcgagtt ttacaagctg ctgtgcgtcg acggcatcat tacctccaaa    1320
actaaatctg acgatgacga taaatttggc ggtttcacgg gcgcacgcaa atcagcgcgt    1380
aaacgtaaga accaggcgct agcgggcggt ggcggtagcg gcggtggcgg tagcggcggt    1440
ggcggtagcg cactagtgct gcagtgtatc aaggttaaca actgggattt attcttcagc    1500
ccgagtgaag acaacttcac caacgacctg aacaaaggtg aagaaatcac ctcagatact    1560
aacatcgaag cagccgaaga aaacatctcg ctggacctga tccagcagta ctacctgacc    1620
tttaatttcg acaacgagcc ggaaaacatt tctatcgaaa acctgagctc tgatatcatc    1680
ggccagctgg aactgatgcc gaacatcgaa cgtttcccaa acggtaaaaa gtacgagctg    1740
gacaaatata ccatgttcca ctacctgcgc gcgcaggaat ttgaacacgg caaatcccgt    1800
atcgcactga ctaactccgt taacgaagct ctgctcaacc cgtcccgtgt atacaccttc    1860
ttctctagcg actacgtgaa aaaggtcaac aaagcgactg aagctgcaat gttcttgggt    1920
tgggttgaac agcttgttta tgattttacc gacgagacgt ccgaagtatc tactaccgac    1980
aaaattgcgg atatcactat catcatcccg tacatcggtc cggctctgaa cattggcaac    2040
atgctgtaca aagacgactt cgttggcgca ctgatcttct ccggtgcggt gatcctgctg    2100
gagttcatcc cggaaatcgc catcccggta ctgggcacct ttgctctggt ttcttacatt    2160
gcaaacaagg ttctgactgt acaaaccatc gacaacgcgc tgagcaaacg taacgaaaaa    2220
tgggatgaag tttacaaata tatcgtgacc aactggctgg ctaaggttaa tactcagatc    2280
gacctcatcc gcaaaaaaat gaaagaagca ctggaaaacc aggcggaagc taccaaggca    2340
atcattaact accagtacaa ccagtacacc gaggaagaaa aaaacaacat caacttcaac    2400
```

```
atcgacgatc tgtcctctaa actgaacgaa tccatcaaca aagctatgat caacatcaac   2460

aagttcctga accagtgctc tgtaagctat ctgatgaact ccatgatccc gtacggtgtt   2520

aaacgtctgg aggacttcga tgcgtctctg aaagacgccc tgctgaaata catttacgac   2580

aaccgtggca ctctgatcgg tcaggttgat cgtctgaagg acaaagtgaa caatacctta   2640

tcgaccgaca tccctttttca gctcagtaaa tatgtcgata accaacgcct tttgtccact   2700

ctagactag                                                           2709
```

<210> SEQ ID NO 76
<211> LENGTH: 902
<212> TYPE: PRT
<213> ORGANISM: Artificial Sequence
<220> FEATURE:
<223> OTHER INFORMATION: Synthetic

<400> SEQUENCE: 76

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300
```

-continued

```
Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Asp Asp Asp Asp Lys
        435                 440                 445

Phe Gly Gly Phe Thr Gly Ala Arg Lys Ser Ala Arg Lys Arg Lys Asn
    450                 455                 460

Gln Ala Leu Ala Gly Gly Gly Gly Ser Gly Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
            500                 505                 510

Gly Glu Glu Ile Thr Ser Asp Thr Asn Ile Glu Ala Ala Glu Glu Asn
        515                 520                 525

Ile Ser Leu Asp Leu Ile Gln Gln Tyr Tyr Leu Thr Phe Asn Phe Asp
    530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
            580                 585                 590

Glu Phe Glu His Gly Lys Ser Arg Ile Ala Leu Thr Asn Ser Val Asn
        595                 600                 605

Glu Ala Leu Leu Asn Pro Ser Arg Val Tyr Thr Phe Phe Ser Ser Asp
    610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Ile Pro Tyr Ile
            660                 665                 670

Gly Pro Ala Leu Asn Ile Gly Asn Met Leu Tyr Lys Asp Asp Phe Val
        675                 680                 685

Gly Ala Leu Ile Phe Ser Gly Ala Val Ile Leu Leu Glu Phe Ile Pro
    690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
                725                 730                 735
```

```
Arg Asn Glu Lys Trp Asp Glu Val Tyr Lys Tyr Ile Val Thr Asn Trp
            740                 745                 750

Leu Ala Lys Val Asn Thr Gln Ile Asp Leu Ile Arg Lys Lys Met Lys
        755                 760                 765

Glu Ala Leu Glu Asn Gln Ala Glu Ala Thr Lys Ala Ile Ile Asn Tyr
    770                 775                 780

Gln Tyr Asn Gln Tyr Thr Glu Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
        835                 840                 845

Ser Leu Lys Asp Ala Leu Leu Lys Tyr Ile Tyr Asp Asn Arg Gly Thr
    850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Asp
            900
```

<210> SEQ ID NO 77
<211> LENGTH: 207
<212> TYPE: DNA
<213> ORGANISM: Artificial Sequence
<220> FEATURE:
<223> OTHER INFORMATION: Synthetic

<400> SEQUENCE: 77

```
ggatccacgc acgtcgacgg catcattacc tccaaaacta aatctctgat agaaggtaga      60

tttggcggtt tcacgggcgc acgcaaatca gcgcgtaaac gtaagaacca ggcgctagcg     120

ggcggtggcg gtagcggcgg tggcggtagc ggcggtggcg gtagcgcact agtgctgcag     180

acgcacggtc tagaatgata aaagctt                                         207
```

<210> SEQ ID NO 78
<211> LENGTH: 2742
<212> TYPE: DNA
<213> ORGANISM: Artificial Sequence
<220> FEATURE:
<223> OTHER INFORMATION: Synthetic

<400> SEQUENCE: 78

```
ggatccgaat tcatgccgat caccatcaac aacttcaact acagcgatcc ggtggataac      60

aaaaacatcc tgtacctgga tacccatctg aataccctgg cgaacgaacc ggaaaaagcg     120

tttcgtatca ccggcaacat ttgggttatt ccggatcgtt ttagccgtaa cagcaacccg     180

aatctgaata aaccgccgcg tgttaccagc ccgaaaagcg gttattacga tccgaactat     240

ctgagcaccg atagcgataa agataccttc ctgaaagaaa tcatcaaact gttcaaacgc     300

atcaacagcc gtgaaattgg cgaagaactg atctatcgcc tgagcaccga tattccgttt     360

ccgggcaaca acaacacccc gatcaacacc tttgatttcg atgtggattt caacagcgtt     420

gatgttaaaa cccgccaggg taacaattgg gtgaaaaccg gcagcattaa cccgagcgtg     480

attattaccg gtccgcgcga aaacattatt gatccggaaa ccagcacctt taaactgacc     540
```

aacaacacct ttgcggcgca ggaaggtttt ggcgcgctga gcattattag cattagcccg 600
cgctttatgc tgacctatag caacgcgacc aacgatgttg gtgaaggccg tttcagcaaa 660
agcgaatttt gcatggaccc gatcctgatc ctgatgcatg aactgaacca tgcgatgcat 720
aacctgtatg gcatcgcgat tccgaacgat cagaccatta gcagcgtgac cagcaacatc 780
ttttacagcc agtacaacgt gaaactggaa tatgcggaaa tctatgcgtt tggcggtccg 840
accattgatc tgattccgaa aagcgcgcgc aaatacttcg aagaaaaagc gctggattac 900
tatcgcagca ttgcgaaacg tctgaacagc attaccaccg cgaatccgag cagcttcaac 960
aaatatatcg gcgaatataa acagaaactg atccgcaaat atcgctttgt ggtggaaagc 1020
agcggcgaag ttaccgttaa ccgcaataaa ttcgtggaac tgtacaacga actgacccag 1080
atcttcaccg aatttaacta tgcgaaaatc tataacgtgc agaaccgtaa aatctacctg 1140
agcaacgtgt ataccccggt gaccgcgaat attctggatg ataacgtgta cgatatccag 1200
aacggcttta acatcccgaa aagcaacctg aacgttctgt ttatgggcca gaacctgagc 1260
cgtaatccgg cgctgcgtaa agtgaacccg gaaaacatgc tgtacctgtt caccaaattt 1320
tgcgtcgacg gcatcattac ctccaaaact aaatctctga tagaaggtag atttggcggt 1380
ttcacgggcg cacgcaaatc agcgcgtaaa cgtaagaacc aggcgctagc gggcggtggc 1440
ggtagcggcg gtggcggtag cggcggtggc ggtagcgcac tagtgctgca gtgtcgtgaa 1500
ctgctggtga aaaacaccga tctgccgttt attggcgata tcagcgatgt gaaaaccgat 1560
atcttcctgc gcaaagatat caacgaagaa accgaagtga tctactaccc ggataacgtg 1620
agcgttgatc aggtgatcct gagcaaaaac accagcgaac atggtcagct ggatctgctg 1680
tatccgagca ttgatagcga aagcgaaatt ctgccgggcg aaaaccaggt gttttacgat 1740
aaccgtaccc agaacgtgga ttacctgaac agctattact acctggaaag ccagaaactg 1800
agcgataacg tggaagattt tacctttacc cgcagcattg aagaagcgct ggataacagc 1860
gcgaaagttt acacctattt tccgaccctg gcgaacaaag ttaatgcggg tgttcagggc 1920
ggtctgtttc tgatgtgggc gaacgatgtg gtggaagatt tcaccaccaa catcctgcgt 1980
aaagataccc tggataaaat cagcgatgtt agcgcgatta ttccgtatat tggtccggcg 2040
ctgaacatta gcaatagcgt gcgtcgtggc aattttaccg aagcgtttgc ggttaccggt 2100
gtgaccattc tgctggaagc gtttccggaa tttaccattc cggcgctggg tgcgtttgtg 2160
atctatagca aagtgcagga acgcaacgaa atcatcaaaa ccatcgataa ctgcctggaa 2220
cagcgtatta aacgctggaa agatagctat gaatggatga tgggcacctg gctgagccgt 2280
attatcaccc agttcaacaa catcagctac cagatgtacg atagcctgaa ctatcaggcg 2340
ggtgcgatta aagcgaaaat cgatctggaa tacaaaaaat acagcggcag cgataaagaa 2400
aacatcaaaa gccaggttga aaacctgaaa aacagcctgg atgtgaaaat tagcgaagcg 2460
atgaataaca tcaacaaatt catccgcgaa tgcagcgtga cctacctgtt caaaaacatg 2520
ctgccgaaag tgatcgatga actgaacgaa tttgatcgca acaccaaagc gaaactgatc 2580
aacctgatcg atagccacaa cattattctg gtgggcgaag tggataaact gaaagcgaaa 2640
gttaacaaca gcttccagaa caccatcccg tttaacatct tcagctatac caacaacagc 2700
ctgctgaaag atatcatcaa cgaatacttc aatctagact ag 2742

<210> SEQ ID NO 79
<211> LENGTH: 913
<212> TYPE: PRT
<213> ORGANISM: Artificial Sequence
<220> FEATURE:

<223> OTHER INFORMATION: Synthetic

<400> SEQUENCE: 79

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
    290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
    370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
```

```
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Gly Ile Ile Thr Ser
        435                 440                 445

Lys Thr Lys Ser Leu Ile Glu Gly Arg Phe Gly Gly Phe Thr Gly Ala
    450                 455                 460

Arg Lys Ser Ala Arg Lys Arg Lys Asn Gln Ala Leu Ala Gly Gly Gly
465                 470                 475                 480

Gly Ser Gly Gly Gly Gly Ser Gly Gly Gly Gly Ser Ala Leu Val Leu
                485                 490                 495

Gln Cys Arg Glu Leu Leu Val Lys Asn Thr Asp Leu Pro Phe Ile Gly
            500                 505                 510

Asp Ile Ser Asp Val Lys Thr Asp Ile Phe Leu Arg Lys Asp Ile Asn
        515                 520                 525

Glu Glu Thr Glu Val Ile Tyr Tyr Pro Asp Asn Val Ser Val Asp Gln
    530                 535                 540

Val Ile Leu Ser Lys Asn Thr Ser Glu His Gly Gln Leu Asp Leu Leu
545                 550                 555                 560

Tyr Pro Ser Ile Asp Ser Glu Ser Glu Ile Leu Pro Gly Glu Asn Gln
                565                 570                 575

Val Phe Tyr Asp Asn Arg Thr Gln Asn Val Asp Tyr Leu Asn Ser Tyr
            580                 585                 590

Tyr Tyr Leu Glu Ser Gln Lys Leu Ser Asp Asn Val Glu Asp Phe Thr
        595                 600                 605

Phe Thr Arg Ser Ile Glu Glu Ala Leu Asp Asn Ser Ala Lys Val Tyr
    610                 615                 620

Thr Tyr Phe Pro Thr Leu Ala Asn Lys Val Asn Ala Gly Val Gln Gly
625                 630                 635                 640

Gly Leu Phe Leu Met Trp Ala Asn Asp Val Val Glu Asp Phe Thr Thr
                645                 650                 655

Asn Ile Leu Arg Lys Asp Thr Leu Asp Lys Ile Ser Asp Val Ser Ala
            660                 665                 670

Ile Ile Pro Tyr Ile Gly Pro Ala Leu Asn Ile Ser Asn Ser Val Arg
        675                 680                 685

Arg Gly Asn Phe Thr Glu Ala Phe Ala Val Thr Gly Val Thr Ile Leu
    690                 695                 700

Leu Glu Ala Phe Pro Glu Phe Thr Ile Pro Ala Leu Gly Ala Phe Val
705                 710                 715                 720

Ile Tyr Ser Lys Val Gln Glu Arg Asn Glu Ile Ile Lys Thr Ile Asp
                725                 730                 735

Asn Cys Leu Glu Gln Arg Ile Lys Arg Trp Lys Asp Ser Tyr Glu Trp
            740                 745                 750

Met Met Gly Thr Trp Leu Ser Arg Ile Ile Thr Gln Phe Asn Asn Ile
        755                 760                 765

Ser Tyr Gln Met Tyr Asp Ser Leu Asn Tyr Gln Ala Gly Ala Ile Lys
    770                 775                 780

Ala Lys Ile Asp Leu Glu Tyr Lys Lys Tyr Ser Gly Ser Asp Lys Glu
785                 790                 795                 800

Asn Ile Lys Ser Gln Val Glu Asn Leu Lys Asn Ser Leu Asp Val Lys
                805                 810                 815

Ile Ser Glu Ala Met Asn Asn Ile Asn Lys Phe Ile Arg Glu Cys Ser
            820                 825                 830
```

-continued

```
Val Thr Tyr Leu Phe Lys Asn Met Leu Pro Lys Val Ile Asp Glu Leu
        835                 840                 845

Asn Glu Phe Asp Arg Asn Thr Lys Ala Lys Leu Ile Asn Leu Ile Asp
    850                 855                 860

Ser His Asn Ile Ile Leu Val Gly Glu Val Asp Lys Leu Lys Ala Lys
865                 870                 875                 880

Val Asn Asn Ser Phe Gln Asn Thr Ile Pro Phe Asn Ile Phe Ser Tyr
                885                 890                 895

Thr Asn Asn Ser Leu Leu Lys Asp Ile Ile Asn Glu Tyr Phe Asn Leu
            900                 905                 910

Asp
```

<210> SEQ ID NO 80
<211> LENGTH: 2673
<212> TYPE: DNA
<213> ORGANISM: Artificial Sequence
<220> FEATURE:
<223> OTHER INFORMATION: Synthetic

<400> SEQUENCE: 80

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc caccggaagc gaaacaggtg ccggtatctt actatgactc cacctacctg     240
tctaccgata acgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg gttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt tccgtctgta ctactataac aagttcaaag atatcgcatc caccctgaac     900
aaagcgaaat ccatcgtggg taccactgct tctctccagt acatgaagaa cgtttttaaa     960
gaaaaatacc tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa aatcaacatc    1140
gtgccgaaag ttaactacac tatctacgat ggtttcaacc tgcgtaacac caacctggct    1200
gctaatttta acggccagaa cacggaaatc aacaacatga acttcacaaa actgaaaaac    1260
ttcactggtc tgttcgagtt ttacaagctg ctgtgcgtcg acggcatcat tacctccaaa    1320
actaaatctc tgatagaagg tagatacggt ggtttcctgg cgctagcggg cggtggcggt    1380
agcggcggtg gcggtagcgg cggtggcggt agcgcactag tgctgcagtg tatcaaggtt    1440
aacaactggg atttattctt cagcccgagt gaagacaact tcaccaacga cctgaacaaa    1500
ggtgaagaaa tcacctcaga tactaacatc gaagcagccg aagaaaacat ctcgctggac    1560
ctgatccagc agtactacct gacctttaat ttcgacaacg agccggaaaa catttctatc    1620
```

```
gaaaacctga gctctgatat catcggccag ctggaactga tgccgaacat cgaacgtttc   1680

ccaaacggta aaaagtacga gctggacaaa tataccatgt tccactacct gcgcgcgcag   1740

gaatttgaac acggcaaatc ccgtatcgca ctgactaact ccgttaacga agctctgctc   1800

aacccgtccc gtgtatacac cttcttctct agcgactacg tgaaaaaggt caacaaagcg   1860

actgaagctg caatgttctt gggttgggtt gaacagcttg tttatgattt taccgacgag   1920

acgtccgaag tatctactac cgacaaaatt gcggatatca ctatcatcat cccgtacatc   1980

ggtccggctc tgaacattgg caacatgctg tacaaagacg acttcgttgg cgcactgatc   2040

ttctccggtg cggtgatcct gctggagttc atcccggaaa tcgccatccc ggtactgggc   2100

acctttgctc tggtttctta cattgcaaac aaggttctga ctgtacaaac catcgacaac   2160

gcgctgagca aacgtaacga aaaatgggat gaagtttaca aatatatcgt gaccaactgg   2220

ctggctaagg ttaatactca gatcgacctc atccgcaaaa aaatgaaaga agcactggaa   2280

aaccaggcgg aagctaccaa ggcaatcatt aactaccagt acaaccagta caccgaggaa   2340

gaaaaaaaca acatcaactt caacatcgac gatctgtcct ctaaactgaa cgaatccatc   2400

aacaaagcta tgatcaacat caacaagttc ctgaaccagt gctctgtaag ctatctgatg   2460

aactccatga tcccgtacgg tgttaaacgt ctggaggact tcgatgcgtc tctgaaagac   2520

gccctgctga aatacattta cgacaaccgt ggcactctga tcggtcaggt tgatcgtctg   2580

aaggacaaag tgaacaatac cttatcgacc gacatccctt ttcagctcag taaatatgtc   2640

gataaccaac gccttttgtc cactctagac tag                                2673


<210> SEQ ID NO 81
<211> LENGTH: 890
<212> TYPE: PRT
<213> ORGANISM: Artificial Sequence
<220> FEATURE:
<223> OTHER INFORMATION: Synthetic

<400> SEQUENCE: 81

Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175
```

-continued

```
Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Tyr Gly Gly Phe Leu Ala Leu Ala Gly Gly Gly Gly Ser Gly Gly Gly
    450                 455                 460

Gly Ser Gly Gly Gly Gly Ser Ala Leu Val Leu Gln Cys Ile Lys Val
465                 470                 475                 480

Asn Asn Trp Asp Leu Phe Phe Ser Pro Ser Glu Asp Asn Phe Thr Asn
                485                 490                 495

Asp Leu Asn Lys Gly Glu Glu Ile Thr Ser Asp Thr Asn Ile Glu Ala
            500                 505                 510

Ala Glu Glu Asn Ile Ser Leu Asp Leu Ile Gln Gln Tyr Tyr Leu Thr
        515                 520                 525

Phe Asn Phe Asp Asn Glu Pro Glu Asn Ile Ser Ile Glu Asn Leu Ser
    530                 535                 540

Ser Asp Ile Ile Gly Gln Leu Glu Leu Met Pro Asn Ile Glu Arg Phe
545                 550                 555                 560

Pro Asn Gly Lys Lys Tyr Glu Leu Asp Lys Tyr Thr Met Phe His Tyr
                565                 570                 575

Leu Arg Ala Gln Glu Phe Glu His Gly Lys Ser Arg Ile Ala Leu Thr
            580                 585                 590

Asn Ser Val Asn Glu Ala Leu Leu Asn Pro Ser Arg Val Tyr Thr Phe
        595                 600                 605
```

```
Phe Ser Ser Asp Tyr Val Lys Lys Val Asn Lys Ala Thr Glu Ala Ala
    610                 615                 620

Met Phe Leu Gly Trp Val Glu Gln Leu Val Tyr Asp Phe Thr Asp Glu
625                 630                 635                 640

Thr Ser Glu Val Ser Thr Thr Asp Lys Ile Ala Asp Ile Thr Ile Ile
                645                 650                 655

Ile Pro Tyr Ile Gly Pro Ala Leu Asn Ile Gly Asn Met Leu Tyr Lys
            660                 665                 670

Asp Asp Phe Val Gly Ala Leu Ile Phe Ser Gly Ala Val Ile Leu Leu
        675                 680                 685

Glu Phe Ile Pro Glu Ile Ala Ile Pro Val Leu Gly Thr Phe Ala Leu
    690                 695                 700

Val Ser Tyr Ile Ala Asn Lys Val Leu Thr Val Gln Thr Ile Asp Asn
705                 710                 715                 720

Ala Leu Ser Lys Arg Asn Glu Lys Trp Asp Glu Val Tyr Lys Tyr Ile
                725                 730                 735

Val Thr Asn Trp Leu Ala Lys Val Asn Thr Gln Ile Asp Leu Ile Arg
            740                 745                 750

Lys Lys Met Lys Glu Ala Leu Glu Asn Gln Ala Glu Ala Thr Lys Ala
        755                 760                 765

Ile Ile Asn Tyr Gln Tyr Asn Gln Tyr Thr Glu Glu Glu Lys Asn Asn
    770                 775                 780

Ile Asn Phe Asn Ile Asp Asp Leu Ser Ser Lys Leu Asn Glu Ser Ile
785                 790                 795                 800

Asn Lys Ala Met Ile Asn Ile Asn Lys Phe Leu Asn Gln Cys Ser Val
                805                 810                 815

Ser Tyr Leu Met Asn Ser Met Ile Pro Tyr Gly Val Lys Arg Leu Glu
            820                 825                 830

Asp Phe Asp Ala Ser Leu Lys Asp Ala Leu Leu Lys Tyr Ile Tyr Asp
        835                 840                 845

Asn Arg Gly Thr Leu Ile Gly Gln Val Asp Arg Leu Lys Asp Lys Val
    850                 855                 860

Asn Asn Thr Leu Ser Thr Asp Ile Pro Phe Gln Leu Ser Lys Tyr Val
865                 870                 875                 880

Asp Asn Gln Arg Leu Leu Ser Thr Leu Asp
                885                 890


<210> SEQ ID NO 82
<211> LENGTH: 2709
<212> TYPE: DNA
<213> ORGANISM: Artificial Sequence
<220> FEATURE:
<223> OTHER INFORMATION: Synthetic

<400> SEQUENCE: 82

ggatccatgg agttcgttaa caaacagttc aactataaag acccagttaa cggtgttgac      60

attgcttaca tcaaaatccc gaacgctggc cagatgcagc cggtaaaggc attcaaaatc     120

cacaacaaaa tctgggttat cccggaacgt gataccttta ctaacccgga agaaggtgac     180

ctgaacccgc caccggaagc gaaacaggtg ccggtatctt actatgactc cacctacctg     240

tctaccgata acgaaaagga caactacctg aaaggtgtta ctaaactgtt cgagcgtatt     300

tactccaccg acctgggccg tatgctgctg actagcatcg ttcgcggtat cccgttctgg     360

ggcggttcta ccatcgatac cgaactgaaa gtaatcgaca ctaactgcat caacgttatt     420

cagccggacg gttcctatcg ttccgaagaa ctgaacctgg tgatcatcgg cccgtctgct     480
```

```
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct tctctccagt acatgaagaa cgtttttaaa    960
gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa aatcaacatc   1140
gtgccgaaag ttaactacac tatctacgat ggtttcaacc tgcgtaacac caacctggct   1200
gctaatttta acggccagaa cacggaaatc aacaacatga acttcacaaa actgaaaaac   1260
ttcactggtc tgttcgagtt ttacaagctg ctgtgcgtcg acggcatcat tacctccaaa   1320
actaaatctc tgatagaagg tagatatggc ggtttcacgg gcgcacgcaa atcagcgcgt   1380
aaattagcta accaggcgct agcgggcggt ggcggtagcg gcggtggcgg tagcggcggt   1440
ggcggtagcg cactagtgct gcagtgtatc aaggttaaca actgggattt attcttcagc   1500
ccgagtgaag acaacttcac caacgacctg aacaaaggtg aagaaatcac ctcagatact   1560
aacatcgaag cagccgaaga aaacatctcg ctggacctga tccagcagta ctacctgacc   1620
tttaatttcg acaacgagcc ggaaaacatt tctatcgaaa acctgagctc tgatatcatc   1680
ggccagctgg aactgatgcc gaacatcgaa cgtttcccaa acggtaaaaa gtacgagctg   1740
gacaaatata ccatgttcca ctacctgcgc gcgcaggaat ttgaacacgg caaatcccgt   1800
atcgcactga ctaactccgt taacgaagct ctgctcaacc cgtcccgtgt atacaccttc   1860
ttctctagcg actacgtgaa aaaggtcaac aaagcgactg aagctgcaat gttcttgggt   1920
tgggttgaac agcttgttta tgattttacc gacgagacgt ccgaagtatc tactaccgac   1980
aaaattgcgg atatcactat catcatcccg tacatcggtc cggctctgaa cattggcaac   2040
atgctgtaca aagacgactt cgttggcgca ctgatcttct ccggtgcggt gatcctgctg   2100
gagttcatcc cggaaatcgc catcccggta ctgggcacct ttgctctggt ttcttacatt   2160
gcaaacaagg ttctgactgt acaaaccatc gacaacgcgc tgagcaaacg taacgaaaaa   2220
tgggatgaag tttacaaata tatcgtgacc aactggctgg ctaaggttaa tactcagatc   2280
gacctcatcc gcaaaaaaat gaaagaagca ctggaaaacc aggcggaagc taccaaggca   2340
atcattaact accagtacaa ccagtacacc gaggaagaaa aaaacaacat caacttcaac   2400
atcgacgatc tgtcctctaa actgaacgaa tccatcaaca aagctatgat caacatcaac   2460
aagttcctga accagtgctc tgtaagctat ctgatgaact ccatgatccc gtacggtgtt   2520
aaacgtctgg aggacttcga tgcgtctctg aaagacgccc tgctgaaata catttacgac   2580
aaccgtggca ctctgatcgg tcaggttgat cgtctgaagg acaaagtgaa caatacctta   2640
tcgaccgaca tccctttca gctcagtaaa tatgtcgata accaacgcct tttgtccact    2700
ctagactag                                                           2709
```

<210> SEQ ID NO 83
<211> LENGTH: 902

<212> TYPE: PRT
<213> ORGANISM: Artificial Sequence
<220> FEATURE:
<223> OTHER INFORMATION: Synthetic

<400> SEQUENCE: 83

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
```

-continued

```
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Tyr Gly Gly Phe Thr Gly Ala Arg Lys Ser Ala Arg Lys Leu Ala Asn
    450                 455                 460

Gln Ala Leu Ala Gly Gly Gly Gly Ser Gly Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
            500                 505                 510

Gly Glu Glu Ile Thr Ser Asp Thr Asn Ile Glu Ala Ala Glu Glu Asn
        515                 520                 525

Ile Ser Leu Asp Leu Ile Gln Gln Tyr Tyr Leu Thr Phe Asn Phe Asp
    530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
            580                 585                 590

Glu Phe Glu His Gly Lys Ser Arg Ile Ala Leu Thr Asn Ser Val Asn
        595                 600                 605

Glu Ala Leu Leu Asn Pro Ser Arg Val Tyr Thr Phe Phe Ser Ser Asp
    610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Ile Pro Tyr Ile
            660                 665                 670

Gly Pro Ala Leu Asn Ile Gly Asn Met Leu Tyr Lys Asp Asp Phe Val
        675                 680                 685

Gly Ala Leu Ile Phe Ser Gly Ala Val Ile Leu Leu Glu Phe Ile Pro
    690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
                725                 730                 735

Arg Asn Glu Lys Trp Asp Glu Val Tyr Lys Tyr Ile Val Thr Asn Trp
            740                 745                 750

Leu Ala Lys Val Asn Thr Gln Ile Asp Leu Ile Arg Lys Lys Met Lys
        755                 760                 765

Glu Ala Leu Glu Asn Gln Ala Glu Ala Thr Lys Ala Ile Ile Asn Tyr
    770                 775                 780

Gln Tyr Asn Gln Tyr Thr Glu Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815
```

```
Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
        835                 840                 845

Ser Leu Lys Asp Ala Leu Leu Lys Tyr Ile Tyr Asp Asn Arg Gly Thr
    850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Asp
            900


<210> SEQ ID NO 84
<211> LENGTH: 2709
<212> TYPE: DNA
<213> ORGANISM: Artificial Sequence
<220> FEATURE:
<223> OTHER INFORMATION: Synthetic

<400> SEQUENCE: 84

ggatccatgg agttcgttaa caaacagttc aactataaag acccagttaa cggtgttgac      60

attgcttaca tcaaaatccc gaacgctggc cagatgcagc cggtaaaggc attcaaaatc     120

cacaacaaaa tctgggttat cccggaacgt gatacccttta ctaacccgga agaaggtgac    180

ctgaacccgc caccggaagc gaaacaggtg ccggtatctt actatgactc cacctacctg     240

tctaccgata acgaaaagga caactacctg aaaggtgtta ctaaactgtt cgagcgtatt     300

tactccaccg acctgggccg tatgctgctg actagcatcg ttcgcggtat cccgttctgg     360

ggcggttcta ccatcgatac cgaactgaaa gtaatcgaca ctaactgcat caacgttatt     420

cagccggacg gttcctatcg ttccgaagaa ctgaacctgg tgatcatcgg cccgtctgct     480

gatatcatcc agttcgagtg taagagcttt ggtcacgaag ttctgaacct cacccgtaac     540

ggctacggtt ccactcagta catccgtttc tctccggact tcaccttcgg ttttgaagaa     600

tccctggaag tagacacgaa cccactgctg ggcgctggta aattcgcaac tgatcctgcg     660

gttaccctgg ctcacgaact gattcatgca ggccaccgcc tgtacggtat cgccatcaat     720

ccgaaccgtg tcttcaaagt taacaccaac gcgtattacg agatgtccgg tctggaagtt     780

agcttcgaag aactgcgtac ttttggcggt cacgacgcta aattcatcga ctctctgcaa     840

gaaaacgagt tccgtctgta ctactataac aagttcaaag atatcgcatc caccctgaac     900

aaagcgaaat ccatcgtggg taccactgct tctctccagt acatgaagaa cgtttttaaa     960

gaaaaatacc tgctcagcga agacacctcc ggcaaattct ctgtagacaa gttgaaattc    1020

gataaacttt acaaaatgct gactgaaatt tacaccgaag acaacttcgt taagttcttt    1080

aaagttctga accgcaaaac ctatctgaac ttcgacaagg cagtattcaa aatcaacatc    1140

gtgccgaaag ttaactacac tatctacgat ggtttcaacc tgcgtaacac caacctggct    1200

gctaatttta acggccagaa cacggaaatc aacaacatga acttcacaaa actgaaaaac    1260

ttcactggtc tgttcgagtt ttacaagctg ctgtgcgtcg acggcatcat tacctccaaa    1320

actaaatctc tgatagaagg tagatatggc ggtttcacgg gcgcacgcaa atcagcgcgt    1380

aaacgtaaga accaggcgct agcgggcggt ggcggtagcg gcggtggcgg tagcggcggt    1440

ggcggtagcg cactagtgct gcagtgtatc aaggttaaca actgggattt attcttcagc    1500

ccgagtgaag acaacttcac caacgacctg aacaaaggtg aagaaatcac ctcagatact    1560
```

```
aacatcgaag cagccgaaga aaacatctcg ctggacctga tccagcagta ctacctgacc   1620

tttaatttcg acaacgagcc ggaaaacatt tctatcgaaa acctgagctc tgatatcatc   1680

ggccagctgg aactgatgcc gaacatcgaa cgtttcccaa acggtaaaaa gtacgagctg   1740

gacaaatata ccatgttcca ctacctgcgc gcgcaggaat ttgaacacgg caaatcccgt   1800

atcgcactga ctaactccgt taacgaagct ctgctcaacc cgtcccgtgt atacaccttc   1860

ttctctagcg actacgtgaa aaaggtcaac aaagcgactg aagctgcaat gttcttgggt   1920

tgggttgaac agcttgttta tgattttacc gacgagacgt ccgaagtatc tactaccgac   1980

aaaattgcgg atatcactat catcatcccg tacatcggtc cggctctgaa cattggcaac   2040

atgctgtaca aagacgactt cgttggcgca ctgatcttct ccggtgcggt gatcctgctg   2100

gagttcatcc cggaaatcgc catcccggta ctgggcacct ttgctctggt ttcttacatt   2160

gcaaacaagg ttctgactgt acaaaccatc gacaacgcgc tgagcaaacg taacgaaaaa   2220

tgggatgaag tttacaaata tatcgtgacc aactggctgg ctaaggttaa tactcagatc   2280

gacctcatcc gcaaaaaaat gaaagaagca ctggaaaacc aggcggaagc taccaaggca   2340

atcattaact accagtacaa ccagtacacc gaggaagaaa aaaacaacat caacttcaac   2400

atcgacgatc tgtcctctaa actgaacgaa tccatcaaca aagctatgat caacatcaac   2460

aagttcctga accagtgctc tgtaagctat ctgatgaact ccatgatccc gtacggtgtt   2520

aaacgtctgg aggacttcga tgcgtctctg aaagacgccc tgctgaaata catttacgac   2580

aaccgtggca ctctgatcgg tcaggttgat cgtctgaagg acaaagtgaa caatacctta   2640

tcgaccgaca tccctttca gctcagtaaa tatgtcgata accaacgcct tttgtccact   2700

ctagactag                                                          2709
```

<210> SEQ ID NO 85
<211> LENGTH: 902
<212> TYPE: PRT
<213> ORGANISM: Artificial Sequence
<220> FEATURE:
<223> OTHER INFORMATION: Synthetic

<400> SEQUENCE: 85

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160
```

-continued

```
Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Tyr Gly Gly Phe Thr Gly Ala Arg Lys Ser Ala Arg Lys Arg Lys Asn
    450                 455                 460

Gln Ala Leu Ala Gly Gly Gly Gly Ser Gly Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
            500                 505                 510

Gly Glu Glu Ile Thr Ser Asp Thr Asn Ile Glu Ala Ala Glu Glu Asn
        515                 520                 525

Ile Ser Leu Asp Leu Ile Gln Gln Tyr Tyr Leu Thr Phe Asn Phe Asp
    530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
            580                 585                 590
```

```
Glu Phe Glu His Gly Lys Ser Arg Ile Ala Leu Thr Asn Ser Val Asn
        595                 600                 605

Glu Ala Leu Leu Asn Pro Ser Arg Val Tyr Thr Phe Phe Ser Ser Asp
    610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Ile Pro Tyr Ile
            660                 665                 670

Gly Pro Ala Leu Asn Ile Gly Asn Met Leu Tyr Lys Asp Asp Phe Val
        675                 680                 685

Gly Ala Leu Ile Phe Ser Gly Ala Val Ile Leu Leu Glu Phe Ile Pro
    690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
                725                 730                 735

Arg Asn Glu Lys Trp Asp Glu Val Tyr Lys Tyr Ile Val Thr Asn Trp
            740                 745                 750

Leu Ala Lys Val Asn Thr Gln Ile Asp Leu Ile Arg Lys Lys Met Lys
        755                 760                 765

Glu Ala Leu Glu Asn Gln Ala Glu Ala Thr Lys Ala Ile Ile Asn Tyr
    770                 775                 780

Gln Tyr Asn Gln Tyr Thr Glu Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
        835                 840                 845

Ser Leu Lys Asp Ala Leu Leu Lys Tyr Ile Tyr Asp Asn Arg Gly Thr
    850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Asp
            900


<210> SEQ ID NO 86
<211> LENGTH: 2889
<212> TYPE: DNA
<213> ORGANISM: Artificial Sequence
<220> FEATURE:
<223> OTHER INFORMATION: Synthetic

<400> SEQUENCE: 86

ggatccttgg tacgagatga cgttgactat caaattttcc gcgactttgc ggaaaataaa      60

ggtaagtttt tcgtcggcgc cacagacctg tccgtcaaaa ataagagagg ccagaacatc     120

ggtaacgcac tgagcaacgt ccctatgatt gattttagtg tagcggacgt taataaacgg     180

attgcaaccg tcgttgatcc gcagtatgct gtcagcgtca aacatgctaa agcggaagtt     240

catacgttct attacgggca atataacggc cataacgatg tggctgataa agaaaatgaa     300
```

-continued

```
tatcgcgtgg tcgagcagaa caattacgaa ccgcacaaag cgtggggcgc gagtaattta    360
ggccgcctgg aggactataa catggcccgt ttcaataaat tcgtgaccga ggtagcaccg    420
atcgccccca cagatgctgg tgggggcctg gatacctaca aagataaaaa ccgcttctct    480
agcttcgtgc gcattggcgc cggtcgtcag ctcgtgtacg agaagggtgt ctatcaccag    540
gaaggtaatg aaaaggggta cgacctccgt gatttgtccc aggcgtatcg ctacgctatt    600
gccggaaccc cgtataaaga tattaatatc gatcaaacca tgaataccga aggcctaatt    660
ggtttcggga atcataataa gcaatatagc gcagaagagc taaagcaggc cctcagccaa    720
gatgcgttaa ccaattacgg agtgttaggc gatagcggca gtccgctgtt tgccttcgat    780
aaacagaaaa atcaatgggt gtttctgggc acttatgatt attgggccgg atatggtaaa    840
aagagctggc aggaatggaa tatttataaa aaggaattcg cagacaaaat caagcagcat    900
gacaacgcag gtacggtgaa ggggaacggc gaacatcact ggaagacgac cggcacgaat    960
agtcatatcg gatcgacggc cgttcgcctg gcgaacaatg agggcgatgc aaacaatggg   1020
caaaacgtga cctttgagga caacggtacc ctggtcctta accagaacat aaatcagggc   1080
gcgggaggct tgttctttaa aggcgactat actgttaagg gagcaaacaa tgacatcacc   1140
tggttagggg ccggtattga cgttgcggat ggaaaaaagg tggtttggca ggttaaaaac   1200
cctaacgggg accggctggc aaaaatcggc aaagggacat tggaaattaa tggtaccggt   1260
gtgaatcagg gtcagctgaa agtgggagat gggaccgtga ttctgaacca gaaagcagac   1320
gctgacaaaa aggtgcaagc ctttagccaa gtaggaattg ttagtggtcg tggcacactc   1380
gtcttgaact caagcaacca aataaatccg gataacctgt actttggatt tcgtggcgga   1440
cgcctggatg ctaacgggaa tgatctgacc tttgaacata tccgtaacgt tgacgagggt   1500
gcgcgcatag ttaatcataa tactgaccat gcatcaacta tcaccttgac cgggaaaagt   1560
ctgattacaa acccaaactc tctgtcagta cattccatcc agaatgatta tgatgaagac   1620
gattactcat actattaccg gccgcgtaga ccaattccac aaggtaaaga tctttattac   1680
aaaaattacc gttattacgc attaaaatcc ggagggcggc tgaatgcacc tatgccggaa   1740
aatggcgtgg ccgaaaacaa tgactggatt tttatgggtt atactcaaga agaggctcgc   1800
aaaaatgcaa tgaaccataa aaataaccga aggatcggtg atttcggcgg atttttcgat   1860
gaggaaaatg gtaaaggtca caatggtgcg ctgaatctaa attttaacgg caaaagtgcc   1920
cagaaacgtt tccttctgac tggtggcgct aatctgaatg gtaaaatcag tgtgacgcag   1980
ggtaacgtgc tgctttctgg ccggccaact ccgcatgcac gtgattttgt aaataaatcg   2040
agcgctcgta aagatgcgca tttttctaaa aataacgagg tcgtgtttga agatgactgg   2100
ataaatcgca cctttaaagc ggcagaaatc gcggttaatc agagtgcgag cttttcatcg   2160
ggtaggaatg tatctgatat tacagcaaac attacagcca ctgataatgc gaaggtcaac   2220
ctgggttata aaaacggtga tgaagtttgt gttcgatcgg attacacggg ctatgttacc   2280
tgcaacactg gcaatctgtc tgataaagcg cttaactctt ttgacgccac gcgcattaac   2340
gggaatgtga acctgaacca aaacgctgcc ttggtacttg gtaaggccgc gttgtggggt   2400
aaaattcagg gccagggcaa ctcccgtgtg tctctgaacc agcactcgaa gtggcacctg   2460
acgggggact cgcaggtgca caacttgtcc ctggccgata gccatattca ccttaacaat   2520
gcgtccgatg cccagtcagc taataaatat catacgatca aaatcaatca cctctctggc   2580
aacggtcact ttcactactt aacggattta gcaaaaaact taggggataa agtcctggta   2640
aaagaatcag cgagcggaca ttatcagtta catgtacaga acaaaaacag cgagccaaat   2700
```

```
caggaaggcc ttgacttatt tgatgcttca tcggtacaag atcgttccag actgttcgtt   2760

tcactcgcga atcactacgt tgatctgggt gcgctgcgct atactataaa gacggaaaat   2820

ggcataacac gcctctataa tccctatgcc ggtaacggcc gtccggtgaa acctgctccc   2880

tgcgtcgac                                                           2889
```

<210> SEQ ID NO 87
<211> LENGTH: 4296
<212> TYPE: DNA
<213> ORGANISM: Artificial Sequence
<220> FEATURE:
<223> OTHER INFORMATION: Synthetic

<400> SEQUENCE: 87

```
ggatccttgg tacgagatga cgttgactat caaattttcc gcgactttgc ggaaaataaa     60

ggtaagtttt tcgtcggcgc cacagacctg tccgtcaaaa ataagagagg ccagaacatc    120

ggtaacgcac tgagcaacgt ccctatgatt gattttagtg tagcggacgt taataaacgg    180

attgcaaccg tcgttgatcc gcagtatgct gtcagcgtca aacatgctaa agcggaagtt    240

catacgttct attacgggca atataacggc cataacgatg tggctgataa agaaaatgaa    300

tatcgcgtgg tcgagcagaa caattacgaa ccgcacaaag cgtggggcgc gagtaattta    360

ggccgcctgg aggactataa catggcccgt ttcaataaat tcgtgaccga ggtagcaccg    420

atcgcccccca cagatgctgg tgggggcctg gatacctaca aagataaaaa ccgcttctct    480

agcttcgtgc gcattggcgc cggtcgtcag ctcgtgtacg agaagggtgt ctatcaccag    540

gaaggtaatg aaaaggggta cgacctccgt gatttgtccc aggcgtatcg ctacgctatt    600

gccggaaccc cgtataaaga tattaatatc gatcaaacca tgaataccga aggcctaatt    660

ggtttcggga atcataataa gcaatatagc gcagaagagc taaagcaggc cctcagccaa    720

gatgcgttaa ccaattacgg agtgttaggc gatagcggca gtccgctgtt tgccttcgat    780

aaacagaaaa atcaatgggt gtttctgggc acttatgatt attgggccgg atatggtaaa    840

aagagctggc aggaatggaa tatttataaa aaggaattcg cagacaaaat caagcagcat    900

gacaacgcag gtacggtgaa ggggaacggc gaacatcact ggaagacgac cggcacgaat    960

agtcatatcg gatcgacggc cgttcgcctg gcgaacaatg agggcgatgc aaacaatggg   1020

caaaacgtga cctttgagga caacggtacc ctggtcctta accagaacat aaatcagggc   1080

gcgggaggct tgttctttaa aggcgactat actgttaagg gagcaaacaa tgacatcacc   1140

tggttagggg ccggtattga cgttgcggat ggaaaaaagg tggtttggca ggttaaaaac   1200

cctaacgggg accggctggc aaaaatcggc aaagggacat tggaaattaa tggtaccggt   1260

gtgaatcagg gtcagctgaa agtgggagat gggaccgtga ttctgaacca gaaagcagac   1320

gctgacaaaa aggtgcaagc ctttagccaa gtaggaattg ttagtggtcg tggcacactc   1380

gtcttgaact caagcaacca aataaatccg gataacctgt actttggatt tcgtggcgga   1440

cgcctggatg ctaacgggaa tgatctgacc tttgaacata tccgtaacgt tgacgagggt   1500

gcgcgcatag ttaatcataa tactgaccat gcatcaacta tcaccttgac cgggaaaagt   1560

ctgattacaa acccaaactc tctgtcagta cattccatcc agaatgatta tgatgaagac   1620

gattactcat actattaccg gccgcgtaga ccaattccac aaggtaaaga tctttattac   1680

aaaaattacc gttattacgc attaaaatcc ggagggcggc tgaatgcacc tatgccggaa   1740

aatggcgtgg ccgaaaacaa tgactggatt tttatgggtt atactcaaga agaggctcgc   1800

aaaaatgcaa tgaaccataa aaataaccga aggatcggtg atttcggcgg atttttcgat   1860
```

gaggaaaatg gtaaaggtca caatggtgcg ctgaatctaa attttaacgg caaaagtgcc 1920
cagaaacgtt tccttctgac tggtggcgct aatctgaatg gtaaaatcag tgtgacgcag 1980
ggtaacgtgc tgctttctgg ccggccaact ccgcatgcac gtgattttgt aaataaatcg 2040
agcgctcgta aagatgcgca tttttctaaa aataacgagg tcgtgtttga agatgactgg 2100
ataaatcgca cctttaaagc ggcagaaatc gcggttaatc agagtgcgag cttttcatcg 2160
ggtaggaatg tatctgatat tacagcaaac attacagcca ctgataatgc gaaggtcaac 2220
ctgggttata aaaacggtga tgaagtttgt gttcgatcgg attacacggg ctatgttacc 2280
tgcaacactg gcaatctgtc tgataaagcg cttaactctt ttgacgccac gcgcattaac 2340
gggaatgtga acctgaacca aaacgctgcc ttggtacttg gtaaggccgc gttgtggggt 2400
aaaattcagg gccagggcaa ctcccgtgtg tctctgaacc agcactcgaa gtggcacctg 2460
acgggggact cgcaggtgca caacttgtcc ctggccgata gccatattca ccttaacaat 2520
gcgtccgatg cccagtcagc taataaatat catacgatca aaatcaatca cctctctggc 2580
aacggtcact ttcactactt aacggattta gcaaaaaact taggggataa agtcctggta 2640
aaagaatcag cgagcggaca ttatcagtta catgtacaga acaaaacagg cgagccaaat 2700
caggaaggcc ttgacttatt tgatgcttca tcggtacaag atcgttccag actgttcgtt 2760
tcactcgcga atcactacgt tgatctgggt gcgctgcgct atactataaa gacggaaaat 2820
ggcataacac gcctctataa tccctatgcc ggtaacggcc gtccggtgaa acctgctccc 2880
tgcgtcgacg gcatcattac ctccaaaact aaatctctga tagaaggtag atttggcggt 2940
ttcacgggcg cacgcaaatc agcgcgtaaa cgtaagaacc aggcgctagc gggcggtggc 3000
ggtagcggcg gtggcggtag cggcggtggc ggtagcgcac tagtgctgca gtgtatcaag 3060
gttaacaact gggatttatt cttcagcccg agtgaagaca acttcaccaa cgacctgaac 3120
aaaggtgaag aaatcacctc agatactaac atcgaagcag ccgaagaaaa catctcgctg 3180
gacctgatcc agcagtacta cctgaccttt aatttcgaca acgagccgga aaacatttct 3240
atcgaaaacc tgagctctga tatcatcggc cagctggaac tgatgccgaa catcgaacgt 3300
ttcccaaacg gtaaaaagta cgagctggac aaatatacca tgttccacta cctgcgcgcg 3360
caggaatttg aacacggcaa atcccgtatc gcactgacta actccgttaa cgaagctctg 3420
ctcaacccgt cccgtgtata caccttcttc tctagcgact acgtgaaaaa ggtcaacaaa 3480
gcgactgaag ctgcaatgtt cttgggttgg gttgaacagc ttgtttatga ttttaccgac 3540
gagacgtccg aagtatctac taccgacaaa attgcggata tcactatcat catcccgtac 3600
atcggtccgg ctctgaacat tggcaacatg ctgtacaaag acgacttcgt tggcgcactg 3660
atcttctccg gtgcggtgat cctgctggag ttcatcccgg aaatcgccat cccggtactg 3720
ggcacctttg ctctggtttc ttacattgca aacaaggttc tgactgtaca aaccatcgac 3780
aacgcgctga gcaaacgtaa cgaaaaatgg gatgaagttt acaaatatat cgtgaccaac 3840
tggctggcta aggttaatac tcagatcgac ctcatccgca aaaaaatgaa agaagcactg 3900
gaaaaccagg cggaagctac caaggcaatc attaactacc agtacaacca gtacaccgag 3960
gaagaaaaaa acaacatcaa cttcaacatc gacgatctgt cctctaaact gaacgaatcc 4020
atcaacaaag ctatgatcaa catcaacaag ttcctgaacc agtgctctgt aagctatctg 4080
atgaactcca tgatcccgta cggtgttaaa cgtctggagg acttcgatgc gtctctgaaa 4140
gacgccctgc tgaaatacat ttacgacaac cgtggcactc tgatcggtca ggttgatcgt 4200
ctgaaggaca aagtgaacaa taccttatcg accgacatcc cttttcagct cagtaaatat 4260

-continued gtcgataacc aacgcctttt gtccactcta gactag 4296

<210> SEQ ID NO 88
<211> LENGTH: 1431
<212> TYPE: PRT
<213> ORGANISM: Artificial Sequence
<220> FEATURE:
<223> OTHER INFORMATION: Synthetic

<400> SEQUENCE: 88

Gly Ser Leu Val Arg Asp Asp Val Asp Tyr Gln Ile Phe Arg Asp Phe
1 5 10 15

Ala Glu Asn Lys Gly Lys Phe Phe Val Gly Ala Thr Asp Leu Ser Val
20 25 30

Lys Asn Lys Arg Gly Gln Asn Ile Gly Asn Ala Leu Ser Asn Val Pro
35 40 45

Met Ile Asp Phe Ser Val Ala Asp Val Asn Lys Arg Ile Ala Thr Val
50 55 60

Val Asp Pro Gln Tyr Ala Val Ser Val Lys His Ala Lys Ala Glu Val
65 70 75 80

His Thr Phe Tyr Tyr Gly Gln Tyr Asn Gly His Asn Asp Val Ala Asp
85 90 95

Lys Glu Asn Glu Tyr Arg Val Val Glu Gln Asn Asn Tyr Glu Pro His
100 105 110

Lys Ala Trp Gly Ala Ser Asn Leu Gly Arg Leu Glu Asp Tyr Asn Met
115 120 125

Ala Arg Phe Asn Lys Phe Val Thr Glu Val Ala Pro Ile Ala Pro Thr
130 135 140

Asp Ala Gly Gly Gly Leu Asp Thr Tyr Lys Asp Lys Asn Arg Phe Ser
145 150 155 160

Ser Phe Val Arg Ile Gly Ala Gly Arg Gln Leu Val Tyr Glu Lys Gly
165 170 175

Val Tyr His Gln Glu Gly Asn Glu Lys Gly Tyr Asp Leu Arg Asp Leu
180 185 190

Ser Gln Ala Tyr Arg Tyr Ala Ile Ala Gly Thr Pro Tyr Lys Asp Ile
195 200 205

Asn Ile Asp Gln Thr Met Asn Thr Glu Gly Leu Ile Gly Phe Gly Asn
210 215 220

His Asn Lys Gln Tyr Ser Ala Glu Glu Leu Lys Gln Ala Leu Ser Gln
225 230 235 240

Asp Ala Leu Thr Asn Tyr Gly Val Leu Gly Asp Ser Gly Ser Pro Leu
245 250 255

Phe Ala Phe Asp Lys Gln Lys Asn Gln Trp Val Phe Leu Gly Thr Tyr
260 265 270

Asp Tyr Trp Ala Gly Tyr Gly Lys Lys Ser Trp Gln Glu Trp Asn Ile
275 280 285

Tyr Lys Lys Glu Phe Ala Asp Lys Ile Lys Gln His Asp Asn Ala Gly
290 295 300

Thr Val Lys Gly Asn Gly Glu His His Trp Lys Thr Thr Gly Thr Asn
305 310 315 320

Ser His Ile Gly Ser Thr Ala Val Arg Leu Ala Asn Asn Glu Gly Asp
325 330 335

Ala Asn Asn Gly Gln Asn Val Thr Phe Glu Asp Asn Gly Thr Leu Val
340 345 350

Leu Asn Gln Asn Ile Asn Gln Gly Ala Gly Gly Leu Phe Phe Lys Gly

-continued

```
        355                 360                 365

Asp Tyr Thr Val Lys Gly Ala Asn Asn Asp Ile Thr Trp Leu Gly Ala
    370                 375                 380

Gly Ile Asp Val Ala Asp Gly Lys Lys Val Val Trp Gln Val Lys Asn
385                 390                 395                 400

Pro Asn Gly Asp Arg Leu Ala Lys Ile Gly Lys Gly Thr Leu Glu Ile
                405                 410                 415

Asn Gly Thr Gly Val Asn Gln Gly Gln Leu Lys Val Gly Asp Gly Thr
            420                 425                 430

Val Ile Leu Asn Gln Lys Ala Asp Ala Asp Lys Lys Val Gln Ala Phe
        435                 440                 445

Ser Gln Val Gly Ile Val Ser Gly Arg Gly Thr Leu Val Leu Asn Ser
    450                 455                 460

Ser Asn Gln Ile Asn Pro Asp Asn Leu Tyr Phe Gly Phe Arg Gly Gly
465                 470                 475                 480

Arg Leu Asp Ala Asn Gly Asn Asp Leu Thr Phe Glu His Ile Arg Asn
                485                 490                 495

Val Asp Glu Gly Ala Arg Ile Val Asn His Asn Thr Asp His Ala Ser
            500                 505                 510

Thr Ile Thr Leu Thr Gly Lys Ser Leu Ile Thr Asn Pro Asn Ser Leu
        515                 520                 525

Ser Val His Ser Ile Gln Asn Asp Tyr Asp Glu Asp Asp Tyr Ser Tyr
    530                 535                 540

Tyr Tyr Arg Pro Arg Arg Pro Ile Pro Gln Gly Lys Asp Leu Tyr Tyr
545                 550                 555                 560

Lys Asn Tyr Arg Tyr Tyr Ala Leu Lys Ser Gly Gly Arg Leu Asn Ala
                565                 570                 575

Pro Met Pro Glu Asn Gly Val Ala Glu Asn Asn Asp Trp Ile Phe Met
            580                 585                 590

Gly Tyr Thr Gln Glu Glu Ala Arg Lys Asn Ala Met Asn His Lys Asn
        595                 600                 605

Asn Arg Arg Ile Gly Asp Phe Gly Gly Phe Phe Asp Glu Glu Asn Gly
    610                 615                 620

Lys Gly His Asn Gly Ala Leu Asn Leu Asn Phe Asn Gly Lys Ser Ala
625                 630                 635                 640

Gln Lys Arg Phe Leu Leu Thr Gly Gly Ala Asn Leu Asn Gly Lys Ile
                645                 650                 655

Ser Val Thr Gln Gly Asn Val Leu Leu Ser Gly Arg Pro Thr Pro His
            660                 665                 670

Ala Arg Asp Phe Val Asn Lys Ser Ser Ala Arg Lys Asp Ala His Phe
        675                 680                 685

Ser Lys Asn Asn Glu Val Val Phe Glu Asp Asp Trp Ile Asn Arg Thr
    690                 695                 700

Phe Lys Ala Ala Glu Ile Ala Val Asn Gln Ser Ala Ser Phe Ser Ser
705                 710                 715                 720

Gly Arg Asn Val Ser Asp Ile Thr Ala Asn Ile Thr Ala Thr Asp Asn
                725                 730                 735

Ala Lys Val Asn Leu Gly Tyr Lys Asn Gly Asp Glu Val Cys Val Arg
            740                 745                 750

Ser Asp Tyr Thr Gly Tyr Val Thr Cys Asn Thr Gly Asn Leu Ser Asp
        755                 760                 765

Lys Ala Leu Asn Ser Phe Asp Ala Thr Arg Ile Asn Gly Asn Val Asn
    770                 775                 780
```

-continued

```
Leu Asn Gln Asn Ala Ala Leu Val Leu Gly Lys Ala Ala Leu Trp Gly
785                 790                 795                 800

Lys Ile Gln Gly Gln Gly Asn Ser Arg Val Ser Leu Asn Gln His Ser
                805                 810                 815

Lys Trp His Leu Thr Gly Asp Ser Gln Val His Asn Leu Ser Leu Ala
            820                 825                 830

Asp Ser His Ile His Leu Asn Asn Ala Ser Asp Ala Gln Ser Ala Asn
        835                 840                 845

Lys Tyr His Thr Ile Lys Ile Asn His Leu Ser Gly Asn Gly His Phe
    850                 855                 860

His Tyr Leu Thr Asp Leu Ala Lys Asn Leu Gly Asp Lys Val Leu Val
865                 870                 875                 880

Lys Glu Ser Ala Ser Gly His Tyr Gln Leu His Val Gln Asn Lys Thr
                885                 890                 895

Gly Glu Pro Asn Gln Glu Gly Leu Asp Leu Phe Asp Ala Ser Ser Val
            900                 905                 910

Gln Asp Arg Ser Arg Leu Phe Val Ser Leu Ala Asn His Tyr Val Asp
        915                 920                 925

Leu Gly Ala Leu Arg Tyr Thr Ile Lys Thr Glu Asn Gly Ile Thr Arg
    930                 935                 940

Leu Tyr Asn Pro Tyr Ala Gly Asn Gly Arg Pro Val Lys Pro Ala Pro
945                 950                 955                 960

Cys Val Asp Gly Ile Ile Thr Ser Lys Thr Lys Ser Leu Ile Glu Gly
                965                 970                 975

Arg Phe Gly Gly Phe Thr Gly Ala Arg Lys Ser Ala Arg Lys Arg Lys
            980                 985                 990

Asn Gln Ala Leu Ala Gly Gly Gly  Gly Ser Gly Gly Gly  Gly Ser Gly
        995                 1000                1005

Gly Gly  Gly Ser Ala Leu Val  Leu Gln Cys Ile Lys  Val Asn Asn
    1010                1015                1020

Trp Asp  Leu Phe Phe Ser Pro  Ser Glu Asp Asn Phe  Thr Asn Asp
    1025                1030                1035

Leu Asn  Lys Gly Glu Glu Ile  Thr Ser Asp Thr Asn  Ile Glu Ala
    1040                1045                1050

Ala Glu  Glu Asn Ile Ser Leu  Asp Leu Ile Gln Gln  Tyr Tyr Leu
    1055                1060                1065

Thr Phe  Asn Phe Asp Asn Glu  Pro Glu Asn Ile Ser  Ile Glu Asn
    1070                1075                1080

Leu Ser  Ser Asp Ile Ile Gly  Gln Leu Glu Leu Met  Pro Asn Ile
    1085                1090                1095

Glu Arg  Phe Pro Asn Gly Lys  Lys Tyr Glu Leu Asp  Lys Tyr Thr
    1100                1105                1110

Met Phe  His Tyr Leu Arg Ala  Gln Glu Phe Glu His  Gly Lys Ser
    1115                1120                1125

Arg Ile  Ala Leu Thr Asn Ser  Val Asn Glu Ala Leu  Leu Asn Pro
    1130                1135                1140

Ser Arg  Val Tyr Thr Phe Phe  Ser Ser Asp Tyr Val  Lys Lys Val
    1145                1150                1155

Asn Lys  Ala Thr Glu Ala Ala  Met Phe Leu Gly Trp  Val Glu Gln
    1160                1165                1170

Leu Val  Tyr Asp Phe Thr Asp  Glu Thr Ser Glu Val  Ser Thr Thr
    1175                1180                1185

Asp Lys  Ile Ala Asp Ile Thr  Ile Ile Ile Pro Tyr  Ile Gly Pro
    1190                1195                1200
```

```
Ala Leu  Asn Ile Gly Asn Met  Leu Tyr Lys Asp Asp  Phe Val Gly
    1205                 1210                 1215

Ala Leu  Ile Phe Ser Gly Ala  Val Ile Leu Leu Glu  Phe Ile Pro
    1220                 1225                 1230

Glu Ile  Ala Ile Pro Val Leu  Gly Thr Phe Ala Leu  Val Ser Tyr
    1235                 1240                 1245

Ile Ala  Asn Lys Val Leu Thr  Val Gln Thr Ile Asp  Asn Ala Leu
    1250                 1255                 1260

Ser Lys  Arg Asn Glu Lys Trp  Asp Glu Val Tyr Lys  Tyr Ile Val
    1265                 1270                 1275

Thr Asn  Trp Leu Ala Lys Val  Asn Thr Gln Ile Asp  Leu Ile Arg
    1280                 1285                 1290

Lys Lys  Met Lys Glu Ala Leu  Glu Asn Gln Ala Glu  Ala Thr Lys
    1295                 1300                 1305

Ala Ile  Ile Asn Tyr Gln Tyr  Asn Gln Tyr Thr Glu  Glu Glu Lys
    1310                 1315                 1320

Asn Asn  Ile Asn Phe Asn Ile  Asp Asp Leu Ser Ser  Lys Leu Asn
    1325                 1330                 1335

Glu Ser  Ile Asn Lys Ala Met  Ile Asn Ile Asn Lys  Phe Leu Asn
    1340                 1345                 1350

Gln Cys  Ser Val Ser Tyr Leu  Met Asn Ser Met Ile  Pro Tyr Gly
    1355                 1360                 1365

Val Lys  Arg Leu Glu Asp Phe  Asp Ala Ser Leu Lys  Asp Ala Leu
    1370                 1375                 1380

Leu Lys  Tyr Ile Tyr Asp Asn  Arg Gly Thr Leu Ile  Gly Gln Val
    1385                 1390                 1395

Asp Arg  Leu Lys Asp Lys Val  Asn Asn Thr Leu Ser  Thr Asp Ile
    1400                 1405                 1410

Pro Phe  Gln Leu Ser Lys Tyr  Val Asp Asn Gln Arg  Leu Leu Ser
    1415                 1420                 1425

Thr Leu  Asp
    1430
```

<210> SEQ ID NO 89
<211> LENGTH: 1357
<212> TYPE: DNA
<213> ORGANISM: Artificial Sequence
<220> FEATURE:
<223> OTHER INFORMATION: Synthetic

<400> SEQUENCE: 89

```
gctagcgggc ggtggcggta gcggcggtgg cggtagcggc ggtggcggta gcgcactagt     60

gctgcagtgt atcaaggtta acaactggga tttattcttc agcccgagtg aagacaactt    120

caccaacgac ctgaacaaag gtgaagaaat cacctcagat actaacatcg aagcagccga    180

agaaaacatc tcgctggacc tgatccagca gtactacctg acctttaatt tcgacaacga    240

gccggaaaac atttctatcg aaaacctgag ctctgatatc atcggccagc tggaactgat    300

gccgaacatc gaacgtttcc caaacggtaa aaagtacgag ctggacaaat ataccatgtt    360

ccactacctg cgcgcgcagg aatttgaaca cggcaaatcc cgtatcgcac tgactaactc    420

cgttaacgaa gctctgctca acccgtcccg tgtatacacc ttcttctcta gcgactacgt    480

gaaaaaggtc aacaaagcga ctgaagctgc aatgttcttg ggttgggttg aacagcttgt    540

ttatgatttt accgacgaga cgtccgaagt atctactacc gacaaaattg cggatatcac    600

tatcatcatc ccgtacatcg gtccggctct gaacattggc aacatgctgt acaaagacga    660
```

cttcgttggc gcactgatct tctccggtgc ggtgatcctg ctggagttca tcccggaaat 720
cgccatcccg gtactgggca cctttgctct ggtttcttac attgcaaaca aggttctgac 780
tgtacaaacc atcgacaacg cgctgagcaa acgtaacgaa aaatgggatg aagtttacaa 840
atatatcgtg accaactggc tggctaaggt taatactcag atcgacctca tccgcaaaaa 900
aatgaaagaa gcactggaaa accaggcgga agctaccaag gcaatcatta actaccagta 960
caaccagtac accgaggaag aaaaaaacaa catcaacttc aacatcgacg atctgtcctc 1020
taaactgaac gaatccatca acaaagctat gatcaacatc aacaagttcc tgaaccagtg 1080
ctctgtaagc tatctgatga actccatgat cccgtacggt gttaaacgtc tggaggactt 1140
cgatgcgtct ctgaaagacg ccctgctgaa atacatttac gacaaccgtg gcactctgat 1200
cggtcaggtt gatcgtctga aggacaaagt gaacaatacc ttatcgaccg acatcccttt 1260
tcagctcagt aaatatgtcg ataaccaacg ccttttgtcc actctagaaa tagaaggtag 1320
aagtgggcac catcaccatc accattaatg aaagctt 1357

<210> SEQ ID NO 90
<211> LENGTH: 2745
<212> TYPE: DNA
<213> ORGANISM: Artificial Sequence
<220> FEATURE:
<223> OTHER INFORMATION: Synthetic

<400> SEQUENCE: 90
ggatccatgg agttcgttaa caaacagttc aactataaag acccagttaa cggtgttgac 60
attgcttaca tcaaaatccc gaacgctggc cagatgcagc cggtaaaggc attcaaaatc 120
cacaacaaaa tctgggttat cccggaacgt gatacctta ctaacccgga agaaggtgac 180
ctgaacccgc caccggaagc gaaacaggtg ccggtatctt actatgactc cacctacctg 240
tctaccgata acgaaaagga caactacctg aaaggtgtta ctaaactgtt cgagcgtatt 300
tactccaccg acctgggccg tatgctgctg actagcatcg ttcgcggtat cccgttctgg 360
ggcggttcta ccatcgatac cgaactgaaa gtaatcgaca ctaactgcat caacgttatt 420
cagccggacg gttcctatcg ttccgaagaa ctgaacctgg tgatcatcgg cccgtctgct 480
gatatcatcc agttcgagtg taagagcttt ggtcacgaag ttctgaacct cacccgtaac 540
ggctacggtt ccactcagta catccgtttc tctccggact tcaccttcgg ttttgaagaa 600
tccctggaag tagacacgaa cccactgctg ggcgctggta aattcgcaac tgatcctgcg 660
gttaccctgg ctcacgaact gattcatgca ggccaccgcc tgtacggtat cgccatcaat 720
ccgaaccgtg tcttcaaagt taacaccaac gcgtattacg agatgtccgg tctggaagtt 780
agcttcgaag aactgcgtac ttttggcggt cacgacgcta aattcatcga ctctctgcaa 840
gaaaacgagt tccgtctgta ctactataac aagttcaaag atatcgcatc caccctgaac 900
aaagcgaaat ccatcgtggg taccactgct tctctccagt acatgaagaa cgtttttaaa 960
gaaaaatacc tgctcagcga agacacctcc ggcaaattct ctgtagacaa gttgaaattc 1020
gataaacttt acaaaatgct gactgaaatt tacaccgaag acaacttcgt taagttcttt 1080
aaagttctga accgcaaaac ctatctgaac ttcgacaagg cagtattcaa aatcaacatc 1140
gtgccgaaag ttaactacac tatctacgat ggtttcaacc tgcgtaacac caacctggct 1200
gctaatttta acggccagaa cacggaaatc aacaacatga acttcacaaa actgaaaaac 1260
ttcactggtc tgttcgagtt ttacaagctg ctgtgcgtcg acggcatcat tacctccaaa 1320
actaaatctc tgatagaagg tagatttggc ggtttcacgg gcgcacgcaa atcagcgcgt 1380

```
aaacgtaaga accaggcgct agcgggcggt ggcggtagcg gcggtggcgg tagcggcggt   1440

ggcggtagcg cactagtgct gcagtgtatc aaggttaaca actgggattt attcttcagc   1500

ccgagtgaag acaacttcac caacgacctg aacaaaggtg aagaaatcac ctcagatact   1560

aacatcgaag cagccgaaga aaacatctcg ctggacctga tccagcagta ctacctgacc   1620

tttaatttcg acaacgagcc ggaaaacatt tctatcgaaa acctgagctc tgatatcatc   1680

ggccagctgg aactgatgcc gaacatcgaa cgtttcccaa acggtaaaaa gtacgagctg   1740

gacaaatata ccatgttcca ctacctgcgc gcgcaggaat ttgaacacgg caaatcccgt   1800

atcgcactga ctaactccgt taacgaagct ctgctcaacc cgtcccgtgt atacaccttc   1860

ttctctagcg actacgtgaa aaaggtcaac aaagcgactg aagctgcaat gttcttgggt   1920

tgggttgaac agcttgttta tgattttacc gacgagacgt ccgaagtatc tactaccgac   1980

aaaattgcgg atatcactat catcatcccg tacatcggtc cggctctgaa cattggcaac   2040

atgctgtaca aagacgactt cgttggcgca ctgatcttct ccggtgcggt gatcctgctg   2100

gagttcatcc cggaaatcgc catcccggta ctgggcacct ttgctctggt ttcttacatt   2160

gcaaacaagg ttctgactgt acaaaccatc gacaacgcgc tgagcaaacg taacgaaaaa   2220

tgggatgaag tttacaaata tatcgtgacc aactggctgg ctaaggttaa tactcagatc   2280

gacctcatcc gcaaaaaaat gaaagaagca ctggaaaacc aggcggaagc taccaaggca   2340

atcattaact accagtacaa ccagtacacc gaggaagaaa aaaacaacat caacttcaac   2400

atcgacgatc tgtcctctaa actgaacgaa tccatcaaca aagctatgat caacatcaac   2460

aagttcctga accagtgctc tgtaagctat ctgatgaact ccatgatccc gtacggtgtt   2520

aaacgtctgg aggacttcga tgcgtctctg aaagacgccc tgctgaaata catttacgac   2580

aaccgtggca ctctgatcgg tcaggttgat cgtctgaagg acaaagtgaa caataccta    2640

tcgaccgaca tccctttca gctcagtaaa tatgtcgata accaacgcct tttgtccact    2700

ctagaaatag aaggtagaag tgggcaccat caccatcacc attaa                   2745
```

<210> SEQ ID NO 91
<211> LENGTH: 914
<212> TYPE: PRT
<213> ORGANISM: Artificial Sequence
<220> FEATURE:
<223> OTHER INFORMATION: Synthetic

<400> SEQUENCE: 91

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125
```

```
Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Arg Lys Arg Lys Asn
    450                 455                 460

Gln Ala Leu Ala Gly Gly Gly Gly Ser Gly Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
            500                 505                 510

Gly Glu Glu Ile Thr Ser Asp Thr Asn Ile Glu Ala Ala Glu Glu Asn
        515                 520                 525

Ile Ser Leu Asp Leu Ile Gln Gln Tyr Tyr Leu Thr Phe Asn Phe Asp
    530                 535                 540

Asn Glu Pro Glu Asn Ile Ser Ile Glu Asn Leu Ser Ser Asp Ile Ile
```

545 550 555 560

Gly Gln Leu Glu Leu Met Pro Asn Ile Glu Arg Phe Pro Asn Gly Lys
565 570 575

Lys Tyr Glu Leu Asp Lys Tyr Thr Met Phe His Tyr Leu Arg Ala Gln
580 585 590

Glu Phe Glu His Gly Lys Ser Arg Ile Ala Leu Thr Asn Ser Val Asn
595 600 605

Glu Ala Leu Leu Asn Pro Ser Arg Val Tyr Thr Phe Phe Ser Ser Asp
610 615 620

Tyr Val Lys Lys Val Asn Lys Ala Thr Glu Ala Ala Met Phe Leu Gly
625 630 635 640

Trp Val Glu Gln Leu Val Tyr Asp Phe Thr Asp Glu Thr Ser Glu Val
645 650 655

Ser Thr Thr Asp Lys Ile Ala Asp Ile Thr Ile Ile Ile Pro Tyr Ile
660 665 670

Gly Pro Ala Leu Asn Ile Gly Asn Met Leu Tyr Lys Asp Asp Phe Val
675 680 685

Gly Ala Leu Ile Phe Ser Gly Ala Val Ile Leu Leu Glu Phe Ile Pro
690 695 700

Glu Ile Ala Ile Pro Val Leu Gly Thr Phe Ala Leu Val Ser Tyr Ile
705 710 715 720

Ala Asn Lys Val Leu Thr Val Gln Thr Ile Asp Asn Ala Leu Ser Lys
725 730 735

Arg Asn Glu Lys Trp Asp Glu Val Tyr Lys Tyr Ile Val Thr Asn Trp
740 745 750

Leu Ala Lys Val Asn Thr Gln Ile Asp Leu Ile Arg Lys Lys Met Lys
755 760 765

Glu Ala Leu Glu Asn Gln Ala Glu Ala Thr Lys Ala Ile Ile Asn Tyr
770 775 780

Gln Tyr Asn Gln Tyr Thr Glu Glu Glu Lys Asn Asn Ile Asn Phe Asn
785 790 795 800

Ile Asp Asp Leu Ser Ser Lys Leu Asn Glu Ser Ile Asn Lys Ala Met
805 810 815

Ile Asn Ile Asn Lys Phe Leu Asn Gln Cys Ser Val Ser Tyr Leu Met
820 825 830

Asn Ser Met Ile Pro Tyr Gly Val Lys Arg Leu Glu Asp Phe Asp Ala
835 840 845

Ser Leu Lys Asp Ala Leu Leu Lys Tyr Ile Tyr Asp Asn Arg Gly Thr
850 855 860

Leu Ile Gly Gln Val Asp Arg Leu Lys Asp Lys Val Asn Asn Thr Leu
865 870 875 880

Ser Thr Asp Ile Pro Phe Gln Leu Ser Lys Tyr Val Asp Asn Gln Arg
885 890 895

Leu Leu Ser Thr Leu Glu Ile Glu Gly Arg Ser Gly His His His His
900 905 910

His His

<210> SEQ ID NO 92
<211> LENGTH: 619
<212> TYPE: DNA
<213> ORGANISM: Artificial Sequence
<220> FEATURE:
<223> OTHER INFORMATION: Synthetic

<400> SEQUENCE: 92

```
gctagcgggc ggtggcggta gcggcggtgg cggtagcggc ggtggcggta gcgcactagt     60

gctgcagtgt atcaatctgg attgggacgt aatccgtgat aagaccaaaa caaaaatcga    120

gtctttgaaa gaacacggcc cgatcaaaaa taagatgtct gaatcaccca ataaaactgt    180

ttcggaggaa aaagcgaaac agtatttgga agagtttcat caaaccgcgc ttgaacatcc    240

ggagctcagt gaactgaaaa cagtgacggg aacgaatcct gtttttgcag gcgcaaacta    300

tgcggcttgg gccgtgaatg ttgcccaagt aattgatagt gagaccgcag acaacctgga    360

aaagacgacc gcagcgttaa gcattttacc ggggattggt tccgtgatgg gtatagcgga    420

tggagcggtc caccataaca ctgaggaaat tgtcgcccag tcaatcgctc tgagttccct    480

gatggttgca caggctatcc cactcgtggg ggaactggtt gacataggtt tcgccgccta    540

caacttcgta gaaagcatta ttaatctttt tcaggtggtg cataacagct acaaccgccc    600

tctagaatga taaaagctt                                                 619
```

<210> SEQ ID NO 93
<211> LENGTH: 1971
<212> TYPE: DNA
<213> ORGANISM: Artificial Sequence
<220> FEATURE:
<223> OTHER INFORMATION: Synthetic

<400> SEQUENCE: 93

```
ggatccatgg agttcgttaa caaacagttc aactataaag acccagttaa cggtgttgac     60

attgcttaca tcaaaatccc gaacgctggc cagatgcagc cggtaaaggc attcaaaatc    120

cacaacaaaa tctgggttat cccggaacgt gataccttta ctaacccgga agaaggtgac    180

ctgaacccgc caccggaagc gaaacaggtg ccggtatctt actatgactc cacctacctg    240

tctaccgata acgaaaagga caactacctg aaaggtgtta ctaaactgtt cgagcgtatt    300

tactccaccg acctgggccg tatgctgctg actagcatcg ttcgcggtat cccgttctgg    360

ggcggttcta ccatcgatac cgaactgaaa gtaatcgaca ctaactgcat caacgttatt    420

cagccggacg gttcctatcg ttccgaagaa ctgaacctgg tgatcatcgg cccgtctgct    480

gatatcatcc agttcgagtg taagagcttt ggtcacgaag ttctgaacct cacccgtaac    540

ggctacggtt ccactcagta catccgtttc tctccggact tcaccttcgg ttttgaagaa    600

tccctggaag tagacacgaa cccactgctg ggcgctggta aattcgcaac tgatcctgcg    660

gttaccctgg ctcacgaact gattcatgca ggccaccgcc tgtacggtat cgccatcaat    720

ccgaaccgtg tcttcaaagt taacaccaac gcgtattacg agatgtccgg tctggaagtt    780

agcttcgaag aactgcgtac ttttggcggt cacgacgcta aattcatcga ctctctgcaa    840

gaaaacgagt tccgtctgta ctactataac aagttcaaag atatcgcatc caccctgaac    900

aaagcgaaat ccatcgtggg taccactgct tctctccagt acatgaagaa cgtttttaaa    960

gaaaaatacc tgctcagcga agacacctcc ggcaaattct ctgtagacaa gttgaaattc   1020

gataaacttt acaaaatgct gactgaaatt tacaccgaag acaacttcgt taagttcttt   1080

aaagttctga accgcaaaac ctatctgaac ttcgacaagg cagtattcaa aatcaacatc   1140

gtgccgaaag ttaactacac tatctacgat ggtttcaacc tgcgtaacac caacctggct   1200

gctaatttta acggccagaa cacggaaatc aacaacatga acttcacaaa actgaaaaac   1260

ttcactggtc tgttcgagtt ttacaagctg ctgtgcgtcg acggcatcat tacctccaaa   1320

actaaatctc tgatagaagg tagatacggt ggtttcctgg cgctagcggg cggtggcggt   1380

agcggcggtg gcggtagcgg cggtggcggt agcgcactag tgctgcagtg tatcaatctg   1440
```

```
gattgggacg taatccgtga taagaccaaa acaaaaatcg agtctttgaa agaacacggc   1500

ccgatcaaaa ataagatgtc tgaatcaccc aataaaactg tttcggagga aaaagcgaaa   1560

cagtatttgg aagagtttca tcaaaccgcg cttgaacatc cggagctcag tgaactgaaa   1620

acagtgacgg gaacgaatcc tgtttttgca ggcgcaaact atgcggcttg ggccgtgaat   1680

gttgcccaag taattgatag tgagaccgca gacaacctgg aaaagacgac cgcagcgtta   1740

agcattttac cggggattgg ttccgtgatg ggtatagcgg atggagcggt ccaccataac   1800

actgaggaaa ttgtcgccca gtcaatcgct ctgagttccc tgatggttgc acaggctatc   1860

ccactcgtgg gggaactggt tgacataggt ttcgccgcct acaacttcgt agaaagcatt   1920

attaatcttt ttcaggtggt gcataacagc tacaaccgcc ctctagaatg a            1971
```

<210> SEQ ID NO 94
<211> LENGTH: 656
<212> TYPE: PRT
<213> ORGANISM: Artificial Sequence
<220> FEATURE:
<223> OTHER INFORMATION: Synthetic

<400> SEQUENCE: 94

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
```

```
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Tyr Gly Gly Phe Leu Ala Leu Ala Gly Gly Gly Gly Ser Gly Gly Gly
    450                 455                 460

Gly Ser Gly Gly Gly Gly Ser Ala Leu Val Leu Gln Cys Ile Asn Leu
465                 470                 475                 480

Asp Trp Asp Val Ile Arg Asp Lys Thr Lys Thr Lys Ile Glu Ser Leu
                485                 490                 495

Lys Glu His Gly Pro Ile Lys Asn Lys Met Ser Glu Ser Pro Asn Lys
            500                 505                 510

Thr Val Ser Glu Glu Lys Ala Lys Gln Tyr Leu Glu Glu Phe His Gln
        515                 520                 525

Thr Ala Leu Glu His Pro Glu Leu Ser Glu Leu Lys Thr Val Thr Gly
    530                 535                 540

Thr Asn Pro Val Phe Ala Gly Ala Asn Tyr Ala Ala Trp Ala Val Asn
545                 550                 555                 560

Val Ala Gln Val Ile Asp Ser Glu Thr Ala Asp Asn Leu Glu Lys Thr
                565                 570                 575

Thr Ala Ala Leu Ser Ile Leu Pro Gly Ile Gly Ser Val Met Gly Ile
            580                 585                 590

Ala Asp Gly Ala Val His His Asn Thr Glu Glu Ile Val Ala Gln Ser
        595                 600                 605

Ile Ala Leu Ser Ser Leu Met Val Ala Gln Ala Ile Pro Leu Val Gly
    610                 615                 620

Glu Leu Val Asp Ile Gly Phe Ala Ala Tyr Asn Phe Val Glu Ser Ile
625                 630                 635                 640

Ile Asn Leu Phe Gln Val Val His Asn Ser Tyr Asn Arg Pro Leu Glu
                645                 650                 655
```

<210> SEQ ID NO 95
<211> LENGTH: 1329
<212> TYPE: DNA
<213> ORGANISM: Artificial Sequence
<220> FEATURE:
<223> OTHER INFORMATION: Synthetic

<400> SEQUENCE: 95

```
ggatccatgc ctattactat taacaatttt cgttatagcg atcccgtcaa caatgacacc      60

attatcatga tggaaccgcc atattgcaaa ggactggaca tttactataa agccttcaag     120

attactgacc gcatttggat tgttccagag cgttacgagt tcgggacgaa accagaagat     180

tttaacccgc cttcatcgct gatcgaagga gcatcagagt attacgatcc gaactatctg     240

cgtacggaca gcgataaaga ccgcttctta cagaccatgg tcaaactttt taaccgtatt     300

aagaacaatg tggccggaga agcactcttg gataagatta tcaacgcgat tccatacctg     360

ggcaattctt acagcctgct ggataaattt gacacaaata gtaattcagt cagctttaac     420

ctgttagaac aagatccgag tggcgcaacc acgaagtctg ccatgctgac aaatctgatc     480

atttttggtc caggtcctgt actgaataaa aatgaagtac gcggcatcgt tctccgcgtg     540

gacaataaga actacttccc atgccgtgac ggcttcggtt cgatcatgca gatggctttc     600

tgtccggagt acgttccgac gtttgataat gttattgaga atatcacgag tttaacaatc     660

ggtaagtcaa aatattttca agatccggcc cttctcctta tgcatgaact gattcacgtg     720

ctgcacggct tatatggtat gcaagtgtcc tcgcatgaaa tcattccgtc caaacaggaa     780

atttatatgc agcataccta cccgatttca gctgaagagt tgtttacgtt tggtggccag     840

gacgcgaatt tgatctccat cgacatcaaa aacgatctgt atgagaaaac attaaatgac     900

tataaagcga ttgcgaacaa actgtctcag gtgactagct gcaacgatcc taacattgat     960

attgattcct acaaacaaat ttatcaacag aaataccagt tcgataaaga cagcaatggt    1020

cagtatatcg taaacgaaga taaatttcag atcctgtata acagcattat gtatggcttt    1080

accgaaattg agttggggaa gaaatttaac attaaaaccc gtctgtctta ttttagtatg    1140

aaccatgatc cggtgaaaat ccccaatctg cttgatgata ccatttataa tgataccgaa    1200

gggttcaaca ttgaatctaa ggatctgaaa tccgaataca aaggccaaaa tatgcgtgtt    1260

aatactaacg ctttccgtaa tgttgatggt agtggactcg tctcgaaact gattgggttg    1320

tgtgtcgac                                                            1329
```

<210> SEQ ID NO 96
<211> LENGTH: 2736
<212> TYPE: DNA
<213> ORGANISM: Artificial Sequence
<220> FEATURE:
<223> OTHER INFORMATION: Synthetic

<400> SEQUENCE: 96

```
ggatccatgc ctattactat taacaatttt cgttatagcg atcccgtcaa caatgacacc      60

attatcatga tggaaccgcc atattgcaaa ggactggaca tttactataa agccttcaag     120

attactgacc gcatttggat tgttccagag cgttacgagt tcgggacgaa accagaagat     180

tttaacccgc cttcatcgct gatcgaagga gcatcagagt attacgatcc gaactatctg     240

cgtacggaca gcgataaaga ccgcttctta cagaccatgg tcaaactttt taaccgtatt     300

aagaacaatg tggccggaga agcactcttg gataagatta tcaacgcgat tccatacctg     360

ggcaattctt acagcctgct ggataaattt gacacaaata gtaattcagt cagctttaac     420

ctgttagaac aagatccgag tggcgcaacc acgaagtctg ccatgctgac aaatctgatc     480

atttttggtc caggtcctgt actgaataaa aatgaagtac gcggcatcgt tctccgcgtg     540

gacaataaga actacttccc atgccgtgac ggcttcggtt cgatcatgca gatggctttc     600

tgtccggagt acgttccgac gtttgataat gttattgaga atatcacgag tttaacaatc     660

ggtaagtcaa aatattttca agatccggcc cttctcctta tgcatgaact gattcacgtg     720
```

ctgcacggct tatatggtat gcaagtgtcc tcgcatgaaa tcattccgtc caaacaggaa 780
atttatatgc agcataccta cccgatttca gctgaagagt tgtttacgtt tggtggccag 840
gacgcgaatt tgatctccat cgacatcaaa aacgatctgt atgagaaaac attaaatgac 900
tataaagcga ttgcgaacaa actgtctcag gtgactagct gcaacgatcc taacattgat 960
attgattcct acaaacaaat ttatcaacag aaataccagt tcgataaaga cagcaatggt 1020
cagtatatcg taaacgaaga taaatttcag atcctgtata acagcattat gtatggcttt 1080
accgaaattg agttggggaa gaaatttaac attaaaaccc gtctgtctta ttttagtatg 1140
aaccatgatc cggtgaaaat ccccaatctg cttgatgata ccatttataa tgataccgaa 1200
gggttcaaca ttgaatctaa ggatctgaaa tccgaataca aaggccaaaa tatgcgtgtt 1260
aatactaacg ctttccgtaa tgttgatggt agtggactcg tctcgaaact gattgggttg 1320
tgtgtcgacg gcatcattac ctccaaaact aaatctctga tagaaggtag atttggcggt 1380
ttcacgggcg cacgcaaatc agcgcgtaaa cgtaagaacc aggcgctagc gggcggtggc 1440
ggtagcggcg gtggcggtag cggcggtggc ggtagcgcac tagtgctgca gtgtatcaag 1500
gttaacaact gggatttatt cttcagcccg agtgaagaca acttcaccaa cgacctgaac 1560
aaaggtgaag aaatcacctc agatactaac atcgaagcag ccgaagaaaa catctcgctg 1620
gacctgatcc agcagtacta cctgaccttt aatttcgaca acgagccgga aaacatttct 1680
atcgaaaacc tgagctctga tatcatcggc cagctggaac tgatgccgaa catcgaacgt 1740
ttcccaaacg gtaaaaagta cgagctggac aaatatacca tgttccacta cctgcgcgcg 1800
caggaatttg aacacggcaa atcccgtatc gcactgacta actccgttaa cgaagctctg 1860
ctcaacccgt cccgtgtata caccttcttc tctagcgact acgtgaaaaa ggtcaacaaa 1920
gcgactgaag ctgcaatgtt cttgggttgg gttgaacagc ttgtttatga ttttaccgac 1980
gagacgtccg aagtatctac taccgacaaa attgcggata tcactatcat catcccgtac 2040
atcggtccgg ctctgaacat tggcaacatg ctgtacaaag acgacttcgt tggcgcactg 2100
atcttctccg gtgcggtgat cctgctggag ttcatcccgg aaatcgccat cccggtactg 2160
ggcacctttg ctctggtttc ttacattgca aacaaggttc tgactgtaca aaccatcgac 2220
aacgcgctga gcaaacgtaa cgaaaaatgg gatgaagttt acaaatatat cgtgaccaac 2280
tggctggcta aggttaatac tcagatcgac ctcatccgca aaaaaatgaa agaagcactg 2340
gaaaaccagg cggaagctac caaggcaatc attaactacc agtacaacca gtacaccgag 2400
gaagaaaaaa acaacatcaa cttcaacatc gacgatctgt cctctaaact gaacgaatcc 2460
atcaacaaag ctatgatcaa catcaacaag ttcctgaacc agtgctctgt aagctatctg 2520
atgaactcca tgatcccgta cggtgttaaa cgtctggagg acttcgatgc gtctctgaaa 2580
gacgccctgc tgaaatacat ttacgacaac cgtggcactc tgatcggtca ggttgatcgt 2640
ctgaaggaca aagtgaacaa taccttatcg accgacatcc cttttcagct cagtaaatat 2700
gtcgataacc aacgcctttt gtccactcta gactag 2736

<210> SEQ ID NO 97
<211> LENGTH: 911
<212> TYPE: PRT
<213> ORGANISM: Artificial Sequence
<220> FEATURE:
<223> OTHER INFORMATION: Synthetic

<400> SEQUENCE: 97

Gly Ser Met Pro Ile Thr Ile Asn Asn Phe Arg Tyr Ser Asp Pro Val

-continued

```
1               5                   10                  15

Asn Asn Asp Thr Ile Ile Met Met Glu Pro Pro Tyr Cys Lys Gly Leu
            20                  25                  30

Asp Ile Tyr Tyr Lys Ala Phe Lys Ile Thr Asp Arg Ile Trp Ile Val
        35                  40                  45

Pro Glu Arg Tyr Glu Phe Gly Thr Lys Pro Glu Asp Phe Asn Pro Pro
    50                  55                  60

Ser Ser Leu Ile Glu Gly Ala Ser Glu Tyr Tyr Asp Pro Asn Tyr Leu
65                  70                  75                  80

Arg Thr Asp Ser Asp Lys Asp Arg Phe Leu Gln Thr Met Val Lys Leu
                85                  90                  95

Phe Asn Arg Ile Lys Asn Asn Val Ala Gly Glu Ala Leu Leu Asp Lys
            100                 105                 110

Ile Ile Asn Ala Ile Pro Tyr Leu Gly Asn Ser Tyr Ser Leu Leu Asp
        115                 120                 125

Lys Phe Asp Thr Asn Ser Asn Ser Val Ser Phe Asn Leu Leu Glu Gln
    130                 135                 140

Asp Pro Ser Gly Ala Thr Thr Lys Ser Ala Met Leu Thr Asn Leu Ile
145                 150                 155                 160

Ile Phe Gly Pro Gly Pro Val Leu Asn Lys Asn Glu Val Arg Gly Ile
                165                 170                 175

Val Leu Arg Val Asp Asn Lys Asn Tyr Phe Pro Cys Arg Asp Gly Phe
            180                 185                 190

Gly Ser Ile Met Gln Met Ala Phe Cys Pro Glu Tyr Val Pro Thr Phe
        195                 200                 205

Asp Asn Val Ile Glu Asn Ile Thr Ser Leu Thr Ile Gly Lys Ser Lys
    210                 215                 220

Tyr Phe Gln Asp Pro Ala Leu Leu Leu Met His Glu Leu Ile His Val
225                 230                 235                 240

Leu His Gly Leu Tyr Gly Met Gln Val Ser Ser His Glu Ile Ile Pro
                245                 250                 255

Ser Lys Gln Glu Ile Tyr Met Gln His Thr Tyr Pro Ile Ser Ala Glu
            260                 265                 270

Glu Leu Phe Thr Phe Gly Gly Gln Asp Ala Asn Leu Ile Ser Ile Asp
        275                 280                 285

Ile Lys Asn Asp Leu Tyr Glu Lys Thr Leu Asn Asp Tyr Lys Ala Ile
    290                 295                 300

Ala Asn Lys Leu Ser Gln Val Thr Ser Cys Asn Asp Pro Asn Ile Asp
305                 310                 315                 320

Ile Asp Ser Tyr Lys Gln Ile Tyr Gln Gln Lys Tyr Gln Phe Asp Lys
                325                 330                 335

Asp Ser Asn Gly Gln Tyr Ile Val Asn Glu Asp Lys Phe Gln Ile Leu
            340                 345                 350

Tyr Asn Ser Ile Met Tyr Gly Phe Thr Glu Ile Glu Leu Gly Lys Lys
        355                 360                 365

Phe Asn Ile Lys Thr Arg Leu Ser Tyr Phe Ser Met Asn His Asp Pro
    370                 375                 380

Val Lys Ile Pro Asn Leu Leu Asp Asp Thr Ile Tyr Asn Asp Thr Glu
385                 390                 395                 400

Gly Phe Asn Ile Glu Ser Lys Asp Leu Lys Ser Glu Tyr Lys Gly Gln
                405                 410                 415

Asn Met Arg Val Asn Thr Asn Ala Phe Arg Asn Val Asp Gly Ser Gly
            420                 425                 430
```

```
Leu Val Ser Lys Leu Ile Gly Leu Cys Val Asp Gly Ile Ile Thr Ser
        435                 440                 445

Lys Thr Lys Ser Leu Ile Glu Gly Arg Phe Gly Gly Phe Thr Gly Ala
    450                 455                 460

Arg Lys Ser Ala Arg Lys Arg Lys Asn Gln Ala Leu Ala Gly Gly Gly
465                 470                 475                 480

Gly Ser Gly Gly Gly Gly Ser Gly Gly Gly Gly Ser Ala Leu Val Leu
                485                 490                 495

Gln Cys Ile Lys Val Asn Asn Trp Asp Leu Phe Phe Ser Pro Ser Glu
            500                 505                 510

Asp Asn Phe Thr Asn Asp Leu Asn Lys Gly Glu Glu Ile Thr Ser Asp
        515                 520                 525

Thr Asn Ile Glu Ala Ala Glu Glu Asn Ile Ser Leu Asp Leu Ile Gln
    530                 535                 540

Gln Tyr Tyr Leu Thr Phe Asn Phe Asp Asn Glu Pro Glu Asn Ile Ser
545                 550                 555                 560

Ile Glu Asn Leu Ser Ser Asp Ile Ile Gly Gln Leu Glu Leu Met Pro
                565                 570                 575

Asn Ile Glu Arg Phe Pro Asn Gly Lys Lys Tyr Glu Leu Asp Lys Tyr
            580                 585                 590

Thr Met Phe His Tyr Leu Arg Ala Gln Glu Phe Glu His Gly Lys Ser
        595                 600                 605

Arg Ile Ala Leu Thr Asn Ser Val Asn Glu Ala Leu Leu Asn Pro Ser
    610                 615                 620

Arg Val Tyr Thr Phe Phe Ser Ser Asp Tyr Val Lys Lys Val Asn Lys
625                 630                 635                 640

Ala Thr Glu Ala Ala Met Phe Leu Gly Trp Val Glu Gln Leu Val Tyr
                645                 650                 655

Asp Phe Thr Asp Glu Thr Ser Glu Val Ser Thr Thr Asp Lys Ile Ala
            660                 665                 670

Asp Ile Thr Ile Ile Ile Pro Tyr Ile Gly Pro Ala Leu Asn Ile Gly
        675                 680                 685

Asn Met Leu Tyr Lys Asp Asp Phe Val Gly Ala Leu Ile Phe Ser Gly
    690                 695                 700

Ala Val Ile Leu Leu Glu Phe Ile Pro Glu Ile Ala Ile Pro Val Leu
705                 710                 715                 720

Gly Thr Phe Ala Leu Val Ser Tyr Ile Ala Asn Lys Val Leu Thr Val
                725                 730                 735

Gln Thr Ile Asp Asn Ala Leu Ser Lys Arg Asn Glu Lys Trp Asp Glu
            740                 745                 750

Val Tyr Lys Tyr Ile Val Thr Asn Trp Leu Ala Lys Val Asn Thr Gln
        755                 760                 765

Ile Asp Leu Ile Arg Lys Lys Met Lys Glu Ala Leu Glu Asn Gln Ala
    770                 775                 780

Glu Ala Thr Lys Ala Ile Ile Asn Tyr Gln Tyr Asn Gln Tyr Thr Glu
785                 790                 795                 800

Glu Glu Lys Asn Asn Ile Asn Phe Asn Ile Asp Asp Leu Ser Ser Lys
                805                 810                 815

Leu Asn Glu Ser Ile Asn Lys Ala Met Ile Asn Ile Asn Lys Phe Leu
            820                 825                 830

Asn Gln Cys Ser Val Ser Tyr Leu Met Asn Ser Met Ile Pro Tyr Gly
        835                 840                 845

Val Lys Arg Leu Glu Asp Phe Asp Ala Ser Leu Lys Asp Ala Leu Leu
    850                 855                 860
```

-continued

```
Lys Tyr Ile Tyr Asp Asn Arg Gly Thr Leu Ile Gly Gln Val Asp Arg
865                 870                 875                 880

Leu Lys Asp Lys Val Asn Asn Thr Leu Ser Thr Asp Ile Pro Phe Gln
                885                 890                 895

Leu Ser Lys Tyr Val Asp Asn Gln Arg Leu Leu Ser Thr Leu Asp
            900                 905                 910
```

```
<210> SEQ ID NO 98
<211> LENGTH: 180
<212> TYPE: DNA
<213> ORGANISM: Artificial Sequence
<220> FEATURE:
<223> OTHER INFORMATION: Synthetic

<400> SEQUENCE: 98

ggatccacgc acgtcgacgc gattgatggt cgttttggcg gtttcacggg cgcacgcaaa     60

tcagcgcgta aacgtaagaa ccaggcgcta gcgggcggtg gcggtagcgg cggtggcggt    120

agcggcggtg gcggtagcgc actagtgctg cagacgcacg gtctagaatg ataaaagctt    180
```

```
<210> SEQ ID NO 99
<211> LENGTH: 2715
<212> TYPE: DNA
<213> ORGANISM: Artificial Sequence
<220> FEATURE:
<223> OTHER INFORMATION: Synthetic

<400> SEQUENCE: 99

ggatccgaat tcatgccgat caccatcaac aacttcaact acagcgatcc ggtggataac     60

aaaaacatcc tgtacctgga tacccatctg aataccctgg cgaacgaacc ggaaaaagcg    120

tttcgtatca ccggcaacat ttgggttatt ccggatcgtt ttagccgtaa cagcaacccg    180

aatctgaata aaccgccgcg tgttaccagc ccgaaaagcg gttattacga tccgaactat    240

ctgagcaccg atagcgataa agataccttc ctgaaagaaa tcatcaaact gttcaaacgc    300

atcaacagcc gtgaaattgg cgaagaactg atctatcgcc tgagcaccga tattccgttt    360

ccgggcaaca acaacacccc gatcaacacc tttgatttcg atgtggattt caacagcgtt    420

gatgttaaaa cccgccaggg taacaattgg gtgaaaaccg gcagcattaa cccgagcgtg    480

attattaccg gtccgcgcga aaacattatt gatccggaaa ccagcacctt taaactgacc    540

aacaacacct ttgcggcgca ggaaggtttt ggcgcgctga gcattattag cattagcccg    600

cgctttatgc tgacctatag caacgcgacc aacgatgttg gtgaaggccg tttcagcaaa    660

agcgaatttt gcatggaccc gatcctgatc ctgatgcatg aactgaacca tgcgatgcat    720

aacctgtatg gcatcgcgat tccgaacgat cagaccatta gcagcgtgac cagcaacatc    780

ttttacagcc agtacaacgt gaaactggaa tatgcggaaa tctatgcgtt tggcggtccg    840

accattgatc tgattccgaa aagcgcgcgc aaatacttcg aagaaaaagc gctggattac    900

tatcgcagca ttgcgaaacg tctgaacagc attaccaccg cgaatccgag cagcttcaac    960

aaatatatcg gcgaatataa acagaaactg atccgcaaat atcgctttgt ggtggaaagc   1020

agcggcgaag ttaccgttaa ccgcaataaa ttcgtggaac tgtacaacga actgacccag   1080

atcttcaccg aatttaacta tgcgaaaatc tataacgtgc agaaccgtaa aatctacctg   1140

agcaacgtgt ataccccggt gaccgcgaat attctggatg ataacgtgta cgatatccag   1200

aacggcttta acatcccgaa aagcaacctg aacgttctgt ttatgggcca gaacctgagc   1260

cgtaatccgg cgctgcgtaa agtgaacccg gaaaacatgc tgtacctgtt caccaaattt   1320
```

-continued

```
tgcgtcgacg cgattgatgg tcgttttggc ggtttcacgg gcgcacgcaa atcagcgcgt   1380

aaacgtaaga accaggcgct agcgggcggt ggcggtagcg gcggtggcgg tagcggcggt   1440

ggcggtagcg cactagtgct gcagtgtcgt gaactgctgg tgaaaaacac cgatctgccg   1500

tttattggcg atatcagcga tgtgaaaacc gatatcttcc tgcgcaaaga tatcaacgaa   1560

gaaaccgaag tgatctacta cccggataac gtgagcgttg atcaggtgat cctgagcaaa   1620

aacaccagcg aacatggtca gctggatctg ctgtatccga gcattgatag cgaaagcgaa   1680

attctgccgg gcgaaaacca ggtgttttac gataaccgta cccagaacgt ggattacctg   1740

aacagctatt actacctgga aagccagaaa ctgagcgata acgtggaaga ttttaccttt   1800

acccgcagca ttgaagaagc gctggataac agcgcgaaag tttacaccta ttttccgacc   1860

ctggcgaaca aagttaatgc gggtgttcag ggcggtctgt ttctgatgtg ggcgaacgat   1920

gtggtggaag atttcaccac caacatcctg cgtaaagata ccctggataa aatcagcgat   1980

gttagcgcga ttattccgta tattggtccg gcgctgaaca ttagcaatag cgtgcgtcgt   2040

ggcaatttta ccgaagcgtt tgcggttacc ggtgtgacca ttctgctgga agcgtttccg   2100

gaatttacca ttccggcgct gggtgcgttt gtgatctata gcaaagtgca ggaacgcaac   2160

gaaatcatca aaaccatcga taactgcctg gaacagcgta ttaaacgctg gaaagatagc   2220

tatgaatgga tgatgggcac ctggctgagc cgtattatca cccagttcaa caacatcagc   2280

taccagatgt acgatagcct gaactatcag gcgggtgcga ttaaagcgaa aatcgatctg   2340

gaatacaaaa aatacagcgg cagcgataaa gaaaacatca aaagccaggt tgaaaacctg   2400

aaaaacagcc tggatgtgaa aattagcgaa gcgatgaata acatcaacaa attcatccgc   2460

gaatgcagcg tgacctacct gttcaaaaac atgctgccga aagtgatcga tgaactgaac   2520

gaatttgatc gcaacaccaa agcgaaactg atcaacctga tcgatagcca caacattatt   2580

ctggtgggcg aagtggataa actgaaagcg aaagttaaca acagcttcca gaacaccatc   2640

ccgtttaaca tcttcagcta taccaacaac agcctgctga aagatatcat caacgaatac   2700

ttcaatctag actag                                                    2715
```

<210> SEQ ID NO 100
<211> LENGTH: 904
<212> TYPE: PRT
<213> ORGANISM: Artificial Sequence
<220> FEATURE:
<223> OTHER INFORMATION: Synthetic

<400> SEQUENCE: 100

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
```

-continued

```
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
    290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
    370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Ala Ile Asp Gly Arg
        435                 440                 445

Phe Gly Gly Phe Thr Gly Ala Arg Lys Ser Ala Arg Lys Arg Lys Asn
    450                 455                 460

Gln Ala Leu Ala Gly Gly Gly Gly Ser Gly Gly Gly Gly Ser Gly Gly
465                 470                 475                 480

Gly Gly Ser Ala Leu Val Leu Gln Cys Arg Glu Leu Leu Val Lys Asn
                485                 490                 495

Thr Asp Leu Pro Phe Ile Gly Asp Ile Ser Asp Val Lys Thr Asp Ile
            500                 505                 510

Phe Leu Arg Lys Asp Ile Asn Glu Glu Thr Glu Val Ile Tyr Tyr Pro
        515                 520                 525

Asp Asn Val Ser Val Asp Gln Val Ile Leu Ser Lys Asn Thr Ser Glu
    530                 535                 540
```

His Gly Gln Leu Asp Leu Leu Tyr Pro Ser Ile Asp Ser Glu Ser Glu
545 550 555 560

Ile Leu Pro Gly Glu Asn Gln Val Phe Tyr Asp Asn Arg Thr Gln Asn
565 570 575

Val Asp Tyr Leu Asn Ser Tyr Tyr Tyr Leu Glu Ser Gln Lys Leu Ser
580 585 590

Asp Asn Val Glu Asp Phe Thr Phe Thr Arg Ser Ile Glu Glu Ala Leu
595 600 605

Asp Asn Ser Ala Lys Val Tyr Thr Tyr Phe Pro Thr Leu Ala Asn Lys
610 615 620

Val Asn Ala Gly Val Gln Gly Gly Leu Phe Leu Met Trp Ala Asn Asp
625 630 635 640

Val Val Glu Asp Phe Thr Thr Asn Ile Leu Arg Lys Asp Thr Leu Asp
645 650 655

Lys Ile Ser Asp Val Ser Ala Ile Ile Pro Tyr Ile Gly Pro Ala Leu
660 665 670

Asn Ile Ser Asn Ser Val Arg Arg Gly Asn Phe Thr Glu Ala Phe Ala
675 680 685

Val Thr Gly Val Thr Ile Leu Leu Glu Ala Phe Pro Glu Phe Thr Ile
690 695 700

Pro Ala Leu Gly Ala Phe Val Ile Tyr Ser Lys Val Gln Glu Arg Asn
705 710 715 720

Glu Ile Ile Lys Thr Ile Asp Asn Cys Leu Glu Gln Arg Ile Lys Arg
725 730 735

Trp Lys Asp Ser Tyr Glu Trp Met Met Gly Thr Trp Leu Ser Arg Ile
740 745 750

Ile Thr Gln Phe Asn Asn Ile Ser Tyr Gln Met Tyr Asp Ser Leu Asn
755 760 765

Tyr Gln Ala Gly Ala Ile Lys Ala Lys Ile Asp Leu Glu Tyr Lys Lys
770 775 780

Tyr Ser Gly Ser Asp Lys Glu Asn Ile Lys Ser Gln Val Glu Asn Leu
785 790 795 800

Lys Asn Ser Leu Asp Val Lys Ile Ser Glu Ala Met Asn Asn Ile Asn
805 810 815

Lys Phe Ile Arg Glu Cys Ser Val Thr Tyr Leu Phe Lys Asn Met Leu
820 825 830

Pro Lys Val Ile Asp Glu Leu Asn Glu Phe Asp Arg Asn Thr Lys Ala
835 840 845

Lys Leu Ile Asn Leu Ile Asp Ser His Asn Ile Ile Leu Val Gly Glu
850 855 860

Val Asp Lys Leu Lys Ala Lys Val Asn Asn Ser Phe Gln Asn Thr Ile
865 870 875 880

Pro Phe Asn Ile Phe Ser Tyr Thr Asn Asn Ser Leu Leu Lys Asp Ile
885 890 895

Ile Asn Glu Tyr Phe Asn Leu Asp
900

<210> SEQ ID NO 101
<211> LENGTH: 30
<212> TYPE: PRT
<213> ORGANISM: Artificial Sequence
<220> FEATURE:
<223> OTHER INFORMATION: Synthetic sequence

<400> SEQUENCE: 101

Gly Trp Thr Leu Asn Ser Ala Gly Tyr Leu Leu Gly Pro His Ala Val

-continued

```
1               5                   10                  15

Gly Asn His Arg Ser Phe Ser Asp Leu Asn Gly Leu Thr Ser
            20                  25                  30
```

<210> SEQ ID NO 102
<211> LENGTH: 16
<212> TYPE: PRT
<213> ORGANISM: Artificial Sequence
<220> FEATURE:
<223> OTHER INFORMATION: Synthetic sequence

<400> SEQUENCE: 102

```
Gly Trp Thr Leu Asn Ser Ala Gly Tyr Leu Leu Gly Pro His Ala Val
1               5                   10                  15
```

<210> SEQ ID NO 103
<211> LENGTH: 2751
<212> TYPE: DNA
<213> ORGANISM: Artificial Sequence
<220> FEATURE:
<223> OTHER INFORMATION: Synthetic sequence

<400> SEQUENCE: 103

```
ggatccatgg agttcgttaa caaacagttc aactataaag acccagttaa cggtgttgac     60

attgcttaca tcaaaatccc gaacgctggc cagatgcagc cggtaaaggc attcaaaatc    120

cacaacaaaa tctgggttat cccggaacgt gataccttta ctaacccgga agaaggtgac    180

ctgaacccgc caccggaagc gaaacaggtg ccggtatctt actatgactc cacctacctg    240

tctaccgata acgaaaagga caactacctg aaaggtgtta ctaaactgtt cgagcgtatt    300

tactccaccg acctgggccg tatgctgctg actagcatcg ttcgcggtat cccgttctgg    360

ggcggttcta ccatcgatac cgaactgaaa gtaatcgaca ctaactgcat caacgttatt    420

cagccggacg gttcctatcg ttccgaagaa ctgaacctgg tgatcatcgg cccgtctgct    480

gatatcatcc agttcgagtg taagagcttt ggtcacgaag ttctgaacct cacccgtaac    540

ggctacggtt ccactcagta catccgtttc tctccggact tcaccttcgg ttttgaagaa    600

tccctggaag tagacacgaa cccactgctg ggcgctggta aattcgcaac tgatcctgcg    660

gttaccctgg ctcacgaact gattcatgca ggccaccgcc tgtacggtat cgccatcaat    720

ccgaaccgtg tcttcaaagt taacaccaac gcgtattacg agatgtccgg tctggaagtt    780

agcttcgaag aactgcgtac ttttggcggt cacgacgcta aattcatcga ctctctgcaa    840

gaaaacgagt tccgtctgta ctactataac aagttcaaag atatcgcatc caccctgaac    900

aaagcgaaat ccatcgtggg taccactgct tctctccagt acatgaagaa cgtttttaaa    960

gaaaaatacc tgctcagcga agacacctcc ggcaaattct ctgtagacaa gttgaaattc   1020

gataaacttt acaaaatgct gactgaaatt tacaccgaag acaacttcgt taagttcttt   1080

aaagttctga accgcaaaac ctatctgaac ttcgacaagg cagtattcaa aatcaacatc   1140

gtgccgaaag ttaactacac tatctacgat ggtttcaacc tgcgtaacac caacctggct   1200

gctaatttta acggccagaa cacggaaatc aacaacatga acttcacaaa actgaaaaac   1260

ttcactggtc tgttcgagtt ttacaagctg ctgtgcgtcg acggcatcat tacctccaaa   1320

actaaatctc tgatagaagg tagaaacaaa gcgctgaacg acctctgtat caaggttaac   1380

aactgggatt tattcttcag cccgagtgaa gacaacttca ccaacgacct gaacaaaggt   1440

gaagaaatca cctcagatac taacatcgaa gcagccgaag aaaacatctc gctggacctg   1500

atccagcagt actacctgac ctttaatttc gacaacgagc cggaaaacat ttctatcgaa   1560
```

-continued

```
aacctgagct ctgatatcat cggccagctg gaactgatgc cgaacatcga acgtttccca   1620

aacggtaaaa agtacgagct ggacaaatat accatgttcc actacctgcg cgcgcaggaa   1680

tttgaacacg gcaaatcccg tatcgcactg actaactccg ttaacgaagc tctgctcaac   1740

ccgtcccgtg tatacacctt cttctctagc gactacgtga aaaaggtcaa caaagcgact   1800

gaagctgcaa tgttcttggg ttgggttgaa cagcttgttt atgattttac cgacgagacg   1860

tccgaagtat ctactaccga caaaattgcg gatatcacta tcatcatccc gtacatcggt   1920

ccggctctga acattggcaa catgctgtac aaagacgact tcgttggcgc actgatcttc   1980

tccggtgcgg tgatcctgct ggagttcatc ccggaaatcg ccatcccggt actgggcacc   2040

tttgctctgg tttcttacat tgcaaacaag gttctgactg tacaaaccat cgacaacgcg   2100

ctgagcaaac gtaacgaaaa atgggatgaa gtttacaaat atatcgtgac caactggctg   2160

gctaaggtta atactcagat cgacctcatc cgcaaaaaaa tgaaagaagc actggaaaac   2220

caggcggaag ctaccaaggc aatcattaac taccagtaca accagtacac cgaggaagaa   2280

aaaaacaaca tcaacttcaa catcgacgat ctgtcctcta aactgaacga atccatcaac   2340

aaagctatga tcaacatcaa caagttcctg aaccagtgct ctgtaagcta tctgatgaac   2400

tccatgatcc cgtacggtgt taaacgtctg gaggacttcg atgcgtctct gaaagacgcc   2460

ctgctgaaat acatttacga caaccgtggc actctgatcg gtcaggttga tcgtctgaag   2520

gacaaagtga acaataccttt atcgaccgac atcccttttc agctcagtaa atatgtcgat   2580

aaccaacgcc ttttgtccac tctagaaggc ggtggcggta gcggcggtgg cggtagcggc   2640

ggtggcggta gcgcactagt gggttggacc ctgaactctg ctggttacct gctgggtccg   2700

cacgctgttg gtaaccaccg ttctttctct gacctgaacg gtctgacctc t            2751
```

<210> SEQ ID NO 104
<211> LENGTH: 2709
<212> TYPE: DNA
<213> ORGANISM: Artificial Sequence
<220> FEATURE:
<223> OTHER INFORMATION: Synthetic sequence

<400> SEQUENCE: 104

```
ggatccatgg agttcgttaa caaacagttc aactataaag acccagttaa cggtgttgac     60

attgcttaca tcaaaatccc gaacgctggc cagatgcagc cggtaaaggc attcaaaatc    120

cacaacaaaa tctgggttat cccggaacgt gataccttta ctaacccgga agaaggtgac    180

ctgaacccgc caccggaagc gaaacaggtg ccggtatctt actatgactc cacctacctg    240

tctaccgata acgaaaagga caactacctg aaaggtgtta ctaaactgtt cgagcgtatt    300

tactccaccg acctgggccg tatgctgctg actagcatcg ttcgcggtat cccgttctgg    360

ggcggttcta ccatcgatac cgaactgaaa gtaatcgaca ctaactgcat caacgttatt    420

cagccggacg gttcctatcg ttccgaagaa ctgaacctgg tgatcatcgg cccgtctgct    480

gatatcatcc agttcgagtg taagagcttt ggtcacgaag ttctgaacct cacccgtaac    540

ggctacggtt ccactcagta catccgtttc tctccggact tcaccttcgg ttttgaagaa    600

tccctggaag tagacacgaa cccactgctg ggcgctggta aattcgcaac tgatcctgcg    660

gttaccctgg ctcacgaact gattcatgca ggccaccgcc tgtacggtat cgccatcaat    720

ccgaaccgtg tcttcaaagt taacaccaac gcgtattacg agatgtccgg tctggaagtt    780

agcttcgaag aactgcgtac ttttggcggt cacgacgcta aattcatcga ctctctgcaa    840

gaaaacgagt tccgtctgta ctactataac aagttcaaag atatcgcatc caccctgaac    900
```

-continued

```
aaagcgaaat ccatcgtggg taccactgct tctctccagt acatgaagaa cgtttttaaa    960

gaaaaatacc tgctcagcga agacacctcc ggcaaattct ctgtagacaa gttgaaattc   1020

gataaacttt acaaaatgct gactgaaatt tacaccgaag acaacttcgt taagttcttt   1080

aaagttctga accgcaaaac ctatctgaac ttcgacaagg cagtattcaa aatcaacatc   1140

gtgccgaaag ttaactacac tatctacgat ggtttcaacc tgcgtaacac caacctggct   1200

gctaatttta acggccagaa cacggaaatc aacaacatga acttcacaaa actgaaaaac   1260

ttcactggtc tgttcgagtt ttacaagctg ctgtgcgtcg acggcatcat tacctccaaa   1320

actaaatctc tgatagaagg tagaaacaaa gcgctgaacg acctctgtat caaggttaac   1380

aactgggatt tattcttcag cccgagtgaa gacaacttca ccaacgacct gaacaaaggt   1440

gaagaaatca cctcagatac taacatcgaa gcagccgaag aaaacatctc gctggacctg   1500

atccagcagt actacctgac ctttaatttc gacaacgagc cggaaaacat ttctatcgaa   1560

aacctgagct ctgatatcat cggccagctg gaactgatgc cgaacatcga acgtttccca   1620

aacggtaaaa agtacgagct ggacaaatat accatgttcc actacctgcg cgcgcaggaa   1680

tttgaacacg gcaaatcccg tatcgcactg actaactccg ttaacgaagc tctgctcaac   1740

ccgtcccgtg tatacacctt cttctctagc gactacgtga aaaaggtcaa caaagcgact   1800

gaagctgcaa tgttcttggg ttgggttgaa cagcttgttt atgattttac cgacgagacg   1860

tccgaagtat ctactaccga caaaattgcg gatatcacta tcatcatccc gtacatcggt   1920

ccggctctga acattggcaa catgctgtac aaagacgact tcgttggcgc actgatcttc   1980

tccggtgcgg tgatcctgct ggagttcatc ccggaaatcg ccatcccggt actgggcacc   2040

tttgctctgg tttcttacat tgcaaacaag gttctgactg tacaaaccat cgacaacgcg   2100

ctgagcaaac gtaacgaaaa atgggatgaa gtttacaaat atatcgtgac caactggctg   2160

gctaaggtta atactcagat cgacctcatc cgcaaaaaaa tgaaagaagc actggaaaac   2220

caggcggaag ctaccaaggc aatcattaac taccagtaca accagtacac cgaggaagaa   2280

aaaaacaaca tcaacttcaa catcgacgat ctgtcctcta aactgaacga atccatcaac   2340

aaagctatga tcaacatcaa caagttcctg aaccagtgct ctgtaagcta tctgatgaac   2400

tccatgatcc cgtacggtgt taaacgtctg gaggacttcg atgcgtctct gaaagacgcc   2460

ctgctgaaat acatttacga caaccgtggc actctgatcg gtcaggttga tcgtctgaag   2520

gacaaagtga acaatacctt atcgaccgac atcccttttc agctcagtaa atatgtcgat   2580

aaccaacgcc ttttgtccac tctagaaggc ggtggcggta gcggcggtgg cggtagcggc   2640

ggtggcggta gcgcactagt gggttggacc ctgaactctg ctggttacct gctgggtccg   2700

cacgctgtt                                                           2709
```

<210> SEQ ID NO 105
<211> LENGTH: 917
<212> TYPE: PRT
<213> ORGANISM: Artificial Sequence
<220> FEATURE:
<223> OTHER INFORMATION: Synthetic sequence

<400> SEQUENCE: 105

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45
```

```
Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Asn Lys Ala Leu Asn Asp Leu Cys Ile Lys Val Asn Asn Trp Asp Leu
    450                 455                 460

Phe Phe Ser Pro Ser Glu Asp Asn Phe Thr Asn Asp Leu Asn Lys Gly
```

```
465                 470                 475                 480

Glu Glu Ile Thr Ser Asp Thr Asn Ile Glu Ala Ala Glu Glu Asn Ile
                485                 490                 495

Ser Leu Asp Leu Ile Gln Gln Tyr Tyr Leu Thr Phe Asn Phe Asp Asn
            500                 505                 510

Glu Pro Glu Asn Ile Ser Ile Glu Asn Leu Ser Ser Asp Ile Ile Gly
        515                 520                 525

Gln Leu Glu Leu Met Pro Asn Ile Glu Arg Phe Pro Asn Gly Lys Lys
    530                 535                 540

Tyr Glu Leu Asp Lys Tyr Thr Met Phe His Tyr Leu Arg Ala Gln Glu
545                 550                 555                 560

Phe Glu His Gly Lys Ser Arg Ile Ala Leu Thr Asn Ser Val Asn Glu
                565                 570                 575

Ala Leu Leu Asn Pro Ser Arg Val Tyr Thr Phe Phe Ser Ser Asp Tyr
            580                 585                 590

Val Lys Lys Val Asn Lys Ala Thr Glu Ala Ala Met Phe Leu Gly Trp
        595                 600                 605

Val Glu Gln Leu Val Tyr Asp Phe Thr Asp Glu Thr Ser Glu Val Ser
    610                 615                 620

Thr Thr Asp Lys Ile Ala Asp Ile Thr Ile Ile Ile Pro Tyr Ile Gly
625                 630                 635                 640

Pro Ala Leu Asn Ile Gly Asn Met Leu Tyr Lys Asp Asp Phe Val Gly
                645                 650                 655

Ala Leu Ile Phe Ser Gly Ala Val Ile Leu Leu Glu Phe Ile Pro Glu
            660                 665                 670

Ile Ala Ile Pro Val Leu Gly Thr Phe Ala Leu Val Ser Tyr Ile Ala
        675                 680                 685

Asn Lys Val Leu Thr Val Gln Thr Ile Asp Asn Ala Leu Ser Lys Arg
    690                 695                 700

Asn Glu Lys Trp Asp Glu Val Tyr Lys Tyr Ile Val Thr Asn Trp Leu
705                 710                 715                 720

Ala Lys Val Asn Thr Gln Ile Asp Leu Ile Arg Lys Lys Met Lys Glu
                725                 730                 735

Ala Leu Glu Asn Gln Ala Glu Ala Thr Lys Ala Ile Ile Asn Tyr Gln
            740                 745                 750

Tyr Asn Gln Tyr Thr Glu Glu Glu Lys Asn Asn Ile Asn Phe Asn Ile
        755                 760                 765

Asp Asp Leu Ser Ser Lys Leu Asn Glu Ser Ile Asn Lys Ala Met Ile
    770                 775                 780

Asn Ile Asn Lys Phe Leu Asn Gln Cys Ser Val Ser Tyr Leu Met Asn
785                 790                 795                 800

Ser Met Ile Pro Tyr Gly Val Lys Arg Leu Glu Asp Phe Asp Ala Ser
                805                 810                 815

Leu Lys Asp Ala Leu Leu Lys Tyr Ile Tyr Asp Asn Arg Gly Thr Leu
            820                 825                 830

Ile Gly Gln Val Asp Arg Leu Lys Asp Lys Val Asn Asn Thr Leu Ser
        835                 840                 845

Thr Asp Ile Pro Phe Gln Leu Ser Lys Tyr Val Asp Asn Gln Arg Leu
    850                 855                 860

Leu Ser Thr Leu Glu Gly Gly Gly Gly Ser Gly Gly Gly Gly Ser Gly
865                 870                 875                 880

Gly Gly Gly Ser Ala Leu Val Gly Trp Thr Leu Asn Ser Ala Gly Tyr
                885                 890                 895
```

Leu Leu Gly Pro His Ala Val Gly Asn His Arg Ser Phe Ser Asp Leu
900 905 910

Asn Gly Leu Thr Ser
915

<210> SEQ ID NO 106
<211> LENGTH: 903
<212> TYPE: PRT
<213> ORGANISM: Artificial Sequence
<220> FEATURE:
<223> OTHER INFORMATION: Synthetic sequence

<400> SEQUENCE: 106

Gly Ser Met Glu Phe Val Asn Lys Gln Phe Asn Tyr Lys Asp Pro Val
1 5 10 15

Asn Gly Val Asp Ile Ala Tyr Ile Lys Ile Pro Asn Ala Gly Gln Met
20 25 30

Gln Pro Val Lys Ala Phe Lys Ile His Asn Lys Ile Trp Val Ile Pro
35 40 45

Glu Arg Asp Thr Phe Thr Asn Pro Glu Glu Gly Asp Leu Asn Pro Pro
50 55 60

Pro Glu Ala Lys Gln Val Pro Val Ser Tyr Tyr Asp Ser Thr Tyr Leu
65 70 75 80

Ser Thr Asp Asn Glu Lys Asp Asn Tyr Leu Lys Gly Val Thr Lys Leu
85 90 95

Phe Glu Arg Ile Tyr Ser Thr Asp Leu Gly Arg Met Leu Leu Thr Ser
100 105 110

Ile Val Arg Gly Ile Pro Phe Trp Gly Gly Ser Thr Ile Asp Thr Glu
115 120 125

Leu Lys Val Ile Asp Thr Asn Cys Ile Asn Val Ile Gln Pro Asp Gly
130 135 140

Ser Tyr Arg Ser Glu Glu Leu Asn Leu Val Ile Ile Gly Pro Ser Ala
145 150 155 160

Asp Ile Ile Gln Phe Glu Cys Lys Ser Phe Gly His Glu Val Leu Asn
165 170 175

Leu Thr Arg Asn Gly Tyr Gly Ser Thr Gln Tyr Ile Arg Phe Ser Pro
180 185 190

Asp Phe Thr Phe Gly Phe Glu Glu Ser Leu Glu Val Asp Thr Asn Pro
195 200 205

Leu Leu Gly Ala Gly Lys Phe Ala Thr Asp Pro Ala Val Thr Leu Ala
210 215 220

His Glu Leu Ile His Ala Gly His Arg Leu Tyr Gly Ile Ala Ile Asn
225 230 235 240

Pro Asn Arg Val Phe Lys Val Asn Thr Asn Ala Tyr Tyr Glu Met Ser
245 250 255

Gly Leu Glu Val Ser Phe Glu Glu Leu Arg Thr Phe Gly Gly His Asp
260 265 270

Ala Lys Phe Ile Asp Ser Leu Gln Glu Asn Glu Phe Arg Leu Tyr Tyr
275 280 285

Tyr Asn Lys Phe Lys Asp Ile Ala Ser Thr Leu Asn Lys Ala Lys Ser
290 295 300

Ile Val Gly Thr Thr Ala Ser Leu Gln Tyr Met Lys Asn Val Phe Lys
305 310 315 320

Glu Lys Tyr Leu Leu Ser Glu Asp Thr Ser Gly Lys Phe Ser Val Asp
325 330 335

Lys Leu Lys Phe Asp Lys Leu Tyr Lys Met Leu Thr Glu Ile Tyr Thr

-continued

```
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Asn Lys Ala Leu Asn Asp Leu Cys Ile Lys Val Asn Asn Trp Asp Leu
    450                 455                 460

Phe Phe Ser Pro Ser Glu Asp Asn Phe Thr Asn Asp Leu Asn Lys Gly
465                 470                 475                 480

Glu Glu Ile Thr Ser Asp Thr Asn Ile Glu Ala Ala Glu Glu Asn Ile
                485                 490                 495

Ser Leu Asp Leu Ile Gln Gln Tyr Tyr Leu Thr Phe Asn Phe Asp Asn
            500                 505                 510

Glu Pro Glu Asn Ile Ser Ile Glu Asn Leu Ser Ser Asp Ile Ile Gly
        515                 520                 525

Gln Leu Glu Leu Met Pro Asn Ile Glu Arg Phe Pro Asn Gly Lys Lys
    530                 535                 540

Tyr Glu Leu Asp Lys Tyr Thr Met Phe His Tyr Leu Arg Ala Gln Glu
545                 550                 555                 560

Phe Glu His Gly Lys Ser Arg Ile Ala Leu Thr Asn Ser Val Asn Glu
                565                 570                 575

Ala Leu Leu Asn Pro Ser Arg Val Tyr Thr Phe Phe Ser Ser Asp Tyr
            580                 585                 590

Val Lys Lys Val Asn Lys Ala Thr Glu Ala Ala Met Phe Leu Gly Trp
        595                 600                 605

Val Glu Gln Leu Val Tyr Asp Phe Thr Asp Glu Thr Ser Glu Val Ser
    610                 615                 620

Thr Thr Asp Lys Ile Ala Asp Ile Thr Ile Ile Ile Pro Tyr Ile Gly
625                 630                 635                 640

Pro Ala Leu Asn Ile Gly Asn Met Leu Tyr Lys Asp Asp Phe Val Gly
                645                 650                 655

Ala Leu Ile Phe Ser Gly Ala Val Ile Leu Leu Glu Phe Ile Pro Glu
            660                 665                 670

Ile Ala Ile Pro Val Leu Gly Thr Phe Ala Leu Val Ser Tyr Ile Ala
        675                 680                 685

Asn Lys Val Leu Thr Val Gln Thr Ile Asp Asn Ala Leu Ser Lys Arg
    690                 695                 700

Asn Glu Lys Trp Asp Glu Val Tyr Lys Tyr Ile Val Thr Asn Trp Leu
705                 710                 715                 720

Ala Lys Val Asn Thr Gln Ile Asp Leu Ile Arg Lys Lys Met Lys Glu
                725                 730                 735

Ala Leu Glu Asn Gln Ala Glu Ala Thr Lys Ala Ile Ile Asn Tyr Gln
            740                 745                 750

Tyr Asn Gln Tyr Thr Glu Glu Glu Lys Asn Asn Ile Asn Phe Asn Ile
        755                 760                 765
```

```
Asp Asp Leu Ser Ser Lys Leu Asn Glu Ser Ile Asn Lys Ala Met Ile
    770                 775                 780

Asn Ile Asn Lys Phe Leu Asn Gln Cys Ser Val Ser Tyr Leu Met Asn
785                 790                 795                 800

Ser Met Ile Pro Tyr Gly Val Lys Arg Leu Glu Asp Phe Asp Ala Ser
                805                 810                 815

Leu Lys Asp Ala Leu Leu Lys Tyr Ile Tyr Asp Asn Arg Gly Thr Leu
            820                 825                 830

Ile Gly Gln Val Asp Arg Leu Lys Asp Lys Val Asn Asn Thr Leu Ser
        835                 840                 845

Thr Asp Ile Pro Phe Gln Leu Ser Lys Tyr Val Asp Asn Gln Arg Leu
    850                 855                 860

Leu Ser Thr Leu Glu Gly Gly Gly Gly Ser Gly Gly Gly Gly Ser Gly
865                 870                 875                 880

Gly Gly Gly Ser Ala Leu Val Gly Trp Thr Leu Asn Ser Ala Gly Tyr
                885                 890                 895

Leu Leu Gly Pro His Ala Val
            900
```

<210> SEQ ID NO 107
<211> LENGTH: 23
<212> TYPE: PRT
<213> ORGANISM: Influenza virus

<400> SEQUENCE: 107

```
Gly Leu Phe Gly Ala Ile Ala Gly Phe Ile Glu Asn Gly Trp Glu Gly
1               5                   10                  15

Met Ile Asp Gly Trp Tyr Gly
            20
```

<210> SEQ ID NO 108
<211> LENGTH: 5
<212> TYPE: PRT
<213> ORGANISM: Artificial Sequence
<220> FEATURE:
<223> OTHER INFORMATION: chemically synthesized enterokinase cleavage site

<400> SEQUENCE: 108

```
Asp Asp Asp Asp Lys
1               5
```

<210> SEQ ID NO 109
<211> LENGTH: 8
<212> TYPE: PRT
<213> ORGANISM: Artificial Sequence
<220> FEATURE:
<223> OTHER INFORMATION: chemically synthesized Factor Xa cleavage site

<400> SEQUENCE: 109

```
Ile Glu Gly Arg Ile Asp Gly Arg
1               5
```

<210> SEQ ID NO 110
<211> LENGTH: 7
<212> TYPE: PRT
<213> ORGANISM: Artificial Sequence
<220> FEATURE:
<223> OTHER INFORMATION: chemically synthesized tobacco etch virus cleavage site

<400> SEQUENCE: 110

Glu Asn Leu Tyr Phe Gln Gly
1 5

<210> SEQ ID NO 111
<211> LENGTH: 6
<212> TYPE: PRT
<213> ORGANISM: Artificial Sequence
<220> FEATURE:
<223> OTHER INFORMATION: chemically synthesized thrombin cleavage site

<400> SEQUENCE: 111

Leu Val Pro Arg Gly Ser
1 5

<210> SEQ ID NO 112
<211> LENGTH: 8
<212> TYPE: PRT
<213> ORGANISM: Artificial Sequence
<220> FEATURE:
<223> OTHER INFORMATION: chemically synthesized PreScission cleavage site

<400> SEQUENCE: 112

Leu Glu Val Leu Phe Gln Gly Pro
1 5

<210> SEQ ID NO 113
<211> LENGTH: 48
<212> TYPE: DNA
<213> ORGANISM: Artificial Sequence
<220> FEATURE:
<223> OTHER INFORMATION: chemically synthesized PCR primer

<400> SEQUENCE: 113
tccaaaacta aatctctgat agaaggtaga aacaaagcgc tgaacgac 48

<210> SEQ ID NO 114
<211> LENGTH: 25
<212> TYPE: DNA
<213> ORGANISM: Artificial Sequence
<220> FEATURE:
<223> OTHER INFORMATION: chemically synthesized PCR primer

<400> SEQUENCE: 114
cttgatgtac tctgtgaacg tgctc 25

<210> SEQ ID NO 115
<211> LENGTH: 48
<212> TYPE: DNA
<213> ORGANISM: Artificial Sequence
<220> FEATURE:
<223> OTHER INFORMATION: chemically synthesized PCR primer

<400> SEQUENCE: 115
gtcgttcagc gctttgtttc taccttctat cagagattta gttttgga 48

<210> SEQ ID NO 116
<211> LENGTH: 24
<212> TYPE: DNA
<213> ORGANISM: Artificial Sequence
<220> FEATURE:
<223> OTHER INFORMATION: chemically synthesized PCR primer

<400> SEQUENCE: 116
atggagttcg ttaacaaaca gttc 24

<210> SEQ ID NO 117
<211> LENGTH: 25
<212> TYPE: PRT
<213> ORGANISM: Artificial Sequence
<220> FEATURE:
<223> OTHER INFORMATION: chemically synthesized activation loop

<400> SEQUENCE: 117

Cys Val Arg Gly Ile Ile Thr Ser Lys Thr Lys Ser Leu Asp Lys Gly
1 5 10 15

Tyr Asn Lys Ala Leu Asn Asp Leu Cys
20 25

<210> SEQ ID NO 118
<211> LENGTH: 5
<212> TYPE: PRT
<213> ORGANISM: Artificial Sequence
<220> FEATURE:
<223> OTHER INFORMATION: chemically synthesized met-enkephalin peptide

<400> SEQUENCE: 118

Tyr Gly Gly Phe Met
1 5

<210> SEQ ID NO 119
<211> LENGTH: 13
<212> TYPE: PRT
<213> ORGANISM: Artificial Sequence
<220> FEATURE:
<223> OTHER INFORMATION: chemically synthesized peptide linker

<400> SEQUENCE: 119

Ala Leu Ala Gly Gly Gly Gly Ser Ala Leu Val Leu Gln
1 5 10

<210> SEQ ID NO 120
<211> LENGTH: 18
<212> TYPE: PRT
<213> ORGANISM: Artificial Sequence
<220> FEATURE:
<223> OTHER INFORMATION: chemically synthesized peptide linker

<400> SEQUENCE: 120

Ala Leu Ala Gly Gly Gly Gly Ser Gly Gly Gly Gly Ser Ala Leu Val
1 5 10 15

Leu Gln

<210> SEQ ID NO 121
<211> LENGTH: 28
<212> TYPE: PRT
<213> ORGANISM: Artificial Sequence
<220> FEATURE:
<223> OTHER INFORMATION: chemically synthesized peptide linker

<400> SEQUENCE: 121

Ala Leu Ala Gly Gly Gly Gly Ser Gly Gly Gly Gly Ser Gly Gly Gly
1 5 10 15

Gly Ser Gly Gly Gly Gly Ser Ala Leu Val Leu Gln
20 25

<210> SEQ ID NO 122
<211> LENGTH: 33
<212> TYPE: PRT
<213> ORGANISM: Artificial Sequence
<220> FEATURE:
<223> OTHER INFORMATION: chemically synthesized peptide linker -continued

```
<400> SEQUENCE: 122

Ala Leu Ala Gly Gly Gly Gly Ser Gly Gly Gly Gly Ser Gly Gly Gly
1               5                   10                  15

Gly Ser Gly Gly Gly Gly Ser Gly Gly Gly Gly Ser Ala Leu Val Leu
            20                  25                  30

Gln


<210> SEQ ID NO 123
<211> LENGTH: 30
<212> TYPE: PRT
<213> ORGANISM: Artificial Sequence
<220> FEATURE:
<223> OTHER INFORMATION: chemically synthesized peptide linker

<400> SEQUENCE: 123

Ala Leu Ala Ala Glu Ala Ala Ala Lys Glu Ala Ala Ala Lys Glu Ala
1               5                   10                  15

Ala Ala Lys Ala Gly Gly Gly Gly Ser Ala Leu Val Leu Gln
            20                  25                  30
```

NON-CYTOTOXIC PROTEIN CONJUGATES

FIELD OF THE INVENTION

This invention relates to a non-cytotoxic protein conjugate, and to the use of said conjugate for treating pain.

BACKGROUND OF THE INVENTION

Toxins may be generally divided into two groups according to the type of effect that they have on a target cell. In more detail, the first group of toxins kill their natural target cells, and are therefore known as cytotoxic toxin molecules. This group of toxins is exemplified inter alia by plant toxins such as ricin, and abrin, and by bacterial toxins such as diphtheria toxin, and *Pseudomonas* exotoxin A. Cytotoxic toxins typically kill their target cells by inhibiting the cellular process of protein synthesis.

In contrast, the second group of toxins, which are known as non-cytotoxic toxins, do not (as their name confirms) kill their natural target cells. Non-cytotoxic toxins have attracted much less commercial interest than have their cytotoxic counterparts, and exert their effects on a target cell by inhibiting cellular processes other than protein synthesis. As with their cytotoxic counterparts, non-cytotoxic toxins are produced from a variety of sources such as plants, and bacteria. Bacterial non-cytotoxic toxins are now described in more detail.

Clostridial neurotoxins are proteins that typically have a molecular mass of the order of 150 kDa. They are produced by various species of bacteria, especially of the genus *Clostridium*, most importantly *C. tetani* and several strains of *C. botulinum, C. butyricum* and *C. argentinense*. There are at present eight different classes of the clostridial neurotoxin, namely: tetanus toxin, and botulinum neurotoxin in its serotypes A, B, $C_1$, D, E, F and G, and they all share similar structures and modes of action.

Clostridial neurotoxins represent a major group of non-cytotoxic toxin molecules, and are synthesised by the host bacterium as single polypeptides that are modified post-translationally by a proteolytic cleavage event to form two polypeptide chains joined together by a disulphide bond. The two chains are termed the heavy chain (H-chain), which has a molecular mass of approximately 100 kDa, and the light chain (L-chain), which has a molecular mass of approximately 50 kDa.

L-chains possess a protease function (zinc-dependent endopeptidase activity) and exhibit high substrate specificity for vesicle and/or plasma membrane associated proteins involved in the exocytic process. L-chains from different clostridial species or serotypes may hydrolyse different but specific peptide bonds in one of three substrate proteins, namely synaptobrevin, syntaxin or SNAP-25. These substrates are important components of the neurosecretory machinery.

Non-cytotoxic toxins are also produced by other bacteria, such as from the genus *Neisseria*, most importantly from the species *N. gonorrhoeae*. For example, *Neisseria* sp. produces the non-cytotoxic toxin IgA protease (see WO99/58571).

It has been well documented in the art that toxin molecules may be re-targeted to a cell that is not the toxin's natural target cell. When so re-targeted, the modified toxin is capable of binding to a desired target cell and, following subsequent translocation into the cytosol, is capable of exerting its effect on the target cell. Said re-targeting is achieved by replacing the natural Targeting Moiety (TM) of the toxin with a different TM. In this regard, the TM is selected so that it will bind to a desired target cell, and allow subsequent passage of the modified toxin into an endosome within the target cell. The modified toxin also comprises a translocation domain to enable entry of the non-cytotoxic protease into the cell cytosol. The translocation domain can be the natural translocation domain of the toxin or it can be a different translocation domain obtained from a microbial protein with translocation activity.

For example, in the context of non-cytotoxic toxin molecules, it has been well documented that a clostridial neurotoxin may be re-targeted by incorporation of a Targeting Moiety (TM), which is not the natural TM of a clostridial neurotoxin. The described chemical conjugation and recombinant methodologies are now regarded as conventional, and reference is made to Hermanson, G. T. (1996), Bioconjugate techniques, Academic Press, and to Wong, S. S. (1991), Chemistry of protein conjugation and cross-linking, CRC Press.

For example, WO94/21300 describes modified clostridial neurotoxin molecules that are capable of regulating Integral Membrane Protein (IMP) density present at the cell surface of the target cell. The modified neurotoxin molecules are thus capable of controlling cell activity (e.g. glucose uptake) of the target cell. WO96/33273 and WO99/17806 describe modified clostridial neurotoxin molecules that target peripheral sensory afferents. The modified neurotoxin molecules are thus capable of demonstrating an analgesic effect. WO00/10598 describes the preparation of modified clostridial neurotoxin molecules that target mucus hypersecreting cells (or neuronal cells controlling said mucus hypersecreting cells), which modified neurotoxins are capable of inhibiting hypersecretion from said cells. WO01/21213 describes modified clostridial neurotoxin molecules that target a wide range of different types of non-neuronal target cells. The modified molecules are thus capable of preventing secretion from the target cells. Additional publications in the technical field of re-targeted toxin molecules include: WO00/62814; WO00/04926; U.S. Pat. No. 5,773,586; WO93/15766; WO00/61192; and WO99/58571.

Thus, from the above-described publications, it will be appreciated that the basic concept of re-targeting a non-cytotoxic protease to a desired target cell, by selecting a TM that has a corresponding receptor present on the target cell, has been well documented.

However, different receptors present on a target cell of interest demonstrate different binding affinities for different TMs. This may be a particular problem with pain-sensing cells, which possess a wide range of receptor types having different binding affinities for different TMs. Thus, a re-targeted conjugate comprising a particular TM (that binds to a receptor on a pain-sensing cell) may demonstrate a low binding affinity for a pain-sensing target cell, which is undesirable.

There is therefore a need to develop modified non-cytotoxic conjugates that address one or more of the above problems. Of particular interest is the development of an improved conjugate for use in treating pain.

SUMMARY OF THE INVENTION

The present invention seeks to address one or more of the above problems by using as the conjugate's Targeting Moiety (TM) an "agonist" of a receptor that is present on the pain-sensing target cell of interest. In preferred embodiments, the pain-sensing target cell is a nociceptive sensory afferent, more preferably a primary nociceptive sensory afferent. In particularly preferred embodiments, the TM is an agonist of the opioid-like receptor-1 ($ORL_1$) receptor.

Accordingly, in a first aspect, the present invention provides a non-cytotoxic conjugate for inhibition or reduction of exocytic fusion in a nociceptive sensory afferent cell, comprising:

(i) a Targeting Moiety (TM),
wherein said TM is an agonist of a receptor present on said nociceptive sensory afferent cell, and wherein said receptor undergoes endocytosis to be incorporated into an endosome within the nociceptive sensory afferent cell;

(ii) a non-cytotoxic protease or a fragment thereof,
wherein the protease or protease fragment is capable of cleaving a protein of the exocytic fusion apparatus of said nociceptive sensory afferent cell; and (iii) a Translocation Domain,
wherein the Translocation Domain translocates the protease or protease fragment from within the endosome, across the endosomal membrane, and into the cytosol of the nociceptive sensory afferent cell.

BRIEF DESCRIPTION OF THE DRAWINGS

SDS-PAGE analysis of expression and purification of recLH$_N$/B from *E. coli*. In FIG. 1, recLH$_N$/B is purified from cell paste using a three column strategy as described in Example 3. Protein samples are separated by SDS-PAGE and visualised by staining with simplyblue safestain coomassie reagent. Crude, soluble MBP-LH$_N$/B fusion protein contained within the clarified extract (lane 2) is loaded onto Q-Sepharose FF anion-exchange resin. Lane 3 represents recombinant MBP-LH$_N$/B fusion eluted from column at 150-200 mM salt. This sample is treated with factor Xa protease to remove MBP affinity tag (lane 4), and cleaved mixture diluted to lower salt concentration prior to loading onto a Q-Sepharose FF anion-exchange column. Material eluted between 120-170 mM salt was rich in LH$_N$/B (lane 5). Protein in lanes 6 and 8 represents LH$_N$/B harvested after treatment with enterokinase and final purification using Benzamidine Sepharose, under non-reducing and reducing conditions respectively. Lanes 1 and 7 represent molecular mass markers [Mark 12 (Invitrogen)].

SDS-PAGE analysis of expression and purification of LH$_N$/C from *E. coli*. In FIG. 2, recLH$_N$/C is purified from *E. coli* cell paste using a two-step strategy described in Example 4. Protein samples are separated by SDS-PAGE and visualised by staining with coomassie blue. Clarified Crude cell lysate (lane 2) is loaded onto Q-Sepharose FF anion-exchange resin. Fusion protein, MBP-LH$_N$/C is eluted with 0.1 M NaCl (lane 3). Eluted material incubated at 22° C. for 16 h with factor Xa protease (New England Biolabs) to cleave fusion tag MBP and nick recLH$_N$/C at the linker site. The protein of interest is further purified from cleaved fusion products (lane 4) using Q-Sepharose FF. Lanes 5 and 7 show purified recLH$_N$/C under non-reducing conditions and reduced with 10 mM DTT respectively, to illustrate disulphide bonding at the linker region between LC and H$_N$ domains after nicking with factor Xa. Lanes 1 and 6 represent molecular mass markers (shown in KDa); Mark 12 (Invitrogen).

SDS-PAGE analysis of expression and purification of N[1-17]-LH$_N$/A from *E. coli*. In FIG. 3, N[1-17]-LH$_N$/A is purified from *E. coli* BL21 cell paste using the methodology outlined in Example 9. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE (Panel A) and Western blotting (Panel B). Anti-nociceptin antisera (obtained from Abcam) were used as the primary antibody for Western blotting. The final purified material in the absence and presence of reducing agent is identified in the lanes marked [−] and [+] respectively.

Using the methodology outlined in Example 26, a LC/A-nociceptin-H$_N$/A fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE (Panel A) and Western blotting (Panel B). Anti-nociceptin antisera (obtained from Abcam) were used as the primary antibody for Western blotting. The final purified material in the absence and presence of reducing agent is identified in the lanes marked [−] and [+] respectively.

Figure 5:
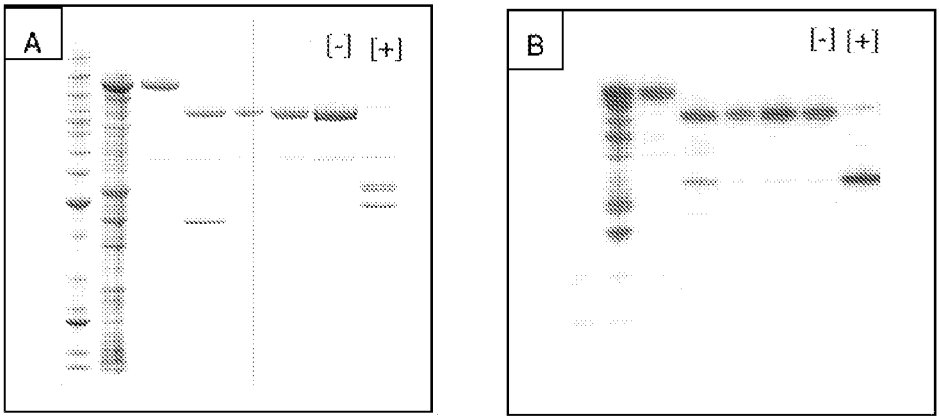

FIG. 5-P*urification* of a Nociceptin-LC/A-H$_N$/A Fusion Protein

Using the methodology outlined in Example 26, a nociceptin-LC/A-H$_N$/A fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE (Panel A) and Western blotting (Panel B). Anti-nociceptin antisera (obtained from Abcam) were used as the primary antibody for Western blotting. The final purified material in the absence and presence of reducing agent is identified in the lanes marked [−] and [+] respectively.

Figure 6:
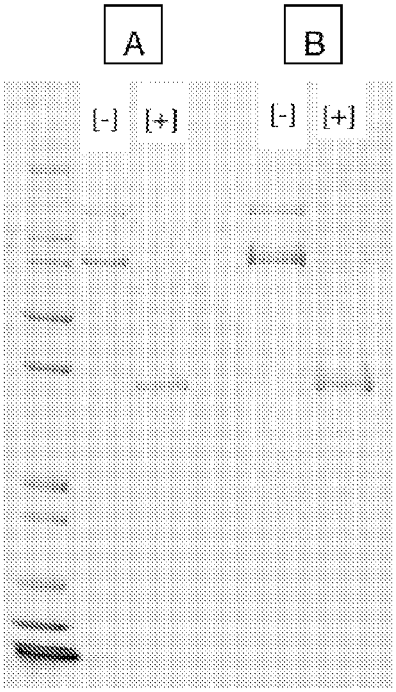

FIG. 6-P*urification* of a LC/C-nociceptin-H$_N$/C Fusion Protein

Using the methodology outlined in Example 26, an LC/C-nociceptin-H$_N$/C fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE (Panel A) and Western blotting (Panel B). Anti-nociceptin antisera (obtained from Abcam) were used as the primary antibody for Western blotting. The final purified material in the absence and presence of reducing agent is identified in the lanes marked [−] and [+] respectively.

Figure 7:
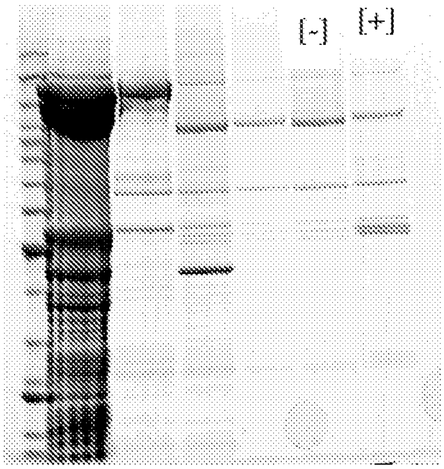

FIG. 7-P*urification* of a LC/A-Met Enkephalin-H$_N$/A Fusion Protein

Using the methodology outlined in Example 26, an LC/A-met enkephalin-H$_N$/A fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

Figure 8:
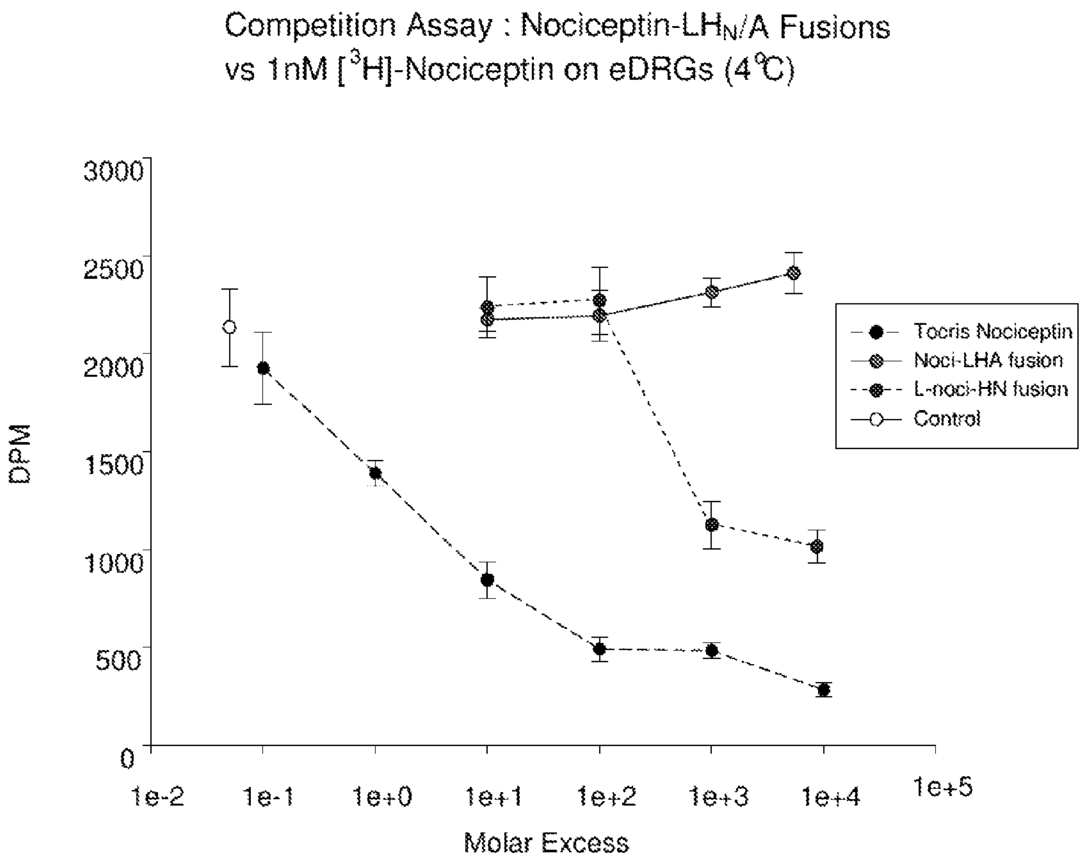

FIG. 8-C*omparison* of Binding Efficacy of a LC/A-nociceptin-$H_N$/A Fusion Protein and a Nociceptin-LC/A-$H_N$/A Fusion Protein The ability of nociceptin fusions to bind to the $ORL_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). It is clear that the LC/A-nociceptin-$H_N$/A fusion is far superior to the nociceptin-LC/A-$H_N$/A fusion at interacting with the $ORL_1$ receptor.

Figure 9:
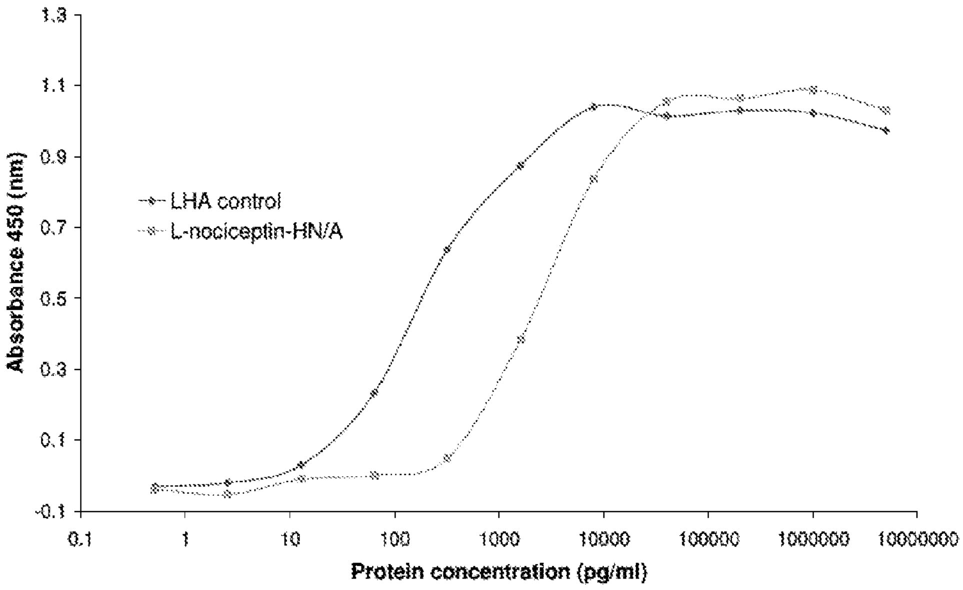

FIG. 9—In Vitro Catalytic Activity of a LC/A-Nociceptin-$H_N$/A Fusion Protein The in vitro endopeptidase activity of the purified LC/A-nociceptin-$H_N$/A fusion protein was determined essentially as described in Chaddock et al 2002, Prot. Express Purif. 25, 219-228. Briefly, SNAP-25 peptide immobilised to an ELISA plate was exposed to varying concentrations of fusion protein for 1 hour at 37° C. Following a series of washes, the amount of cleaved SNAP-25 peptide was quantified by reactivity with a specific antisera.

Figure 10:
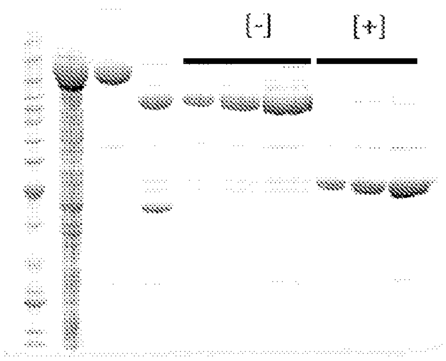

FIG. 10-P*urification* of a LC/A-Nociceptin Variant-$H_N$/A Fusion Protein

Using the methodology outlined in Example 26, an LC/A-nociceptin variant-$H_N$/A fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

Figure 11:
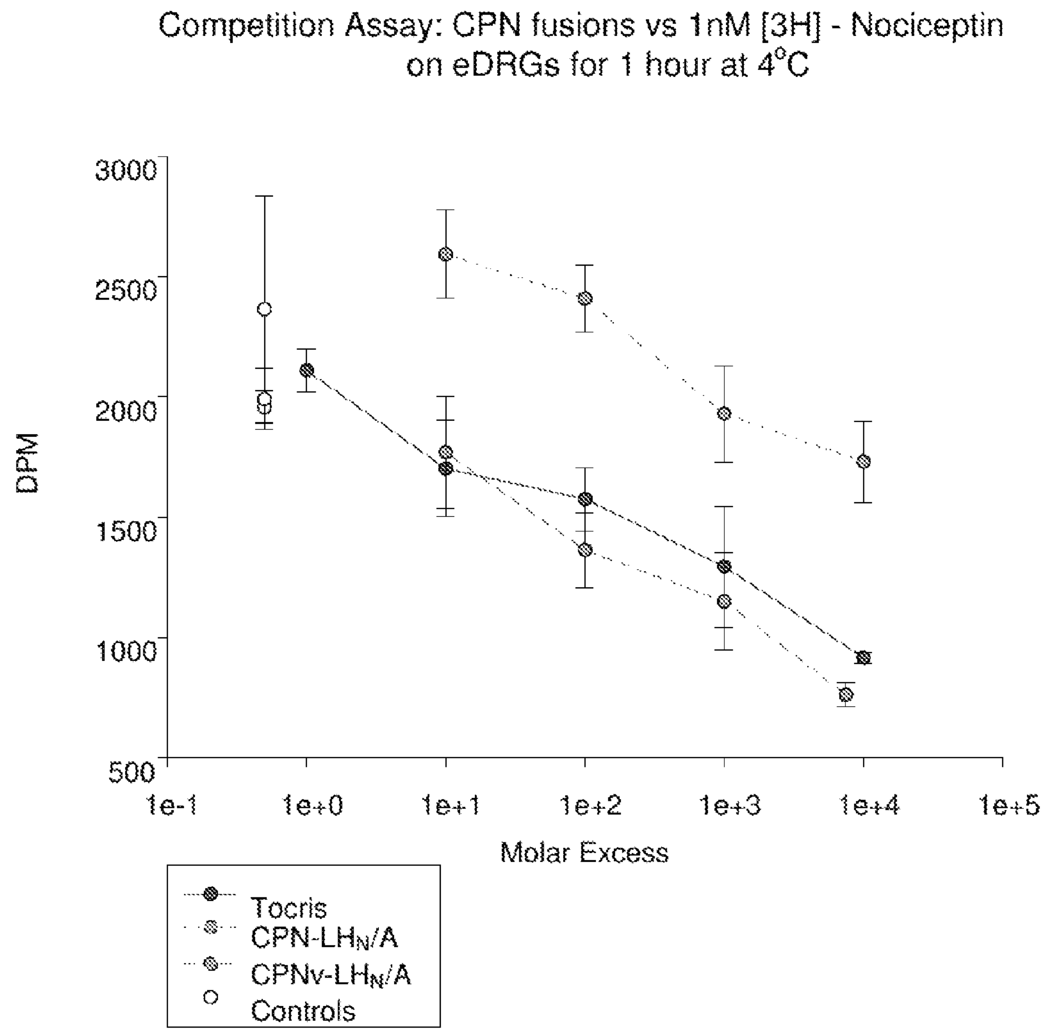

FIG. 11-C*omparison* of Binding Efficacy of a LC/A-Nociceptin-$H_N$/A Fusion Protein and a LC/A-Nociceptin Variant-$H_N$/A Fusion Protein The ability of nociceptin fusions to bind to the $ORL_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). It is clear that the LC/A-nociceptin variant-$H_N$/A fusion (CPNv-LHA) is superior to the LC/A-nociceptin variant-$H_N$/A fusion (CPN-LHA) at interacting with the $ORL_1$ receptor.

Figure 12:
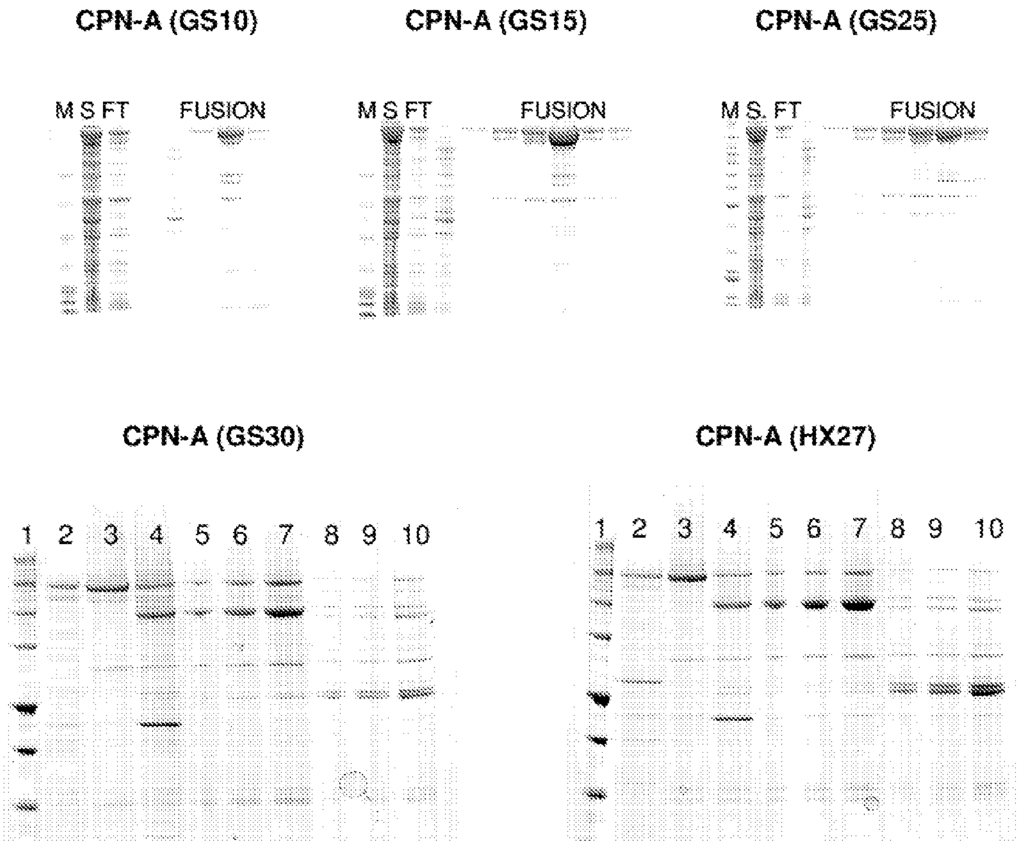

FIG. 12-Expressed/Purified LC/A-Nociceptin-$H_N$/A Fusion Protein Family with Variable Spacer Length Product(s)

Using the methodology outlined in Example 26, variants of the LC/A-CPN-$H_N$/A fusion consisting of GS10, GS30 and HX27 are purified from *E. coli* cell paste. Samples from the purification of LC/A-CPN(GS10)-$H_N$/A, LC/A-CPN (GS15)-$H_N$/A, LC/A-CPN(GS25)-$H_N$/A, LC/A-CPN (GS30)-$H_N$/A and LC/A-CPN(HX27)-$H_N$/A were assessed by SDS-PAGE prior to staining with Coomassie Blue. The electrophoresis profile indicates purification of a disulphide-bonded di-chain species of the expected molecular mass of CPBE-A. Top panel: M=benchmark molecular mass markers; S=total *E. coli* protein soluble fraction; FT=proteins that did not bind to the $Ni^{2+}$-charged Sepharose column; FUSION=fusion protein eluted by the addition of imidazole. Bottom panel: Lane 1=benchmark molecular mass markers; Lane 2=total *E. coli* protein soluble fraction; Lane 3=purified material following initial capture on $Ni^{2+}$-charged Sepharose; Lane 4=Factor Xa treated material prior to final capture on $Ni^{2+}$-charged Sepharose; Lane 5=purified final material post activation with Factor Xa (5 μl); Lane 6=purified final material post activation with Factor Xa (10 μl); Lane 7=purified final material post activation with Factor Xa (20 μl); Lane 8=purified final material post activation with Factor Xa+DTT (5 μl); Lane 9=purified final material post activation with Factor Xa+DTT (10 μl); Lane 10=purified final material post activation with Factor Xa+DTT (20 μl).

Figure 13:
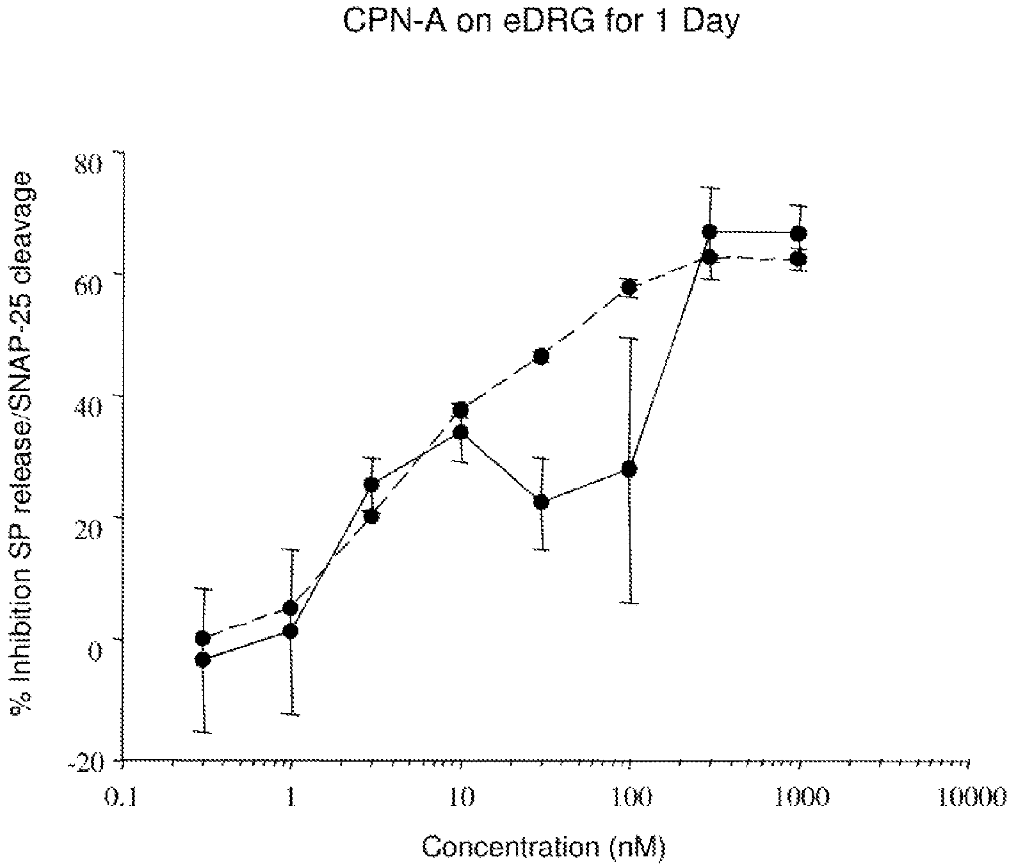

FIG. 13-I*nhibition* of SP Release and Cleavage of SNAP-25 by CPN-A

Briefly, primary cultures of dorsal root ganglia (DRG) were exposed to varying concentrations of CPN-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis and plotted against fusion concentration (dashed line). Material was also recovered for an analysis of substance P content using a specific EIA kit. Inhibition of substance P release is illustrated by the solid line. The fusion concentration required to achieve 50% maximal SNAP-25 cleavage is estimated to be 6.30±2.48 nM.

Figure 14:
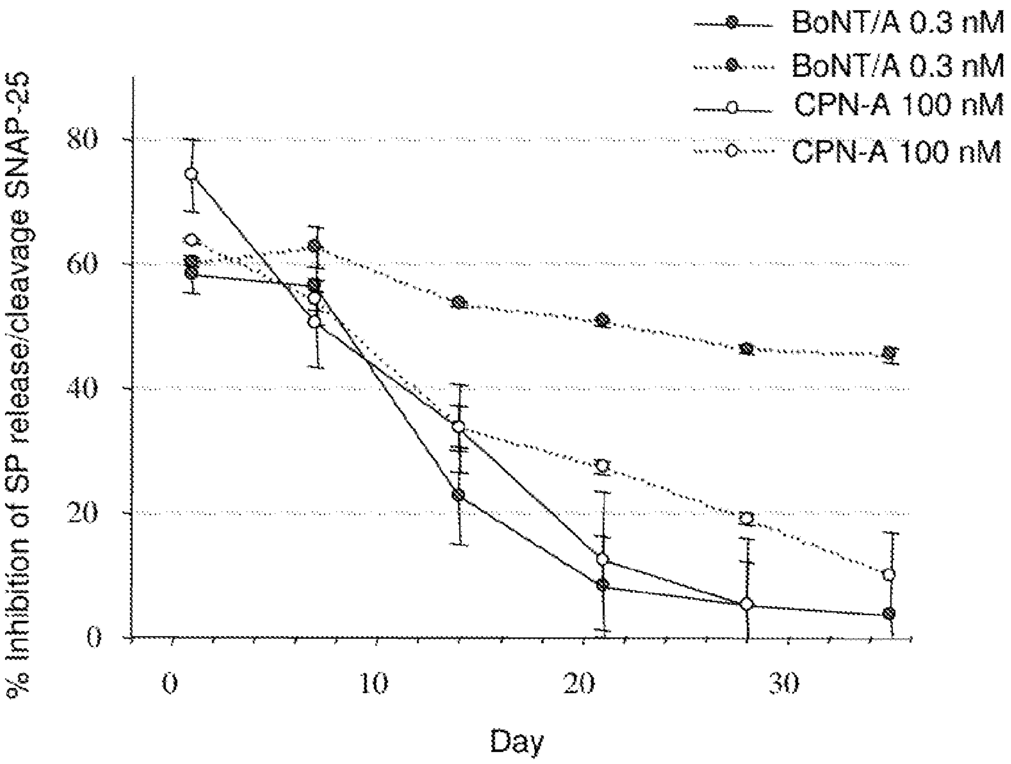

FIG. 14-I*nhibition* of SP Release and Cleavage of SNAP-25 Over Extended Time Periods after Exposure of DRG to CPN-A Primary cultures of dorsal root ganglia (DRG) were exposed to varying concentrations of CPN-A for 24 hours. Botulinum neurotoxin (BoNT/A) was used as a control. After this initial exposure, extracellular material was removed by washing, and the cells incubated at 37° C. for varying periods of time. At specific time points, cellular proteins were separated by SDS-PAGE, Western blotted, and probed with anti-SNAP-25 to facilitate an assessment of SNAP-25 cleavage. The percentage of cleaved SNAP-25 was calculated by densitometric analysis and illustrated by the dotted lines. Material was also recovered for an analysis of substance P content using a specific EIA kit. Inhibition of substance P release is illustrated by the solid lines.

Figure 15:
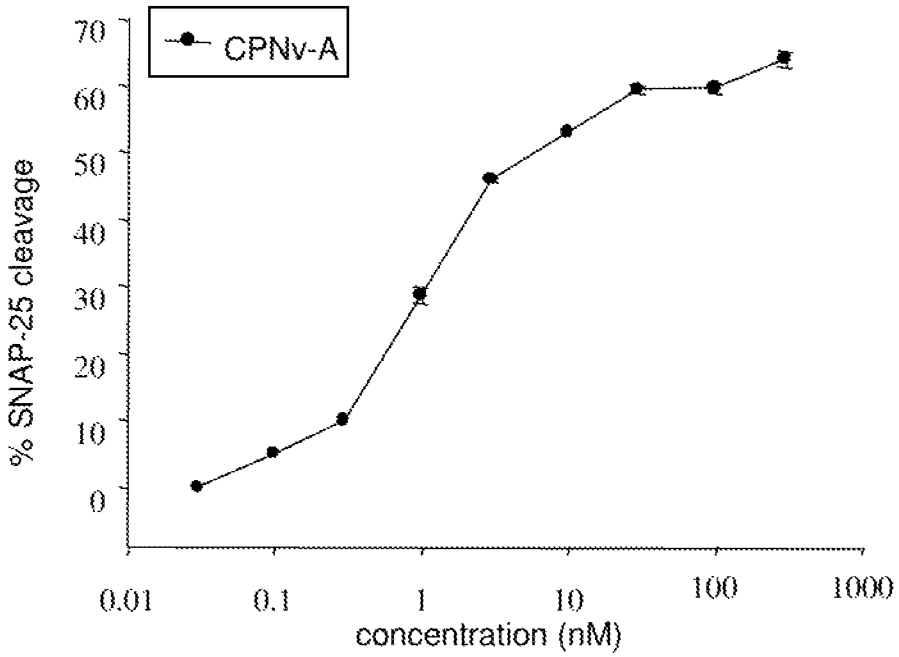

FIG. 15-C*leavage* of SNAP-25 by CPNv-A

Primary cultures of dorsal root ganglia (DRG) were exposed to varying concentrations of CPNv-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. The fusion concentration required to achieve 50% maximal SNAP-25 cleavage is estimated to be 1.38±0.36 nM.

Figure 16:
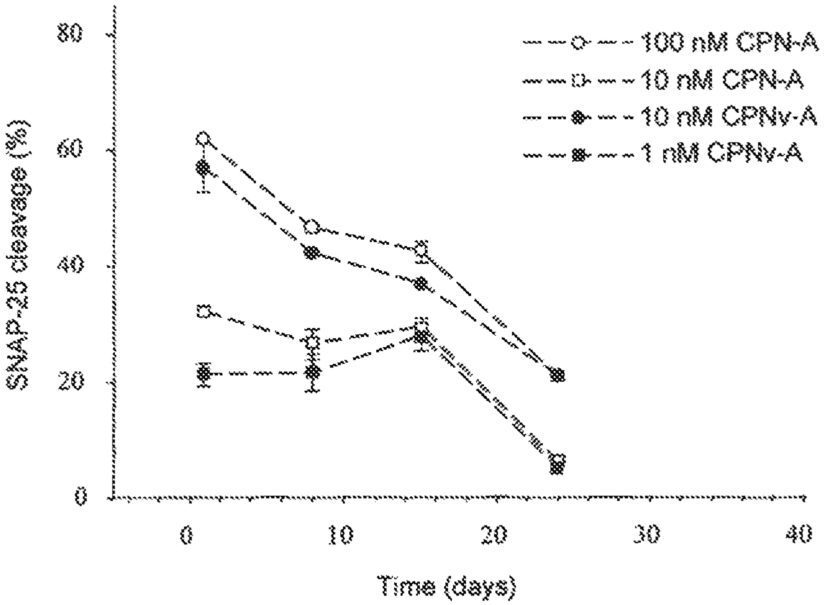

FIG. 16-C*leavage* of SNAP-25 Over Extended Time Periods after Exposure of DRG to CPNv-A Primary cultures of dorsal root ganglia (DRG) were exposed to varying concentrations of CPNv-A for 24 hours. CPN-A was used as a control. After this initial exposure, extracellular material was removed by washing, and the cells incubated at 37° C. for varying periods of time. At specific time points, cellular proteins were separated by SDS-PAGE, Western blotted, and probed with anti-SNAP-25 to facilitate an assessment of SNAP-25 cleavage. The percentage of cleaved SNAP-25 was calculated by densitometric analysis.

Figure 17:
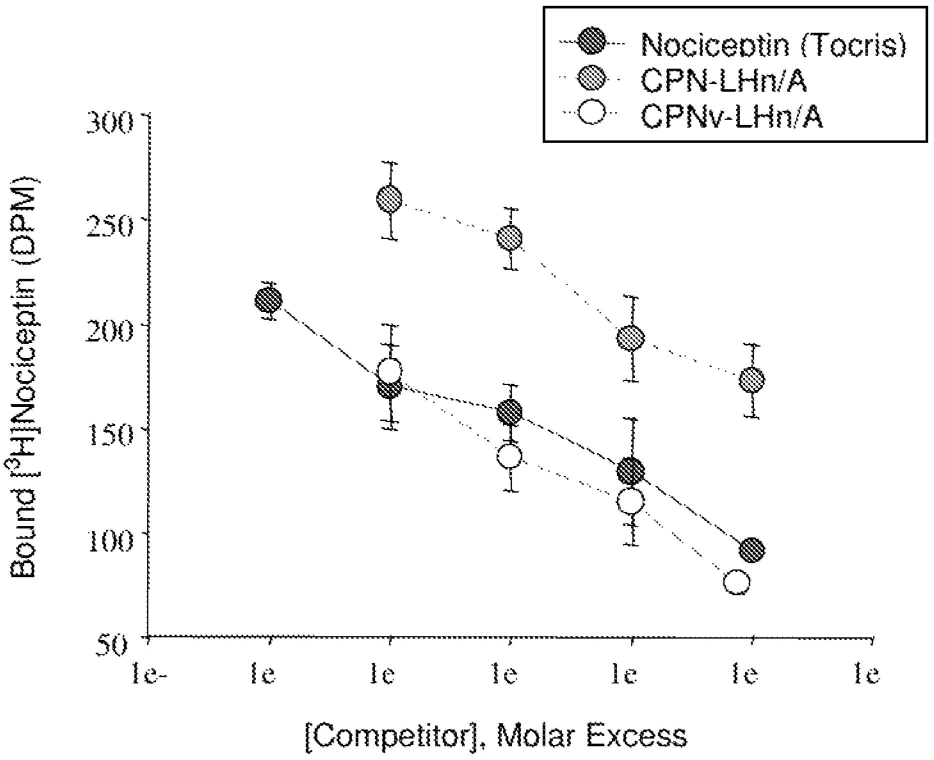

FIG. 17-CPN*v*-A Fusion-Mediated Displacement of [3H]-Nociceptin Binding

The ability of nociceptin fusions to bind to the $ORL_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). It is clear that the LC/A-nociceptin variant-$H_N$/A fusion (labelled as CPNv-LHnA) is superior to the LC/A-nociceptin-$H_N$/A fusion (labelled as CPN-LHnA) at interacting with the $ORL_1$ receptor.

Figure 18:
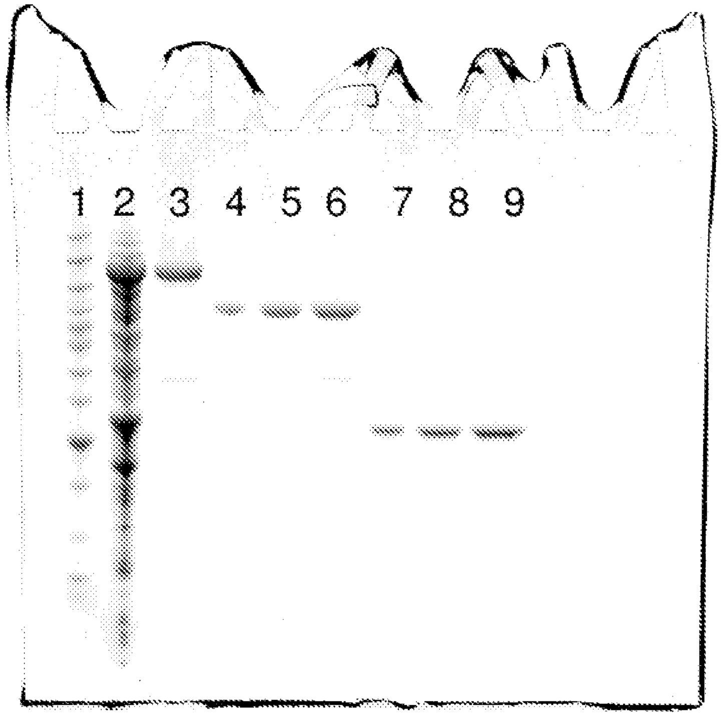

FIG. 18-Expressed/Purified CPNv(Ek)-A Product

Proteins were subjected to SDS-PAGE prior to staining with Coomassie Blue. The electrophoresis profile indicates purification of a disulphide-bonded di-chain species of the expected molecular mass of CPNv(Ek)-A. Lane 1=benchmark molecular mass markers; Lane 2=total *E. coli* protein soluble fraction; Lane 3=purified material following initial capture on $Ni^{2+}$-charged Sepharose; Lane 4=purified final material post activation with enterokinase (5 μl); Lane 5=purified final material post activation with enterokinase (10 μl); Lane 6=purified final material post activation with enterokinase (20 μl); Lane 7=purified final material post activation with enterokinase+DTT (5 μl); Lane 8=purified final material post activation with enterokinase+DTT (10 μl); Lane 9=purified final material post activation with enterokinase+DTT (20 μl).

Figure 19:
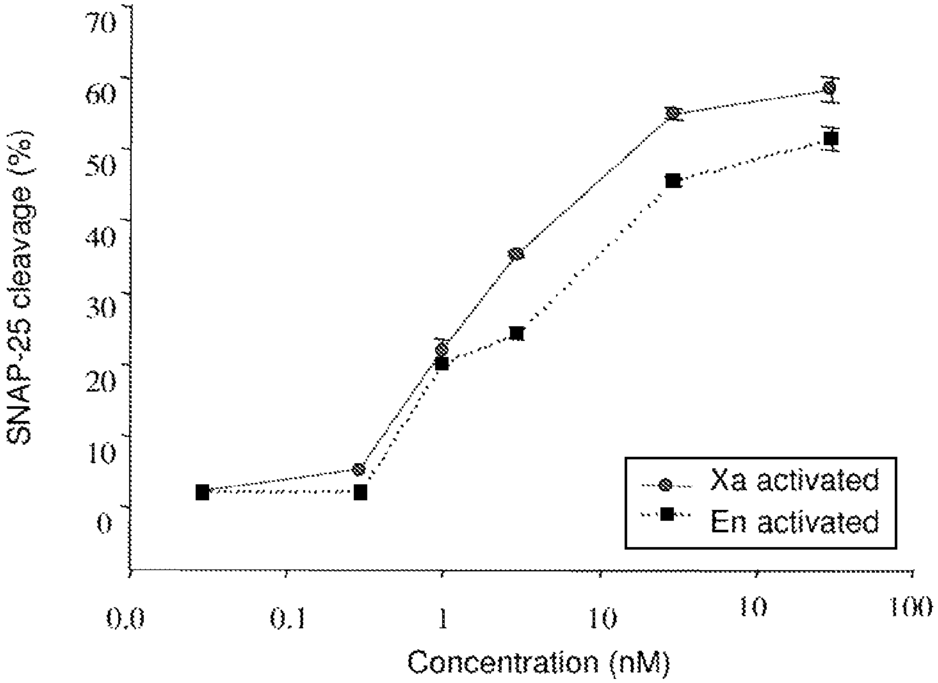

FIG. 19-C*leavage* of SNAP-25 by CPNv(Ek)-A

Primary cultures of dorsal root ganglia (DRG) were exposed to varying concentrations of CPNv(Ek)-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. CPNv-A as prepared in Example 26 was used for comparison purposes. The percentage cleavage of SNAP-25 by CPNv(Ek)-A (labelled as En activated) and CPNv-A (labelled as Xa activated) are illustrated.

Figure 20:
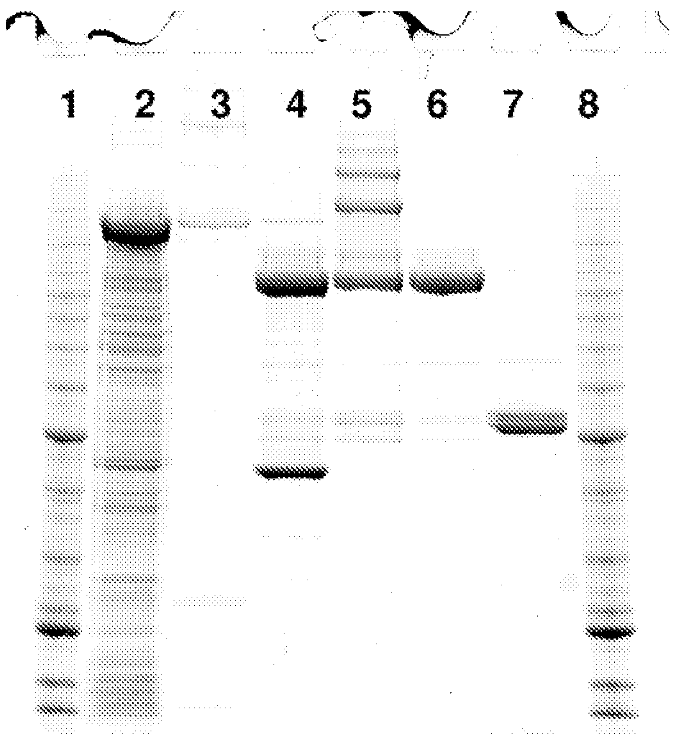

FIG. 20-Expressed/Purified CPNv-C Product

Proteins were subjected to SDS-PAGE prior to staining with Coomassie Blue. The electrophoresis profile indicates purification of a disulphide-bonded di-chain species of the expected molecular mass of CPNv-C. Lane 1=benchmark molecular mass markers; Lane 2=total *E. coli* protein soluble fraction; Lane 3=purified material following initial capture on $Ni^{2+}$-charged Sepharose; Lane 4=Factor Xa treated material prior to final capture on $Ni^{2+}$-charged Sepharose; Lane 5=purified material following second capture on $Ni^{2+}$-charged Sepharose; Lane 6=final purified material; Lane 7=final purified material+DTT; Lane 8=is benchmark molecular mass markers.

Figure 21:
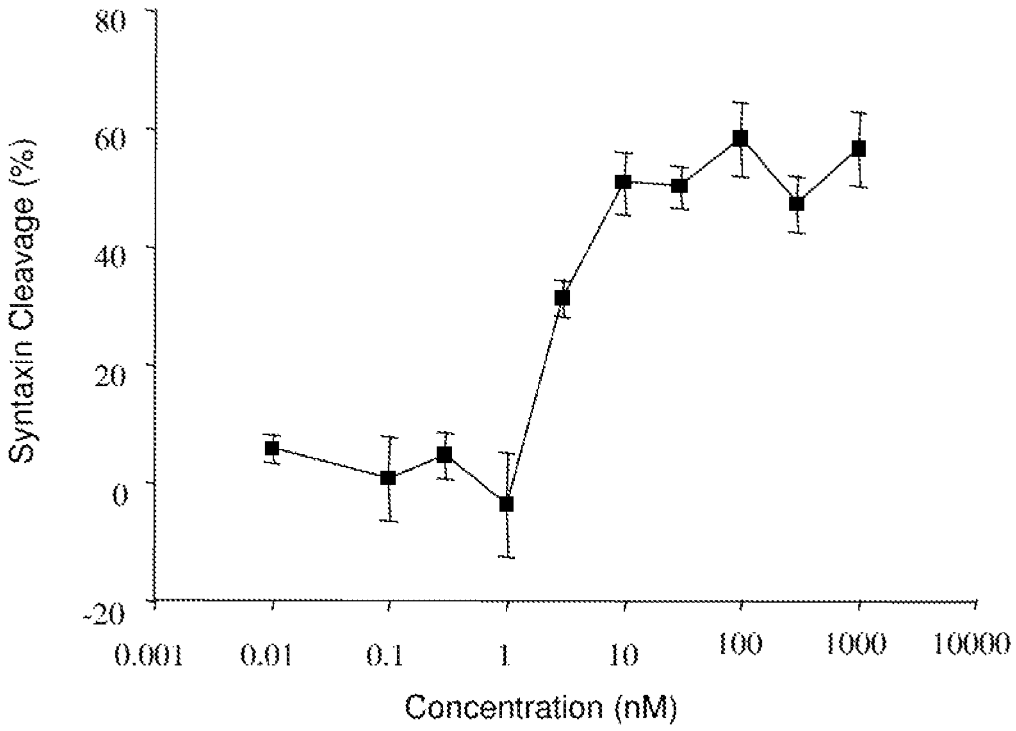

FIG. 21-C*leavage* of Syntaxin by CPNv-C

Primary cultures of dorsal root ganglia (DRG) were exposed to varying concentrations of CPNv-C for 24 hours. Cellular proteins were separated by SDS-PAGE, Western blotted, and probed with anti-syntaxin to facilitate an assessment of syntaxin cleavage. The percentage of cleaved syntaxin was calculated by densitometric analysis. The fusion concentration required to achieve 50% maximal syntaxin cleavage is estimated to be 3.13±1.96 nM.

Figure 22:
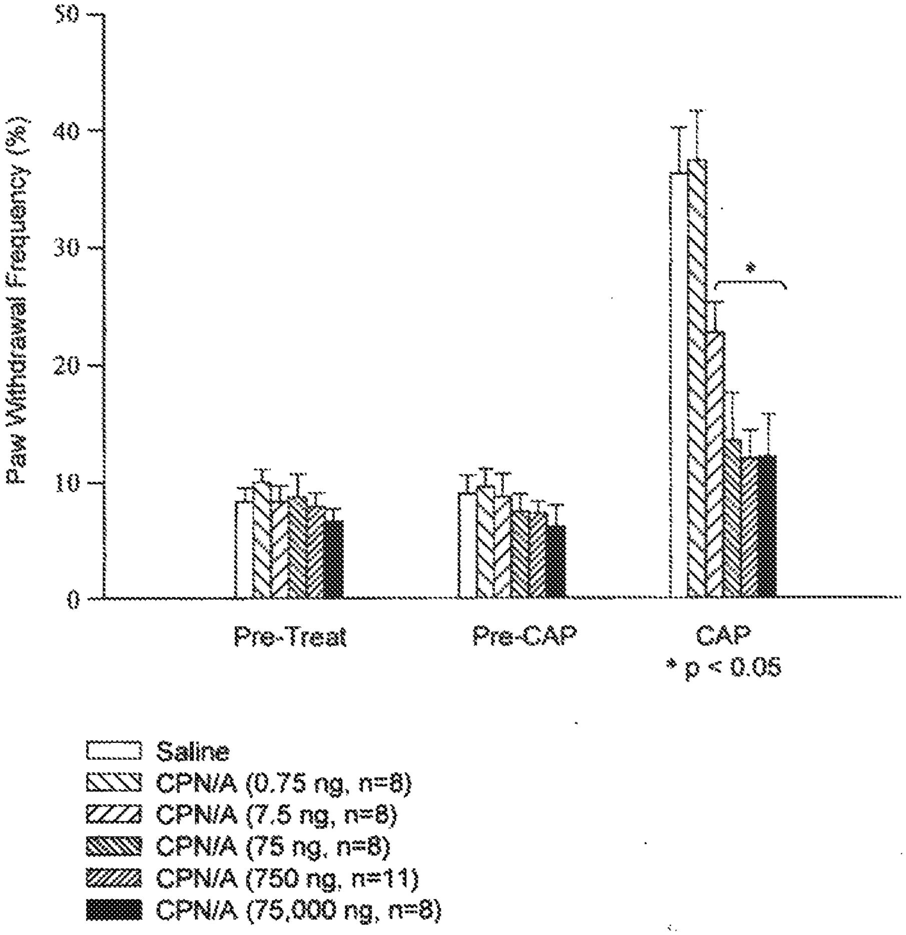

FIG. 22-CPN-A efficacy in the Acute Capsaicin-Induced Mechanical Allodynia Model The ability of an LC/A-nociceptin-$H_N$/A fusion (CPN/A) to inhibit capsaicin-induced mechanical allodynia was evaluated following subcutaneous intraplantar injection in the rat hind paw. Test animals were evaluated for paw withdrawal frequency (PWF %) in response to a 10 g Von Frey filament stimulus series (10 stimuli×3 trials) prior to recruitment into the study (Pre-Treat); after subcutaneous intraplantar treatment with CPN/A but before capsaicin (Pre-CAP); and following capsaicin challenge post-injection of CPN/A (average of responses at 15' and 30'; CAP). Capsaicin challenge was achieved by injection of 10 μL of a 0.3% solution. Sample dilutions were prepared in 0.5% BSA/saline.

Figure 23:
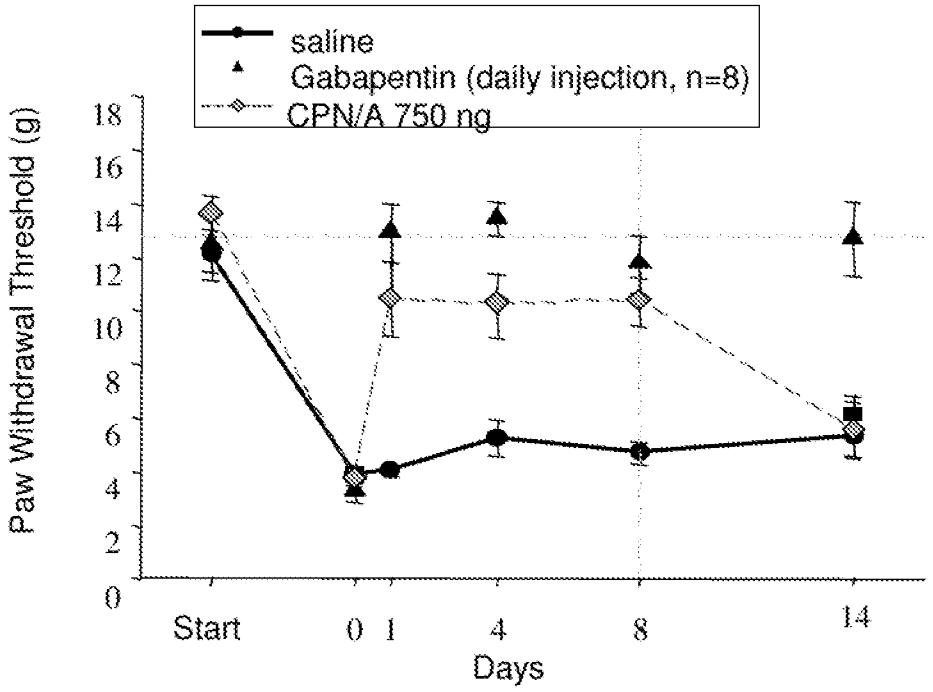

FIG. 23-CPN-A efficacy in the Streptozotocin (STZ)-Induced Peripheral Diabetic Neuropathy (Neuropathic Pain) Model Male Sprague-Dawley rats (250-300 g) are treated with 65 mg/kg STZ in citrate buffer (I.V.) and blood glucose and lipid are measured weekly to define the readiness of the model. Paw Withdrawal Threshold (PWT) is measured in response to a Von Frey filament stimulus series over a period of time. Allodynia is said to be established when the PWT on two consecutive test dates (separated by 1 week) measures below 6 g on the scale. At this point, rats are randomized to either a saline group (negative efficacy control), gabapentin group (positive efficacy control) or a test group (CPN/A). Test materials (20-25 μl) are injected subcutaneously as a single injection (except gabapentin) and the PWT is measured at 1 day post-treatment and periodically thereafter over a 2 week period. Gabapentin (30 mg/kg i.p.@ 3 ml/kg injection volume) is injected daily, 2 hours prior to the start of PWT testing.

Figure 24:
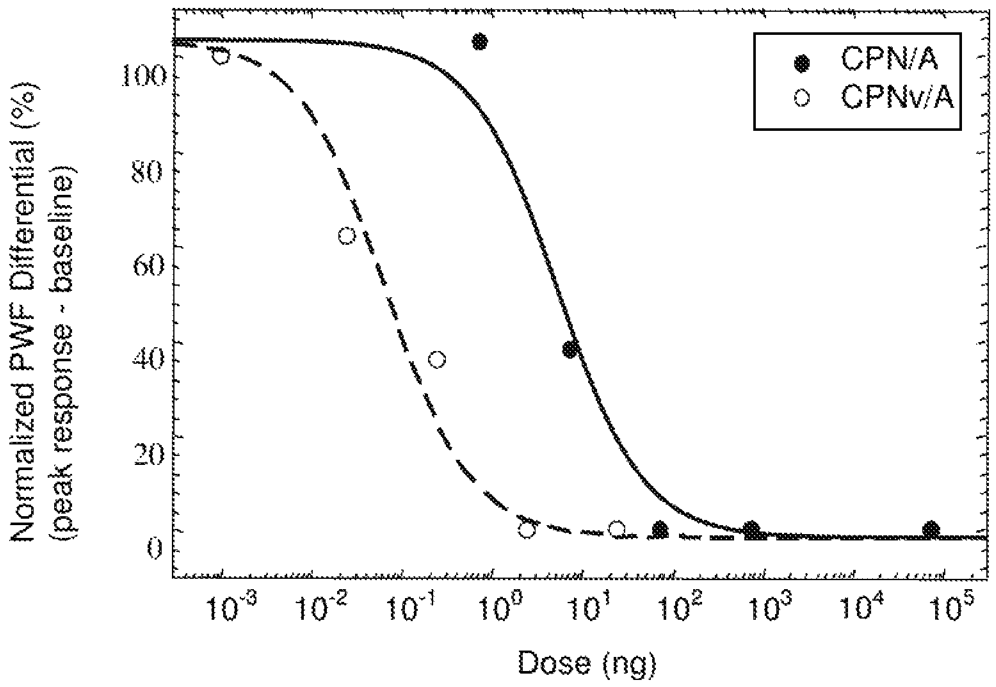

FIG. 24-CPN*v*-A Efficacy in the Acute Capsaicin-Induced Mechanical Allodynia model The ability of an LC/A-nociceptin variant-$H_N$/A fusion (CPNv/A) to inhibit capsaicin-induced mechanical allodynia was evaluated following subcutaneous intraplantar injection in the rat hind paw. Test animals were evaluated for paw withdrawal frequency (PWF %) in response to a 10 g Von Frey filament stimulus series (10 stimuli×3 trials) prior to recruitment into the study (Pre-Treat), after subcutaneous intraplantar treatment with CPNv/A but before capsaicin (Pre-CAP), and following capsaicin challenge post-injection of CPNv/A (average of responses at 15' and 30'; CAP). Capsaicin challenge was achieved by injection of 10 μL of a 0.3% solution. Sample dilutions were prepared in 0.5% BSA/saline. These data are expressed as a normalized paw withdrawal frequency differential, in which the difference between the peak response (post-capsaicin) and the baseline response (pre-capsaicin) is expressed as a percentage. With this analysis, it can be seen that CPNv/A is more potent than CPN/A since a lower dose of CPNv/A is required to achieve similar analgesic effect to that seen with CPN/A.

Figure 25:
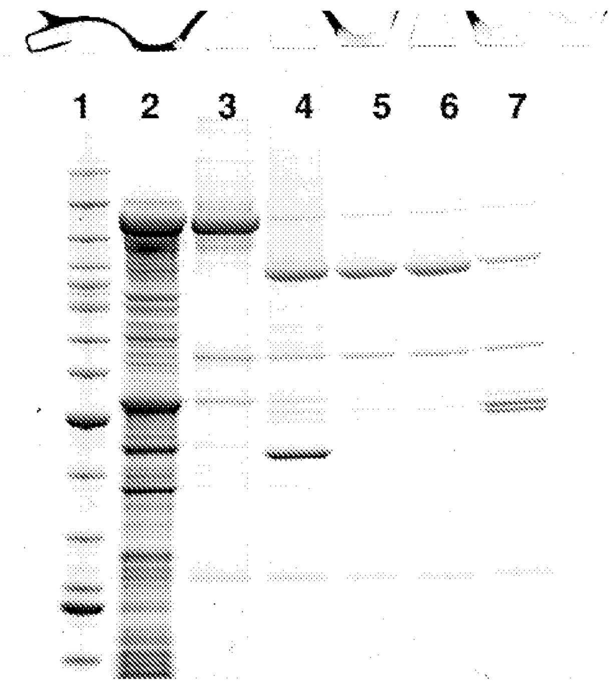

FIG. 25-Expressed/Purified LC/A-CPLE-$H_N$/A Product

Proteins were subjected to SDS-PAGE prior to staining with Coomassie Blue. The electrophoresis profile indicates purification of a disulphide-bonded di-chain species of the expected molecular mass of CPLE-A. Lane 1=benchmark molecular mass markers; Lane 2=total *E. coli* protein soluble fraction; Lane 3=purified material following initial capture on $Ni^{2+}$-charged Sepharose; Lane 4=Factor Xa treated material prior to final capture on $Ni^{2+}$-charged Sepharose; is Lane 5=purified material following second capture on $Ni^{2+}$-charged Sepharose; Lane 6=final purified material; Lane 7=final purified material+DTT.

Figure 26:
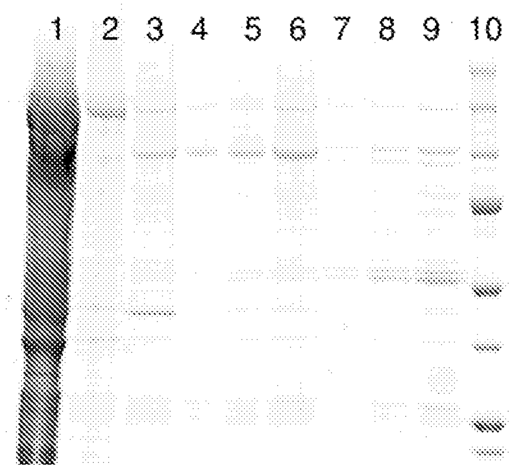

FIG. 26-Expressed/Purified LC/A-CPBE-$H_N$/A Product

Proteins were subjected to SDS-PAGE prior to staining with Coomassie Blue. The electrophoresis profile indicates purification of a disulphide-bonded di-chain species of the expected molecular mass of CPBE-A. Lane 1=total *E. coli* protein soluble fraction; Lane 2=purified material following initial capture on $Ni^{2+}$-charged Sepharose; Lane 3=Factor Xa treated material prior to final capture on $Ni^{2+}$-charged Sepharose; Lane 4=purified final material post activation with Factor Xa (5 μl); Lane 5=purified final material post activation with Factor Xa (10 μl); Lane 6=purified final material post activation with Factor Xa (20 μl); Lane 7=purified final material post activation with Factor Xa+DTT (5 μl); Lane 8=purified final material post activation with Factor Xa+DTT (10 μl); Lane 9=purified final material post activation with Factor Xa+DTT (20 μl); Lane 10=benchmark molecular mass markers.

Figure 27:
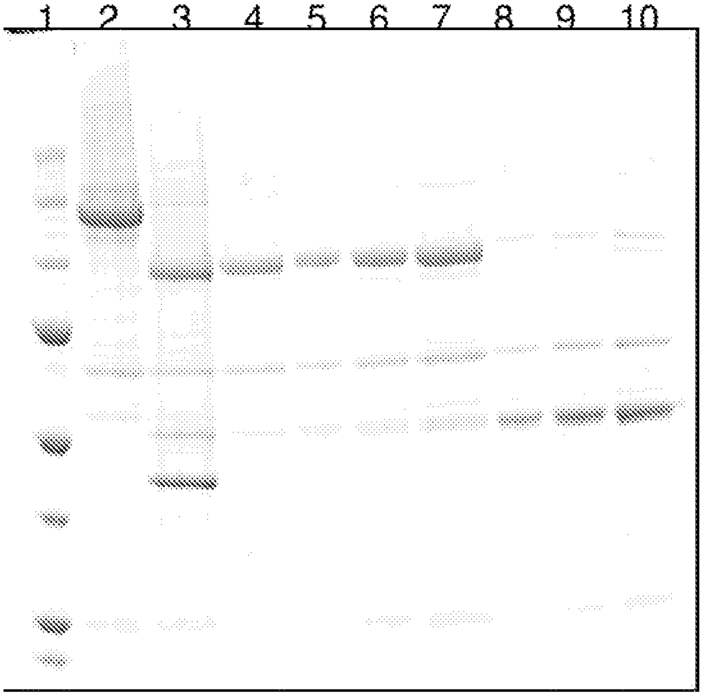

FIG. 27-Expressed/Purified CPOP-A Product Proteins were subjected to SDS-PAGE prior to staining with Coomassie Blue. The electrophoresis profile indicates purification of a disulphide-bonded di-chain species of the expected molecular mass of CPOP-A. Lane 1=benchmark molecular mass markers; Lane 2=purified material following initial capture on $Ni^{2+}$-charged Sepharose; Lane 3=Factor Xa treated material prior to final capture on $Ni^{2+}$-charged Sepharose; Lane 4=purified material following second capture on $Ni^{2+}$-charged Sepharose; Lane 5=purified final material post activation with Factor Xa (5 μl); Lane 6=purified final material post activation with Factor Xa (10 μl); Lane 7=purified final material post activation with Factor Xa (20 μl); Lane 8=purified final material post activation with Factor Xa+DTT (5 μl); Lane 9=purified final material post activation with Factor Xa+DTT (10 μl); Lane 10=purified final material post activation with Factor Xa+DTT (20 μl).

Figure 28:
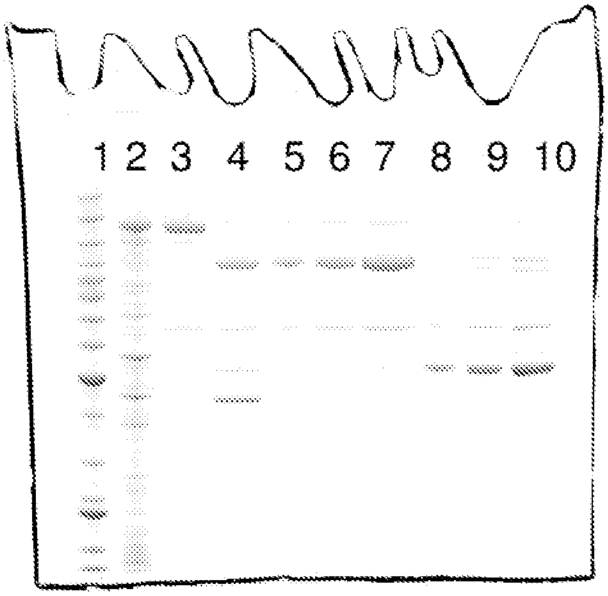

FIG. 28-Expressed/Purified CPOPv-A Product

Proteins were subjected to SDS-PAGE prior to staining with Coomassie Blue. The electrophoresis profile indicates purification of a disulphide-bonded di-chain species of the expected molecular mass of CPOPv-A. Lane 1=benchmark molecular mass markers; Lane 2=total *E. coli* protein soluble fraction; Lane 3=purified material following initial capture on $Ni^{2+}$-charged Sepharose; Lane 4=Factor Xa treated material prior to final capture on $Ni^{2+}$-charged Sepharose; Lane 5=purified final material post activation with Factor Xa (5 μl); Lane 6=purified final material post activation with Factor Xa (10 μl); Lane 7=purified final material post activation with Factor Xa (20 μl); Lane 8=purified final material post activation with Factor Xa+DTT (5 μl); Lane 9=purified final material post activation with Factor Xa+DTT (10 μl); Lane 10=purified final material post activation with Factor Xa+DTT (20 μl).

Figure 29:
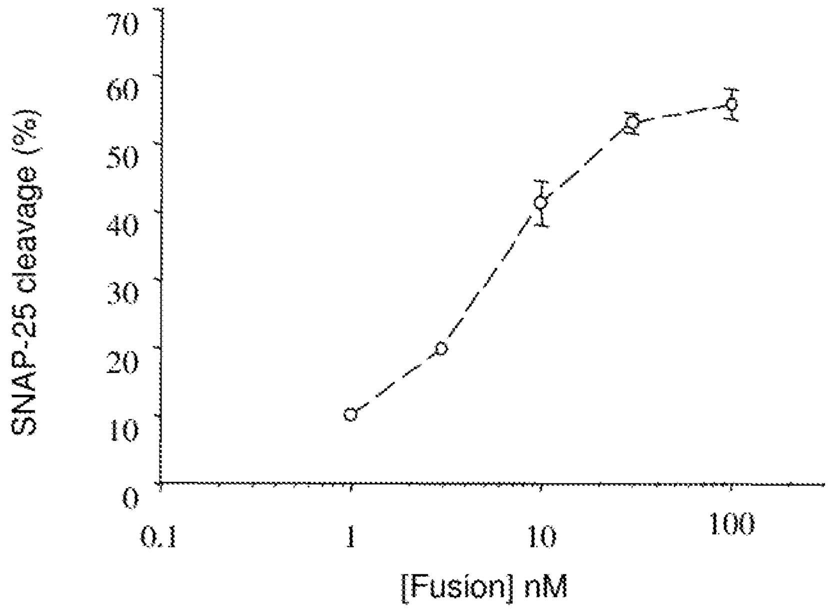

FIG. 29—In Vitro SNAP-25 Cleavage in a DRG Cell Model

Primary cultures of dorsal root ganglia (DRG) were exposed to varying concentrations of CPOPv-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis.

Figure 30:
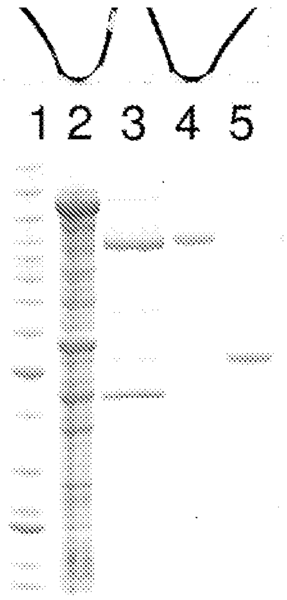

FIG. 30-Expressed/Purified CPNv-A-FXa-HT (Removable his-Tag)

Proteins were subjected to SDS-PAGE prior to staining with Coomassie Blue. The electrophoresis profile indicates purification of a disulphide-bonded di-chain species of the expected molecular mass of CPNv-A-FXa-HT. Lane 1=benchmark molecular mass markers; Lane 2=total *E. coli* protein soluble to fraction; Lane 3=Factor Xa treated material prior to final capture on $Ni^{2+}$-charged Sepharose; Lane 4=purified final material post activation with Factor Xa; Lane 5=purified final material post activation with Factor Xa+DTT.

Figure 31:
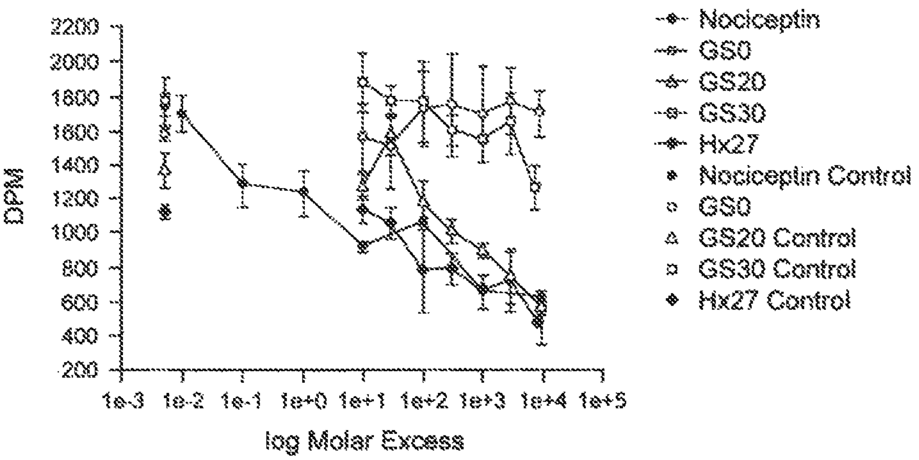
Figure 31:
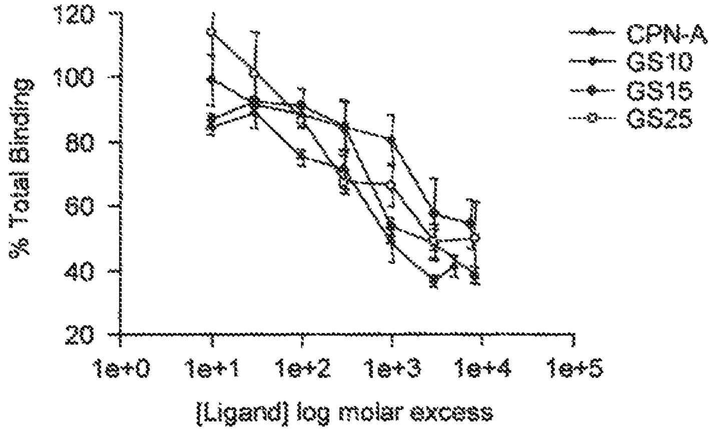

FIG. 31—In Vitro Efficacy of LC/A-Nociceptin-$H_N$/A Fusion Proteins with Variable Spacer Length, as Assessed by Ligand Competition Assay The ability of LC/A-nociceptin-$H_N$/A fusions of variable spacer length to bind to the $ORL_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). The upper panel illustrates the displacement characteristics of the GS0, GS20, GS30 and Hx27 spacers, whilst the lower panel illustrates the displacement achieved by the GS10, GS15 and GS25 spaced fusion proteins. It is concluded that the GS0 and GS30 spacers are ineffective, and the GS10 is poorly effective, at displacing nociceptin from the $ORL_1$ receptor.

Figure 32:
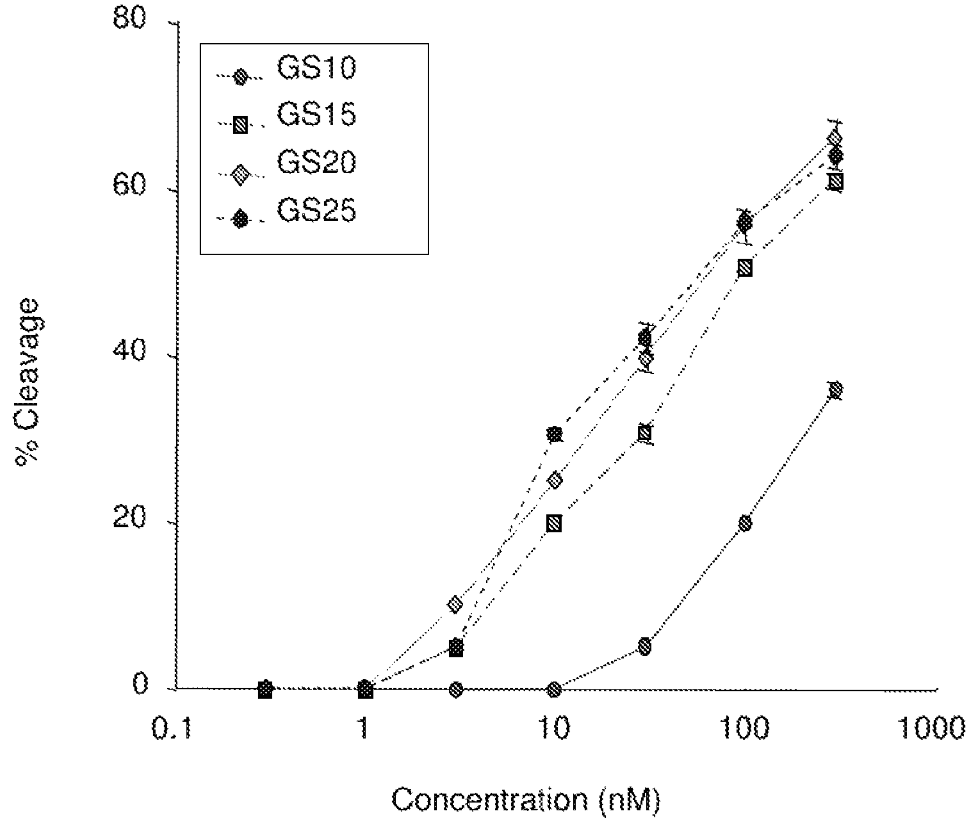

FIG. 32—In Vitro Efficacy of LC/A-Nociceptin-$H_N$/A Fusion Proteins with Variable Spacer Length, as Assessed by In Vitro SNAP-25 Cleavage Primary cultures of dorsal root ganglia (DRG) were exposed to varying concentrations of CPN-A (of variable spacer length) for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. The poorly effective binding characteristics of the GS10 spaced fusion protein (see FIG. 28) are reflected in the higher concentrations of fusion required to achieve cleavage of intracellular SNAP-25. GS0 and GS30 spaced fusion proteins were completely ineffective (date not shown). GS15, 20 and 25 spaced fusion proteins were similarly effective.

Figure 33:
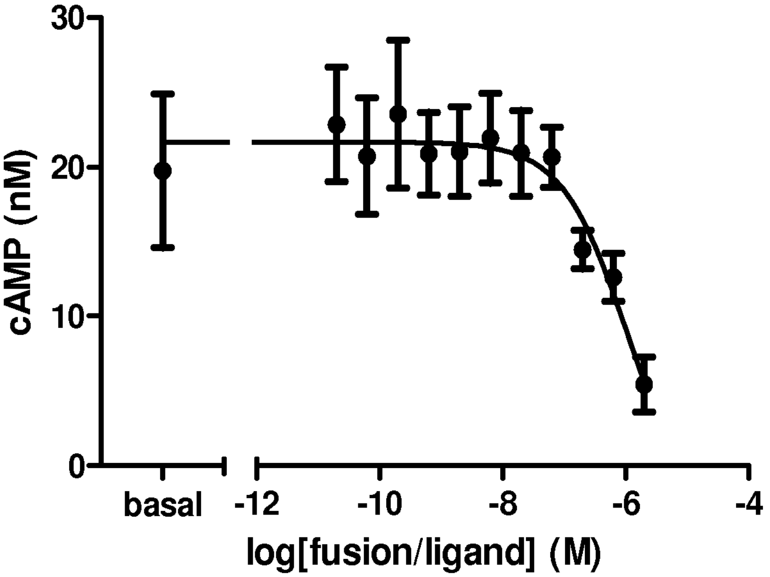

FIG. 33—GALR1 Receptor Activation Studies with a Galanin Fusion Protein

Chinese hamster ovary (CHO) cells were transfected so that they express the GALR1 receptor and SNAP-25. Said cells were used to measure cAMP depletion that occurs when the receptor is activated with a galanin ligand, using a FRET-based cAMP kit (LANCE kit from Perkin Elmer). The transfected cells were exposed to varying concentrations of a galanin-16 (GA16) fusion protein of the present invention for 2 hours. cAMP levels were then detected by addition of a detection mix containing a fluorescently labelled cAMP tracer (Europium-streptavidin/biotin-cAMP) and fluorescently (Alexa) labelled anti-cAMP antibody and incubating at room temperature for 24 hours. Then samples are excited at 320 nM and emitted light measured at 665 nM to determine cAMP levels. It is clear from data that the GALR1 receptor is activated by the galanin fusion protein.

Figure 34:
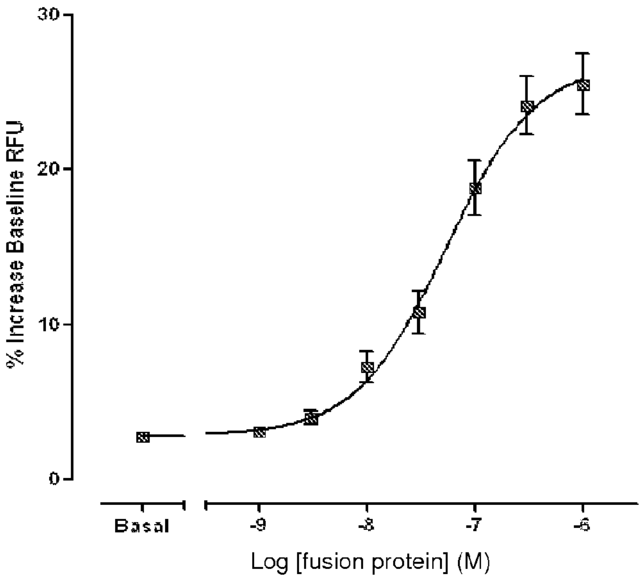

FIG. 34—GALR2 Receptor Activation Studies with a Galanin Fusion Protein

Chinese hamster ovary (CHO) cells were transfected so that they express the GALR2 receptor. Said cells were used to measure calcium mobilisation that occurs when the receptor is activated with a galanin ligand, using a fluorescence imaging assay using a Flexstation 3 microplate reader (Molecular devices). The transfected cells were pre-loaded with a calcium sensitive dye and then exposed to varying concentrations of galanin-16 (GA16) fusion proteins of the present invention. Calcium mobilisation was then detected in real time by the Flexstation by excitation at 485 nm and emitted light measured at 525 nM. It is clear from data that the GALR2 receptor is activated by the galanin fusion protein.

DETAILED DESCRIPTION OF THE INVENTION

The use of an "agonist", which would normally stimulate a biological process, particularly exocytosis (for example, an increase in cellular secretion, or an up-regulation in membrane protein expression), is an exciting development in the technical field of re-targeted toxins. Furthermore, it is particularly surprising that to an agonist may be employed in a therapeutic composition to achieve a reduction or inhibition of a biological process that the agonist would normally stimulate.

The agonist-containing conjugates of the present invention represent a distinct sub-set of toxin conjugates. In more detail, the conjugates of the present invention comprise TMs that have been selected on the basis of specific agonist properties rather than on the simple basis that they have a corresponding receptor on a pain-sensing target cell of interest.

Conventionally, an agonist has been considered any molecule that can either increase or decrease activities within a cell, namely any molecule that simply causes an alteration of cell activity. For example, the conventional meaning of an agonist would include: a chemical substance capable of combining with a receptor on a cell and initiating a reaction or activity, or a drug that induces an active response by activating receptors, whether the response is an increase or decrease in cellular activity.

However, for the purposes of this invention, an agonist is more specifically defined as a molecule that is capable of stimulating the process of exocytic fusion in a pain-sensing target cell, which process is susceptible to inhibition by a protease (or fragment thereof) capable of cleaving a protein of the exocytic fusion apparatus in said target cell.

Accordingly, the particular agonist definition of the present invention would exclude many molecules that would be conventionally considered as agonists. For example, nerve growth factor (NGF) is an agonist in respect of its ability to promote neuronal differentiation via binding to a TrkA receptor. However, NGF is not an agonist when assessed by the above criteria because it is not a principal inducer of exocytic fusion. In addition, the process that NGF stimulates (i.e. cell differentiation) is not susceptible to inhibition by the protease activity of a non-cytotoxic toxin molecule.

In use, an agonist-containing conjugate of the present invention does not deactivate an agonist receptor on a pain-sensing target cell, but rather the protease activity of the conjugate serves to negate the agonist-mediated response.

Furthermore, once delivered to the cytosol of the pain-sensing target cell, the protease component of a conjugate of the present invention inhibits or blocks the action of all subsequent agonists capable of causing the same effect (i.e. increased exocytic fusion) in the same target cell. This is advantageous and means that the conjugates of the present invention have application in situations where multiple agonists may be responsible for causing the sensation of pain. Thus, when designing a conjugate of the present invention, the TM that is selected for delivery need not necessarily be the principal agonist involved in causing the sensation of pain.

Agonist-mediated delivery according to the present invention provides the following significant advantage over previous non-cytotoxic protease-containing therapeutics:

use of an agonist may confer preferential binding and/or internalisation properties on the conjugate. This, in turn, may result in more efficient delivery of the protease component to a pain-sensing target cell.

In addition, use of an agonist as a TM is self-limiting with respect to side-effects. In more detail, binding of an agonist to a pain-sensing target cell increases exocytic fusion, which may exacerbate the sensation of pain. However, the exocytic process that is stimulated by agonist binding is subsequently reduced or inhibited by the protease component of the conjugate.

In preferred embodiments of the invention, the TM is an agonist of the $ORL_1$ receptor. The $ORL_1$ receptor is present on pain-sensing cells in the body.

The $ORL_1$ receptor is a member of the G-protein-coupled class of receptors, and has a seven transmembrane domain structure. The properties of the $ORL_1$ receptor are discussed in detail in Mogil & Pasternak (2001), *Pharmacological Reviews*, Vol. 53, No. 3, pages 381-415.

Throughout this specification, reference to the "$ORL_1$ receptor" embraces all members of the $ORL_1$ receptor family. Members of the $ORL_1$ receptor family typically have a seven transmembrane domain structure, and are coupled to G-proteins of the $G_i$ and $G_o$ families. A method for determining the G-protein-stimulating activity of ligands of the $ORL_1$ receptor is given in Example 17. A method for measuring reduction in cellular cAMP levels following $ORL_1$ activation is given in Example 16. A further characteristic of members of the $ORL_1$ receptor family is that they are typically able to bind nociceptin (the natural ligand of $ORL_1$). As an example, all alternative splice variants of the $ORL_1$ receptor, are members of the $ORL_1$ receptor family.

The conjugates of the present invention generally demonstrate a reduced binding affinity (in the region of up to 100-fold) for nociceptive sensory afferent target cells when compared with the corresponding 'free' TM. However, despite this observation, the conjugates of the present invention surprisingly demonstrate good efficacy. This can be attributed to two principal features. First, the non-cytotoxic protease component is catalytic—thus, the therapeutic effect of a few such molecules is rapidly amplified. Secondly, the receptors present on the nociceptive sensory afferents need only act as a gateway for entry of the therapeutic, and need not necessarily be stimulated to a level required in order to achieve a ligand-receptor mediated pharmacological response. Accordingly, the conjugates of the present invention may be administered at a dosage that is much lower that would be employed for other types of analgesic molecules such as NSAIDS, morphine, and gabapentin. The latter molecules are typically administered at high microgram to milligram (even up to hundreds of milligram) quantities, whereas the conjugates of the present invention may be administered at much lower dosages, typically at least 10-fold lower, and more typically at 100-fold lower.

In a particularly preferred embodiment of the invention, the TM of the conjugate is nociceptin—the natural ligand for the $ORL_1$ receptor. Nociceptin targets the $ORL_1$ receptor with high affinity.

Examples of other preferred TMs include:

| Code | Sequence | Ref. | SEQ ID NO: |
|---|---|---|---|
| Nociceptin 1-17 | FGGFTGARKSARKLANQ | [1] | 1, 2 |
| Nociceptin 1-11 | FGGFTGARKSA | [1] | 3, 4 |
| Nociceptin [Y10]1-11 | FGGFTGARKYA | [1] | 5, 6 |

-continued

| Code | Sequence | Ref. | SEQ ID NO: |
|---|---|---|---|
| Nociceptin [Y11]1-11 | FGGFTGARKSY | [1] | 7, 8 |
| Nociceptin [Y14]1-17 | FGGFTGARKSARKYANQ | [1] | 9, 10 |
| Nociceptin 1-13 | FGGFTGARKSARK | [2] | 11, 12 |
| Nociceptin [R14K15] 1-17 (also known as "variant" nociceptin) | FGGFTGARKSARKRKNQ | [3, 4] | 13, 14 |
| Nociceptin 1-13-$NH_2$ | FGGFTGARKSARK-$NH_2$ | [5] | 12 |
| Nociceptin Phe (p-$NO_2$) 1-17 | (p$NO_2$) FGGFTGARKSARKLANQ | [5] | 2 |
| Lofentanil | Non-peptide agonists | [5] | — |
| Etorphine | Non-peptide agonists | [5] | — |
| Peptide agonist | Peptide agonists from combinatorial library approach | [6] | — |

[1] Mogil & Pasternak, 2001, Pharmacol. Rev., 53, 381-415
[2] Maile et al., 2003, Neurosci. Lett., 350, 190-192
[3] Rizzi et al., 2002, J. Pharmacol. Exp. Therap., 300, 57-63
[4] Okada et al., 2000, Biochem. Biophys. Res. Commun., 278, 493-498
[5] Zaveri, 2003, Life Sci., 73, 663-678.
[6] Dooley et al., 1997, J Pharmacol Exp Ther. 283(2), 735-41.

The TM preferably comprises a maximum of 50 amino acid residues, more to preferably a maximum of 40 amino acid residues, particularly preferably a maximum of 30 amino acid residues, and most preferably a maximum of 20 amino acid residues. For example, nociceptin is a 17 amino acid residue peptide.

The above-identified "variant" TM demonstrates particularly good binding affinity (when compared with natural nociceptin) for nociceptive sensory afferents. Generally speaking, a TM-containing conjugate will demonstrate an approximate 100-fold reduction in binding ability vis-à-vis the TM per se. The above-mentioned "variant" TM per se demonstrates an approximate 3- to 10-fold increase in binding ability for a nociceptive sensory afferent vis-à-vis natural nociceptin. Thus, a "variant" TM-containing fusion might be expected to demonstrate an approximate 10-fold reduction in binding ability for a nociceptive sensory afferent vis-à-vis 'free' nociceptin. However, the present inventors have demonstrated that conjugates comprising said "variant" TM demonstrate a binding ability that (most surprisingly) closely mirrors that of 'free' nociceptin—see FIG. 17.

In the context of the present invention, the term opiod or an agonist of the $ORL_1$ receptor (such as nociceptin, or any one of the peptides listed in the table above) embraces molecules having at least 70%, preferably at least 80%, more preferably at least 90%, and most preferably at least 95% amino acid sequence acid identity/homology with said opiod or agonist. The agonist homologues is retain the agonist properties of nociceptin at the $ORL_1$ receptor, which may be tested using the methods provided in Examples 16 and 17. Similarly, an opioid homologue substantially retains the binding function of the opioid with which it shows high amino acid sequence identity/homology.

The invention also encompasses fragments, variants, and derivatives of any one of the TMs described above. These fragments, variants, and derivatives will substantially retain the properties that are ascribed to said TMs.

In addition to the above-mentioned opioid and non-opioid classes of TMs, a variety of other polypeptides are suitable for targeting the conjugates of the present invention to nociceptive sensory afferents (e.g. to nociceptors). In this regard, particular reference is made to galanin and derivatives of galanin. Galanin receptors are found pre- and post-synaptically in DRGs (Liu & Hokfelt, (2002), Trends Pharm. Sci., 23(10), 468-74), and are enhanced in expression during neuropathic pain states. Proteinase-activated receptors (PARs) are also a preferred group of TMs of the present invention, most particularly PAR-2. It is known that agonists of PAR-2 induce/elicit acute inflammation, in part via a neurogenic mechanism. PAR2 is expressed by primary spinal afferent neurons, and PAR2 agonists stimulate release of substance P(SP) and calcitonin gene-related peptide (CGRP) in peripheral tissues.

A particularly preferred set of TMs of the present invention includes:

| Ligand | Reference |
|---|---|
| Nociceptin | Guerrini, et al., (1997) J. Med. Chem., 40, pp. 1789-1793 |
| β-endorphin | Blanc, et al., (1983) J. Biol. Chem., 258(13), pp. 8277-8284 |
| Endomorphin-1; Endomorphin-2 | Zadina, et al., (1997). Nature, 386, pp. 499-502 |
| Dynorphin | Fields & Basbaum (2002) Chapter 11, In The Textbook of Pain, Wall & Melzack eds. |
| Met-enkephalin | Fields & Basbaum (2002) Chapter 11, In The Textbook of Pain, Wall & Melzack eds. |
| Leu-enkephalin | Fields & Basbaum (2002) Chapter 11, In The Textbook of Pain, Wall & Melzack eds. |
| Galanin | Xu et al., (2000) Neuropeptides, 34 (3&4), 137-147 |
| PAR-2 peptide | Vergnolle et al., (2001) Nat. Med., 7(7), 821-826 |

In a preferred embodiment of the invention, the target for the TM is the GALR1 and/or the GALR2 receptor. These receptors are members of the G-protein-coupled class of receptors, and have a seven transmembrane domain structure.

In one embodiment, the TM is a molecule that binds (preferably that specifically binds) to the GALR1 receptor and/or the GALR2 receptor. More preferably, the TM is an "agonist" of the GALR1 receptor and/or the GALR2 receptor. The term "agonist" in this context is as defined herein.

In one embodiment, the TM comprises or consists of a galanin peptide. Wild-type human galanin peptide is a 30 amino acid peptide, abbreviated herein as "GA30" (represented by SEQ ID NO: 101). In one embodiment, the TM comprises or consists of SEQ ID NO: 101.

The invention also encompasses fragments, variants, and derivatives of the galanin TM described above. These fragments, variants, and derivatives substantially retain the properties that are ascribed to said galanin TM. For example, the fragments, variants, and derivatives may retain the ability to bind to the GALR1 receptor and/or GALR2 receptor. In one embodiment, the galanin TM of the invention comprises or consists of a 16 amino acid fragment of full-length galanin peptide and is referred to herein as GA16 (represented by SEQ ID NO: 102).

In one embodiment, the TM comprises or consist of an amino acid sequence having at least 70%, preferably at least 80% (such as at least 82, 84, 85, 86, 88 or 89%), more preferably at least 90% (such as at least 91, 92, 93 or 94%), and most preferably at least 95% (such as at least 96, 97, 98, 99 or 100%) amino acid sequence acid identity to SEQ ID NO: 101 or SEQ ID NO: 102.

In one embodiment, the Targeting Moiety comprises or consists of an amino acid sequence according to SEQ ID NO. 101 or a fragment comprising or consisting of at least 16 (such as at least 10, 11, 12, 13, 14 or 15) contiguous amino acid residues thereof, or a variant amino acid sequence of said SEQ ID NO: 101 or said fragment having a maximum of 6 (such as a maximum of 5, 4, 3, 2 or 1) conservative amino acid substitutions.

The agonist properties of a TM can be confirmed using the methods described in Example 1. These methods are based on previous experiments (see Inoue et al. (1998) Proc. Natl. Acad. Sci., 95, 10949-10953), which confirm that the natural agonist of the $ORL_1$ receptor, nociceptin, causes the induction of substance P release from nociceptive primary afferent neurons. This is supported by the facts that:

- the nociceptin-induced responses are abolished by specific NK1 receptor (the substance P receptor) antagonists; and
- pre-treatment of the cells with capsaicin (which depletes substance P from small diameter primary afferent neurons) attenuates the nociceptin-induced responses.

Similarly, Inoue et al. confirm that an intraplantar injection of botulinum neurotoxin type A abolishes the nociceptin-induced responses. Since it is known that BoNT inhibits the release of substance P from primary afferent neurons (Welch et al., (2000), Toxicon, 38, 245-258), this confirms the link between nociceptin-$ORL_i$ is interaction and subsequent release of substance P.

Thus, a TM can be said to have agonist activity at the $ORL_1$ receptor if the TM causes an induction in the release of substance P from a nociceptive sensory afferent neuron (see Example 1).

In another embodiment, opioids represent a preferred group of TMs of the present invention. Within this family of peptides is included enkephalins (met and leu), endomorphins 1 and 2, β-endorphin and dynorphin. Opioid peptides are frequently used in the clinic to modify the activity to nociceptors, and other cells involved in the pain response. As exemplified by the three-step World Health Organisation Analgesic Ladder, opioids have entry points into the pharmacological treatment of chronic cancer and non-cancer pain at all three stages, underlining their importance to the treatment of pain. Reference to opioids embraces fragments, variants and derivatives thereof, which retain the ability to bind to nociceptive sensory afferents.

The protease of the present invention embraces all naturally-occurring non-cytotoxic proteases that are capable of cleaving one or more proteins of the exocytic fusion apparatus in eukaryotic cells.

The protease of the present invention is preferably a bacterial protease.

More preferably, the bacterial protease is selected from the genera *Clostridium* or *Neisseria* (e.g. a clostridial L-chain, or a neisserial IgA protease preferably from *N. gonorrhoeae*).

The present invention also embraces modified non-cytotoxic proteases, which include amino acid sequences that do not occur in nature and/or synthetic amino acid residues, so long as the modified proteases still demonstrate the above-mentioned protease activity.

The protease of the present invention preferably demonstrates a serine or metalloprotease activity (e.g. endopeptidase activity). The protease is preferably specific for a SNARE protein (e.g. SNAP-25, synaptobrevin/VAMP, or syntaxin).

Particular mention is made to the protease domains of neurotoxins, for example the protease domains of bacterial neurotoxins. Thus, the present invention embraces the use of neurotoxin domains, which occur in nature, as well as recombinantly prepared versions of said naturally-occurring neurotoxins.

Exemplary neurotoxins are produced by clostridia, and the term clostridial neurotoxin embraces neurotoxins produced by *C. tetani* (TeNT), and by *C. botulinum* (BoNT) serotypes A-G, as well as the closely related BoNT-like neurotoxins produced by *C. baratii* and *C. butyricum*. The above-mentioned abbreviations are used throughout the present specification. For example, the nomenclature BoNT/A denotes the source of neurotoxin as BoNT (serotype A). Corresponding nomenclature applies to other BoNT serotypes.

The term L-chain fragment means a component of the L-chain of a neurotoxin, which fragment demonstrates a metalloprotease activity and is capable of proteolytically cleaving a vesicle and/or plasma membrane associated protein involved in cellular exocytosis.

A Translocation Domain is a molecule that enables translocation of a protease (or fragment thereof) into a pain-sensing target cell such that a functional expression of protease activity occurs within the cytosol of the target cell. Whether any molecule (e.g. a protein or peptide) possesses the requisite translocation function to of the present invention may be confirmed by any one of a number of conventional assays.

For example, Shone C. (1987) describes an in vitro assay employing liposomes, which are challenged with a test molecule. Presence of the requisite translocation function is confirmed by release from the liposomes of $K^+$ and/or labelled NAD, which may be readily monitored (see Shone C. (1987) Eur. J. Biochem; vol. 167(1): pp. 175-180).

A further example is provided by Blaustein R. (1987), which describes a simple in vitro assay employing planar phospholipid bilayer membranes. The membranes are challenged with a test molecule and the requisite translocation function is confirmed by an increase in conductance across said membranes (see Blaustein (1987) FEBS Letts; vol. 226, no. 1: pp. 115-120).

Additional methodology to enable assessment of membrane fusion and thus identification of Translocation Domains suitable for use in the present invention are provided by Methods in Enzymology, Vols. 220 and 221, Membrane Fusion Techniques, Parts A and B, Academic Press 1993.

The Translocation Domain is preferably capable of formation of ion-permeable pores in lipid membranes under conditions of low pH. Preferably, it has been found to use only those portions of the protein molecule capable of pore-formation within the endosomal membrane.

The Translocation Domain may be obtained from a microbial protein source, in particular from a bacterial or viral protein source. Hence, in one embodiment, the Translocation Domain is a translocating domain of an enzyme, such as a bacterial toxin or viral protein.

It is well documented that certain domains of bacterial toxin molecules are to capable of forming such pores. It is also known that certain translocation domains of virally expressed membrane fusion proteins are capable of forming such pores. Such domains may be employed in the present invention.

The Translocation Domain may be of a clostridial origin, namely the $H_N$ domain is (or a functional component thereof).

$H_N$ means a portion or fragment of the H-chain of a clostridial neurotoxin approximately equivalent to the amino-terminal half of the H-chain, or the domain corresponding to that fragment in the intact H-chain. Examples of suitable clostridial Translocation Domains include:

Botulinum type A neurotoxin—amino acid residues (449-871)

Botulinum type B neurotoxin—amino acid residues (441-858)

Botulinum type C neurotoxin—amino acid residues (442-866)

Botulinum type D neurotoxin—amino acid residues (446-862)

Botulinum type E neurotoxin—amino acid residues (423-845)

Botulinum type F neurotoxin—amino acid residues (440-864)

Botulinum type G neurotoxin—amino acid residues (442-863)

Tetanus neurotoxin—amino acid residues (458-879)

For further details on the genetic basis of toxin production in *Clostridium botulinum* and *C. tetani*, we refer to Henderson et al. (1997) in *The Clostridia: Molecular Biology and Pathogenesis*, Academic press.

The term $H_N$ embraces naturally-occurring neurotoxin $H_N$ portions, and modified $H_N$ portions having amino acid sequences that do not occur in nature and/or synthetic amino acid residues, so long as the modified $H_N$ portions still demonstrate the above-mentioned translocation function.

Alternatively, the Translocation Domain may be of a non-clostridial origin (see table below). Examples of non-clostridial Translocation Domain origins include, but are not restricted to, the translocation domain of diphtheria toxin [O'Keefe et al., Proc. Natl. Acad. Sci. USA (1992) 89, 6202-6206; Silverman et al., J. Biol. Chem. (1993) 269, 22524-22532; and London, E. (1992) *Biochem. Biophys. Acta.,* 1112, pp. 25-51], the translocation domain of *Pseudomonas* exotoxin type A [Prior et al. Biochemistry (1992) 31, 3555-3559], the translocation domains of anthrax toxin [Blanke et al. Proc. Natl. Acad. Sci. USA (1996) 93, 8437-8442], a variety of fusogenic or hydrophobic peptides of translocating function [Plank et al. J. Biol. Chem. (1994) 269, 12918-12924; and Wagner et al (1992) *PNAS,* 89, pp. 7934-7938], and amphiphilic peptides [Murata et al (1992) *Biochem.,* 31, pp. 1986-1992]. The Translocation Domain may mirror the Translocation Domain present in a naturally-occurring protein, or may include amino acid variations so long as the variations do not destroy the translocating ability of the Translocation Domain.

Particular examples of viral Translocation Domains suitable for use in the present invention include certain translocating domains of virally expressed membrane fusion proteins. For example, Wagner et al. (1992) and Murata et al. (1992) describe the translocation (i.e. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded "spike proteins" have particular application in the context of the present invention, for example, the E1 protein of SFV and the G protein of VSV.

Use of the Translocation Domains (listed below) includes use of sequence variants thereof. A variant may comprise one or more conservative nucleic acid substitutions and/or nucleic acid deletions or insertions, with the proviso that the variant possesses the requisite translocating function. A variant may also to comprise one or more amino acid substitutions and/or amino acid deletions or insertions, so long as the variant possesses the requisite translocating function.

| Translocation Domain source | Amino acid residues | References |
|---|---|---|
| Diphtheria toxin | 194-380 | Silverman et al., 1994, J. Biol. Chem. 269, 22524-22532<br>London E., 1992, Biochem. Biophys. Acta., 1113, 25-51 |
| Domain II of pseudomonas exotoxin | 405-613 | Prior et al., 1992, Biochemistry 31, 3555-3559<br>Kihara & Pastan, 1994, Bioconj Chem. 5, 532-538 |
| Influenza virus haemagglutinin | GLFGAIAGFIENGWE GMIDGWYG (SEQ ID NO: 107), and Variants thereof | Plank et al., 1994, J. Biol. Chem. 269, 12918-12924<br>Wagner et al., 1992, PNAS, 89, 7934-7938<br>Murata et al., 1992, Biochemistry 31, 1986-1992 |
| Semliki Forest virus fusogenic protein | Translocation domain | Kielian et al., 1996, J Cell Biol. 134(4), 863-872 |
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glycoprotein | Translocation domain | Picard-Maureau et al., 2003, J Virol. 77(8), 4722-4730 |

Once a potential receptor agonist (e.g. an $ORL_1$ agonist) has been identified, one or more of the following optional steps may be carried out:

(A) confirming that the putative agonist molecule or agonist is capable of being combined with a non-cytotoxic protease (or a fragment thereof) and optionally a Translocation Domain to form a conjugate of the present invention; and/or (B) confirming that said putative agonist molecule or agonist binds to the receptor on the pain-sensing target cell, which receptor is susceptible to receptor-mediated endocytosis; and/or (C) confirming that said putative agonist molecule or agonist is able to deliver a non-cytotoxic protease (or fragment thereof) into the cytosol of a pain-sensing target cell.

The above steps (A)-(C) may be confirmed by routine tests that would be readily available to a skilled person.

For example, step (A) may be performed by a simple chemical conjugation experiment using conventional conjugation reagents and/or linker molecules, followed by native polyacrylamide gel electrophoresis to confirm that a conjugate of the present invention is formed that has the anticipated molecular weight. The conjugate components are typically linked together (optionally via linker molecules) by covalent bonds.

For example, step (B) may be performed by any one of a range of methodologies for assessment of binding of a ligand. Standard text, for example "Receptor-Ligand Interactions. A Practical Approach. Ed. E. C. Hulme, IRL Press, 1992" are available that describe such approaches in detail. In brief, the agonist or putative agonist molecule is labelled (for example, with 125-iodine) and applied to a cell preparation in vitro in the presence of an excess of unlabelled agonist. The purpose of the unlabelled material is to saturate any non-specific binding sites. The agonist is incubated with the cell preparation for sufficient time to achieve equilibrium, and the amount of label bound to the cells assessed by measuring cell associated radioactivity, for example by scintillation or gamma counting.

A further example involves gold-labelling of the agonist (or putative agonist), followed by the use of electron microscopy to monitor the cellular transport progress of the labelled agonist [see the basic methodology described by Rabinowitz S. (1992); J. Cell. Biol. 116(1): pp. 95-112; and that described by van Deurs (1986); J. Cell. Biol. 102: pp. 37-47].

For example, step (C) may be performed by contacting the conjugate prepared in step (A) with a suitable target cell and assessing cleavage of the substrate. This is performed by extraction of the SNARE proteins, followed by Western blotting of SDS-PAGE-separated samples. Cleavage of substrate is indicative of delivery of the protease into the target cell. In this regard, cleavage may be monitored by disappearance of substrate and/or appearance of cleavage product. A particularly useful antibody that selectively binds to the cleaved substrate product is described in WO95/33850.

Preparation of a conjugate according to the present invention is now discussed.

It is known in the art that the $H_C$ portion of a neurotoxin molecule can be removed from the other portion of the H-chain, known as $H_N$, such that the $H_N$ fragment remains disulphide linked to the L-chain of the neurotoxin providing a fragment known as $LH_N$. Thus, in one embodiment of the present invention the $LH_N$ fragment of a neurotoxin is covalently linked, using linkages which may include one or more spacer regions, to a TM.

In another embodiment of the invention, the $H_C$ domain of a neurotoxin is mutated, blocked or modified, e.g. by chemical modification, to reduce or preferably incapacitate its ability to bind the neurotoxin to receptors at the neuromuscular junction. This modified neurotoxin is then covalently linked, using linkages which may include one or more spacer regions, to a TM.

In another embodiment of the invention, the H-chain of a neurotoxin, in which the $H_C$ domain is mutated, blocked or modified, e.g. by chemical modification, to reduce or preferably incapacitate its native binding ability, is combined with the L-chain of a different neurotoxin, or another protease capable of cleaving a protein of the exocytic fusion apparatus (e.g. IgA protease of *N. gonorrhoeae*). This hybrid, modified neurotoxin is then covalently linked, using linkages which may include one or more spacer regions, to a TM.

In another embodiment of the invention, the $H_N$ domain of a neurotoxin is combined with the L-chain of a different neurotoxin, or another protease capable of cleaving a protein of the exocytic fusion apparatus (e.g. IgA protease of *N. gonorrhoeae*). This hybrid is then covalently linked, using linkages which may include one or more spacer regions, to a TM.

In another embodiment of the invention, the protease (for example the L-chain component of a neurotoxin) is covalently linked, using linkages that may include one or more spacer regions, to a TM that can also effect the internalisation of the protease into the cytoplasm of the relevant target cell(s).

In another embodiment of the invention, the protease (for example the L-chain component of a neurotoxin) is covalently linked, using linkages which may include one or more spacer regions, to a translocation domain to effect transport of the protease fragment into the cytosol.

In use, the domains of a conjugate according to the present invention are associated with each other. In one embodiment, two or more of the domains may be joined together either directly (e.g. by a covalent linkage), or via a linker molecule.

A variety of different linker/spacer molecules may be employed in any of the is fusion proteins of the present invention. Examples of such spacer molecules include those illustrated in FIGS. 31 and 32. Particular mention here is made to GS15, GS20, GS25, and Hx27—see FIGS. 31 and 32.

The present inventors have unexpectedly found that non-cytotoxic protease-TM conjugates (e.g. CPNv/A) may demonstrate an improved binding activity for nociceptive sensory afferents when the size of the spacer is selected so that (in use) the TM (preferably the C-terminus thereof) and the translocation domain (preferably the N-terminus thereof) are separated from one another by 40-105 angstroms, preferably by 50-100 angstroms, and more preferably by 50-90 angstroms. In another embodiment, the preferred spacers have an amino acid sequence of 11-29 amino acid residues, preferably 15-27 amino acid residues, and more preferably 20-27 amino acid residues. Suitable spacers may be routinely identified and obtained according to Crasto, C. J. and Feng, J. A. (2000) May, 13(5), pp. 309-312—see also the website having a URL ending in: fccc.edu/research/labs/feng/linker.html.

Conjugation techniques suitable for use in the present invention have been well documented and are routine for a person skilled in the art.

The methodology involved in coupling two protein molecules (A and B) together is simple, and is achieved through the use of a cross-linking agent (also known as a chemical coupling agent). For example, molecules A and B are separately contacted with a cross-linking agent, which chemically modifies a specific surface group on each of molecules A and B thereby forming derivatised molecules A' and B'. The modified surface group on molecule A' is capable of covalently bonding with the modified surface group on molecule B'. Thus, the coupling reaction is completed by mixing together the two protein molecules A' and B'.

Chemical conjugation is illustrated by reference to the following embodiments, where P=non-cytotoxic protease component, T=translocation component, and TM=targeting moiety.

In one embodiment, a single chain P-T is prepared, which is then conjugated to a TM. In another embodiment, a single chain TM-T (or T-TM) is prepared, which is then conjugated to a P. In a further embodiment, a single chain P-TM (or TM-P) is prepared, which is then conjugated to a T. Another particularly preferred conjugate has the structure P-TM-T (with an optional protease cleavage site between P and TM).

Where the T and P components are prepared as a single chain polypeptide, a protease cleavage site is typically included between said components. Any protease cleavage site may be employed in this regard.

In an alternative embodiment, the three components may be simultaneously or sequentially conjugated together. Thus, the conjugation may be a one- or two-step process, and may include one or more different coupling agents.

In one embodiment, the invention provides a non-cytotoxic protein conjugate comprising (or consisting of) any one of SEQ ID NOs: 105 and/or 106, and/or a non-cytotoxic protein conjugate having at least 80% (such as at least 85, 90, 92, 94, 95, 96, 97, 98, 99 or 100%) sequence identity thereto.

Chemical coupling agents and cross-linking agents have been commercially available for many years.

Example 5 of the present invention describes in detail the use of one such coupling agent, namely SPDP, to chemically couple two protein molecules (nociceptin, and the $LH_N$ of botulinum neurotoxin). The two molecules are separately contacted with SPDP, and then mixed together to allow covalent conjugation.

The conjugate described in Example 6 confirms that another coupling agent, PDPH/EDAC, or Traut's reagent, may be employed as an alternative coupling agent to SPDP.

SPDP and Traut's reagent are popular and well-documented coupling agents in the technical field of protein conjugation chemistry and are presented here simply as two examples of a well known class of compounds that may be employed to covalently link together the Targeting Moiety component and the clostridial neurotoxin component of the conjugate of the present invention. Other suitable agents include SMPB, SMCC (succinimidyl 4-(N-maleimidomethyl)cyclohexan-1-carboxylate), and LC-SPDP.

In more detail, commercially available members of the well-known coupling agents may be used for conjugation purposes to produce a conjugate of the invention. Details of such agents can be found in the following publications:

Hermanson, G. T. (1996), Bioconjugate techniques, Academic Press;

Wong, S. S. (1991), Chemistry of protein conjugation and cross-linking, CRC Press;

Thorpe et al (1987), Cancer Res, 1987, 47, 5924-31. This paper describes the use of SMBT (sodium S-4-succinimidyloxycarbonyl-alpha-methyl benzyl thiosulfate) and SMPT (4-succinimidyloxycarbonyl-alpha-methyl-alpha(2-pyridyldithio)toluene); and Peeters et al (1989), J Immunol Methods. 1989, 120, 133-43. This paper describes the use of 4 coupling reagents, MHS (succinimidyl 6-(N-maleimido)-n-hexanoate), SMCC (succinimidyl 4-(N-maleimidomethyl)-cyclohexane-1-carboxylate), MBS (succinimidyl m-maleimidobenzoate), and SPDP.

The conjugates according to the present invention may also be prepared recombinantly, as detailed in Examples 9 to 12.

In one embodiment, the preparation of a recombinant conjugate involves arrangement of the coding sequences of a selected TM, a selected non-cytotoxic protease component, and a translocation component (in any order) in a single genetic construct. These coding sequences may be arranged in-frame so that subsequent transcription and translation is continuous through both coding sequences and results in a fusion protein. All constructs would have a 5' ATG codon to encode an N-terminal methionine, and a C-terminal translational stop codon.

Thus, the recombinant preparation method results in the generation of a single chain polypeptide. In order to activate this polypeptide, a protease cleavage site is present between the non-cytotoxic protease component and the translocation component. Cleavage of this site generates a di-chain polypeptide in which the protease and translocation domains are linked together by way of a covalent bond, preferably a disulphide bond. In this regard, any protease cleavage site may be employed.

In the single polypeptide aspect of the present invention, the TM is preferably either N- or C-terminally located with respect to the fusion protein. In other words, it is preferred that the TM is not located between the P and T components of the single polypeptide fusion protein. In a particularly preferred embodiment, the TM is N-terminally located with respect to the fusion protein.

In one embodiment, an L-chain of a clostridial neurotoxin or another protease capable of cleaving a protein of the exocytic fusion apparatus (e.g. an IgA protease), or a fragment/variant thereof, may be expressed recombinantly as a fusion protein with a TM, which TM can also effect the internalisation of the L-chain component into the cytoplasm of the relevant target cell(s) responsible for secretion. Alternatively, the fusion protein may further comprise a Translocation Domain. The expressed fusion protein may include one or more spacer regions.

By way of example, the following information is required to produce, recombinantly, an agent of the present invention:

(I) DNA sequence data relating to a selected TM;

(II) DNA sequence data relating to the protease component;

(III) DNA sequence data relating to the translocation domain; and (IV) a protocol to permit construction and expression of the construct comprising (I), (II) and (III).

All of the above basic information (I)-(IV) are either readily available, or are readily determinable by conventional methods. For example, both WO98/07864 and WO99/17806 exemplify recombinant technology suitable for use in the present application.

In addition, methods for the construction and expression of the constructs of the present invention may employ information from the following references and others:

Lorberboum-Galski, H., FitzGerald, D., Chaudhary, V., Adhya, S., Pastan, I. (1988), Cytotoxic activity of an interleukin 2-Pseudomonas exotoxin chimeric protein produced in *Escherichia coli*. Proc. Natl. Acad. Sci. USA, 85(6):1922-6;

Murphy, J. R. (1988), Diphtheria-related peptide hormone gene is fusions: a molecular genetic approach to chimeric toxin development. Cancer Treat. Res.; 37:123-40;

Williams, D. P., Parker, K., Bacha, P., Bishai, W., Borowski, M., Genbauffe, F., Strom, T. B., Murphy, J. R. (1987), Diphtheria toxin receptor binding domain substitution with interleukin-2: genetic construction and properties of a diphtheria toxin-related interleukin-2 fusion protein. Protein Eng; 1(6):493-8;

Arora, N., Williamson, L. C., Leppla, S. H., Halpern, J. L. (1994), Cytotoxic effects of a chimeric protein consisting of tetanus toxin light chain and anthrax toxin lethal factor in non-neuronal cells J. Biol. Chem., 269(42): 26165-71;

Brinkmann, U., Reiter, Y., Jung, S. H., Lee, B., Pastan, I. (1993), A recombinant immunotoxin containing a disulphide-stabilized Fv fragment. Proc. Natl. Acad. Sci. USA, 90(16):7538-42; and O'Hare, M., Brown, A. N., Hussain, K., Gebhardt, A., Watson, G., Roberts, L. M., Vitetta, E. S., Thorpe, P. E., Lord, J. M. (1990), Cytotoxicity of a recombinant ricin-A-chain fusion protein containing a proteolytically-cleavable spacer sequence. FEBS Lett October 29; 273 (1-2):200-4.

Suitable clostridial neurotoxin sequence information relating to L- and $LH_N$-chains may be obtained from, for example, Kurazono, H. (1992) *J. Biol. Chem., vol.* 267, No. 21, pp. 14721-14729; and Popoff, M. R., and Marvaud, J.-C. (1999) The *Comprehensive Sourcebook of Bacterial Protein Toxins,* 2nd edition (ed. Alouf, J. E., and Freer, J. H.), Academic Press, pp. 174-201.

All of the aforementioned publications are hereby incorporated into the present is specification by reference thereto.

Similarly, suitable TM sequence data are widely available in the art. Alternatively, any necessary sequence data may be obtained by techniques which are well-known to the skilled person.

For example, DNA encoding the TM component may be cloned from a source organism by screening a cDNA library for the correct coding region (for example by using specific oligonucleotides based on the known sequence information to probe the library), isolating the TM DNA, sequencing this DNA for confirmation purposes, and then placing the isolated DNA in an appropriate expression vector for expression in the chosen host.

As an alternative to isolation of the sequence from a library, the available sequence information may be employed to prepare specific primers for use in PCR, whereby the coding sequence is then amplified directly from the source material and, by suitable use of primers, may be cloned directly into an expression vector.

Another alternative method for isolation of the coding sequence is to use the existing sequence information and synthesise a copy, possibly incorporating alterations, using DNA synthesis technology. For example, DNA sequence data may be generated from existing protein and/or RNA sequence information. Using DNA synthesis technology to do this (and the alternative described above) enables the codon bias of the coding sequence to be modified to be optimal for the chosen expression host. This may give rise to superior expression levels of the fusion protein.

Optimisation of the codon bias for the expression host may be applied to the DNA sequences encoding the TM and clostridial components of the construct. Optimisation of the codon bias is possible by application of the protein sequence into freely available DNA/protein database software, e.g. programs available from Genetics Computer Group, Inc.

Having prepared a conjugate of the invention, it is a matter of routine to confirm that the various domains have retained their specified function.

Protease function after conjugation may be tested by using, for example, any one of the following routine tests:

SNAP-25 (or synaptobrevin, or syntaxin) may be challenged with a conjugate to be tested, and then analysed by SDS-PAGE peptide separation techniques. Subsequent detection of peptides (e.g. by silver staining) having molecular weights corresponding to the cleaved products of SNAP-25 (or other component of the neurosecretory machinery) would confirm the presence of a functional L-chain.

As a further alternative, the conjugate may be tested by assaying for SNAP-25 (or synaptobrevin, or syntaxin) cleavage products via antibody-specific binding (see WO95/33850). In more detail, a specific antibody is employed for detecting cleavage of SNAP-25. Since the antibody recognises cleaved SNAP-25, but not uncleaved SNAP-25, identification of the cleaved product by the antibody confirms the presence of L-chain proteolytic function. By way of exemplification, such a method is described in Examples 2 and 3 of WO96/33273.

Translocation component function after conjugation may be tested using, for example, any one of the following routine tests:

Suitable methods are, for example, described by Shone et al. (1987) Eur. J. Biochem. 167, pp. 175-180; and by Blaustein et al. (1987) FEBS 226 (1), pp. 115-120.

The Shone et al. method employs artificial liposomes loaded with potassium phosphate buffer (pH 7.2) and radiolabelled NAD. Release of K+ and NAD from the liposomes correlates with a positive result for channel forming activity and hence translocation activity. In this regard, K+ release from liposomes may be measured using an electrode and NAD release calculated by measuring the radioactivity in the supernatant (see page 176, column 1, line 33-column 2, line 17).

The Blaustein et al. method employs planar phospholipid bilayer membranes, which are used to test for channel forming activity. In more detail, salt solutions on either side of the membrane are buffered at a different pH—on the cis side, pH 4.7 or 5.5 and on the trans side, pH 7.4. The "conjugate" to be tested is added to the cis side of the membrane and electrical measurements are made under voltage clamp conditions, in order to monitor the flow of current across the membrane (see paragraph 2.2, pages 116-118). The presence of an active translocation function is confirmed by a steady rate of channel turn-on (i.e. a positive result for channel formation)—see paragraph 3, page 118.

Targeting Moiety (TM) function after conjugation may be tested by assaying for the agonist function inherent to the TM. Suitable methods include those described in Example 1.

The ability of the conjugate of the invention to inhibit substance P release from nociceptive afferent cells can be assessed using the methods described in Example 15.

In Example 15, a nociceptin-LHN/A conjugate according to the first aspect of the invention is assessed for its ability to inhibit the release of substance P from primary nociceptive sensory afferent neurons. As can be seen from Table 1, incubation of the conjugate with cultures of nociceptive afferent neurons results in a significant inhibition of release of substance P (when compared to incubation of the cells with LHN/A alone). The experiment therefore confirms that the conjugate is inhibiting substance P release from these cells.

In use of the present invention, a pain-sensing target cell is selected in which it is desired to reduce or inhibit the process of exocytic fusion, which exocytic process contributes to the symptoms associated with the sensation of pain. For example, the target cell in question may demonstrate an undesirable phenotype (e.g. an undesirable secretion, or the expression of an undesirable concentration of membrane receptor, transporter or membrane channel), which contributes to the symptoms associated with pain. Alternatively, a target cell may be selected in which the process of exocytic fusion contributes to the sensation of pain.

In preferred embodiments of the invention, the target cell is a nociceptive sensory afferent cell, preferably a primary nociceptive afferent cell (e.g. an A-fibre such as an Aδ-fibre or a C-fibre). Thus, the conjugates of the present invention are capable of inhibiting neurotransmitter or neuromodulator (e.g. glutamate, substance P, calcitonin-gene related peptide (CGRP), and/or neuropeptide Y) release from discrete populations of nociceptive sensory afferent neurons. In use, the conjugates reduce or prevent the transmission of sensory afferent signals (e.g. neurotransmitters or neuromodulators) from peripheral to central pain fibres, and therefore have application as therapeutic molecules for the treatment of pain, in particular chronic pain.

It is routine to confirm that a TM binds to a nociceptive sensory afferent. For example, a simple radioactive displacement experiment may be employed in which tissue or cells representative of the nociceptive sensory afferent (for example DRGs) are exposed to labelled (e.g. tritiated) ligand in the presence of an excess of unlabelled ligand. In such an experiment, the relative proportions of non-specific and specific binding may be assessed, thereby allowing confirmation that the ligand binds to the nociceptive sensory afferent target cell. Optionally, the assay may include one or more binding antagonists, and the assay may further comprise observing a loss of ligand binding. Examples of this type of experiment can be found in Hulme, E. C. (1990), Receptor-binding studies, a brief outline, pp 303-311, in Receptor biochemistry, A Practical Approach, Ed. E. C. Hulme, Oxford University Press.

According to a second aspect, the present invention provides a non-cytotoxic conjugate for inhibition or reduction of exocytotic fusion in a nociceptive sensory afferent cell, comprising:

(i) a Targeting Moiety (TM),
 wherein said TM is an agonist of a receptor that is present on said nociceptive sensory afferent cell, and wherein said receptor undergoes endocytosis to be incorporated into an endosome within the nociceptive sensory afferent cell;

(ii) a DNA sequence encoding a non-cytotoxic protease or a fragment thereof,
 wherein the DNA sequence is expressible in the nociceptive sensory afferent cell and when so expressed provides a protease or protease fragment capable of cleaving a protein of the exocytic fusion apparatus of said nociceptive sensory afferent cell; and (iii) a Translocation Domain,
 wherein the Translocation Domain translocates the DNA sequence encoding the protease or protease fragment from within the endosome, across the endosomal membrane, and into the nociceptive sensory afferent cell.

In a preferred embodiment, the receptor is an $ORL_1$ receptor.

In a preferred embodiment of the invention, the target for the TM is the GALR1 and/or the GALR2 receptor. These receptors are members of the G-protein-coupled class of receptors, and have a seven transmembrane domain structure.

In one embodiment, the TM is a molecule that binds (preferably that specifically binds) to the GALR1 receptor and/or the GALR2 receptor. More preferably, the TM is an "agonist" of the GALR1 receptor and/or the GALR2 receptor. The term "agonist" in this context is defined as above.

In one embodiment, the TM comprises or consists of a galanin peptide. Wild-type human galanin peptide is a 30 amino acid peptide, abbreviated herein as "GA30" (represented by SEQ ID NO: 101). In one embodiment, the TM comprises or consists of SEQ ID NO: 101.

The invention also encompasses fragments, variants, and derivatives of the galanin TM described above. These fragments, variants, and derivatives substantially retain the properties that are ascribed to said galanin TM. For example, the fragments, variants, and derivatives may retain the ability to bind to the GALR1 receptor and/or GALR2 receptor. In one embodiment, the galanin TM of the invention comprises or consists of a 16 amino acid fragment of full-length galanin peptide and is referred to herein as GA16 (represented by SEQ ID NO: 102).

In one embodiment, the TM comprises or consist of an amino acid sequence having at least 70%, preferably at least 80% (such as at least 82, 84, 85, 86, 88 or 89%), more preferably at least 90% (such as at least 91, 92, 93 or 94%), and most preferably at least 95% (such as at least 96, 97, 98, 99 or 100%) amino acid sequence acid identity to SEQ ID NO: 101 or SEQ ID NO: 102.

In one embodiment, the Targeting Moiety comprises or consists of an amino acid sequence according to SEQ ID NO. 101 or a fragment comprising or consisting of at least 16 (such as at least 10, 11, 12, 13, 14 or 15) contiguous amino acid residues thereof, or a variant amino acid sequence of said SEQ ID NO: 101 or said fragment having a maximum of 6 (such as a maximum of 5, 4, 3, 2 or 1) conservative amino acid substitutions.

DNA encoding a protein of interest can be transfected into eukaryotic cells through receptor-mediated endocytosis of a protein-DNA conjugate, as confirmed by Cotton et al. (Cotton, M., Wagner, E. and Birnstiel, L. (1993) Receptor-mediated transport of DNA into eukaryotic cells. Methods in Enzymol. 217, 619-645). Several methods exist for condensing DNA to a suitable size using polycationic ligands. These include: polylysine, various cationic peptides and cationic liposomes. Of these, polylysine was used in the present study because of its successfully reported use in receptor-mediated transfection studies (Cotton et al., 1993).

The DNA sequence encoding the non-cytotoxic protease component may be expressed under the control of an operably linked promoter present as part of the agent (e.g. as part of the protease DNA sequence upstream of the coding region). Alternatively, expression of the protease component in the target cell may rely on a promoter present in the target cell.

The DNA sequence encoding the protease component may integrate into a DNA sequence of the target cell. One or more integration site(s) may be provided as part of the conjugate (e.g. as part of the protease DNA sequence).

The TM, Translocation Domain and protease components of this second aspect of the invention are as defined for the first aspect of the invention. Examples 13 and 14 describe the preparation of conjugates according to the second aspect of is the invention.

According to a third aspect, the present invention provides a pharmaceutical composition comprising a conjugate according to the first and/or second aspect of the present invention.

The pharmaceutical composition may further comprise a pharmaceutically-acceptable carrier, and/or a suitable diluent and/or excipient, although the exact form of the composition may be tailored to the mode of administration. Administration is preferably to a mammal, more preferably to a human.

The components of the composition may, for example, be employed in the form of an aerosol or nebulisable solution for inhalation or a sterile solution for parenteral administration, intra-articular administration or intra-cranial administration.

The composition may also be administered by i.v. injection, which includes the use of pump systems. Spinal injection (e.g. epidural or intrathecal) or indwelling pumps may also be used.

The dosage ranges for administration of the components of the present invention are those to produce the desired therapeutic effect. It will be appreciated that the dosage range required depends on the precise nature of the components, the route of administration, the nature of the formulation, the age of the patient, the nature, extent or severity of the patient's condition, contraindications, if any, and the judgement of the attending physician.

Suitable daily dosages (for each component) are in the range 0.0001-1 mg/kg, preferably 0.0001-0.5 mg/kg, more preferably 0.002-0.5 mg/kg, and particularly preferably 0.004-0.5 mg/kg. The unit dosage can vary from less than 1 microgram to 30 mg, but typically will be in the region of 0.01 to 1 mg per dose, is which may be administered daily or preferably less frequently, such as weekly or six monthly.

A particularly preferred dosing regimen is based on 2.5 ng of fusion protein (e.g. CPNv/A) as the 1× dose. In this regard, preferred dosages are in the range 1×-100× (i.e. 2.5-250 ng). This dosage range is significantly lower (i.e. at least 10-fold, typically 100-fold lower) than would be employed with other types of analgesic molecules such as NSAIDS, morphine, and gabapentin. Moreover, the above-mentioned difference is considerably magnified when the same comparison is made on a molar basis—this is because the fusion proteins of the present invention have a considerably greater Mw than do conventional 'small' molecule therapeutics.

Wide variations in the required dosage, however, are to be expected depending on the precise nature of the components, and the differing efficiencies of various routes of administration. For example, oral administration would be expected to require higher dosages than administration by intravenous injection.

Variations in these dosage levels can be adjusted using standard empirical routines for optimisation, as is well understood in the art.

Compositions suitable for injection may be in the form of solutions, suspensions or emulsions, or dry powders which are dissolved or suspended in a suitable vehicle prior to use.

Fluid unit dosage forms are typically prepared utilising a pyrogen-free sterile to vehicle.

The active ingredients, depending on the vehicle and concentration used, can be either dissolved or suspended in the vehicle.

Solutions may be used for all forms of parenteral administration, and are is particularly used for intravenous injection. In preparing solutions the components can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving.

Advantageously additives such as buffering, solubilising, stabilising, preservative or bactericidal, suspending or emulsifying agents and/or local anaesthetic agents may be dissolved in the vehicle.

Dry powders which are dissolved or suspended in a suitable vehicle prior to use may be prepared by filling pre-sterilised drug substance and other ingredients into a sterile container using aseptic technique in a sterile area.

Alternatively the components of the composition may be dissolved in an aqueous vehicle, the solution is sterilized by filtration and distributed into suitable containers using aseptic technique in a sterile area. The product is then freeze-dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

Advantageously, a suspending agent for example polyvinylpyrrolidone is included in the composition(s) to facilitate uniform distribution of the components.

Compositions suitable for administration via the respiratory tract include aerosols, nebulisable solutions or microfine powders for insufflation. In the latter case, particle size of less than 50 microns, especially less than 10 microns, is preferred. Such compositions may be made up in a conventional manner and employed in conjunction with conventional administration devices.

The compositions described in this invention can be used in vivo, either directly or as a pharmaceutically acceptable salt, for the treatment of conditions involving exocytosis (for example secretion, or the delivery of proteins such as receptors, transporters, and membrane channels to the plasma membrane of a cell).

According to a fourth aspect, the present invention provides a DNA construct that encodes a conjugate according to the first or second aspects of the invention.

By expressing the construct in a host cell, conjugates of the invention may be prepared.

According to a fifth aspect, the present invention provides a method of treatment of pain by administration to a patient of a conjugate, composition, or construct according to the first to fourth aspects of the invention, or any combination thereof.

In a preferred embodiment, the invention provides a method of treating chronic pain.

According to a sixth aspect, the present invention provides for the use of a conjugate, composition or construct according to the first to fourth aspects of the invention, for the manufacture of a medicament for treating pain, preferably chronic pain.

According to a further aspect of the present invention, there is provided use of a conjugate of the invention, for the manufacture of a medicament for treating, preventing or ameliorating pain.

According to a related aspect, there is provided a method of treating, preventing or ameliorating pain in a subject, comprising administering to said patient a therapeutically effective amount of a conjugate or composition of the invention.

The conjugates and compositions described here may be used to treat a patient suffering from one or more types of chronic pain including neuropathic pain, inflammatory pain, headache pain, somatic pain, visceral pain, and referred pain.

To "treat," as used here, means to deal with medically. It includes, for example, administering a compound of the invention to prevent pain or to lessen its severity.

The term "pain," as used here, means any unpleasant sensory experience, usually associated with a physical disorder. The physical disorder may or may not be apparent to a clinician. Pain is of two types: chronic and acute. An "acute pain" is a pain of short duration having a sudden onset. One type of acute pain, for example, is cutaneous pain felt on injury to the skin or other superficial tissues, such as caused by a cut or a burn. Cutaneous nociceptors terminate just below the skin, and due to the high concentration of nerve endings, produce a well-defined, localized pain of short duration. "Chronic pain" is a pain other than an acute pain. Chronic pain includes neuropathic pain, inflammatory pain, headache pain, somatic pain visceral pain and referred pain.

I. Neuropathic Pain

The compounds of the invention may be used to treat pain caused by or otherwise associated with any of the following neuropathic pain conditions. "Neuropathic pain" means abnormal sensory input, resulting in discomfort, from the peripheral nervous system, central nervous systems, or both.

A. Symptoms of Neuropathic Pain

Symptoms of neuropathic pain can involve persistent, spontaneous pain, as well as allodynia (a painful response to a stimulus that normally is not painful), hyperalgesia (an accentuated response to a painful stimulus that usually causes only a mild discomfort, such as a pin prick), or hyperpathia (where a short discomfort becomes a prolonged severe pain).

B. Causes of Neuropathic Pain

Neuropathic pain may be caused by any of the following.

1. A traumatic insult, such as, for example, a nerve compression injury (e.g., a nerve crush, a nerve stretch, a nerve entrapment or an incomplete nerve transection); a spinal cord injury (e.g., a hemisection of the spinal cord); a limb amputation; a contusion; an inflammation (e.g., an inflammation of the spinal cord); or a surgical procedure.
2. An ischemic event, including, for example, a stroke and heart attack.
3. An infectious agent.
4. Exposure to a toxic agent, including, for example, a drug, an alcohol, a heavy metal (e.g., lead, arsenic, mercury), an industrial agent (e.g., a solvent, fumes from a glue) or nitrous oxide.

5. A disease, including, for example, an inflammatory disorder, a neoplastic tumor, an acquired immune deficiency syndrome (AIDS), Lymes disease, a leprosy, a metabolic disease, a peripheral nerve disorder, like neuroma, a mononeuropathy or a polyneuropathy.

C. Types of Neuropathic Pain

1. Neuralgia.

A neuralgia is a pain that radiates along the course of one or more specific nerves usually without any demonstrable pathological change in the nerve structure. The causes of neuralgia are varied. Chemical irritation, inflammation, trauma (including surgery), compression by nearby structures (for instance, tumors), and infections may all lead to neuralgia. In many cases, however, the cause is unknown or unidentifiable. Neuralgia is most common in elderly persons, but it may occur at any age. A neuralgia, includes, without limitation, a trigeminal neuralgia, a post-herpetic neuralgia, a postherpetic neuralgia, a glossopharyngeal neuralgia, a sciatica and an atypical facial pain.

Neuralgia is pain in the distribution of a nerve or nerves. Examples are trigeminal neuralgia, atypical facial pain, and postherpetic neuralgia (caused by shingles or herpes). The affected nerves are responsible for sensing touch, temperature and pressure in the facial area from the jaw to the forehead. The disorder generally causes short episodes of excruciating pain, usually for less than two minutes and on only one side of the face. The pain can be described in a variety of ways such as "stabbing," "sharp," "like lightning," "burning," and even "itchy". In the atypical form of TN, the pain can also present as severe or merely aching and last for extended periods. The pain associated with TN is recognized as one the most excruciating pains that can be experienced.

Simple stimuli such as eating, talking, washing the face, or any light touch or sensation can trigger an attack (even the sensation of a gentle breeze). The attacks can occur in clusters or as an isolated attack.

Symptoms include sharp, stabbing pain or constant, burning pain located anywhere, usually on or near the surface of the body, in the same location for each episode; pain along the path of a specific nerve; impaired function of affected body part due to pain, or muscle weakness due to concomitant motor nerve damage; increased sensitivity of the skin or numbness of the affected skin to area (feeling similar to a local anesthetic such as a Novacaine shot); and any touch or pressure is interpreted as pain. Movement may also be painful.

Trigeminal neuralgia is the most common form of neuralgia. It affects the main sensory nerve of the face, the trigeminal nerve ("trigeminal" literally means "three origins", referring to the division of the nerve into 3 branches). This condition involves sudden and short attacks of severe pain on the side of the face, along the area supplied by the trigeminal nerve on that side. The pain attacks may be severe enough to cause a facial grimace, which is classically referred to as a painful tic (tic douloureux). Sometimes, the cause of trigeminal neuralgia is a blood vessel or small tumor pressing on the nerve. Disorders such as multiple sclerosis (an inflammatory disease affecting the brain and spinal cord), certain forms of arthritis, and diabetes (high blood sugar) may also cause trigeminal neuralgia, but a cause is not always identified. In this condition, certain movements such as chewing, talking, swallowing, or touching an area of the face may trigger a spasm of excruciating pain.

A related but rather uncommon neuralgia affects the glosso-pharyngeal nerve, which provides sensation to the throat. Symptoms of this neuralgia are short, shock-like episodes of pain located in the throat.

Neuralgia may occur after infections such as shingles, which is caused by the varicella-zoster virus, a type of herpesvirus. This neuralgia produces a constant burning pain after the shingles rash has healed. The pain is worsened by movement of or contact with the affected area. Not all of those diagnosed with shingles go on to experience postherpetic neuralgia, which can be more painful than shingles. The pain and sensitivity can last for months or even years. The pain is usually in the form of an intolerable sensitivity to any touch but especially light touch. Postherpetic neuralgia is not restricted to the face; it can occur anywhere on the body but usually occurs at the location of the shingles rash. Depression is not uncommon due to the pain and social isolation during the illness.

Postherpetic neuralgia may be debilitating long after signs of the original herpes infection have disappeared. Other infectious diseases that may cause neuralgia are syphilis and Lyme disease.

Diabetes is another common cause of neuralgia. This very common medical problem affects almost 1 out of every 20 Americans during adulthood. Diabetes damages the tiny arteries that supply circulation to the nerves, resulting in nerve fiber malfunction and sometimes nerve loss. Diabetes can produce almost any neuralgia, including trigeminal neuralgia, carpal tunnel syndrome (pain and numbness of the hand and wrist), and meralgia paresthetica (numbness and pain in the thigh due to damage to the lateral femoral cutaneous nerve). Strict control of blood sugar may prevent diabetic nerve damage and may accelerate recovery in patients who do develop neuralgia.

Other medical conditions that may be associated with neuralgias are chronic renal insufficiency and porphyria—a hereditary disease in which the body cannot rid itself of certain substances produced after the normal breakdown of blood in the body. Certain drugs may also cause this problem.

2. Deafferentation.

Deafferentation indicates a loss of the sensory input from a portion of the body, and can be caused by interruption of either peripheral sensory fibres or nerves from the central nervous system. A deafferentation pain syndrome, includes, without limitation, an injury to the brain or spinal cord, a post-stroke pain, a phantom pain, a paraplegia, a brachial plexus avulsion injuries, lumbar radiculopathies.

3. Complex Regional Pain Syndromes (CRPSs)

CRPS is a chronic pain syndrome resulting from sympathetically-maintained pain, and presents in two forms. CRPS 1 currently replaces the term "reflex sympathetic dystrophy syndrome". It is a chronic nerve disorder that occurs most often in the arms or legs after a minor or major injury. CRPS 1 is associated with severe pain; changes in the nails, bone, and skin; and an increased sensitivity to is touch in the affected limb. CRPS 2 replaces the term causalgia, and results from an identified injury to the nerve. A CRPS, includes, without limitation, a CRPS Type I (reflex sympathetic dystrophy) and a CRPS Type II (causalgia).

4. Neuropathy.

A neuropathy is a functional or pathological change in a nerve and is characterized clinically by sensory or motor neuron abnormalities.

Central neuropathy is a functional or pathological change in the central nervous system.

Peripheral neuropathy is a functional or pathological change in one or more peripheral nerves. The peripheral nerves relay information from your central nervous system (brain and spinal cord) to muscles and other organs and from your skin, joints, and other organs back to your brain. Peripheral neuropathy occurs when these nerves fail to carry information to and from the brain and spinal cord, resulting in pain, loss of sensation, or inability to control muscles. In some cases, the failure of nerves that control blood vessels, intestines, and other organs results in abnormal blood pressure, digestion problems, and loss of other basic body processes. Risk factors for neuropathy include diabetes, heavy alcohol use, and exposure to certain chemicals and drugs. Some people have a hereditary predisposition for neuropathy. Prolonged pressure on a nerve is another risk for developing a nerve injury. Pressure injury may be caused by prolonged immobility (such as a long surgical procedure or lengthy illness) or compression of a nerve by casts, splints, braces, crutches, or other devices. Polyneuropathy implies a widespread process that usually affects both sides of the body equally. The symptoms depend on which type of nerve is affected. The three main types of nerves are sensory, motor, and autonomic. Neuropathy can affect any one or a combination of all three types of nerves. Symptoms also depend on whether the condition affects the whole body or just one nerve (as from an injury). The cause of chronic inflammatory polyneuropathy is an is abnormal immune response. The specific antigens, immune processes, and triggering factors are variable and in many cases are unknown. It may occur in association with other conditions such as HIV, inflammatory bowel disease, lupus erythematosis, chronic active hepatitis, and blood cell abnormalities.

Peripheral neuropathy may involve a function or pathological change to a single nerve or nerve group (mononeuropathy) or a function or pathological change affecting multiple nerves (polyneuropathy).

Peripheral Neuropathies
Hereditary Disorders
- Charcot-Marie-Tooth disease
- Friedreich's ataxia Systemic or Metabolic Disorders
- Diabetes (diabetic neuropathy)
- Dietary deficiencies (especially vitamin B-12)
- Excessive alcohol use (alcoholic neuropathy)
- Uremia (from kidney failure)
- Cancer Infectious or Inflammatory Conditions
- AIDS
- Hepatitis
- Colorado tick fever
- diphtheria
- Guillain-Barre syndrome
- HIV infection without development of AIDS
- leprosy
- Lyme
- polyarteritis nodosa
- rheumatoid arthritis
- sarcoidosis
- Sjogren syndrome
- syphilis
- systemic lupus erythematosus
- amyloid Exposure to Toxic Compounds
- sniffing glue or other toxic compounds
- nitrous oxide
- industrial agents—especially solvents
- heavy metals (lead, arsenic, mercury, etc.)
- Neuropathy secondary to drugs like analgesic nephropathy Miscellaneous Causes
- ischemia (decreased oxygen/decreased blood flow)
- prolonged exposure to cold temperature a. Polyneuropathy Polyneuropathy is a peripheral neuropathy involving the loss of movement or sensation to an area caused by damage or destruction to multiple peripheral nerves. Polyneuropathic pain, includes, without limitation, post-polio syndrome, post-mastectomy syndrome, diabetic neuropathy, alcohol neuropathy, amyloid, toxins, AIDS, hypothyroidism, uremia, vitamin deficiencies, chemotherapy-induced pain, 2',3'-dideoxycytidine (ddC) treatment, Guillain-Barré syndrome or Fabry's disease.

b. Mononeuropathy

Mononeuropathy is a peripheral neuropathy involving loss of movement or sensation to an area caused by damage or destruction to a single peripheral nerve or nerve group. Mononeuropathy is most often caused by damage to a local area resulting from injury or trauma, although occasionally systemic disorders may cause isolated nerve damage (as with mononeuritis multiplex). The usual causes are direct trauma, prolonged pressure on the nerve, and compression of the nerve by swelling or injury to nearby body structures. The damage includes destruction of the myelin sheath (covering) of the nerve or of part of the nerve cell (the axon). This damage slows or prevents conduction of is impulses through the nerve. Mononeuropathy may involve any part of the body. Mononeuropathic pain, includes, without limitation, a sciatic nerve dysfunction, a common peroneal nerve dysfunction, a radial nerve dysfunction, an ulnar nerve dysfunction, a cranial mononeuropathy VI, a cranial mononeuropathy VII, a cranial mononeuropathy III (compression type), a cranial mononeuropathy III (diabetic type), an axillary nerve dysfunction, a carpal tunnel syndrome, a femoral nerve dysfunction, a tibial nerve dysfunction, a Bell's palsy, a thoracic outlet syndrome, a carpal tunnel syndrome and a sixth (abducent) nerve palsy.

c. Generalized Peripheral Neuropathies

Generalized peripheral neuropathies neuropathis are symmetrical, and usually due to various systematic illnesses and disease processes that affect the peripheral nervous system in its entirety. They are further subdivided into several categories:

i. Distal axonopathies are the result of some metabolic or toxic derangement of neurons. They may be caused by metabolic diseases such as diabetes, renal failure, deficiency syndromes such as malnutrition and alcoholism, or the effects of toxins or drugs. Distal axonopathy (aka dying back neuropathy) is a type of peripheral neuropathy that results from some metabolic or toxic derangement of peripheral nervous system (PNS) neurons. It is the most common response of nerves to metabolic or toxic disturbances, and as such may be caused by metabolic diseases such as diabetes, renal failure, deficiency syndromes such as malnutrition and alcoholism, or the effects of toxins or drugs. The most common cause of distal axonopathy is diabetes, and the most common distal axonopathy is diabetic neuropathy.

ii. Myelinopathies are due to a primary attack on myelin causing an acute failure of impulse conduction. The most common cause is acute inflammatory demyelinating polyneuropathy (AIDP; aka Guillain-Barré syndrome), though other causes include chronic inflammatory demyelinating syndrome (CIDP), genetic metabolic disorders (e.g., leukodystrophy), or toxins. Myelinopathy is due to primary destruction of myelin or the myelinating Schwann cells, which leaves the axon intact, but causes an acute failure of impulse conduction. This demyelination slows down or completely blocks the conduction of electrical impulses through the nerve. The most common cause is acute inflammatory demyelinating polyneuropathy (AIDP, better known as Guillain-Barré syndrome), though other causes include chronic inflammatory demyelinating polyneuropathy (CIDP), genetic metabolic disorders (e.g., leukodystrophy or Charcot-Marie-Tooth disease), or toxins.

iii. Neuronopathies are the result of destruction of peripheral nervous system (PNS) neurons. They may be caused by motor neuron diseases, sensory neuronopathies (e.g., Herpes zoster), toxins or autonomic dysfunction. Neurotoxins may cause neuronopathies, such as the chemotherapy agent vincristine. Neuronopathy is dysfunction due to damage to neurons of the peripheral nervous system (PNS), resulting in a peripheral neuropathy. It may be caused by motor neuron diseases, sensory neuronopathies (e.g., Herpes zoster), toxic substances or autonomic dysfunction. A person with neuronopathy may present in different ways, depending on the cause, the way it affects the nerve cells, and the type of nerve cell that is most affected.

iv. Focal entrapment neuropathies (e.g., carpal tunnel syndrome).

II. Inflammatory Pain

The compounds of the invention may be used to treat pain caused by or otherwise associated with any of the following inflammatory conditions.

A. Arthritic Disorder

Arthritic disorders include, for example, a rheumatoid arthritis; a juvenile rheumatoid arthritis; a systemic lupus erythematosus (SLE); a gouty arthritis; a scleroderma; an osteoarthritis; a psoriatic arthritis; an ankylosing spondylitis; a to Reiter's syndrome (reactive arthritis); an adult Still's disease; an arthritis from a viral infection; an arthritis from a bacterial infection, such as, e.g., a gonococcal arthritis and a non-gonococcal bacterial arthritis (septic arthritis); a Tertiary Lyme disease; a tuberculous arthritis; and an arthritis from a fungal infection, such as, e.g. a blastomycosis.

B. Autoimmune Diseases

Autoimmune diseases include, for example, a Guillain-Barré syndrome, a Hashimoto's thyroiditis, a pernicious anemia, an Addison's disease, a type I diabetes, a systemic lupus erythematosus, a dermatomyositis, a Sjogren's syndrome, a lupus erythematosus, a multiple sclerosis, a myasthenia gravis, a Reiter's syndrome and a Grave's disease.

C. Connective Tissue Disorder

Connective tissue disorders include, for example, a spondyloarthritis a dermatomyositis, and a fibromyalgia.

D. Injury

Inflammation caused by injury, including, for example, a crush, puncture, stretch of a tissue or joint, may cause chronic inflammatory pain.

E. Infection

Inflammation caused by infection, including, for example, a tuberculosis or an interstitial keratitis may cause chronic inflammatory pain.

F. Neuritis

Neuritis is an inflammatory process affecting a nerve or group of nerves. Symptoms depend on the nerves involved, but may include pain, paresthesias, paresis, or hypesthesia (numbness).

Examples include:

a. Brachial neuritis b. Retrobulbar neuropathy, an inflammatory process affecting the part of the optic nerve lying immediately behind the eyeball.

c. Optic neuropathy, an inflammatory process affecting the optic nerve causing sudden, reduced vision in the affected eye. The cause of optic neuritis is unknown. The sudden inflammation of the optic nerve (the nerve connecting the eye and the brain) leads to swelling and destruction of the myelin sheath. The inflammation may occasionally be the result of a viral infection, or it may be caused by autoimmune diseases such as multiple sclerosis. Risk factors are related to the possible causes.

d. Vestibular neuritis, a viral infection causing an inflammatory process affecting the vestibular nerve.

G. Joint Inflammation

Inflammation of the joint, such as that caused by bursitis or tendonitis, for example, may cause chronic inflammatory pain.

III. Headache Pain

The compounds of the invention may be used to treat pain caused by or otherwise associated with any of the following headache conditions. A headache (medically known as cephalgia) is a condition of mild to severe pain in the head; sometimes neck or upper back pain may also be interpreted as a headache. It may indicate an underlying local or systemic disease or be a disorder in itself.

A. Muscular/Myogenic Headache

Muscular/myogenic headaches appear to involve the tightening or tensing of facial and neck muscles; they may radiate to the forehead. Tension headache is the most common form of myogenic headache.

A tension headache is a condition involving pain or discomfort in the head, scalp, or neck, usually associated with muscle tightness in these areas. Tension headaches result from the contraction of neck and scalp muscles. One cause of this muscle contraction is a response to stress, depression or anxiety. Any activity that causes the head to be held in one position for a long time without moving can cause a headache. Such activities include typing or use of computers, fine work with the hands, and use of a microscope. Sleeping in a cold room or sleeping with the neck in an abnormal position may also trigger this type of headache. A tension-type headache, includes, without limitation, an episodic tension headache and a chronic tension headache.

B. Vascular Headache

The most common type of vascular headache is migraine. Other kinds of vascular headaches include cluster headaches, which cause repeated episodes of intense pain, and headaches resulting from high blood pressure.

1. Migraine

A migraine is a heterogeneous disorder that generally involves recurring headaches. Migraines are different from other headaches because they occur with other symptoms, such as, e.g., nausea, vomiting, or sensitivity to light. In most people, a throbbing pain is felt only on one side of the head. Clinical features such as type of aura symptoms, presence of prodromes, or associated symptoms such as vertigo, may be seen in subgroups of patients with different underlying pathophysiological and genetic mechanisms. A migraine headache, includes, without limitation, a migraine without aura (common migraine), a migraine with aura (classic migraine), a menstrual migraine, a migraine equivalent (acephalic headache), a complicated migraine, an abdominal migraine and a mixed tension migraine.

2. Cluster Headache

Cluster headaches affect one side of the head (unilateral) and may be associated with tearing of the eyes and nasal congestion. They occur in clusters, happening repeatedly every day at the same time for several weeks and then remitting.

D. High Blood Pressure Headache

E. Traction and inflammatory headache

Traction and inflammatory headaches are usually symptoms of other disorders, ranging from stroke to sinus infection.

F. Hormone Headache

G. Rebound Headache

Rebound headaches, also known as medication overuse headaches, occur when medication is taken too frequently to relieve headache. Rebound headaches frequently occur daily and can be very painful.

H. Chronic Sinusitis Headache

Sinusitis is inflammation, either bacterial, fungal, viral, allergic or autoimmune, of the paranasal sinuses. Chronic sinusitis is one of the most common complications of the common cold. Symptoms include: Nasal congestion; facial pain; headache; fever; general malaise; thick green or yellow discharge; feeling of facial 'fullness' worsening on bending over. In a small number of cases, chronic maxillary sinusitis can also be brought on by the spreading of bacteria from a dental infection. Chronic hyperplastic eosinophilic sinusitis is a noninfective form of chronic sinusitis.

I. An Organic Headache

J. Ictal Headaches

Ictal headaches are headaches associated with seizure activity.

IV. Somatic Pain

The compounds of the invention may be used to treat pain caused by or otherwise associated with any of the following somatic pain conditions. Somatic pain originates from ligaments, tendons, bones, blood vessels, and even nerves themselves. It is detected with somatic nociceptors. The scarcity of pain receptors in these areas produces a dull, poorly-localized pain of longer duration than cutaneous pain; examples include sprains and broken bones. Additional examples include the following.

A. Excessive Muscle Tension

Excessive muscle tension can be caused, for example, by a sprain or a strain.

B. Repetitive Motion Disorders

Repetitive motion disorders can result from overuse of the hands, wrists, elbows, shoulders, neck, back, hips, knees, feet, legs, or ankles.

C. Muscle Disorders

Muscle disorders causing somatic pain include, for example, a polymyositis, a dermatomyositis, a lupus, a fibromyalgia, a polymyalgia rheumatica, and a rhabdomyolysis.

D. Myalgia

Myalgia is muscle pain and is a symptom of many diseases and disorders. The most common cause for myalgia is either overuse or over-stretching of a muscle or group of muscles. Myalgia without a traumatic history is often due to viral infections. Longer-term myalgias may be indicative of a metabolic myopathy, some nutritional deficiencies or chronic fatigue syndrome.

E. Infection

Infection can cause somatic pain. Examples of such infection include, for example, an abscess in the muscle, a trichinosis, an influenza, a Lyme disease, a malaria, a Rocky Mountain spotted fever, Avian influenza, the common cold, community-acquired pneumonia, meningitis, monkeypox, Severe Acute Respiratory Syndrome, toxic shock syndrome, trichinosis, typhoid fever, and upper respiratory tract infection.

F. Drugs

Drugs can cause somatic pain. Such drugs include, for example, cocaine, a statin for lowering cholesterol (such as atorvastatin, simvastatin, and lovastatin), and an ACE inhibitor for lowering blood pressure (such as enalapril and captopril).

V. Visceral Pain

The compounds of the invention may be used to treat pain caused by or otherwise associated with any of the following visceral pain conditions. Visceral pain originates from body's viscera, or organs. Visceral nociceptors are located within body organs and internal cavities. The even greater scarcity of nociceptors in these areas produces pain that is usually more aching and of a longer duration than somatic pain. Visceral pain is extremely difficult to localise, and several injuries to visceral tissue exhibit "referred" pain, where the sensation is localised to an area completely unrelated to the site of injury. Examples of visceral pain include the following.

A. Functional Visceral Pain

Functional visceral pain includes, for example, an irritable bowel syndrome and a chronic functional abdominal pain (CFAP), a functional constipation and a functional dyspepsia, a non-cardiac chest pain (NCCP) and a chronic abdominal pain.

B. Chronic Gastrointestinal Inflammation

Chronic gastrointestinal inflammation includes, for example, a gastritis, an inflammatory bowel disease, like, e.g., a Crohn's disease, an ulcerative colitis, a microscopic colitis, a diverticulitis and a gastroenteritis; an interstitial cystitis; an intestinal ischemia; a cholecystitis; an appendicitis; a gastroesophageal reflux; an ulcer, a nephrolithiasis, an urinary tract infection, a pancreatitis and a hernia.

C. Autoimmune Pain

Autoimmune pain includes, for example, a sarcoidosis and a vasculitis.

D. Organic Visceral Pain

Organic visceral pain includes, for example, pain resulting from a traumatic, inflammatory or degenerative lesion of the gut or produced by a tumor impinging on sensory innervation.

E. Treatment-Induced Visceral Pain

Treatment-induced visceral pain includes, for example, a pain attendant to chemotherapy therapy or a pain attendant to radiation therapy.

VI. Referred Pain

The compounds of the invention may be used to treat pain caused by or otherwise associated with any of the following referred pain conditions.

Referred pain arises from pain localized to an area separate from the site of pain stimulation. Often, referred pain arises when a nerve is compressed or damaged at or near its origin. In this circumstance, the sensation of pain will generally be felt in the territory that the nerve serves, even though the damage originates elsewhere. A common example occurs in intervertebral disc herniation, in which a nerve root arising from the spinal cord is compressed by adjacent disc material. Although pain may arise from the damaged disc itself, pain will also be felt in the region served by the compressed nerve (for example, the thigh, knee, or foot). Relieving the pressure on the nerve root may ameliorate the referred pain, provided that permanent nerve damage has not occurred. Myocardial ischaemia (the loss of blood flow to a part of the heart muscle tissue) is possibly the best known example of referred pain; the sensation can occur in the upper chest as a restricted feeling, or as an ache in the left shoulder, arm or even hand.

Definitions Section

Exocytic fusion is a process by which intracellular molecules are transported from the cytosol of a pain-sensing target cell to the plasma (i.e. cell) membrane thereof. Thereafter, the intracellular molecules may become displayed on the outer surface of the plasma membrane, or may be secreted into the extracellular environment.

In a healthy individual, the rate of exocytic fusion is carefully regulated and allows control of the transport of molecules between the cytosol and the plasma membrane of a pain-sensing cell. For example, regulation of the exocytic cycle allows control of the density of receptors, transporters, or membrane channels present at the cell's surface, and/or allows control of the secretion rate of intracellular components (e.g. neurotransmitters) from the cytosol of the cell.

However, in an unhealthy individual, the regulation of exocytic fusion may be modified. For example, exocytic fusion may cause affected pain-sensing cells to enter a state of hypersecretion. Alternatively, exocytic fusion may result in the display of an increased concentration of receptors, transporters, or membrane channels present on the surface of the pain-sensing, which may expose the cell to undesirable external stimuli. Thus, the process of exocytic fusion may contribute to the progression and/or severity of pain, and therefore provides a target for therapeutic intervention.

It should also be appreciated that otherwise normal rates of cellular exocytic fusion may contribute to the progression and severity of pain in compromised patients. Thus, by targeting exocytic fusion in accordance with the present invention, it is also possible to provide therapy in such patients.

Targeting Moiety (TM) means any chemical structure associated with a conjugate that functionally interacts with a receptor, e.g. an $ORL_1$ receptor, to cause a to physical association between the conjugate and the surface of a pain-sensing target cell. The term TM embraces any molecule (i.e. a naturally occurring molecule, or a chemically/physically modified variant thereof) that is capable of binding to a receptor on the target cell, which receptor is capable of internalisation (e.g. endosome formation)—also referred to as receptor-mediated endocytosis. The TM may possess an endosomal membrane translocation domain, in which case separate TM and Translocation Domain components need not be present in an agent of the present invention. The TM of the present invention binds (preferably specifically binds) to a nociceptive sensory afferent (e.g. a primary nociceptive afferent). In this regard, specifically binds means that the TM binds to a nociceptive sensory afferent (e.g. a primary nociceptive afferent) with a greater affinity than it binds to other neurons such as non-nociceptive afferents, and/or to motor neurons (i.e. the natural target for clostridial neurotoxin holotoxin). The term "specifically binding" can also mean that a given TM binds to a given receptor, for example the GALR1 and/or GALR2 receptor, with a binding affinity (Ka) of $10^6$ $M^{-1}$ or greater, preferably $10^7$ $M^{-1}$ or greater, more preferably $10^8$ $M^{-1}$ or greater, and most preferably, $10^9$ $M^{-1}$ or greater.

The term "fragment" means a peptide having at least thirty-five, preferably at least twenty-five, more preferably at least twenty, and most preferably at least 19, 18, 17, 16, 15, 14, 13, 12, 11 or 10 amino acid residues of the protein (e.g. TM) in question. In one embodiment, the first amino acid residue of the fragment is the N-terminal amino acid residue of the TM from which the fragment has been derived.

An example of a "variant" is a peptide or peptide fragment of a TM that contains one or more analogues of an amino acid (e.g. an unnatural amino acid), or a substituted linkage.

A "derivative" comprises the TM in question, and a further peptide sequence. The further peptide sequence should preferably not interfere with the basic folding and thus conformational structure of the TM. Two or more peptides (or fragments, or variants) may be joined together to form a derivative. Alternatively, a peptide (or fragment, or variant) may be joined to an unrelated molecule (e.g. a second, unrelated peptide). Derivatives may be chemically synthesized, but will be typically prepared by recombinant nucleic acid methods. Additional components such as lipid, and/or polysaccharide, and/or polyketide components may be included.

The term non-cytotoxic means that the protease molecule in question does not kill the pain-sensing target cell to which it has been re-targeted.

The "protease cleavage site" of the present invention allows cleavage (preferably controlled cleavage) of the conjugate at a position between the non-cytotoxic protease component and the TM component. In one embodiment, the conjugate may include more than one proteolytic cleavage site. However, where two or more such sites exist, they are different, thereby substantially preventing the occurrence of multiple cleavage events in the presence of a single protease. In another embodiment, it is preferred that the conjugate has a single protease cleavage site. The protease cleavage sequence(s) may be introduced (and/or any inherent cleavage sequence removed) at the DNA level by conventional means, such as by site-directed mutagenesis. Screening to confirm the presence of cleavage sequences may be performed manually or with the assistance of computer software (e.g. the MapDraw program by DNASTAR, Inc.).

Whilst any protease cleavage site may be employed, the following are preferred:

| | |
|---|---|
| Enterokinase | SEQ ID NO: 108 (DDDDK↓) |
| Factor Xa | SEQ ID NO: 109 (IEGR↓/IDGR↓) |
| TEV(Tobacco Etch virus) | SEQ ID NO: 110 (ENLYFQ↓G) |
| Thrombin | SEQ ID NO: 111 (LVPR↓GS) |
| PreScission | SEQ ID NO: 112 (LEVLFQ↓GP). |

Also embraced by the term protease cleavage site is an intein, which is a self-cleaving sequence. The self-splicing reaction is controllable, for example by varying the concentration of reducing agent present.

The present invention is now described by reference to the following Examples and Figures, without intended limitation thereto.

SEQ ID NOs:

Where an initial Met amino acid residue or a corresponding initial codon is indicated in any of the following SEQ ID NOs, said residue/codon is optional.

SEQ ID NO:1 DNA sequence of N[1-17]
SEQ ID NO:2 Protein Sequence of N[1-17]
SEQ ID NO:3 DNA sequence of N[1-11]
SEQ ID NO:4 Protein sequence of N[1-11]
SEQ ID NO:5 DNA sequence of N[[Y10]1-11]
SEQ ID NO:6 Protein sequence of N[[Y10]1-11]
SEQ ID NO:7 DNA sequence of N[[Y11]1-11]
SEQ ID NO:8 Protein sequence of N[[Y11]1-11]
SEQ ID NO:9 DNA sequence of N[[Y14]1-17]
SEQ ID NO:10 Protein sequence of N[[Y14]1-17]
SEQ ID NO:11 DNA sequence of N[1-13]
SEQ ID NO:12 Protein sequence of N[1-13]
SEQ ID NO:13 DNA sequence of Nv (also known as N[[R14K15]1-17])
SEQ ID NO:14 Protein sequence of Nv (also known as N[[R14K15]1-17])
SEQ ID NO:15 DNA sequence of N[1-17]-$LH_N$/A fusion protein
SEQ ID NO:16 Protein sequence of N[1-17]-$LH_N$/A fusion protein
SEQ ID NO:17 DNA sequence of N[[Y11]1-11]-LHN/A fusion protein
SEQ ID NO:18 Protein sequence of N[[Y11]1-11]-LHN/A fusion protein
SEQ ID NO:19 DNA sequence of N[1-13]-LHN/A fusion protein
SEQ ID NO:20 Protein sequence of N[1-13]-LHN/A fusion protein SEQ ID NO:21 DNA sequence of LHN/A-N[1-17] fusion protein
SEQ ID NO:22 Protein sequence of LHN/A-N[1-17] fusion protein
SEQ ID NO:23 DNA sequence of LHN/C-N[1-11] fusion protein
SEQ ID NO:24 Protein sequence of LHN/C-N[1-11] fusion protein
SEQ ID NO:25 DNA sequence of N[[Y14]1-17]-LHN/C fusion protein
SEQ ID NO:26 Protein sequence of N[[Y14]1-17]-LHN/C fusion protein
SEQ ID NO:27 DNA sequence of the LC/A
SEQ ID NO:28 DNA sequence of the $H_N$/A
SEQ ID NO:29 DNA sequence of the LC/B
SEQ ID NO:30 DNA sequence of the $H_N$/B
SEQ ID NO:31 DNA sequence of the LC/C
SEQ ID NO:32 DNA sequence of the $H_N$/C
SEQ ID NO:33 DNA sequence of the CPN-A linker
SEQ ID NO:34 DNA sequence of the A linker
SEQ ID NO:35 DNA sequence of the N-terminal presentation nociceptin insert
SEQ ID NO:36 DNA sequence of the CPN-C linker
SEQ ID NO:37 DNA sequence of the CPBE-A linker
SEQ ID NO:38 DNA sequence of the CPNvar-A linker
SEQ ID NO:39 DNA sequence of the LC/A-CPN-$H_N$/A fusion
SEQ ID NO:40 Protein sequence of the LC/A-CPN-$H_N$/A fusion
SEQ ID NO:41 DNA sequence of the N-LC/A-$H_N$/A fusion
SEQ ID NO:42 Protein sequence of the N-LC/A-$H_N$/A fusion
SEQ ID NO:43 DNA sequence of the LC/C-CPN-$H_N$/C fusion
SEQ ID NO:44 Protein sequence of the LC/C-CPN-$H_N$/C fusion
SEQ ID NO:45 DNA sequence of the LC/C-CPN-$H_N$/C (A-linker) fusion
SEQ ID NO:46 Protein sequence of the LC/C-CPN-$H_N$/C (A-linker) fusion
SEQ ID NO:47 DNA sequence of the LC/A-CPME-$H_N$/A fusion
SEQ ID NO:48 Protein sequence of the LC/A-CPME-$H_N$/A fusion
SEQ ID NO:49 DNA sequence of the LC/A-CPBE-$H_N$/A fusion
SEQ ID NO:50 Protein sequence of the LC/A-CPBE-$H_N$/A fusion
SEQ ID NO:51 DNA sequence of the LC/A-CPNv-$H_N$/A fusion
SEQ ID NO:52 Protein sequence of the LC/A-CPNv-$H_N$/A fusion
SEQ ID NO:53 DNA sequence of the LC/A-CPN[1-11]-HN/A fusion
SEQ ID NO:54 Protein sequence of the LC/A-CPN[1-11]-HN/A fusion
SEQ ID NO:55 DNA sequence of the LC/A-CPN[[Y10]1-11]-HN/A fusion
SEQ ID NO:56 Protein sequence of the LC/A-CPN[[Y10]1-11]-HN/A fusion
SEQ ID NO:57 DNA sequence of the LC/A-CPN[[Y11]1-11]-HN/A fusion
SEQ ID NO:58 Protein sequence of the LC/A-CPN[[Y11]1-11]-HN/A fusion
SEQ ID NO:59 DNA sequence of the LC/A-CPN[[Y14]1-17]-HN/A fusion
SEQ ID NO:60 Protein sequence of the LC/A-CPM[[Y14]1-17]-HN/A fusion
SEQ ID NO:61 DNA sequence of the LC/A-CPN[1-13]-HN/A fusion
SEQ ID NO:62 Protein sequence of the LC/A-CPN[1-13]-HN/A fusion
SEQ ID NO:63 DNA sequence of the nociceptin-spacer-LC/A-$H_N$/A fusion
SEQ ID NO:64 Protein sequence of the nociceptin-spacer-LC/A-$H_N$/A fusion
SEQ ID NO:65 DNA sequence of the CPN-A GS10 linker
SEQ ID NO:66 DNA sequence of the CPN-A GS15 linker
SEQ ID NO:67 DNA sequence of the CPN-A GS25 linker
SEQ ID NO:68 DNA sequence of the CPN-A GS30 linker
SEQ ID NO:69 DNA sequence of the CPN-A HX27 linker
SEQ ID NO:70 DNA sequence of the LC/A-CPN(GS15)-$H_N$/A fusion
SEQ ID NO:71 Protein sequence of the LC/A-CPN(GS15)-$H_N$/A fusion
SEQ ID NO:72 DNA sequence of the LC/A-CPN(GS25)-$H_N$/A fusion
SEQ ID NO:73 Protein sequence of the LC/A-CPN(GS25)-$H_N$/A fusion
SEQ ID NO:74 DNA sequence of the CPNvar-A Enterokinase activatable linker
SEQ ID NO:75 DNA sequence of the LC/A-CPNv(Ek)-$H_N$/A fusion
SEQ ID NO:76 Protein sequence of the LC/A-CPNv(Ek)-$H_N$/A fusion
SEQ ID NO:77 DNA sequence of the CPNvar-A linker
SEQ ID NO:78 DNA sequence of the LC/C-CPNv-$H_N$/C fusion (act. A)
SEQ ID NO:79 Protein sequence of the LC/C-CPNv-$H_N$/C fusion (act. A)
SEQ ID NO:80 DNA sequence of the LC/A-CPLE-$H_N$/A fusion
SEQ ID NO:81 Protein sequence of the LC/A-CPLE-$H_N$/A fusion
SEQ ID NO:82 DNA sequence of the LC/A-CPOP-$H_N$/A fusion
SEQ ID NO:83 Protein sequence of the LC/A-CPOP-$H_N$/A fusion
SEQ ID NO:84 DNA sequence of the LC/A-CPOPv-$H_N$/A fusion
SEQ ID NO:85 Protein sequence of the LC/A-CPOPv-$H_N$/A fusion
SEQ ID NO:86 DNA sequence of the IgA protease
SEQ ID NO:87 DNA sequence of the IgA-CPNv-$H_N$/A fusion
SEQ ID NO:88 Protein sequence of the IgA-CPNv-$H_N$/A fusion
SEQ ID NO:89 DNA sequence of the FXa-HT
SEQ ID NO:90 DNA sequence of the CPNv-A-FXa-HT
SEQ ID NO:91 Protein sequence of the CPNv-A-FXa-HT fusion
SEQ ID NO:92 DNA sequence of the DT translocation domain
SEQ ID NO:93 DNA sequence of the CPLE-DT-A
SEQ ID NO:94 Protein sequence of the CPLE-DT-A fusion
SEQ ID NO:95 DNA sequence of the TeNT LC
SEQ ID NO:96 DNA sequence of the CPNv-TENT LC
SEQ ID NO:97 Protein sequence of the CPNV-TeNT LC fusion
SEQ ID NO:98 DNA sequence of the CPNvar-C linker
SEQ ID NO:99 DNA sequence of the LC/C-CPNv-$H_N$/C fusion (act. C)
SEQ ID NO:100 Protein sequence of the LC/C-CPNv-$H_N$/C fusion (act. C)
SEQ ID NO:101 Protein sequence of galanin GA30
SEQ ID NO:102 Protein sequence of galanin GA16
SEQ ID NO:103 DNA sequence of LC/A-$H_N$/A-GS20-GA30 fusion
SEQ ID NO:104 DNA sequence of LC/A-$H_N$/A-GS20-GA16 fusion SEQ ID NO:105 Protein sequence of LC/A-$H_N$/A-GS20-GA30 fusion SEQ ID NO:106 Protein sequence of LC/A-$H_N$/A-GS20-GA16 fusion

EXAMPLES

Example 1

Confirmation of TM Agonist Activity by Measuring Release of Substance P from Neuronal Cell Cultures Materials Substance P EIA is obtained from R&D Systems, UK.

Methods

Primary neuronal cultures of eDRG are established as described previously (Duggan et al., 2002). Substance P release from the cultures is assessed by EIA, essentially as described previously (Duggan et al., 2002). The TM of interest is added to the neuronal cultures (established for at least 2 weeks prior to treatment); control cultures are performed in parallel by addition of vehicle in place of TM. Stimulated (100 mM KCl) and basal release, together with total cell lysate content, of substance P are obtained for both control and TM treated cultures. Substance P immunoreactivity is measured using Substance P Enzyme Immunoassay Kits (Cayman Chemical Company, USA or R&D Systems, UK) according to manufacturers' instructions.

The amount of Substance P released by the neuronal cells in the presence of the TM of interest is compared to the release obtained in the presence and absence of 100 mM KCl. Stimulation of Substance P release by the TM of interest above the basal release, establishes that the TM of interest is an "agonist ligand" as defined in this specification. If desired the stimulation of Substance P release by the TM of interest can be compared to a standard Substance P release-curve produced using the natural ORL-1 receptor ligand, nociceptin (Tocris).

Example 2

Expression and purification of catalytically active $LH_N$/A

Materials

Synthetic DNA obtained from Sigma Genosys.

Restriction enzymes obtained from New England Biolabs.

Methods

The expression and purification of catalytically active $LH_N$/A was carried out essentially as described in Sutton et al., (2005), Prot. Express. Purif., 40, pp 31-41.

Briefly, DNA encoding the light chain plus 423 amino acids from the N-terminal of the heavy chain of BoNT/A was synthesised by Sigma-Genosys to produce a synthetic $LH_N$/A gene with an *E. coli* codon bias. The linker region between the light chain and $H_N$ domain was engineered to contain a Factor Xa cleavage site by splice-overlap extension PCR. Two PCR products were generated using primer pairs consisting of a long, mutagenic primer and a shorter, non-mutagenic primer:

```
(5'-tccaaaactaaatctctgATAGAAGGTAGAaacaaagcgctgaacgac; SEQ ID NO: 113)
with

(5'-CTTGATGTACTCTGTGAACGTGCTC; SEQ ID NO: 114);
and

(5'-gtcgttcagcgctttgttTCTACCTTCTATcagagatttagttttgga; SEQ ID NO: 115)
with

(5'-ATGGAGTTCGTTAACAAACAGTTC; SEQ ID NO: 116).
```

The products from these two reactions were used as templates for the splice-overlap extension PCR. A further PCR reaction was set up to add BamHI and SalI sites at either end of the activatable rec$LH_N$/A gene and these sites were used for insertion into an Invitrogen gateway entry vector. The entry vector was then used, along with a gateway recombination site adapted pMAL c2 x, in a LR clonase reaction to form pMAL c2x rec$LH_N$/A. The pMAL c2x rec$LH_N$/A was modified to incorporate a 6'HIS tag at the N-terminus of the MBP. This was achieved by the insertion of annealed oligonucleotides encoding the HIS tag into the NdeI site of pMAL.

The expression vector expressing $LH_N$/A was transformed into *E. coli* HMS174 or AD494(DE3) (Novagen). Cultures were grown in Terrific broth complex medium supplemented with $ZnCl_2$ (1 μM), ampicillin (100 μg/ml), 0.2% (w/v) glucose. Parameters for expression of all the constructs were initially determined in shake flask cultures before transferring into 8 L fermentor systems. Starter cultures is were grown for 16 hours at 37° C., 220 rpm and used to inoculate 1 L in which growth was continued at 37° C., 250 rpm. At an OD600 nm of 0.6 the temperature was reduced to 25° C. for 30 minutes before induction with 1 mM IPTG. Induction was continued for 4 hours before the cells were harvested and stored at −70° C.

Typically 16 g of cell paste was suspended in 160 ml PBS and lysed by sonication (MSE Soniprep 150). The resulting lysate was clarified by centrifugation prior loading onto a 25 ml amylose column and eluted with 10 mM maltose in PBS. The eluant contained approx. 50% pure fusion protein and was treated with Factor Xa (1 unit Factor Xa/100 μg fusion protein; 20 hours; 26° C.) to remove the HISMBP and cleave the LC-$H_N$ junction to activate the protein. After incubation the sample was filtered (0.45 mm) and diluted two fold with water to give a 0.5×PBS buffer composition. The cleaved, filtered and diluted rec$LH_N$/A was processed through a Q Sepharose FF column (10 ml) and eluted with a step gradient of 80 mM NaCl containing HISMBP and 120 mM NaCl containing approx. 75% pure rec$LH_N$/A. The addition of His tag to MBP overcame previous co-elution problems with $LH_N$/A and MBP. As a final polishing step to ensure complete removal of the HISMBP, the 120 mM NaCl elution from the Q Sepharose column was passed through a Nickel charged 5 ml H isTrap column (Amersham). The flow through from the HisTrap column contained approx. 95% pure rec$LH_N$/A (see the Figures in Sutton et al., (2005), Prot. Express. Purif., 40, pp 31-41 for an illustration of the purification scheme for LHN/A).

Example 3

Expression and Purification of Catalytically Active Recombinant $LH_N$/B

The methodology described below will purify catalytically active $LH_N$/B protease from *E. coli* transformed with the appropriate plasmid encoding the $LH_N/B$ polypeptide. It should be noted that various sequences of suitable $LH_N/B$ polypeptides have been described in PCT/GB97/02273, granted U.S. Pat. No. 6,461,617 and U.S. patent application Ser. No. 10/241,596, incorporated herein by reference.

Methods

The coding region for $LH_N/B$ is inserted in-frame to the 3' of the gene encoding maltose binding protein (MBP) in the expression vector pMAL (New England Biolabs) to create pMAL-c2x-$LH_N/B$. In this construct, the expressed MBP and $LH_N/B$ polypeptides are separated by a Factor Xa cleavage site, and the LC and $H_N$ domains are separated by a peptide that is susceptible to cleavage with enterokinase. The expression clone is termed pMAL-c2X-syn$LH_N/B$.

pMAL-c2X-syn$LH_N/B$ is transformed into *E. coli* HMS174 and cultured in Terrific broth complex medium in 8 L fermentor systems. Pre-induction bacterial growth is maintained at 37° C. to an OD600 nm of 5.0, at which stage expression of recMBP-$LH_N/B$ is induced by addition of IPTG to 0.5 mM and a reduction in temperature to 30° C. After four hours at 30° C. the bacteria are harvested by centrifugation and the resulting paste stored at −70° C.

The cell paste is resuspended in 20 mM Hepes pH 7.2, 125 mM NaCl, 1 μM $ZnCl_2$ and cell disruption achieved using an APV-Gaulin lab model 1000 homogeniser or a MSE Soniprep 150 sonicator. The resulting suspension is clarified by centrifugation prior to purification.

Following cell disruption, the MBP-fusion protein is captured either on an amylose affinity resin in 20 mM Hepes pH 7.2, 125 mM NaCl, 1 μM $ZnCl_2$, or on a Q-Sepharose FF anion-exchange resin in 50 mM Hepes pH 7.2, 1 μM $ZnCl_2$ with no salt. A single peak is eluted from the amylose resin in the same buffer plus 10 mM maltose and from the Q-Sepharose in 150-200 mM salt. Cleavage of the MBP-$LH_N/B$ junction is completed in an 18 hours incubation step at 22° C. with Factor Xa (NEB) at 1 U/50 μg fusion protein. A substrate (MBP-$LH_N/B$) concentration of at least 4 mg/ml is desirable for efficient cleavage to take place.

Figure 1:
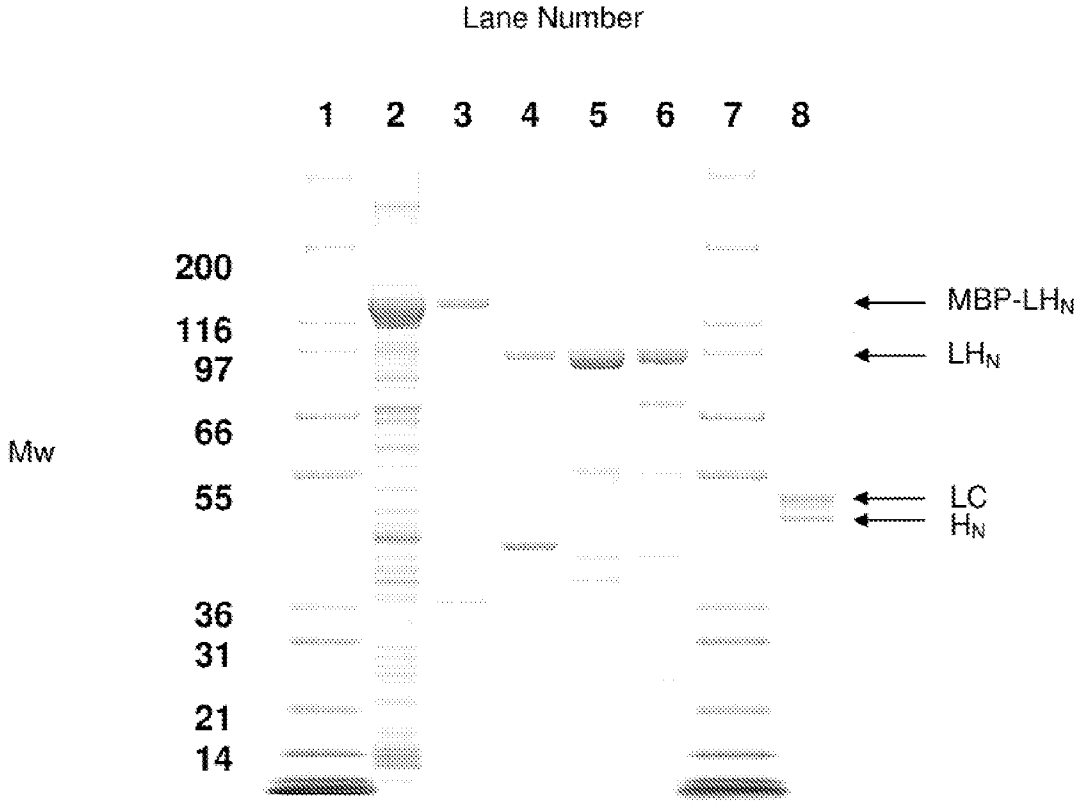
FIG. 1-E*xpression* and Purification of recLH$_N$/B Fusion Protein

The cleaved protein is diluted with 20 mM Hepes to a buffer composition of 20 mM Hepes, 25 mM NaCl, 1 μM $ZnCl_2$, pH 7.2 and processed through a Q Sepharose column to separate the MBP from $LH_N/B$. The $LH_N/B$ is eluted from the Q-Sepharose column with 120-170 mM salt. The linker between the light chain and $H_N$ domain is then nicked by incubation with enterokinase at 1 U/100 μg of $LH_N/B$ at 22° C. for 16 hours. Finally, the enterokinase is separated from the nicked $LH_N/B$ and other contaminating proteins on a Benzamidine Sepharose column, the enzyme preferentially binding to the resin over an incubation of 30 minutes at 4° C. Purified $LH_N/B$ is stored at −20° C. until required. See FIG. 1 for an illustration of the purification scheme for rec$LH_N/B$.

Example 4

Expression and Purification of Catalytically Active Recombinant $LH_N/C$

The coding region for $LH_N/C$ is inserted in-frame to the 3' of the gene encoding maltose binding protein (MBP) in the expression vector pMAL (New England Biolabs) to create pMAL-c2x-$LH_N/C$. In this construct the expressed MBP and $LH_N/C$ polypeptides are separated by a Factor Xa cleavage site.

pMAL-c2x-$LH_N/C$ is transformed into *E. coli* AD494 (DE3, IRL) and cultured in Terrific broth complex medium in 8 L fermentor systems. Pre-induction bacterial growth are maintained at 30° C. to an OD600 nm of 8.0, at which stage expression of recMBP-c2x-$LH_N/C$ is induced by addition of IPTG to 0.5 mM and a reduction in temperature of culture to 25° C. After 4 hours at 25° C. the bacteria are harvested by centrifugation and the resulting paste stored at −70° C.

The cell paste is resuspended in 50 mM Hepes pH 7.2, 1 μM $ZnCl_2$ at 1:6 (w/v) and cell disruption is achieved using an APV-Gaulin lab model 1000 homogeniser or a MSE Soniprep 150 sonicator. The resulting suspension is clarified by centrifugation prior to purification.

Figure 2:
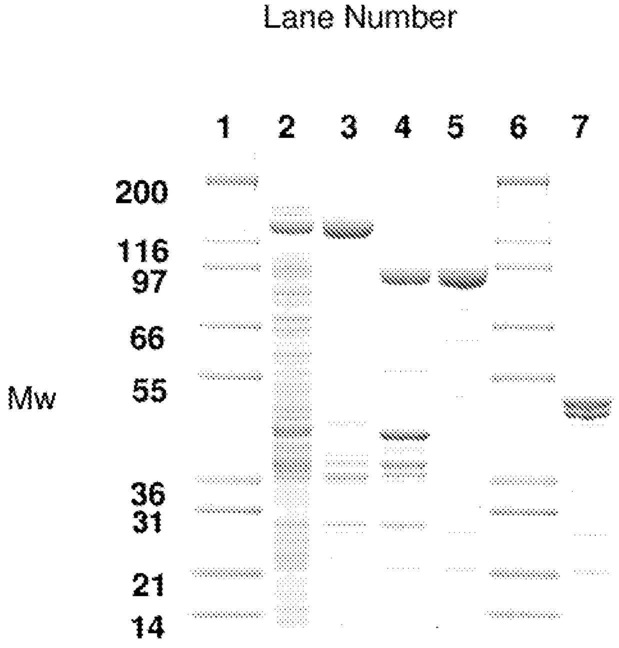
FIG. 2-E*xpression* and Purification of LH$_N$/C Fusion Protein

Following cell disruption and clarification, the MBP-fusion protein is separated on a Q-Sepharose Fast Flow anion-exchange resin in 50 mM Hepes pH 7.2, 1 μM $ZnCl_2$ and eluted with the same buffer plus 100 mM NaCl. A double point cleavage is performed at the MBP-$LH_N/C$ junction and the $H_N$-LC linker in a single incubation step with Factor Xa. The reaction is completed in a 16-hour incubation step at 22° C. with Factor Xa (NEB) at 1 U/100 ìg fusion protein. The cleaved protein is diluted with 20 mM Hepes to a buffer composition of 20 mM Hepes, 25 mM NaCl, pH 7.2 and processed through a second Q-Sepharose column to separate the MBP from $LH_N/C$. Activated (disulphide-bonded cleaved linker) $LH_N/C$ is eluted from the Q-Sepharose column by a salt gradient (20 mM Hepes, 500 mM NaCl, 1 μM $ZnCl_2$, pH 7.2) in 120-170 mM salt. See FIG. 2 for an illustration of the purification of $LH_N/C$.

Example 5

Production of a Chemical Conjugate of Nociceptin and $LH_N/A$

Materials

C-terminally extended nociceptin peptide obtained from Sigma Genosys. Conjugation chemicals obtained from Pierce.

Methods

In order to couple the nociceptin peptide via a C-terminal Cys, the peptide was first synthesised (by standard procedures, commercially obtainable) to include a Cys as the final C-terminal amino acid.

This peptide was then used as the second component in a sulphydryl based coupling reaction as described below (see also previous publications WO 99/17806 and WO 96/33273 and Duggan et al., (2002), J. Biol. Chem. 277, 24846-34852 and Chaddock et al., (2000), Infect Immun., 68, 2587-2593).

Sulphydryl Based Coupling Reaction

Briefly, approximately two reactive leaving groups were introduced into $LH_N/A$ (5 mg/ml in phosphate-buffered saline) by reaction with N-succinimidyl-3-(2-pyridyldithio) propionate (SPDP).

Derivatised material was isolated from excess SPDP by size exclusion chromatography. Reconstituted cysteine-tagged nociceptin ligand was mixed with the derivatised $LH_N/A$ in a 4:1 molar ratio, and incubated at room temperature for 1 hour with gentle agitation in order to create a chemical conjugate through a reducible covalent disulphide bond. Initial fractionation of the conjugate mixture to remove unconjugated peptide was performed by size exclusion chromatography (Superose-12, or Superdex G-200 depending on scale of conjugation).

Example 6

Production of a Chemical Conjugate of Nociceptin and $LH_N/B$

Materials

C-terminally extended nociceptin peptide obtained from Sigma Genosys. Conjugation chemicals obtained from Pierce.

Methods

Lyophilised nociceptin was dissolved by the addition of water and dialysed into MES buffer (0.1 M MES, 0.1 M NaCl, pH 5.0). To this solution (at a concentration of about 0.3 mg/ml) was added PDPH (100 mg/ml in DMF) to a final concentration of 1 mg/ml. After mixing, solid EDAC was added to produce a final concentration of about 0.2 mg/ml. The reaction was allowed to proceed for at least 30 minutes at room temperature. Excess PDPH was then removed by desalting over a PD-10 column (Pharmacia) previously equilibrated with MES buffer.

An amount of $LH_N/B$ equivalent to half the weight of nociceptin used dissolved in triethanolamine buffer (0.02 M triethanolamine/HCl, 0.1 M sodium chloride, pH 7.8) at a concentration of about 1 mg/ml, was reacted with Traut's reagent (100 mM stock solution in 1 M triethanolamine/HCl, pH 8.0) at a final concentration of 2 mM. After 1 hour, the $LH_N/B$ was desalted into PBSE (phosphate buffered saline with 1 mM EDTA) using a PD-10 column (Pharmacia). The protein peak from the column eluate was concentrated using a Microcon 50 (Amicon) to a concentration of about 2 mg/ml.

The derivatised nociceptin was subjected to a final concentration step resulting in a reduction in volume to less than 10% of the starting volume and then mixed with the derivatised $LH_N/B$ overnight at room temperature. The products of the reaction were analysed by polyacrylamide gel electrophoresis in the presence of sodium dodecyl-sulphate (SDS-PAGE).

The conjugate resulting from the above reaction was partially purified by size exclusion chromatography over Bio-Gel P-100 (BioRad). The elution profile was followed by measuring the optical density at 280 nm and SDS-PAGE analysis of the fractions. This allowed the separation of conjugate from free nociceptin and by-products of the reaction.

Example 7

Production of a Chemical Conjugate of Nociceptin 1-11 and $LH_N/B$

Materials

C-terminally extended nociceptin 1-11 peptide obtained from Sigma Genosys. Conjugation chemicals obtained from Pierce.

Methods

In order to couple the nociceptin 1-11 peptide via a C-terminal Cys, the peptide was first synthesised (by standard procedures, commercially obtainable) to include a Cys as the final C-terminal amino acid.

This peptide was then used as the second component in a sulphydryl based coupling reaction as described in Example 5.

Example 8

Production of a Chemical Conjugate of Nociceptin N[[Y14]1-17] and $LH_N/C$

Materials

C-terminally extended nociceptin N[[Y14]1-17] peptide obtained from Sigma Genosys.

Conjugation chemicals obtained from Pierce.

Methods

In order to couple the peptide via a C-terminal Cys, the peptide was first synthesised (by standard procedures, commercially obtainable) to include a Cys as the final C-terminal amino acid.

This peptide was then used as the second component in a sulphydryl based coupling reaction as described in Example 5.

Example 9

Recombinant Production of a Single Polypeptide Fusion of Nociceptin-$LH_N/A$ (SEQ ID NO:15 and SEQ ID NO:16)

The DNA sequence for the nociceptin-$LH_N/A$ was designed by back translation of the LC/A, $H_N/A$, and nociceptin amino acid sequences. The complete ORF containing the nociceptin-LC/A-activation loop-$H_N/A$ sequence was assembled within standard DNA sequence manipulation software (EditSeq). The activation loop between the LC/A cysteine and the $H_N/A$ cysteine (CVRGIITSKTKSLDKGYNKALNDLC; SEQ ID NO:117) was modified to incorporate a Factor Xa protease recognition site.

Restriction sites appropriate to facilitate cloning into the required expression vector (for example BamHIH/SalI) were incorporated at the 5' and 3' ends is respectively of the sequence maintaining the correct reading frame. The DNA sequence was screened (using software such as MapDraw, DNASTAR Inc.) for restriction enzyme cleavage sequences incorporated during the back translation. Any cleavage sequences that were found to be common to those required by the cloning system were removed manually from the proposed coding sequence ensuring common *E. coli* codon usage was maintained. *E. coli* codon usage was assessed by reference to software programs such as Graphical Codon Usage Analyser (Geneart), and the % GC content and codon usage ratio assessed by reference to published codon usage tables (for example GenBank Release 143, 13 Sep. 2004).

This optimised DNA sequence containing the nociceptin-LC/A-activation loop-$H_N/A$ open reading frame (ORF) was then commercially synthesized and provided in the pCR 4 vector.

The DNA encoding the nociceptin-$LH_N/A$ fusion was isolated from pCR 4 and transferred into pMAL vector backbone to facilitate protein expression. The resultant pMAL NO-LHN/A vector was transformed into competent *E. coli* BL21 and correct transformants selected. A single colony of pMAL NO-$LH_N/A$ was grown in Terrific broth complex medium supplemented with $ZnCl_2$ (1 mM), ampicillin (100 μg/ml), 0.2% (w/v) glucose. Expression of the insert was induced by the addition of IPTG (0.1 mM) and the culture maintained at 16° C. for 16 hours. After this period of expression the bacteria were isolated by centrifugation and the cell pellet stored at −20° C. until use.

10 g of *E. coli* BL21 cell paste was defrosted in a falcon tube containing 25 ml 50 mM HEPES, pH 7.2, 200 mM NaCl. The thawed cell paste was made up to 80 ml with 50 mM HEPES, pH 7.2, 200 mM NaCl and sonicated on ice 30 seconds on, 30 seconds off for 10 cycles at a power of 22 microns ensuring the sample remained cool. The lysed cells were centrifuged at 18 000 rpm, 4° C. for 30 minutes. The supernatant was loaded onto a 0.1 M $NiSO_4$ charged chelating column (20-30 ml column is sufficient) and equilibrated with 50 mM HEPES, pH 7.2, 200 mM NaCl.

Using a step gradient of 10 and 40 mM imidazol, the non-specific bound protein was washed away and the fusion protein eluted with 100 mM imidazol. The eluted fusion protein was dialysed against 5 L of 50 mM HEPES, pH 7.2, 200 mM NaCl at 4° C. overnight and the OD of the dialysed fusion protein measured. 1 unit of Factor Xa was added per 100 μg fusion protein and incubated at 25° C. static overnight.

The cleavage mixture was loaded onto a 0.1 M $NiSO_4$ charged Chelating column (20-30 ml column is sufficient) and equilibrated with 50 mM HEPES, pH 7.2, 200 mM NaCl.

Using a step gradient of 10 and 40 mM imidazol, the non-specific bound protein was washed away and the fusion protein eluted with 100 mM imidazol. The eluted fusion protein was dialysed against 5 L of 50 mM HEPES, pH 7.2, 200 mM NaCl at 4° C. overnight and the fusion concentrated to about 2 mg/ml, aliquoted and stored at −20° C.

Figure 3:
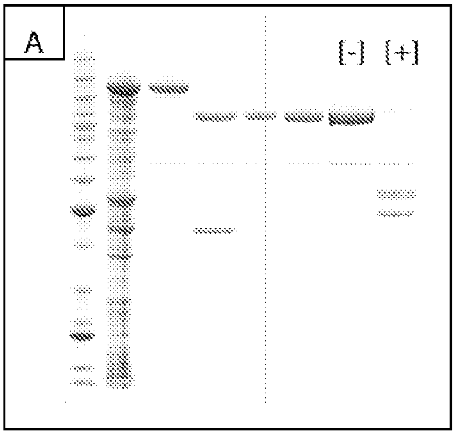
FIG. 3-E*xpression* and Purification of N[1-17]-LH$_N$/A Fusion Protein
Figure 3:
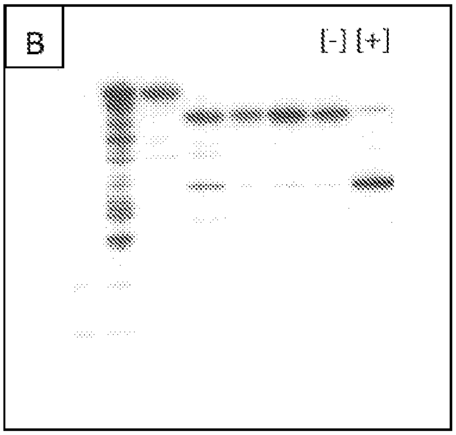
Figure 4:
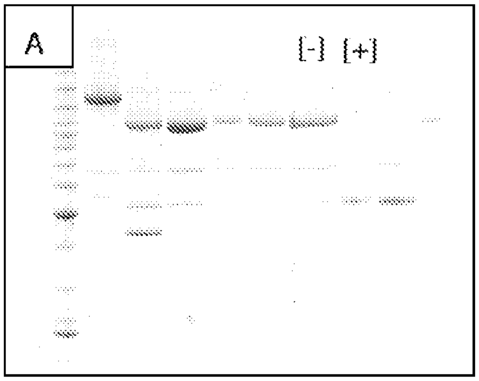
FIG. 4-P*urification* of a LC/A-Nociceptin-H$_N$/A Fusion Protein
Figure 4:
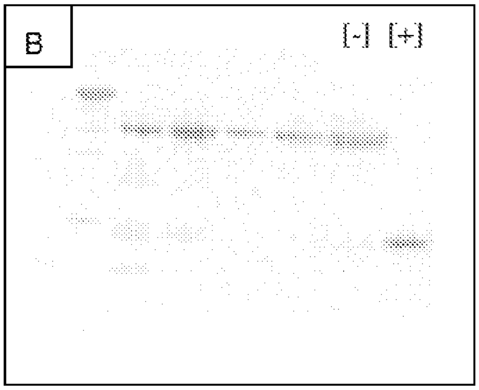

FIG. 3 shows the SDS-PAGE analysis of expression and purification of N[1-17]-$LH_N$/A.

Example 10

Recombinant Production of a Single Polypeptide Fusion of (Nociceptin 1-11)-$LH_N$/B The DNA sequence for the (nociceptin 1-11)-$LH_N$/B was designed by back translation of the LC/B, $H_N$/B, and nociceptin 1-11 amino acid sequences. The complete ORF containing the (nociceptin1-11)-LC/B-activation loop-$H_N$/B sequence was assembled within standard DNA sequence manipulation software (EditSeq). The activation loop between the LC/B cysteine and the $H_N$/B cysteine was modified to incorporate a Factor Xa protease recognition site.

The recombinant fusion protein was then produced essentially as described in Example 9.

Example 11

Recombinant Production of a Single Polypeptide Fusion of (Nociceptin N[[Y14]1-17])-$LH_N$/C (SEQ ID NO:25 and SEQ ID NO:26)

The DNA sequence for the nociceptin N[[Y14]1-17] was designed by back translation of the LC/C, $H_N$/C, and nociceptin N[[Y14]1-17] amino acid sequences. The complete ORF containing the (nociceptin N[[Y14]1-17])-LC/C-activation loop-$H_N$/C sequence was assembled within standard DNA sequence manipulation software (EditSeq). The activation loop between the LC/C cysteine and the $H_N$/C cysteine was modified to incorporate a Factor Xa protease recognition site.

The recombinant fusion protein was then produced essentially as described in Example 9.

Example 12

Recombinant Production of a Single Polypeptide Fusion of $LH_N$/C-(nociceptin 1-11) (SEQ ID NO:23 and SEQ ID NO:24)

The DNA sequence for the $LH_N$/C-(nociceptin 1-11) was designed by back translation of the LC/C, $H_N$/C and nociceptin 1-11 amino acid sequences. The complete ORF (SEQ ID NO:23) containing the LC/C-activation loop-$H_N$/C-flexible spacer-(nociceptin 1-11) was assembled within standard DNA sequence manipulation software (EditSeq).

The recombinant fusion protein (SEQ ID NO:24) was then produced essentially as described in Example 9.

Example 13

Production of a Conjugate for Delivery of DNA Encoding LC/C into a Cell

The construction of a nociceptin-$H_N$-[LC/C] conjugate is described below, where [LC/C] represents the polylysine condensed DNA encoding the light chain of botulinum neurotoxin type C.

Materials

SPDP is from Pierce Chemical Co.

Additional reagents are obtained from Sigma Ltd.

Methods

Using a plasmid containing the gene encoding LC/C under the control of a CMV (immediate early) promoter, condensation of DNA was achieved using SPDP-derivatised polylysine to a ratio of 2 DNA to 1 polylysine. Conjugates were then prepared by mixing condensed DNA (0.4 mg/ml) with $H_N$-nociceptin (100 µg/ml) for 16 h at 25° C. The SPDP-derivatised polylysine and the free —SH group present on the $H_N$ domain combine to facilitate covalent attachment of the DNA and protein.

Example 14

Production of a Conjugate for Delivery of DNA Encoding LC/B into a Cell

The construction of a (nociceptin 1-11)-$H_N$-[LC/B] conjugate is described below, where [LC/B] represents the polylysine condensed DNA encoding the light chain of botulinum neurotoxin type B.

Materials

SPDP is from Pierce Chemical Co.

Additional reagents are obtained from Sigma Ltd.

Methods

Using a plasmid containing the gene encoding LC/B under the control of a CMV (immediate early) promoter, condensation of DNA was achieved using SPDP-derivatised polylysine to a ratio of 2 DNA to 1 polylysine. Conjugates were then prepared by mixing condensed DNA (0.4 mg/ml) with $H_N$-(nociceptin 1-11) (100 µg/ml) for 16 h at 25° C. The SPDP-derivatised polylysine and the free —SH group present on the $H_N$ domain combine to facilitate covalent attachment of the DNA and protein.

Example 15

Assessment of the Activity of Nociceptin-$LH_N$/A in Substance P Releasing Neuronal Cells Using methodology described in Duggan et al., (2002, J. Biol. Chem., 277, 34846-34852), the activity of nociceptin-$LH_N$/A in substance P releasing neuronal cells was assessed.

Nociceptin-$LH_N$/A fusion protein was applied to 2-week old dorsal root ganglia neuronal cultures, and incubated at 37° C. for 16 hours. Following the incubation, the media was removed and the ability of the cells to undergo stimulated release of substance P(SP) was assessed.

The release of SP from the neuronal cells incubated with the nociceptin-$LH_N$/A fusion protein was assayed in comparison to (i) $LH_N$/A-only treated cells and (ii) cells treated with media alone. This allowed the % inhibition of substance P from the eDRG to be calculated. The ability of the nociceptin-$LH_N$/A fusion protein to inhibit SP release (relative to cells treated with media alone) was reported in Table 1. The data represent the mean of 3 determinations:

TABLE 1

| Test Material (µM) | nociceptin-$LH_N$/A fusion protein % Inhibition | $LH_N$/A-only % Inhibition |
|---|---|---|
| 1.0 | 47.3 | 25.6 |
| 0.1 | 13.8 | −11.5 |

Example 16

Confirmation of $ORL_1$ Receptor Activation by Measuring Forskolin-Stimulated cAMP Production Confirmation that a given TM is acting via the $ORL_1$ receptor is provided by the following test, in which the TMs ability to inhibit forskolin-stimulated cAMP production is assessed.

Materials

[$^3$H]adenine and [$^{14}$C]cAMP are obtained from GE Healthcare

Methods

The test is conducted essentially as described previously by Meunier et al. [Isolation and structure of the endogenous agonist of opioid receptor-like $ORL_1$ receptor. Nature 377: 532-535, 1995] in intact transfected-CHO cells plated on 24-well plastic plates.

To the cells is added [3H]adenine (1.0 μCi) in 0.4 ml of culture medium. The cells remain at 37° C. for 2 h to allow the adenine to incorporate into the intracellular ATP pool. After 2 h, the cells are washed once with incubation buffer containing: 130 mM NaCl, 4.8 mM KCl, 1.2 mM $KH_2PO_4$, 1.3 mM $CaCl_2$, 1.2 mM $MgSO_4$, 10 mM glucose, 1 mg/ml bovine serum albumin and 25 mM HEPES, pH 7.4, and replaced with buffer containing forskolin (10 μM) and isobutylmethylxanthine (50 μM) with or without the TM of interest. After 10 min., the medium is aspirated and replaced with 0.5 ml, 0.2 M HCl. Approximately 1000 cpm of [$^{14}$C]cAMP is added to each well and used as an internal standard. The contents of the wells are then transferred to columns of 0.65 g dry alumina powder. The columns are eluted with 4 ml of 5 mM HCl, 0.5 ml of 0.1 M ammonium acetate, then two additional milliliters of ammonium acetate. The final eluate is collected into scintillation vials is and counted for $^{14}$C and tritium. Amounts collected are corrected for recovery of [$^{14}$C]cAMP. TMs that are agonists at the $ORL_1$ receptor cause a reduction in the level of cAMP produced in response to forskolin.

Example 17

Confirmation of $ORL_1$ Receptor Activation using a GTPγS Binding Functional Assay Confirmation that a given TM is acting via the $ORL_1$ receptor is also provided by the following test, a GTPγS binding functional assay.

Materials

[$^{35}$S]GTPγS is obtained from GE Healthcare

Wheatgerm agglutinin-coated (SPA) beads are obtained from GE Healthcare

Methods

This assay is carried out essentially as described by Traynor and Nahorski [Modulation by μ-opioid agonists of guanosine-5-O-(3-[$^{35}$S]thio)triphosphate binding to membranes from human neuroblastoma SH-SY5Y cells. Mol. Pharmacol. 47: 848-854, 1995].

Cells are scraped from tissue culture dishes into 20 mM HEPES, 1 mM ethylenediaminetetraacetic acid, then centrifuged at 500×g for 10 min. Cells are resuspended in this buffer and homogenized with a Polytron Homogenizer.

The homogenate is centrifuged at 27,000×g for 15 min., and the pellet resuspended in buffer A, containing: 20 mM HEPES, 10 mM $MgCl_2$, 100 mM NaCl, pH 7.4. The suspension is recentrifuged at 20,000×g and suspended once more in buffer A. For the binding assay, membranes (8-15 μg protein) are incubated with [$^{35}$S]GTP S (50 μM), GDP (10 μM), with and without the TM of interest, in a total volume of 1.0 ml, for 60 min. at 25° C. Samples are filtered over glass fibre filters and counted as described for the binding assays.

Example 18

Preparation of a LC/A and $H_N$/A Backbone Clones

The following procedure creates the LC and $H_N$ fragments for use as the component backbone for multidomain fusion expression. This example is based on preparation of a serotype A based clone (SEQ ID NO:27 and SEQ ID NO:28), though the procedures and methods are equally applicable to the other serotypes [illustrated by the sequence listing for serotype B (SEQ ID NO:29 and SEQ ID NO:30) and serotype C (SEQ ID NO:31 and SEQ ID NO:32)].

Preparation of Cloning and Expression Vectors pCR 4 (Invitrogen) is the chosen standard cloning vector, selected due to the lack of restriction sequences within the vector and adjacent sequencing primer sites for easy construct confirmation. The expression vector is based on the pMAL (NEB) expression vector, which has the desired restriction sequences within the multiple cloning site in the correct orientation for construct insertion (BamHI-SalI-PstI-HindIII). A fragment of the expression vector has been removed to create a non-mobilisable plasmid and a variety of different fusion tags have been inserted to increase purification options.

Preparation of Protease (e.g. LC/A) Insert

The LC/A (SEQ ID NO:27) is created by one of two ways:

The DNA sequence is designed by back translation of the LC/A amino acid sequence [obtained from freely available database sources such as GenBank (accession number P10845) or Swissprot (accession locus BXA1_CLOBO) using one of a variety of reverse translation software tools (for example EditSeq best E. coli reverse translation (DNASTAR Inc.), or Backtranslation tool v2.0 (Entelechon)]. BamHI/SalI recognition sequences are incorporated at the 5' and 3' ends respectively of the sequence, maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the LC/A open reading frame (ORF) is then commercially synthesized (for example by Entelechon, Geneart or Sigma-Genosys) and is provided in the pCR 4 vector.

The alternative method is to use PCR amplification from an existing DNA sequence with BamHI and SalI restriction enzyme sequences incorporated into the 5' and 3' PCR primers respectively. Complementary oligonucleotide primers are chemically synthesised by a supplier (for example MWG or Sigma-Genosys), so that each pair has the ability to hybridize to the opposite strands (3' ends pointing "towards" each other) flanking the stretch of *Clostridium* target DNA, one oligonucleotide for each of the two DNA strands. To generate a PCR product the pair of short oligonucleotide primers specific for the *Clostridium* DNA sequence are mixed with the *Clostridium* DNA template and other reaction components and placed in a machine (the 'PCR machine') that can change the incubation temperature of the reaction tube automatically, cycling between approximately 94° C. (for denaturation), 55° C. (for oligonucleotide annealing), and 72° C. (for synthesis). Other reagents required for amplification of a PCR product include a DNA polymerase (such as Taq or Pfu polymerase), each of the four nucleotide dNTP building blocks of DNA in equimolar amounts (50-200 μM) and a buffer appropriate for the enzyme optimised for $Mg^{2+}$ concentration (0.5-5 mM).

The amplification product is cloned into pCR 4 using either, TOPO TA cloning for Taq PCR products or Zero Blunt TOPO cloning for Pfu PCR products (both kits commercially available from Invitrogen). The resultant clone is checked by sequencing. Any additional restriction sequences which are not compatible with is the cloning system are then removed using site directed mutagenesis [for example, using Quickchange (Stratagene Inc.)].

Preparation of Translocation (e.g. $H_N$) Insert

The $H_N$/A (SEQ ID NO:28) is created by one of two ways:

The DNA sequence is designed by back translation of the $H_N$/A amino acid sequence [obtained from freely available database sources such as GenBank (accession number P10845) or Swissprot (accession locus BXA1_CLOBO)] using one of a variety of reverse translation software tools [for example EditSeq best *E. coli* reverse translation (DNASTAR Inc.), or Backtranslation tool v2.0 (Entelechon)]. A PstI restriction sequence added to the N-terminus and XbaI-stop codon-HindIII to the C-terminus ensuring the correct reading frame is maintained. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector.

The alternative method is to use PCR amplification from an existing DNA sequence with PstI and XbaI-stop codon-HindIII restriction enzyme sequences incorporated into the 5' and 3' PCR primers respectively. The PCR amplification is performed as described above. The PCR product is inserted into pCR 4 vector and checked by sequencing. Any additional restriction sequences which are not compatible with the cloning system are then removed using site directed mutagenesis [for example using Quickchange (Stratagene Inc.)].

Example 19

Preparation of a LC/A-Nociceptin-$H_N$/A Fusion Protein (Nociceptin is N-Terminal of the $H_N$-Chain)

Preparation of Linker-Nociceptin-Spacer Insert

The LC-$H_N$ linker can be designed from first principle, using the existing sequence information for the linker as the template. For example, the serotype A linker (in this case defined as the inter-domain polypeptide region that exists between the cysteines of the disulphide bridge between LC and $H_N$) is 23 amino acids long and has the sequence VRGIITSKTKSLDKGYNKALNDL (amino acids 2-24 of SEQ ID NO:117). Within this sequence, it is understood that proteolytic activation in nature leads to an $H_N$ domain that has an N-terminus of the sequence ALNDL. This sequence information is freely available from available database sources such as GenBank (accession number P10845) or Swissprot (accession locus BXA1_CLOBO). Into this linker a Factor Xa site, nociceptin and spacer are incorporated; and using one of a variety of reverse translation software tools [for example EditSeq best *E. coli* reverse translation (DNASTAR Inc.), or Backtranslation tool v2.0 (Entelechon)], the DNA sequence encoding the linker-ligand-spacer region is determined. Restriction sites are then incorporated into the DNA sequence and can be arranged as BamHI-SalI-linker-protease site-nociceptin-NheI-spacer-SpeI-PstI-XbaI-stop codon-HindIII (SEQ ID NO:33). It is important to ensure the correct reading frame is maintained for the spacer, nociceptin and restriction sequences and that the XbaI sequence is not preceded by the bases, TC, which would result on DAM methylation. The DNA sequence is screened for restriction sequence incorporation, and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example, GenBank Release 143, 13 Sep. 2004). This optimised DNA sequence is then commercially synthesized (for example by Entelechon, Geneart or Sigma-Genosys) and is provided in the pCR 4 vector.

Preparation of the LC/A-Nociceptin-$H_N$/A Fusion

In order to create the LC-linker-nociceptin-spacer-$H_N$ construct (SEQ ID NO:39), the pCR 4 vector encoding the linker (SEQ ID NO:33) is cleaved with BamHI+SalI restriction enzymes. This cleaved vector then serves as the recipient vector for insertion and ligation of the LC/A DNA (SEQ ID NO:27) cleaved with BamHI+SalI. The resulting plasmid DNA is then cleaved with PstI+XbaI restriction enzymes and serves as the recipient vector for the insertion and ligation of the $H_N$/A DNA (SEQ ID NO:28) cleaved with PstI+XbaI. The final construct contains the LC-linker-nociceptin-spacer-$H_N$ ORF (SEQ ID NO:39) for transfer into expression vectors for expression to result in a fusion protein of the sequence illustrated in SEQ ID NO:40.

Example 20

Preparation of a Nociceptin-LC/A-$H_N$/A Fusion Protein (Nociceptin is N-Terminal of the LC-Chain)

The LC/A-$H_N$/A backbone is constructed as described in Example 19 using the synthesised A serotype linker with the addition of a Factor Xa site for activation, arranged as BamHI-Sail-linker-protease site-linker-PstI-XbaI-stop codon-HindIII (SEQ ID NO:34). The LC/A-$H_N$/A backbone and the synthesised N-terminal presentation nociceptin insert (SEQ ID NO:35) are cleaved with BamHI+HindIII restriction enzymes, gel purified and ligated together to create a nociceptin-spacer-LC-linker-$H_N$. The ORF (SEQ ID NO:41) is then cut out using restriction enzymes AvaI+XbaI for transfer into expression vectors for expression to result in a fusion protein of the sequence illustrated in SEQ ID NO:42.

Example 21

Preparation of a LC/C-Nociceptin-$H_N$/C Fusion Protein

Following the methods used in Examples 1 and 2, the LC/C (SEQ ID NO:31) and $H_N$/C (SEQ ID NO:32) are created and inserted into the C serotype linker arranged as BamHI-Sail-linker-protease site-nociceptin-NheI-spacer-SpeI-PstI-XbaIstop codon-HindIII (SEQ ID NO:36). The final construct contains the LC-linker-nociceptin-spacer-$H_N$ ORF (SEQ ID NO:43) for expression as a protein of the sequence illustrated in SEQ ID NO:44.

Example 22

Preparation of a LC/C-Nociceptin-$H_N$/C Fusion Protein with a Serotype A Activation Sequence Following the methods used in Examples 1 and 2, the LC/C (SEQ ID NO:31) and $H_N$/C (SEQ ID NO:32) are created and inserted into the A serotype linker arranged as BamHI-Sail-linker-protease site-nociceptin-NheI-spacer-SpeI-PstI-XbaI-stop codon-HindIII (SEQ ID NO:33). The final construct contains the LC-linker-nociceptin-spacer-$H_N$ ORF (SEQ ID NO:45) for expression as a protein of the sequence illustrated in SEQ ID NO:46.

Example 23

Preparation of a LC/A-Met Enkephalin-$H_N$/A Fusion Protein

Due to the small, five-amino acid, size of the met-enkephalin ligand the LC/A-met enkephalin-$H_N$/A fusion is created by site directed mutagenesis [for example using Quickchange (Stratagene Inc.)] using the LC/A-nociceptin-$H_N$/A fusion (SEQ ID NO:39) as a template. Oligonucleotides are designed encoding the YGGFM met-enkephalin peptide (SEQ ID NO:118), ensuring standard *E. coli* codon usage is maintained and no additional restriction sites are incorporated, flanked by sequences complimentary to the linker region of the LC/A-nociceptin-$H_N$/A fusion (SEQ ID NO:39) either side on the nociceptin section. The SDM product is checked by sequencing and the final construct containing the LC-linker-met enkephalin-spacer-$H_N$ ORF (SEQ ID NO:47) for expression as a protein of the sequence illustrated in SEQ ID NO:48.

Example 24

Preparation of a LC/A-6 Endorphin-$H_N$/A Fusion Protein

Following the methods used in Examples 1 and 2, the LC/A (SEQ ID NO:27) and $H_N$/A (SEQ ID NO:28) are created and inserted into the A serotype β endorphin linker arranged as BamHI-Sail-linker-protease site-β endorphin-NheI-spacer-SpeI-PstI-XbaI-stop codon-HindIII (SEQ ID NO:37). The final construct contains the LC-linker-β endorphin-spacer-$H_N$ ORF (SEQ ID NO:49) for expression as a protein of the sequence illustrated in SEQ ID NO:50.

Example 25

Preparation of a LC/A-Nociceptin Variant-$H_N$/A Fusion Protein

Following the methods used in Examples 1 and 2, the LC/A (SEQ ID NO:27) and $H_N$/A (SEQ ID NO:28) are created and inserted into the A serotype nociceptin variant linker arranged as BamHI-Sail-linker-protease site-nociceptin variant-NheI-spacer-SpeI-PstI-XbaI-stop codon-HindIII (SEQ ID NO:38). The final construct contains the LC-linker-nociceptin variant-spacer-$H_N$ ORF (SEQ ID NO:51) for expression as a protein of the sequence illustrated in SEQ ID NO:52.

Example 26

Purification Method for LC/A-Nociceptin-$H_N$/A Fusion Protein

Defrost falcon tube containing 25 ml 50 mM HEPES pH 7.2, 200 mM NaCl and approximately 10 g of *E. coli* BL21 cell paste. Make the thawed cell paste up to 80 ml with 50 mM HEPES pH 7.2, 200 mM NaCl and sonicate on ice 30 seconds on, 30 seconds off for 10 cycles at a power of 22 microns ensuring the sample remains cool. Spin the lysed cells at 18 000 rpm, 4° C. for 30 minutes. Load the supernatant onto a 0.1 M $NiSO_4$ charged Chelating column (20-30 ml column is sufficient) equilibrated with 50 mM HEPES pH 7.2, 200 mM NaCl. Using a step gradient of 10 and 40 mM imidazol, wash away the non-specific bound protein and elute the fusion protein with 100 mM imidazol. Dialyse the eluted fusion protein against 5 L of 50 mM HEPES pH 7.2, 200 mM NaCl at 4° C. overnight and measure the OD of the dialysed fusion protein. Add 1 unit of factor Xa per 100 μg fusion protein and Incubate at 25° C. static overnight. Load onto a 0.1 M $NiSO_4$ charged Chelating column (20-30 ml column is sufficient) equilibrated with 50 mM HEPES pH 7.2, 200 mM NaCl. Wash column to baseline with 50 mM HEPES pH 7.2, 200 mM NaCl. Using a step gradient of 10 and 40 mM imidazol, wash away the non-specific bound protein and elute the fusion protein with 100 mM imidazol. Dialyse the eluted fusion protein against 5 L of 50 mM HEPES pH 7.2, 200 mM NaCl at 4° C. overnight and concentrate the fusion to about 2 mg/ml, aliquot sample and freeze at −20° C. Test purified protein using OD, BCA, purity analysis and SNAP-25 assessments.

Example 27

Preparation of a LC/A-Nociceptin-$H_N$/A Fusion Protein (Nociceptin is N-Terminal of the $H_N$-Chain)

The linker-nociceptin-spacer insert is prepared as described in Example 19.

Preparation of the LC/A-Nociceptin-$H_N$/A Fusion

In order to create the LC-linker-nociceptin-spacer-$H_N$ construct (SEQ ID NO:39), the pCR 4 vector encoding the linker (SEQ ID NO:33) is cleaved with BamHI+SalI restriction enzymes. This cleaved vector then serves as the recipient for insertion and ligation of the LC/A DNA (SEQ ID NO:27) also cleaved with BamHI+SalI. The resulting plasmid DNA is then cleaved with BamHI+HindIII restriction enzymes and the LC/A-linker fragment inserted into a similarly cleaved vector containing a unique multiple cloning site for BamHI, SalI, PstI, and HindIII such as the pMAL vector (NEB). The $H_N$/A DNA (SEQ ID NO:28) is then cleaved with PstI+HindIII restriction enzymes and inserted into the similarly cleaved pMAL-LC/A-linker construct. The final construct contains the LC-linker-nociceptin-spacer-$H_N$ ORF (SEQ ID NO:39) for expression as a protein of the sequence illustrated in SEQ ID NO:40.

Example 28

Preparation of a Nociceptin-LC/A-$H_N$/A Fusion Protein (Nociceptin is N-Terminal of the LC-Chain)

In order to create the nociceptin-spacer-LC/A-$H_N$/A construct, an A serotype linker with the addition of a Factor Xa site for activation, arranged as BamHI-Sail-linker-protease site-linker-PstI-XbaI-stop codon-HindIII (SEQ ID NO:34) is synthesised as described in Example 27. The pCR 4 vector encoding the linker is cleaved with BamHI+SalI restriction enzymes. This cleaved vector then serves as the recipient for insertion and ligation of the LC/A DNA (SEQ ID NO:27) also cleaved with BamHI+SalI. The resulting plasmid DNA is then cleaved with BamHI+HindIII restriction enzymes and the LC/A-linker fragment inserted into a similarly cleaved vector containing the synthesised N-terminal presentation nociceptin insert (SEQ ID NO:35). This construct is then cleaved with AvaI+HindIII and inserted into an expression vector such as the pMAL plasmid (NEB). The $H_N$/A DNA (SEQ ID NO:28) is then cleaved with PstI+HindIII restriction enzymes and inserted into the similarly cleaved pMAL-nociceptin-LC/A-linker construct. The final construct contains the nociceptin-spacer-LC/A-$H_N$/A ORF (SEQ ID NO:63) for expression as a protein of the sequence illustrated in SEQ ID NO:64.

Example 29

Preparation and Purification of an LC/A-Nociceptin-$H_N$/A Fusion Protein Family with Variable Spacer Length Using the same strategy as employed in Example 19, a range of DNA linkers were prepared that encoded nociceptin and variable spacer content. Using one of a variety of reverse translation software tools [for example EditSeq best *E. coli* reverse translation (DNASTAR Inc.), or Backtranslation tool v2.0 (Entelechon)], the DNA sequence encoding the linker-ligand-spacer region is determined. Restriction sites are then incorporated into the DNA sequence and can be arranged as BamHI-SalI-linker-protease site-nociceptin-NheI-spacer-SpeI-PstI-XbaI-stop codon-HindIII (SEQ ID NO:65 to SEQ ID NO:69). It is important to ensure the correct reading frame is maintained for the spacer, nociceptin and restriction sequences and that the XbaI sequence is not preceded by the bases, TC which would result on DAM methylation. The DNA sequence is screened for restriction sequence incorporation and any additional sequences are removed is manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector.

The spacers that were created included:

TABLE 2

| Code | Protein sequence of the linker | SEQ ID NO: of the linker DNA |
|---|---|---|
| GS10 | ALAGGGGSALVLQ | 119 |
| GS15 | ALAGGGGSGGGGSALVLQ | 120 |
| GS25 | ALAGGGGSGGGGSGGGGSGGGGSALVLQ | 121 |
| GS30 | ALAGGGGSGGGGSGGGGSGGGGSGGGGSALVLQ | 122 |
| HX27 | ALAAEAAAKEAAAKEAAAKAGGGGSALVLQ | 123 |

By way of example, in order to create the LC/A-CPN (GS15)-$H_N$/A fusion construct (SEQ ID NO:70), the pCR 4 vector encoding the linker (SEQ ID NO:66) is cleaved with BamHI+SalI restriction enzymes. This cleaved vector then serves as the recipient vector for insertion and ligation of the LC/A DNA (SEQ ID NO:27) also cleaved with BamHI+SalI. The resulting plasmid DNA is then cleaved with BamHI+HindIII restriction enzymes and the LC/A-linker fragment inserted into a similarly cleaved vector containing a unique multiple cloning site for BamHI, SalI, PstI, and HindIII such as the pMAL vector (NEB). The $H_N$/A DNA (SEQ ID NO:28) is then cleaved with PstI+HindIII restriction enzymes and inserted into the similarly cleaved pMAL-LC/A-linker construct. The final construct contains the LC/A-CPN(GS15)-$H_N$/A ORF (SEQ ID NO:70) for expression as a protein of the sequence illustrated in SEQ ID NO:71.

As a further example, to create the LC/A-CPN(GS25)-$H_N$/A fusion construct (SEQ ID NO:72), the pCR 4 vector encoding the linker (SEQ ID NO:67) is cleaved with BamHI+SalI restriction enzymes. This cleaved vector then serves as the recipient vector for insertion and ligation of the LC/A DNA (SEQ ID NO:27) cleaved with BamHI+SalI. The resulting plasmid DNA is then cleaved with BamHI+HindIII restriction enzymes and the LC/A-linker fragment inserted into a similarly cleaved vector containing a unique multiple cloning site for BamHI, SalI, PstI, and HindIII such as the pMAL vector (NEB). The $H_N$/A DNA (SEQ ID NO:28) is then cleaved with PstI+HindIII restriction enzymes and inserted into the similarly cleaved pMAL-LC/A-linker construct. The final construct contains the LC/A-CPN(GS25)-$H_N$/A ORF (SEQ ID NO:72) for expression as a protein of the sequence illustrated in SEQ ID NO:73.

Variants of the LC/A-CPN-$H_N$/A fusion consisting of GS10, GS30 and HX27 are similarly created. Using the purification methodology described in Example 26, fusion protein is purified from *E. coli* cell paste. FIG. 12 illustrates the purified product obtained in the case of LC/A-CPN(GS10)-$H_N$/A, LC/A-CPN(GS15)-$H_N$/A, LC/A-CPN(GS25)-$H_N$/A, LC/A-CPN(GS30)-$H_N$/A and LC/A-CPN(HX27)-$H_N$/A.

Example 30

Assessment of in Vitro Efficacy of an LC/A-Nociceptin-$H_N$/A Fusion

Fusion protein prepared according to Examples 2 and 9 was assessed in the eDRG neuronal cell model.

Assays for the inhibition of substance P release and cleavage of SNAP-25 have been previously reported (Duggan et al., 2002, *J. Biol. Chem.*, 277, 34846-34852). Briefly, dorsal root ganglia neurons are harvested from 15-day-old fetal Sprague-Dawley rats and dissociated cells plated onto 24-well plates coated with Matrigel at a density of $1\times10^6$ cells/well. One day post-plating the cells are treated with 10 μM cytosine β-D-arabinofuranoside for 48 h. Cells are maintained in Dulbecco's minimal essential medium supplemented with 5% heat-inactivated fetal bovine serum, 5 mM L-glutamine, 0.6% D-glucose, 2% B27 supplement, and 100 ng/ml 2.5S mouse nerve growth factor. Cultures are maintained for 2 weeks at 37° C. in 95% air/5% $CO_2$ before addition of test materials.

Release of substance P from eDRG is assessed by enzyme-linked immunosorbent assay. Briefly, eDRG cells are washed twice with low potassium-balanced salt solution (BSS: 5 mM KCl, 137 mM NaCl, 1.2 mM $MgCl_2$, 5 mM glucose, 0.44 mM $KH_2PO_4$, 20 mM HEPES, pH 7.4, 2 mM $CaCl_2$). Basal samples are obtained by incubating each well for 5 min. with 1 ml of low potassium BSS. After removal of this buffer, the cells are stimulated to release by incubation with 1 ml of high potassium buffer (BSS as above with modification to include 100 mM KCl isotonically balanced with NaCl) for 5 min. All samples are removed to tubes on ice prior to assay of substance P. Total cell lysates are prepared by addition of 250 μl of 2 M acetic acid/0.1% trifluoroacetic acid to lyse the cells, centrifugal evaporation, and resuspension in 500 μl of assay buffer. Diluted samples are assessed for substance P content. Substance P immunoreactivity is measured using Substance P Enzyme Immunoassay Kits (Cayman Chemical Company or R&D Systems) according to manufacturers' instructions. Substance P is expressed in pg/ml relative to a standard substance P curve run in parallel.

SDS-PAGE and Western blot analysis were performed using standard protocols (Novex). SNAP-25 proteins were resolved on a 12% Tris/glycine polyacrylamide gel (Novex) and subsequently transferred to nitrocellulose membrane. The membranes were probed with a monoclonal antibody (SMI-81) that recognises cleaved and intact SNAP-25. Specific binding was visualised using peroxidase-conjugated secondary antibodies and a chemiluminescent detection system. Cleavage of SNAP-25 was quantified by scanning densitometry (Molecular is Dynamics Personal SI, ImageQuant data analysis software). Percent SNAP-25 cleavage was calculated according to the formula: (Cleaved SNAP-25/(Cleaved+Intact SNAP-25))×100.

Following exposure of eDRG neurons to an LC/A-nociceptin-$H_N$/A fusion (termed CPN-A), both inhibition of substance P release and cleavage of SNAP-25 are observed (FIG. 13). After 24 h exposure to the fusion, 50% of maximal SNAP-25 cleavage is achieved by a fusion concentration of 6.3±2.5 nM.

The effect of the fusion is also assessed at defined time points following a 16 h exposure of eDRG to CPN-A. FIG. 14 illustrates the prolonged duration of action of the CPN-A fusion protein, with measurable activity still being observed at 28 days post exposure.

Example 31

Assessment of In Vitro Efficacy of an LC/A-Nociceptin Variant-$H_N$/A fusion Fusion protein prepared according to Examples 8 and 9 was assessed in the eDRG neuronal cell mode using the method described in Example 30.

Following exposure of eDRG neurons to an LC/A-nociceptin variant-$H_N$/A fusion (termed CPNv-A), both inhibition of substance P release and cleavage of SNAP-25 are observed. After 24 h exposure to the fusion, 50% of maximal SNAP-25 cleavage is achieved by a fusion concentration of 1.4±0.4 nM (FIG. 15).

The effect of the fusion is also assessed at defined time points following a 16 h exposure of eDRG to CPN-A. FIG. 16 illustrates the prolonged duration of action of the CPN-A fusion protein, with measurable activity still being observed at 24 days post exposure.

The binding capability of the CPNv-A fusion protein is also assessed in comparison to the CPN-A fusion. FIG. 17 illustrates the results of a competition experiment to determine binding efficacy at the ORL-1 receptor. CPNv-A is demonstrated to displace [3H]-nociceptin, thereby confirming that access to the receptor is possible with the ligand in the central presentation format.

Example 32

Preparation of an LC/A-Nociceptin Variant-$H_N$/A Fusion Protein that is Activated by Treatment with Enterokinase Following the methods used in Examples 1 and 2, the LC/A (SEQ ID NO:27) and $H_N$/A (SEQ ID NO:28) are created and inserted into the A serotype nociceptin variant linker arranged as BamHI-SalI-linker-enterokinase protease site-nociceptin variant-NheI-spacer-SpeI-PstI-XbaI-stop codon-HindIII (SEQ ID NO:74). The final construct contains the LC-linker-nociceptin variant-spacer-$H_N$ ORF sequences (SEQ ID NO:75) for expression as a protein of the sequence illustrated in SEQ ID NO:76. The fusion protein is termed CPNv(Ek)-A. FIG. 18 illustrates the purification of CPNv(Ek)-A from *E. coli* following the methods used in Example 26 but using Enterokinase for activation at 0.00064 μg per 100 μg of fusion protein.

Example 33

Assessment of In Vitro Efficacy of an LC/A-Nociceptin Variant-$H_N$/A Fusion that has been Activated by Treatment with Enterokinase The CPNv(Ek)-A prepared in Example 32 is obtained in a purified form and applied to the eDRG cell model to assess cleavage of SNAP-25 (using methodology from Example 30). FIG. 19 illustrates the cleavage of SNAP-25 following 24 h exposure of eDRG to CPNv(Ek)-A. The efficiency of cleavage is to observed to be similar to that achieved with the Factor Xa-cleaved material, as recorded in Example 31.

Example 34

Preparation of an LC/C-Nociceptin Variant-$H_N$/C Fusion Protein with a Factor Xa Activation Linker Derived from Serotype A Following the methods used in Example 21, the LC/C (SEQ ID NO:31) and $H_N$/C (SEQ ID NO:32) are created and inserted into the A serotype nociceptin variant linker arranged as BamHI-SalI-linker-nociceptin variant-NheI-spacer-SpeI-PstI-XbaI-stop codon-HindIII (SEQ ID NO:77). The final construct contains the LC-linker-nociceptin variant-spacer-$H_N$ ORF sequences (SEQ ID NO:78) for expression as a protein of the sequence illustrated in SEQ ID NO:79. The fusion protein is termed CPNv-C (act. A). FIG. 20 illustrates the purification of CPNv-C (act. A) from *E. coli* following the methods used in Example 26.

Example 35

Assessment of In Vitro Efficacy of an LC/C-Nociceptin Variant-$H_N$/C Fusion Protein Following the methods used in Example 26, the CPNv-C (act. A) prepared in Example 34 is obtained in a purified form and applied to the eDRG cell model to assess cleavage of SNAP-25 (using methodology from Example 30). After 24 h exposure to the fusion, 50% of maximal syntaxin cleavage is achieved by a fusion concentration of 3.1±2.0 nM. FIG. 21 illustrates the cleavage of syntaxin following 24 h exposure of eDRG to CPNv-C (act. A).

Example 36

Assessment of In Vivo Efficacy of an LC/A-Nociceptin-HN/A Fusion

The ability of an LC/A-nociceptin-$H_N$/A fusion (CPN/A) to inhibit acute capsaicin-induced mechanical allodynia is evaluated following subcutaneous intraplantar injection in the rat hind paw. Test animals are evaluated for paw withdrawal frequency (PWF %) in response to a 10 g Von Frey filament stimulus series (10 stimuli×3 trials) prior to recruitment into the study, after subcutaneous treatment with CPN/A but before capsaicin, and following capsaicin challenge post-injection of CPN/A (average of responses at 15' and 30'). Capsaicin challenge is achieved by injection of 10 μL of a 0.3% solution. Sample dilutions are prepared in 0.5% BSA/saline. FIG. 22 illustrates the reversal of mechanical allodynia that is achieved by pre-treatment of the animals with a range of concentrations of LC/A-nociceptin-H N/A fusion.

The ability of an LC/A-nociceptin-HN/A fusion (CPN/A) to inhibit streptozotocin (STZ)—induced mechanical (tactile) allodynia in rats is evaluated. STZ—induced mechanical allodynia in rats is achieved by injection of streptozotocin (i.p. or i.v.) which yields destruction of pancreatic β-cells leading to loss of insulin production, with concomitant metabolic stress (hyperglycemia and hyperlipidemia). As such, STZ induces Type I diabetes. In addition, STZ treatment leads to progressive development of neuropathy, which serves as a model of chronic pain with hyperalgesia and allodynia that may reflect signs observed in diabetic humans (peripheral diabetic neuropathy).

Male Sprague-Dawley rats (250-300 g) are treated with 65 mg/kg STZ in citrate buffer (I.V.) and blood glucose and lipid are measured weekly to define the readiness of the model. Paw Withdrawal Threshold (PWT) is measured in response to a Von Frey filament stimulus series over a period of time. Allodynia is said to be established when the PWT on two consecutive test dates (separated by 1 week) measures below 6 g on the scale. At this point, rats are randomized to either a saline group (negative efficacy control), gabapentin group (positive efficacy control) or a test group (CPN/A). Test materials (20-25 μl) are injected subcutaneously as a single injection (except gabapentin) and the PWT is measured at 1 day post-treatment and periodically thereafter over a 2-week period. Gabapentin (30 mg/kg i.p.@ 3 ml/kg injection volume) is injected daily, 2 hours prior to the start of PWT testing. FIG. 23 illustrates the reversal of allodynia achieved by pre-treatment of the animals with 750 ng of CPN/A. Data were obtained over a 2-week period after a single injection of CPN/A.

Example 37

Assessment of In Vivo Efficacy of an LC/A-Nociceptin Variant-$H_N$/A Fusion

The ability of an LC/A-nociceptin variant-$H_N$/A fusion (CPNv/A) to inhibit capsaicin-induced mechanical allodynia is evaluated following subcutaneous intraplantar injection in the rat hind paw. Test animals are evaluated for paw withdrawal frequency (PWF %) in response to a 10 g Von Frey filament stimulus series (10 stimuli×3 trials) prior to recruitment into the study (Pre-Treat); after subcutaneous intraplantar treatment with CPNv/A but before capsaicin (Pre-CAP); and following capsaicin challenge post-injection of CPNv/A (average of responses at 15' and 30'; CAP). Capsaicin challenge is achieved by injection of 10 μL of a 0.3% solution. Sample dilutions are prepared in 0.5% BSA/saline.

FIG. 24 illustrates the reversal of allodynia that is achieved by pre-treatment of the animals with a range of concentrations of LC/A-nociceptin variant-$H_N$/A fusion in comparison to the reversal achieved with the addition of LC/A-nociceptin-$H_N$/A fusion. These data are expressed as a normalized paw withdrawal frequency differential, in which the difference between the peak response (post-capsaicin) and the baseline response (pre-capsaicin) is expressed as a percentage. With this analysis, it can be seen that CPNv/A is more potent than CPN/A since a lower dose of CPNv/A is required to achieve similar analgesic effect to that seen with CPN/A.

Example 38

Preparation of an LC/A-Leu Enkephalin-$H_N$/A Fusion Protein

Due to the small, five-amino acid, size of the leu-enkephalin ligand the LC/A-leu enkephalin-$H_N$/A fusion is created by site directed mutagenesis [for example using Quickchange (Stratagene Inc.)] using the LC/A-nociceptin-$H_N$/A fusion (SEQ ID NO:39) as a template. Oligonucleotides are designed encoding the YGGFL leu-enkephalin peptide, ensuring standard *E. coli* codon usage is maintained and no additional restriction sites are incorporated, flanked by sequences complimentary to the linker region of the LC/A-nociceptin-$H_N$/A fusion (SEQ ID NO:39) either side on the nociceptin section. The SDM product is checked by sequencing and the final construct containing the LC-linker-leu enkephalin-spacer-$H_N$ ORF (SEQ ID NO:80) for expression as a protein of the sequence illustrated in SEQ ID NO:81. The fusion protein is termed CPLE-A. FIG. 25 illustrates the purification of CPLE-A from *E. coli* following the methods used in Example 26.

Example 39

Expression and Purification of an LC/A-Beta-Endorphin-$H_N$/A Fusion Protein

Following the methods used in Example 26, and with the LC/A-beta-endorphin-$H_N$/A fusion protein (termed CPBE-A) created in Example 24, the CPBE-A is purified from *E. coli*. FIG. 26 illustrates the purified protein as analysed by SDS-PAGE.

Example 40

Preparation of an LC/A-Nociceptin Mutant-$H_N$/A Fusion Protein

Due to the single amino acid modification necessary to mutate the nociceptin sequence at position 1 from a Phe to a Tyr, the LC/A-nociceptin mutant-$H_N$/A fusion is created by site directed mutagenesis [for example using Quickchange (Stratagene Inc.)] using the LC/A-nociceptin-$H_N$/A fusion (SEQ ID NO:39) as a template. Oligonucleotides are designed encoding tyrosine at position 1 of the nociceptin sequence, ensuring standard *E. coli* codon usage is maintained and no additional restriction sites are incorporated, flanked by sequences complimentary to the linker region of the LC/A-nociceptin-$H_N$/A fusion (SEQ ID NO:39) either side on the nociceptin section. The SDM product is checked by sequencing and the final construct containing the LC/A-nociceptin mutant-spacer-$H_N$/A fusion ORF (SEQ ID NO:82) for expression as a protein of the sequence illustrated in SEQ ID NO:83. The fusion protein is termed CPOP-A. FIG. 27 illustrates the purification of CPOP-A from *E. coli* following the methods used in Example 26.

Example 41

Preparation and Assessment of an LC/A-Nociceptin Variant Mutant-$H_N$/A Fusion Protein Due to the single amino acid modification necessary to mutate the nociceptin sequence at position 1 from a Phe to a Tyr, the LC/A-nociceptin variant mutant-$H_N$/A fusion is created by site directed mutagenesis [for example using Quickchange (Stratagene Inc.)] using the LC/A-nociceptin variant-$H_N$/A fusion (SEQ ID NO:51) as a template. Oligonucleotides are designed encoding tyrosine at position 1 of the nociceptin sequence, ensuring standard *E. coli* codon usage is maintained and no additional restriction sites are incorporated, flanked by sequences complimentary to the linker region of the LC/A-nociceptin variant-$H_N$/A fusion (SEQ ID NO:51) either side on the nociceptin section. The SDM product is checked by sequencing and the final construct containing the LC/A-nociceptin mutant-spacer-$H_N$/A fusion ORF (SEQ ID NO:84) for expression as a protein of the sequence illustrated in SEQ ID NO:85. The fusion protein is termed CPOPv-A. FIG. 28 illustrates the purification of CPOPv-A from *E. coli* following the methods used in Example 26.

Using methodology described in Example 30, CPOPv-A is assessed for its ability to cleave SNAP-25 in the eDRG cell model. FIG. 29 illustrates that CPOPv-A is able to cleave SNAP-25 in the eDRG model, achieving cleavage of 50% of the maximal SNAP-25 after exposure of the cells to approximately 5.9 nM fusion for 24 h.

Example 42

Preparation of an IgA Protease-Nociceptin Variant-$H_N$/A Fusion Protein

The IgA protease amino acid sequence was obtained from freely available database sources such as GenBank (accession number P09790). Information regarding the structure of the *N. Gonorrhoeae* IgA protease gene is available in the literature (Pohlner et al., Gene structure and extracellular secretion of *Neisseria gonorrhoeae* IgA protease, *Nature,* 1987, 325 (6103), 458-62). Using Backtranslation tool v2.0 (Entelechon), the DNA sequence encoding the IgA protease modified for *E. coli* expression was determined. A BamHI recognition sequence was incorporated at the 5' end and a codon encoding a cysteine amino acid and SalI recognition sequence were incorporated at the 3' end of the IgA DNA. The DNA sequence was screened using MapDraw, (DNASTAR Inc.) for restriction enzyme cleavage sequences incorporated during the back translation. Any cleavage sequences that are found to be common to those required for cloning were removed manually from the proposed coding sequence ensuring common *E. coli* codon usage is maintained. *E. coli* codon usage was assessed Graphical Codon Usage Analyser (Geneart), and the % GC content and codon usage ratio assessed by reference to published codon usage tables. This optimised DNA sequence (SEQ ID NO:86) containing the IgA open reading frame (ORF) is then commercially synthesized.

The IgA (SEQ ID NO:86) is inserted into the LC-linker-nociceptin variant-spacer-$H_N$ ORF (SEQ ID NO:51) using BamHI and SalI restriction enzymes to replace the LC with the IgA protease DNA. The final construct contains the IgA-linker-nociceptin variant-spacer-$H_N$ ORF (SEQ ID NO:87) for expression as a protein of the sequence illustrated in SEQ ID NO:88.

Example 43

Preparation and Assessment of a Nociceptin Targeted Endopeptidase Fusion Protein with a Removable Histidine Purification Tag DNA was prepared that encoded a Factor Xa removable his-tag (his6), although it is clear that alternative proteases site such as Enterokinase and alternative purification tags such as longer histidine tags are also possible. Using one of a variety of reverse translation software tools [for example EditSeq best *E. coli* reverse translation (DNASTAR Inc.), or Backtranslation tool v2.0 (Entelechon)], the DNA sequence encoding the Factor Xa removable his-tag region is determined. Restriction sites are then incorporated into the DNA sequence and can be arranged as NheI-linker-SpeI-PstI-$H_N$/A-XbaI-LEIEGRSGHHHHHHStop codon-HindIII (SEQ ID NO:89). The DNA sequence is screened for restriction sequence incorporated and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector. In order to create CPNv-A-FXa-HT (SEQ ID NO:90, removable his-tag construct) the pCR 4 vector encoding the removable his-tag is cleaved with NheI and HindIII. The NheI-HindIII fragment is then inserted into the LC/A-CPNv-$H_N$/A vector (SEQ ID NO:51) that has also been cleaved by NheI and HindIII. The final construct contains the LC/A-linker-nociceptin variant-spacer-$H_N$-FXa-Histag-HindIII ORF sequences (SEQ ID NO:90) for expression as a protein of the sequence illustrated in SEQ ID NO:91. FIG. 30 illustrates the purification of CPNv-A-FXa-HT from *E. coli* following the methods used in Example 26.

Example 44

Preparation of a Leu-Enkephalin Targeted Endopeptidase Fusion Protein Containing a Translocation Domain Derived from Diphtheria Toxin The DNA sequence is designed by back translation of the amino acid sequence of the translocation domain of the diphtheria toxin (obtained from freely available to database sources such as GenBank (accession number 1×DTT) using one of a variety of reverse translation software tools [for example EditSeq best *E. coli* reverse translation (DNASTAR Inc.), or Backtranslation tool v2.0 (Entelechon)]. Restriction sites are then incorporated into the DNA sequence and can be arranged as NheI-Linker-SpeI-PstI-diphtheria translocation domain-XbaI-stop codon-HindIII (SEQ ID NO:92). PstI/XbaI recognition sequences are incorporated at the 5' and 3' ends of the translocation domain respectively of the sequence maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the diphtheria translocation domain is then commercially synthesized as NheI-Linker-SpeI-PstI-diphtheria translocation domain-XbaI-stop codon-HindIII (for example by Entelechon, Geneart or Sigma-Genosys) and is provided in the pCR 4 vector (Invitrogen). The pCR 4 vector encoding the diphtheria translocation domain is cleaved with NheI and XbaI. The NheI-XbaI fragment is then inserted into the LC/A-CPLE-$H_N$/A vector (SEQ ID NO:80) that has also been cleaved by NheI and XbaI. The final construct contains the LC/A-leu-enkephalin-spacer-diphtheria translocation domain ORF sequences (SEQ ID NO:93) for expression as a protein of the sequence illustrated in SEQ ID NO:94.

Example 45

Preparation of a Nociceptin Variant Targeted Endopeptidase Fusion Protein Containing a LC Domain Derived from Tetanus Toxin The DNA sequence is designed by back translation of the tetanus toxin LC amino to acid sequence (obtained from freely available database sources such as GenBank (accession number X04436) using one of a variety of reverse translation software tools [for example EditSeq best *E. coli* reverse translation (DNASTAR Inc.), or Backtranslation tool v2.0 (Entelechon)]. BamHI/SalI recognition sequences are incorporated at the 5' and 3' ends respectively of the sequence maintaining the correct reading frame (SEQ ID NO:95). The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the tetanus toxin LC open reading frame (ORF) is then commercially synthesized (for example by Entelechon, Geneart or Sigma-Genosys) and is provided in the pCR 4 vector (Invitrogen). The pCR 4 vector encoding the TeNT LC is cleaved with BamHI and SalI. The BamHI-SalI fragment is then inserted into the LC/A-CPNv-$H_N$/A vector (SEQ ID NO:51) that has also been cleaved by BamHI and SalI. The final construct contains the TeNT LC-linker-nociceptin variant-spacer-$H_N$ ORF sequences (SEQ ID NO:96) for expression as a protein of the sequence illustrated in SEQ ID NO:97.

Example 46

Preparation of an LC/C-Nociceptin Variant-$H_N$/C Fusion Protein with a Native Serotype C Linker that is Susceptible to Factor Xa Cleavage Following the methods used in Example 21, the LC/C (SEQ ID NO:31) and $H_N$/C (SEQ ID NO:32) are created and inserted into the C serotype nociceptin variant linker arranged as BamHI-Sail-linker-nociceptin variant-NheI-spacer-SpeI-PstI-XbaI-stop codon-HindIII (SEQ ID NO:98). The final construct contains the LC-linker-nociceptin variant-spacer-$H_N$ ORF sequences (SEQ ID NO:99) for expression as a protein of the sequence illustrated in SEQ ID NO:100. The fusion protein is termed CPNv-C (act. C).

Example 47

Construction of CHO-K1 GALR1 & GALR2 Receptor Activation Assay and SNAP-25 Cleavage Assay Cell-Line Creation CHO-K1 cells stably expressing either the human galanin 1 receptor (CHO-K1-Gal-1R; product number ES-510-C) or human galanin 2 receptor (CHO-K1-Gal-2R; product number ES-511-C) were purchased from Perkin-Elmer (Bucks, UK). Where required, cells were transfected with SNAP-25 DNA using Lipofectamine™ 2000 and incubated for 4 hours before media replacement. After 24 hours, cells were transferred to a T175 flask. 100 ug/ml Zeocin was added after a further 24 hours to begin selection of SNAP-25 expressing cells, and 5 ug/ml Blasticidin added to maintain selective pressure for the receptor. Cells were maintained in media containing selection agents for two weeks, passaging cells every two to three days to maintain 30-70% confluence. Cells were then diluted in selective media to achieve 0.5 cell per well in a 96 well microplate. After a few days, the plates were examined under a microscope, and those containing single colonies were marked. Media in these wells was changed weekly. As cells became confluent in the wells, they were transferred to T25 flasks. When they had expanded sufficiently each clone was seeded to 24 wells of a 96 well plate, plus a frozen stock vial created. Galanin conjugates of the invention and LC/A-$H_N$A (LHA) were applied to the cells for 24 hours, and then western blots performed to detect SNAP-25 cleavage. Clones from which SNAP-25 bands were strong and cleavage levels were high with fusion were maintained for further investigation. Full dose curves were run on these, and the clone with the highest differential between galanin conjugates and LC/A-$H_N$A cleavage levels was selected.

GALR1 Receptor Activation Assay

The GALR1 receptor activation assay measures the potency and intrinsic efficacy of ligands at the GALR1 receptor in transfected CHO-K1 cells by quantifying the reduction of forskolin-stimulated intracellular cAMP using a FRET-based cAMP (Perkin Elmer LANCE cAMP kit). After stimulation, a fluorescently labelled cAMP tracer (Europium-streptavidin/biotin-cAMP) and fluorescently (Alexa) labelled anti-cAMP antibody are added to the cells in a lysis buffer. cAMP from the cells competes with the cAMP tracer for antibody binding sites. When read, a light pulse at 320 nm excites the fluorescent portion (Europium) of the cAMP tracer. The energy emitted from the europium is transferred to the Alexa fluor-labelled antibodies bound to the tracer, generating a TR-FRET signal at 665 nm (Time-resolved fluorescence resonance energy transfer is based on the proximity of the donor label, europium, and the acceptor label, Alexa fluor, which have been brought together by a specific binding reaction). Residual energy from the europium produces light at 615 nm. In agonist treated cells there will be less cAMP to compete with the tracer so a dose dependant increase in signal at 665 nm will be observed compared with samples treated with forskolin alone. The signal at 665 nm signal is converted to cAMP concentration by interpolation to a cAMP standard curve which is included in each experiment.

Using Gilson pipettes and Sigmacoted or lo-bind tips, test materials and standards were diluted to the appropriate concentrations in the wells of the first two columns of an eppendorf 500 μl deep-well lo-bind plate, in assay buffer containing 10 μM forskolin. The chosen concentrations in columns one and two were half a log unit apart. From these, serial 1:10 dilutions were made across the plate (using an electronic eight channel pipette with sigmacote or lo-bind tips) until eleven concentrations at half log intervals had been created. In the twelfth column, assay buffer only was added as a 'basal'. Using a 12 channel digital pipette, 10 μl of sample from the lo-bind plate was transferred to the optiplate 96 well microplate.

To wells containing the standard curve, 10 ul of assay buffer was added using a multichannel digital pipette. To wells containing the test materials, 10 ul of cells in assay buffer at the appropriate concentration were added. Plates were sealed and incubated for 120 min at room temperature, for the first hour on an IKA MTS 2/4 orbital shaker set to maximum speed.

LANCE Eu-W8044 labelled streptavidin (Eu-SA) and Biotin-cAMP (b-cAMP) were diluted in cAMP Detection Buffer (both from Perkin Elmer LANCE cAMP kit) to create sub-stocks, at dilution ratios of 1:17 and 1:5, respectively. The final detection mix was prepared by diluting from the two sub stocks into detection buffer at a ratio of 1:125. The mixture was incubated for 15-30 min at room temperature before addition of 1:200 Alexa Fluor® 647-anti cAMP Antibody (Alexa-Fluor Ab). After briefly vortex mixing, 20 μl was immediately added to each well using a digital multichannel pipette. Microplate sealers were applied and plates incubated for 24 h at room temperature (for the first hour on an IKA MTS 2/4 orbital shaker set to maximum speed). Plate sealers were removed prior to reading on the Envision.

GALR2 Receptor Activation Assay

The GALR2 receptor activation assay measures the potency and intrinsic efficacy of ligands at GALR2 receptor in transfected CHO-K1 cells by measuring the calcium mobilisation that occurs when the receptor is activated. The transfected cells are pre-loaded with a calcium sensitive dye (FLIPR) before treatment. When read using Flexstation 3 microplate reader (Molecular devices) a light pulse at 485 nm excites the fluorescent dye and causes an emission at 525 nm. This provides real-time fluorescence data from changes in intracellular calcium. In agonist treated cells there will be activation of the receptor, leading to an increase in calcium mobilisation. This will be measured as an increase in the relative fluorescence units (RFU) at 525 nM.

Culture of Cells for Receptor Activation Assay:

Cells were seeded and cultured in T175 flasks containing Ham F12 with Glutamax, 10% Foetal bovine serum, 5 μg ml-1 Blasticidin and 100 μml-1 Zeocin. The flasks were incubated at 37° C. in a humidified environment containing 5% $CO_2$ until 60-80% confluent. On the day of harvest the media was removed and the cells washed twice with 25 ml PBS. The cells were removed from the flask by addition of 10 ml of Tryple Express, and incubation at 37° C. for 10 min followed by gentle tapping of the flask. The dislodged cells were transferred to a 50 ml centrifuge tube and the flask washed twice with 10 ml media which was added to the cell suspension. The tube was centrifuged at 1300×g for 3 min and the supernatant removed. Cells were gently re-suspended in 10 ml media (if freezing cells) or assay buffer (if using 'fresh' cells in assay), and a sample was removed for counting using a nucleocounter (ChemoMetec). Cells for use 'fresh' in an assay were diluted further in assay buffer to the appropriate concentration. Cells harvested for freezing were re-centrifuged (1300×g; 3 min), the supernatant removed and cells re-suspended in Synth-a-freeze at 4° C. to 3×106 cells/ml. Cryovials containing 1 ml suspension each were placed in a chilled Nalgene Mr Frosty freezing container (−1° C./minute cooling rate), and left overnight in a −80° C. freezer. The following day vials were transferred to the vapour phase of a liquid nitrogen storage tank.

FIGS. 33-34 demonstrate that galanin conjugates of the present invention having different galanin ligands (i.e. galanin-16 and galanin-30) activate both the GALR1 and the GALR2 receptors.

CHO-K1 GALR1SNAP-25 Cleavage Assays

Cultures of cells were exposed to varying concentrations of galanin conjugates for 24 hours. Cellular proteins were separated by SDS-PAGE and western blotted with anti-SNAP-25 antibody to facilitate assessment of SNAP-25 cleavage. SNAP-25 cleavage calculated by densitometric analysis (Syngene).

Plating Cells

Prepare cells at 2×10e5 cells/ml and seed 125 μl per well of 96 well plate. Use the following media: 500 ml Gibco Ham F12 with Glutamax (product code 31765068), 50 ml FBS, 5 ug/ml Blasticidin (250 μl aliquot from box in freezer, G13) (Calbiochem #203351, 10 ml at 10 mg/ml), 100 ug/ml Zeocin (500 μl from box in freezer, G35). (Invitrogen from Fisher, 1 g in 8×1.25 ml tubes at 100 mg/ml product code VXR25001). Allow cells to grow for 24 hrs (37° C., 5% $CO_2$, humidified atmosphere).

Cell Treatment

Prepare dilutions of test protein for a dose range of each test proteins (make up double (2×) the desired final concentrations because 125 μl will be applied directly onto 125 μl of media already in each well). Filter sterilize CHO GALR1 feeding medium (20 ml syringe, 0.2 μm syringe filter) to make the dilutions. Add the filtered medium into 5 labelled bijoux's (7 ml tubes), 0.9 ml each using a Gilson pipette or multi-stepper. Dilute the stock test protein to 2000 nM (working stock solution 1) and 600 nM (working stock solution 2). Using a Gilson pipette prepare 10-fold serial dilutions of each working stock, by adding 100 μl to the next concentration in the series. Pipette up and down to mix thoroughly. Repeat to obtain 4 serial dilutions for solution 1, and 3 serial dilutions for solution 2. A 0 nM control (filtered feeding medium only) should also be prepared as a negative control for each plate. Repeat the above for each test protein. In each experiment a 'standard' batch of material must be included as control/reference material, this is unliganded LC/A-$H_N$/A.

Apply Diluted Sample to CHO GALR1 Plates

Apply 125 μl of test sample (double concentration) per well. Each test sample should be applied to triplicate wells and each dose range should include a 0 nM control. Incubate for 24 hrs (37° C., 5% $CO_2$, humidified atmosphere).

Cell Lysis

Prepare fresh lysis buffer (20 mls per plate) with 25% (4×) NuPAGE LDS sample buffer, 65% $dH_2O$ and 10% 1 M DTT. Remove medium from the CHO GALR1 plate by inverting over a waste receptacle. Drain the remaining media from each well using a fine-tipped pipette. Lyse the cells by adding 125 μl of lysis is buffer per well using a multi-stepper pipette. After a minimum of 20 mins, remove the buffer from each well to a 1.5 ml microcentrifuge tube. Tubes must be numbered to allowing tracking of the CHO GALR1 treatments throughout the blotting procedure. A1-A3 down to H1-H3 numbered 1-24, A4-A6 down to H4-H6 numbered 25-48, A7-A9 down to H7-H93 numbered 49-72, A10-A12 down to H10-H12 numbered 73-96. Vortex each sample and heat at 90° C. for 5-10 mins in a prewarmed heat block. Store at −20° C. or use on the same day on an SDS gel.

Gel Electrophoresis

If the sample has been stored o/n or longer, put in a heat block prewarmed to 90° C. for 5-10 mins. Set up SDS page gels, use 1 gel per 12 samples, prepare running buffer (1×, Invitrogen NuPAGE MOPS SDS Running Buffer (20×) (NP0001))≈800 ml/gel tank. Add 500 μl of NuPAGE antioxidant to the upper buffer chamber. Load 15 ul samples onto gel lanes from left to right as and load 2.5 ul of Invitrogen Magic Marker XP and 5 μl Invitrogen See Blue Plus 2 pre-stained standard and 15 ul of non-treated control. It is important to maximize the resolution of separation during SDS-PAGE. This can be achieved by running 12% bis-tris gels at 200 V for 1 hour and 25 minutes (until the pink (17 kDa) marker reaches the bottom of the tank).

Western Blotting

Complete a Semi-dry transfer: using an Invitrogen iBlot (use iBlot Programme 3 for 6 minutes). Put the nitrocellulose membranes in individual small trays. Incubate the membranes with blocking buffer solution (5 g Marvel milk powder per 100 ml 0.1% PBS/Tween) at room temperature, on a rocker, for 1 hour. Apply primary antibody (Anti-SNAP-25 1:1000 dilution) and incubate the membranes with primary antibody (diluted in blocking buffer) for 1 hour on a rocker at room temperature. Wash the membranes by rinsing 3 times with PBS/Tween (0.1%). Then apply the secondary (Anti-Rabbit-HRP conjugate diluted 1:1000) and incubate the membranes with secondary antibody (diluted in blocking buffer) at is room temperature, on a rocker, for 1 hour. Wash the membranes by rinsing 3 times with PBS/Tween (0.1%), leave membrane a minimum of 20 mins for the last wash. Detect the bound antibody using Syngene: Drain blots of PBS/Tween, mix WestDura reagents 1:1 and add to blots for 5 minutes. Ensure enough solution is added to the membranes to completely cover them. Place membrane in Syngene tray, set up Syngene software for 5 min expose time.

Example 48

Construction and Activation of Galanin Conjugates

Preparation of a LC/A and $H_N$/A Backbone Clones

The following procedure creates the LC and $H_N$ fragments for use as the component backbone for multidomain fusion expression. This example is based on preparation of a serotype A based clone (SEQ ID NO: 27 and SEQ ID NO: 28), though the procedures and methods are equally applicable to the other serotypes [illustrated by the sequence listing for serotype B (SEQ ID NO: 29 and SEQ ID NO:30) and serotype C (SEQ ID NO: 31 and SEQ ID NO: 32)].

Preparation of Cloning and Expression Vectors pCR 4 (Invitrogen) is the chosen standards cloning vector, selected due to the lack of restriction sequences within the vector and adjacent sequencing primer sites for easy construct confirmation. The expression vector is based on the pMAL (NEB) expression vector, which has the desired restriction sequences within the multiple cloning site in the correct orientation for construct insertion (BamHI-SalI-PstI-HindIII). A fragment of the expression vector has been removed to create a non-mobilisable plasmid and a variety of different fusion tags have been inserted to increase purification options.

Preparation of Protease (e.g. LC/A) Insert

The LC/A (SEQ ID NO:27) is created by one of two ways:

The DNA sequence is designed by back translation of the LC/A amino acid sequence [obtained from freely available database sources such as GenBank (accession number P10845) or Swissprot (accession locus BXA1_CLOBO) using is one of a variety of reverse translation software tools (for example EditSeq best E. coli reverse translation (DNASTAR Inc.), or Backtranslation tool v2.0 (Entelechon)]. BamHIH/SalI recognition sequences are incorporated at the 5' and 3' ends respectively of the sequence, maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the LC/A open reading frame (ORF) is then commercially synthesized (for example by Entelechon, Geneart or Sigma-Genosys) and is provided in the pCR 4 vector. The alternative method is to use PCR amplification from an existing DNA sequence with BamHI and SalI restriction enzyme sequences incorporated into the 5' and 3' PCR primers respectively. Complementary oligonucleotide primers are chemically synthesised by a supplier (for example MWG or Sigma-Genosys), so that each pair has the ability to hybridize to the opposite strands (3' ends pointing “towards” each other) flanking the stretch of *Clostridium* target DNA, one oligonucleotide for each of the two DNA strands. To generate a PCR product the pair of short oligonucleotide primers specific for the *Clostridium* DNA sequence are mixed with the *Clostridium* DNA template and other reaction components and to placed in a machine (the ‘PCR machine’) that can change the incubation temperature of the reaction tube automatically, cycling between approximately 94° C. (for denaturation), 55° C. (for oligonucleotide annealing), and 72° C. (for synthesis). Other reagents required for amplification of a PCR product include a DNA polymerase (such as Taq or Pfu polymerase), each of the four nucleotide dNTP building blocks of DNA in equimolar amounts (50-200 μM) and a buffer appropriate for the enzyme optimised for $Mg^{2+}$ concentration (0.5-5 mM).

The amplification product is cloned into pCR 4 using either, TOPO TA cloning for Taq PCR products or Zero Blunt TOPO cloning for Pfu PCR products (both kits commercially available from Invitrogen). The resultant clone is checked by sequencing. Any additional restriction sequences which are not compatible with the cloning system are then removed using site directed mutagenesis [for example, using Quickchange (Stratagene Inc.)].

Preparation of Translocation (e.g. $H_N$) Insert

The $H_N$/A (SEQ ID NO:28) is created by one of two ways:

The DNA sequence is designed by back translation of the $H_N$/A amino acid sequence [obtained from freely available database sources such as GenBank (accession number P10845) or Swissprot (accession locus BXA1_CLOBO)] using one of a variety of reverse translation software tools [for example EditSeq best *E. coli* reverse translation (DNASTAR Inc.), or Backtranslation tool v2.0 (Entelechon)]. A PstI restriction sequence added to the N-terminus and XbaI-stop codon-HindIII to the C-terminus ensuring the correct reading frame is maintained. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector.

The alternative method is to use PCR amplification from an existing DNA sequence with PstI and XbaI-stop codon-HindIII restriction enzyme sequences incorporated into the 5' and 3' PCR primers respectively. The PCR amplification is performed as described above. The PCR product is inserted into pCR 4 vector and checked by sequencing. Any additional restriction sequences which are not compatible with the cloning system are then removed using site directed mutagenesis [for example using Quickchange (Stratagene Inc.)].

Preparation of LC/A-$H_N$/A-GS20-GA30 and LC/A-$H_N$/A-GS20-GA16 Fusion

In order to create the LC/A-$H_N$/A-GS20-GA30 construct, an A serotype linker with the addition of a Factor Xa site for activation, arranged as BamH I-Sail-linker-protease site-linker-PstI-XbaI-stop codon-HindIII (SEQ ID NO: 34) is synthesised. The pCR 4 vector encoding the linker is cleaved with BamHI+SalI restriction enzymes. This cleaved vector then serves as the recipient for insertion and ligation of the LC/A DNA (SEQ ID NO:27) also cleaved with BamHI+SalI. This construct is then cleaved with BamHI+HindIII and inserted into an expression vector such as the pMAL plasmid (NEB). The resulting plasmid DNA is then cleaved with PstI+XbaI restriction enzymes and the $H_N$/A DNA (SEQ ID NO:28) is then cleaved with PstI+XbaI restriction enzymes and inserted into the similarly cleaved pMAL vector to create pMAL-LC/A-HN/A-XbaI-stop codon-HindIII. The final construct contains the GS20 spacer-GA30 ORF for expression as a protein of the sequence illustrated in SEQ ID NO: 105, therefore, XbaI-Spacer-GA30-Stop-HindIII was synthesised. The pCR4 vector encoding this spacer and ligand is cleaved with XbaI and HindIII for insertion into pMAL-LC/A-HN/A-XbaI-stop codon-HindIII to create LC/A-$H_N$/A-GS20-GA30 (SEQ ID NO: 103). Alternatively, LC/A-$H_N$/A-GS20-GA16 (SEQ ID92) was created by synthesising XbaI-Spacer-GA16-Stop-HindIII and cleaving the pCR4 vector encoding this spacer and ligand with XbaI and HindIII for insertion into pMAL-LC/A-HN/A-XbaI-stop codon-HindIII. The final construct contains the GS20 spacer-GA16 ORF for expression as a protein of the sequence illustrated in SEQ ID NO: 106.

Example 49

Purification Method for Galanin Conjugate

Defrost falcon tube containing 25 ml 50 mM HEPES pH 7.2, 200 mM NaCl and approximately 10 g of *E. coli* BL21 cell paste. Make the thawed cell paste up to 80 ml with 50 mM HEPES pH 7.2, 200 mM NaCl and sonicate on ice 30 seconds on, 30 seconds off for 10 cycles at a power of 22 microns ensuring the sample remains cool. Spin the lysed cells at 18 000 rpm, 4° C. for 30 minutes. Load the supernatant onto a 0.1 M $NiSO_4$ charged Chelating column (20-30 ml column is sufficient) equilibrated with 50 mM HEPES pH 7.2, 200 mM NaCl. Using a step gradient of 10 and 40 mM imidazol, wash away the non-specific bound protein and elute the fusion protein with 100 mM imidazol. Dialyse the eluted fusion protein against 5 L of 50 mM HEPES pH 7.2, 200 mM NaCl at 4° C. overnight and measure the OD of the dialysed fusion protein. Add 3.2 μl of enterokinase (2 μg/ml) per 1 mg conjugate and Incubate at 25° C. static overnight. Load onto a 0.1 M $NiSO_4$ charged Chelating column (20-30 ml column is sufficient) equilibrated with 50 mM HEPES pH 7.2, 200 mM NaCl. Wash column to baseline with 50 mM HEPES pH 7.2, 200 mM NaCl. Using a step gradient of 10 and 40 mM imidazol, wash away the non-specific bound protein and elute the fusion protein with 100 mM imidazol. Dialyse the eluted conjugate against 5 L of 50 mM HEPES pH 7.2, 200 mM NaCl at 4° C. overnight and concentrate the conjugate to about 2 mg/ml, aliquot sample and freeze at −20° C. Test purified protein using OD, BCA, purity analysis and SNAP-25 assessments.

Example 50

A method of treating, preventing or ameliorating pain in a subject, comprising administration to said patient a therapeutic effective amount of non-cytotoxic protein conjugate, wherein said pain is selected from the group consisting of: to chronic pain arising from malignant disease, chronic pain not caused by malignant disease (peripheral neuropathies).

Patient A

A 73 year old woman suffering from severe pain caused by posthepatic neuralgia is treated by a peripheral injection with non-cytotoxic protein conjugate to reduce neurotransmitter release at the synapse of nerve terminals to reduce the pain. The patient experiences good analgesic effect within 2 hours of said injection.

Patient B

A 32 year old male suffering from phantom limb pain after having his left arm amputated following a car accident is treated by peripheral injection with non-cytotoxic protein conjugate to reduce the pain. The patient experiences good analgesic effect within 1 hour of said injection.

Patient C

A 55 year male suffering from diabetic neuropathy is treated by a peripheral injection with non-cytotoxic protein conjugate to reduce neurotransmitter release at the synapse of nerve terminals to reduce the pain. The patient experiences good analgesic effect within 4 hours of said injection.

Patient D

A 63 year old woman suffering from cancer pain is treated by a peripheral injection with non-cytotoxic protein conjugate to reduce neurotransmitter release at the synapse of nerve terminals to reduce the pain. The patient experiences good analgesic effect within 4 hours of said injection.

All documents, books, manuals, papers, patents, published patent applications, guides, abstracts and other reference materials cited herein are incorporated by reference in their entirety. While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. A non-cytotoxic protein conjugate for inhibition or reduction of exocytic fusion in a nociceptive sensory afferent cell, comprising:

(i) a galanin Targeting Moiety (TM),
wherein said TM is an agonist of a receptor present on said nociceptive sensory afferent cell, and wherein said receptor undergoes endocytosis to be incorporated into an endosome within the nociceptive sensory afferent cell;

(ii) a non-cytotoxic protease or a protease fragment thereof,
wherein the protease or protease fragment cleaves a protein of the exocytic fusion apparatus of said nociceptive sensory afferent cell; and (iii) a Translocation Domain,
wherein the Translocation Domain translocates the protease or protease fragment from within the endosome, across the endosomal membrane, and into the cytosol of the nociceptive sensory afferent cell.

2. The non-cytotoxic conjugate of claim 1, wherein the non-cytotoxic protease is selected from a clostridial neurotoxin, or an IgA protease.

3. The non-cytotoxic conjugate of claim 1, wherein the Translocation Domain is a botulinum $H_N$ domain.

4. The non-cytotoxic conjugate of claim 1, wherein the receptor is a GALR1 and/or a GALR2 receptor.

5. The non-cytotoxic conjugate of claim 1, wherein the galanin TM comprises an amino acid sequence having at least 70% or at least 80% sequence identity to the amino acid sequence set forth in SEQ ID NO: 101 or SEQ ID NO: 102, or a fragment or variant thereof.

6. The non-cytotoxic conjugate of claim 1, wherein the galanin TM comprises an amino acid sequence having at least 90% sequence identity to the amino acid sequence set forth in SEQ ID NO:101 or SEQ ID NO: 102 or a fragment or variant thereof.

7. The non-cytotoxic conjugate of claim 1, wherein the galanin TM comprises an amino acid sequence having at least 95% sequence identity to the amino acid sequence set forth in SEQ ID NO:101 or SEQ ID NO: 102, or a fragment or variant thereof.

8. The non-cytotoxic conjugate of claim 1, wherein the galanin TM comprises the amino acid sequence set forth in SEQ ID NO:101 or SEQ ID NO: 102.

9. The non-cytotoxic conjugate of claim 1, wherein the nociceptive sensory afferent cell is a primary nociceptive sensory afferent cell.

10. The non-cytotoxic conjugate of claim 1, wherein said conjugate comprises an amino acid sequence having at least 90% sequence identity to the amino acid sequence set forth in SEQ ID NO: 105 or SEQ ID NO: 106.

11. A pharmaceutical composition, comprising a conjugate according to claim 1, and a pharmaceutically acceptable carrier.

12. A method for treating or ameliorating pain in a subject, comprising administering to said subject a therapeutically effective amount of a conjugate according to claim 1, thereby treating or ameliorating pain in the subject.

13. The method according to claim 12, wherein the pain is chronic pain selected from the group consisting of neuropathic pain, inflammatory pain, headache pain, somatic pain, visceral pain and referred pain.

14. A method for treating or ameliorating pain in a subject, comprising administering to said subject a therapeutically effective amount of a pharmaceutical composition according to claim 11, thereby treating or ameliorating pain in the subject.

15. The method according to claim 14, wherein the pain is chronic pain selected from the group consisting of neuropathic pain, inflammatory pain, headache pain, somatic pain, visceral pain and referred pain.

* * * * *